(12) United States Patent
Akioka et al.

(10) Patent No.: US 9,907,307 B2
(45) Date of Patent: *Mar. 6, 2018

(54) AROMATIC COMPOUND AND USES THEREOF

(71) Applicant: SUMITOMO CHEMICAL COMPANY, LIMITED, Tokyo (JP)

(72) Inventors: Yuki Akioka, Takarazuka (JP); Takayuki Shioda, Takarazuka (JP); Sadayuki Arimori, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/128,641

(22) PCT Filed: Mar. 26, 2015

(86) PCT No.: PCT/JP2015/060404
§ 371 (c)(1),
(2) Date: Sep. 23, 2016

(87) PCT Pub. No.: WO2015/147336
PCT Pub. Date: Oct. 1, 2015

(65) Prior Publication Data
US 2017/0105416 A1    Apr. 20, 2017

(30) Foreign Application Priority Data
Mar. 28, 2014    (JP) .................. 2014-067942

(51) Int. Cl.
*A01N 43/713* (2006.01)
*C07D 401/12* (2006.01)

(52) U.S. Cl.
CPC ......... *A01N 43/713* (2013.01); *C07D 401/12* (2013.01)

(58) Field of Classification Search
None
See application file for complete search history.

(56) References Cited

U.S. PATENT DOCUMENTS 5,824,705 A    10/1998    Mueller et al.
5,861,359 A    1/1999    Theodoridis
(Continued)

FOREIGN PATENT DOCUMENTS

JP    7-502747 A    3/1995
JP    2002-506060 A    2/2002
(Continued)

OTHER PUBLICATIONS

International Preliminary Report on Patentability and English translation of the Written Opinion of the International Searching Authority (forms PCT/IB/373 and PCT/ISA/237), dated Oct. 4, 2016, for International Application No. PCT/JP2015/059820.
(Continued)

*Primary Examiner* — Samantha L Shterengarts
(74) *Attorney, Agent, or Firm* — Birch, Stewart, Kolasch & Birch, LLP

(57) ABSTRACT

A pest control agent comprising an aromatic compound represented by formula (1) wherein $R^1$ represents a C1-C4 alkyl group, etc.; $R^3$ represents a hydrogen atom, etc.; $R^7$ represents a C1-C3 alkyl group, etc.;

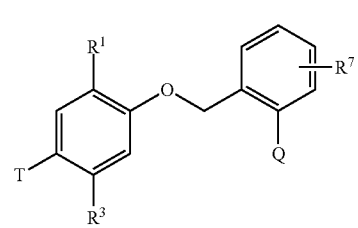

(1)

T represents the following group T1, T2, or T3;

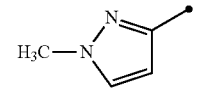

T1

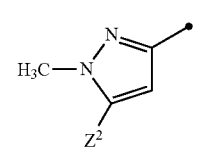

T2

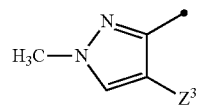

T3

$Z^2$ represents a halogen atom, etc.; $Z^3$ represents a C1-C3 alkyl group, etc.;
Q represents the following group Q1, Q2, or Q3;

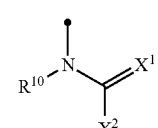

Q1

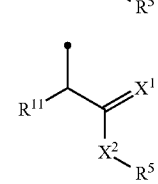

Q2

(Continued)

-continued

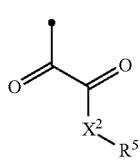

$R^5$ represents a C1-C3 alkyl group, etc.; $R^{10}$ represents a hydrogen atom, etc.; $R^{11}$ represents a hydrogen atom, etc.; $X^1$ represents an oxygen atom, etc.; $X^2$ represents a direct bond, etc.; and $R^{12}$ represents a C1-C3 alkyl group, etc. has excellent control activity.

15 Claims, No Drawings

(56) References Cited

U.S. PATENT DOCUMENTS

| | | | |
|---|---|---|---|
| 5,948,819 | A | 9/1999 | Ohtsuka et al. |
| 6,252,083 | B1 | 6/2001 | Mueller et al. |
| 6,583,090 | B1 | 6/2003 | Gewehr et al. |
| 9,314,023 | B2 | 4/2016 | Arimori et al. |
| 2011/0183978 | A1 | 7/2011 | Sudau et al. |
| 2013/0129839 | A1 | 5/2013 | Long et al. |
| 2013/0281455 | A1 | 10/2013 | Sudau et al. |
| 2015/0203511 | A1 | 7/2015 | Arimori et al. |
| 2015/0305339 | A1 | 10/2015 | Long et al. |
| 2016/0081340 | A1 | 3/2016 | Arimori et al. |

FOREIGN PATENT DOCUMENTS

| | | |
|---|---|---|
| JP | 2003-12416 A | 1/2003 |
| JP | 2007-284384 A | 11/2007 |
| JP | 2011-1292 A | 1/2011 |
| JP | 2011-1294 A | 1/2011 |
| JP | 2013-507334 A | 3/2013 |
| JP | 2013-536866 A | 9/2013 |
| WO | WO 95/27693 A1 | 10/1995 |
| WO | WO 97/05115 A1 | 10/1995 |
| WO | WO 2014/051161 A1 | 4/2014 |
| WO | WO 2014/051165 A1 | 4/2014 |
| WO | WO 2014/192953 A1 | 12/2014 |
| WO | WO 2015/050039 A1 | 4/2015 |

OTHER PUBLICATIONS

International Preliminary Report on Patentability and English translation of the Written Opinion of the International Searching Authority (forms PCT/IB/373 and PCT/ISA/237), dated Oct. 4, 2016, for International Application No. PCT/JP2015/060404.
International Search Report (form PCT/ISA/210), dated Jun. 23, 2015, International Application No. PCT/JP2015/060404.
International Search Report, (form PCT/ISA 210), dated May 19, 2015, International Application No. PCT/JP2015/059820.
U.S. Appl. No. 15/128,681, filed Sep. 23, 2016.
International Search Report, issued in PCT/JP2015/060404, dated Jun. 23, 2015.
Extended European Search Report, dated Jul. 28, 2017, for European Application No. 15768170.1.

AROMATIC COMPOUND AND USES THEREOF

TECHNICAL FIELD

The present invention relates to an aromatic compound and uses thereof.

BACKGROUND ART

Heretofore, various chemicals have been developed so as to control pests and provided in practice use, but in some cases, these chemicals may not exert enough activity.

Meanwhile, there have been known, as compounds having an aromatic group, compounds represented by the following formula (X):

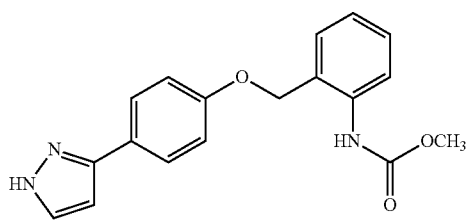

(see JPH07-502747-A)

The present invention provides a compound having excellent control activity against pests.

DISCLOSURE OF THE INVENTION

The present inventors have intensively studied so as to find compounds having excellent control activity against pests, and found that an aromatic compound represented by formula (1) shown below has excellent control activity against pests.

The present invention is as follows.

[1] An aromatic compound represented by formula (1):

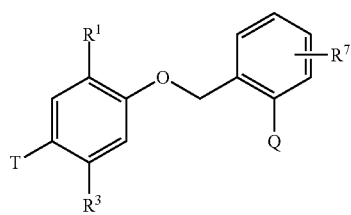

wherein $R^1$ represents a halogen atom or a C1-C4 alkyl group optionally having one or more halogen atoms; $R^3$ represents a hydrogen atom, a halogen atom, or a C1-C4 alkyl group optionally having one or more halogen atoms; $R^7$ represents a C1-C3 alkyl group optionally having one or more halogen atoms, a hydrogen atom, a halogen atom, a C1-C3 alkoxy group optionally having one or more halogen atoms, or a C3-C4 cycloalkyl group optionally having one or more halogen atoms; T represents the following group T1, T2, or T3;

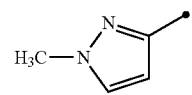

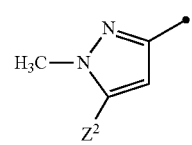

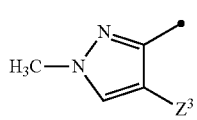

$Z^2$ and $Z^3$ each independently represents a halogen atom, a C1-C3 alkyl group optionally having one or more halogen atoms, or a C1-C3 alkoxy group optionally having one or more halogen atoms; Q represents the following group Q1, Q2, or Q3;

$R^5$ represents a C1-C3 alkyl group optionally having one or more halogen atoms; $R^{10}$ represents a hydrogen atom, a hydroxyl group, or a methyl group; $R^{11}$ represents a hydrogen atom, a hydroxyl group, a methyl group, or a methoxy group; $X^1$ represents an oxygen atom or a sulfur atom; $X^2$ represents an oxygen atom, a sulfur atom, $NR^{12}$, or a direct bond; and $R^{12}$ represents a C1-C3 alkyl group optionally having one or more halogen atoms, or a hydrogen atom.

[2] An aromatic compound represented by formula (2):

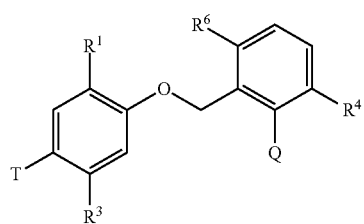

wherein $R^1$, $R^3$, T, and Q are the same as defined above; and $R^4$ and $R^6$ each independently represents a C1-C3 alkyl group optionally having one or more halogen atoms, a hydrogen atom, a halogen atom, a C1-C3 alkoxy group optionally having one or more halogen atoms, or a C3-C4 cycloalkyl group optionally having one or more halogen atoms.

[3] The aromatic compound according to [2], wherein Q is a group Q1 or Q3.

[4] An aromatic compound represented by formula (3):

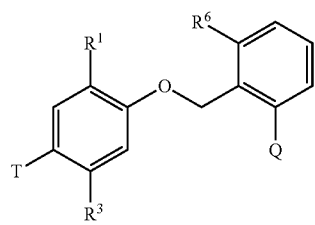

(3)

wherein $R^1$, $R^3$, $R^6$, T, and Q are the same as defined above.

[5] The aromatic compound according to [4], wherein $R^1$ is a C1-C4 alkyl group optionally having one or more halogen atoms; and $X^1$ is an oxygen atom.

[6] A pest control agent comprising the aromatic compound according to any one of [1] to [5].

[7] A method for controlling pests, which comprises treating plants or soil with an effective amount of the aromatic compound according to any one of [1] to [5].

[8] Use of the aromatic compound according to any one of [1] to [5] for controlling pests.

According to the present invention, pests can be controlled.

MODE FOR CARRYING OUT THE INVENTION

In the present invention, a compound represented by formula (1) is referred to as the present compound, and a pest control agent containing the present compound is referred to as the present control agent.

Substituents as used herein will be mentioned below.

The halogen atom represents a fluorine atom, a chlorine atom, a bromine atom, and an iodine atom.

Examples of the C1-C4 alkyl group optionally having one or more halogen atoms include a methyl group, an ethyl group, a propyl group, an isopropyl group, a butyl group, an isobutyl group, a sec-butyl group, a tert-butyl group, a fluoromethyl group, a chloromethyl group, a dichloromethyl group, a difluoromethyl group, a trifluoromethyl group, a trichloromethyl group, a 2-fluoroethyl group, a 2,2,2-trifluoroethyl group, and a 1-trifluoromethyl-2,2,2-trifluoroethyl group.

Examples of the C3-C4 cycloalkyl group optionally having one or more halogen atoms include a cyclopropyl group, a cyclobutyl group, a 2,2-dichlorocyclopropyl group, and a 2,2-difluorocyclopropyl group.

The C1-C3 alkyl group represents a methyl group, an ethyl group, a propyl group, and an isopropyl group.

Examples of the C1-C3 alkyl group optionally having one or more halogen atoms include a methyl group, an ethyl group, a propyl group, an isopropyl group, a fluoromethyl group, a chloromethyl group, a bromomethyl group, a difluoromethyl group, a trifluoromethyl group, a trichloromethyl group, a 2,2,2-trifluoroethyl group, a 2,2,2-trifluoro-1-trifluoromethylethyl group, a 1,2,2,2-tetra fluoro-1-trifluoromethylethyl group, and a 3-fluorobutyl group.

The C1-C3 alkoxy group represents a methoxy group, an ethoxy group, a propyloxy group, and an isopropyloxy group.

Examples of the C1-C3 alkoxy group optionally having one or more halogen atoms include a methoxy group, an ethoxy group, a propyloxy group, an isopropyloxy group, a trifluoromethoxy group, a difluoromethoxy group, a 2-fluoroethoxy group, a 2,2,2-trifluoroethoxy group, and a 3-chloropropoxy group.

Examples of Aspect of the present compound include the following compounds.

An aromatic compound in which $X^1$ is an oxygen atom in formula (1).

An aromatic compound in which $X^1$ is an oxygen atom and $R^5$ is a methyl group in formula (1).

An aromatic compound in which $X^1$ is an oxygen atom and $R^5$ is an ethyl group in formula (1).

An aromatic compound in which Q is Q1 or Q3 in formula (1).

An aromatic compound in which Q is Q1 in formula (1).
An aromatic compound in which Q is Q2 in formula (1).
An aromatic compound in which Q is Q3 in formula (1).
An aromatic compound in which T is T1 in formula (1).
An aromatic compound in which T is T2 in formula (1).
An aromatic compound in which T is T3 in formula (1).

An aromatic compound in which $Z^2$ and $Z^3$ are each independently a halogen atom or a C1-C3 alkoxy group in formula (1).

An aromatic compound in which $Z^2$ is a halogen atom or a C1-C3 alkoxy group in formula (1).

An aromatic compound in which $Z^2$ is a halogen atom in formula (1).

An aromatic compound in which $Z^2$ is a C1-C3 alkoxy group in formula (1).

An aromatic compound in which $Z^3$ is a C1-C3 alkyl group in formula (1).

An aromatic compound in which $R^1$ is a halogen atom in formula (1).

An aromatic compound in which $R^1$ is a C1-C4 alkyl group optionally having one or more halogen atoms in formula (1).

An aromatic compound in which $R^3$ is a hydrogen atom in formula (1).

An aromatic compound in which $R^3$ is a C1-C4 alkyl group optionally having one or more halogen atoms in formula (1).

An aromatic compound in which $R^1$ is a C1-C4 alkyl group optionally having one or more halogen atoms and $R^3$ is a hydrogen atom or a C1-C4 alkyl group optionally having one or more halogen atoms in formula (1).

An aromatic compound in which $R^7$ is a C1-C3 alkyl group optionally having one or more halogen atoms, a hydrogen atom, or a C1-C3 alkoxy group optionally having one or more halogen atoms in formula (1).

An aromatic compound in which $R^7$ is a C1-C3 alkyl group optionally having one or more halogen atoms in formula (1).

An aromatic compound in which $R^7$ is a halogen atom in formula (1).

An aromatic compound in which $R^7$ is a C1-C3 alkoxy group optionally having one or more halogen atoms in formula (1).

An aromatic compound in which $R^7$ is a C3-C4 cycloalkyl group optionally having one or more halogen atoms in formula (1).

An aromatic compound in which Q is Q1, $R^{10}$ is a hydrogen atom, and $X^1$ is an oxygen atom in formula (1).

An aromatic compound in which Q is Q1, $R^{10}$ is a hydrogen atom, $X^1$ is an oxygen atom, and $X^2$ is an oxygen atom in formula (1).
An aromatic compound in which Q is Q1, $R^{10}$ is a hydrogen atom, and $X^1$ is a sulfur atom in formula (1).
An aromatic compound in which Q is Q1, $R^{10}$ is a hydroxyl group, and $X^1$ is an oxygen atom in formula (1).
An aromatic compound in which Q is Q1, $R^{10}$ is a hydroxyl group, and $X^1$ is a sulfur atom in formula (1).
An aromatic compound in which Q is Q1, $R^{10}$ is a methyl group, and $X^1$ is an oxygen atom in formula (1).
An aromatic compound in which Q is Q1, $R^{10}$ is a methyl group, and $X^1$ is a sulfur atom in formula (1).
An aromatic compound in which Q is Q3 and $X^2$ is an oxygen atom in formula (1).
An aromatic compound in which Q is Q3 and $X^2$ is $NR^{12}$ in formula (1).
An aromatic compound in which Q is Q3 and $X^2$ is a direct bond in formula (1).
An aromatic compound in which $R^1$ is a C1-C4 alkyl group optionally having one or more halogen atoms, $R^3$ is a hydrogen atom, and $R^7$ is a hydrogen atom or an alkyl group optionally having one or more halogen atoms in formula (1).
An aromatic compound in which $R^1$ is a methyl group, $R^3$ is a hydrogen atom or a methyl group, and $R^7$ is a hydrogen atom or an alkyl group optionally having one or more halogen atoms in formula (1).
An aromatic compound in which $X^1$ is an oxygen atom in formula (2).
An aromatic compound in which $X^1$ is an oxygen atom and $R^5$ is a methyl group in formula (2).
An aromatic compound in which $X^1$ is an oxygen atom and $R^5$ is an ethyl group in formula (2).
An aromatic compound in which Q is Q1 in formula (2).
An aromatic compound in which Q is Q3 in formula (2).
An aromatic compound in which T is T1 in formula (2).
An aromatic compound in which T is T2 in formula (2).
An aromatic compound in which T is T3 in formula (2).
An aromatic compound in which $Z^2$ and $Z^3$ are each independently a halogen atom or a C1-C3 alkoxy group in formula (2).
An aromatic compound in which $Z^2$ is a halogen atom or a C1-C3 alkoxy group in formula (2).
An aromatic compound in which $Z^2$ is a halogen atom in formula (2).
An aromatic compound in which $Z^2$ is a C1-C3 alkoxy group in formula (2).
An aromatic compound in which $Z^3$ is a C1-C3 alkyl group in formula (2).
An aromatic compound in which $R^1$ is a halogen atom in formula (2).
An aromatic compound in which $R^1$ is a C1-C4 alkyl group optionally having one or more halogen atoms in formula (2).
An aromatic compound in which $R^3$ is a hydrogen atom in formula (2).
An aromatic compound in which $R^3$ is a C1-C4 alkyl group optionally having one or more halogen atoms in formula (2).
An aromatic compound in which $R^6$ is a C1-C3 alkyl group optionally having one or more halogen atoms, a hydrogen atom, a halogen atom, or a C1-C3 alkoxy group optionally having one or more halogen atoms, and $R^4$ is a hydrogen atom in formula (2).
An aromatic compound in which $R^6$ is a C1-C3 alkyl group optionally having one or more halogen atoms, a hydrogen atom, or a C1-C3 alkoxy group optionally having one or more halogen atoms, and $R^4$ is a hydrogen atom in formula (2).
An aromatic compound in which $R^4$ is a C1-C3 alkyl group optionally having one or more halogen atoms, a hydrogen atom, a halogen atom, or a C1-C3 alkoxy group optionally having one or more halogen atoms, and $R^6$ is a hydrogen atom in formula (2).
An aromatic compound in which $R^4$ is a C1-C3 alkyl group optionally having one or more halogen atoms, a hydrogen atom, or a C1-C3 alkoxy group optionally having one or more halogen atoms, and $R^6$ is a hydrogen atom in formula (2).
An aromatic compound in which $R^6$ is a C1-C3 alkyl group optionally having one or more halogen atoms in formula (2).
An aromatic compound in which $R^6$ is a halogen atom in formula (2).
An aromatic compound in which $R^6$ is a C1-C3 alkoxy group optionally having one or more halogen atoms in formula (2).
An aromatic compound in which $R^4$ is a C1-C3 alkyl group optionally having one or more halogen atoms in formula (2).
An aromatic compound in which Q is Q1, $R^{10}$ is a hydrogen atom, and $X^1$ is an oxygen atom in formula (2).
An aromatic compound in which Q is Q1, $R^{10}$ is a hydrogen atom, $X^1$ is an oxygen atom, and $X^2$ is an oxygen atom in formula (2).
An aromatic compound in which Q is Q1, $R^{10}$ is a hydroxyl group, and $X^1$ is an oxygen atom in formula (2).
An aromatic compound in which Q is Q3 and $X^2$ is an oxygen atom in formula (2).
An aromatic compound in which $R^4$ is a C1-C4 alkyl group optionally having one or more halogen atoms, $R^3$ is a hydrogen atom or a methyl group, and $R^6$ is a hydrogen atom or an alkyl group optionally having one or more halogen atoms in formula (2).
An aromatic compound in which $R^4$ is a C1-C4 alkyl group optionally having one or more halogen atoms, or a halogen atom, $R^3$ is a hydrogen atom or a methyl group, $R^6$ is a C1-C3 alkyl group optionally having one or more halogen atoms, a hydrogen atom, a halogen atom, a C1-C3 alkoxy group optionally having one or more halogen atoms, a C3-C4 cycloalkyl group optionally having one or more halogen atoms, Q is Q1 or Q2, $R^{40}$ is a hydrogen atom, and $X^1$ is an oxygen atom in formula (2).
An aromatic compound in which $R^4$ is a C1-C4 alkyl group optionally having one or more halogen atoms, $R^3$ is a hydrogen atom or a methyl group, $R^6$ is a C1-C3 alkyl group optionally having one or more halogen atoms, a hydrogen atom, a halogen atom, a C1-C3 alkoxy group optionally having one or more halogen atoms, or a C3-C4 cycloalkyl group optionally having one or more halogen atoms, Q is Q1, $R^{10}$ is a hydrogen atom, and $X^1$ is an oxygen atom in formula (2).
An aromatic compound in which $R^1$ is a C1-C4 alkyl group optionally having one or more halogen atoms, $R^3$ is a hydrogen atom or a methyl group, $R^6$ is a C1-C3 alkyl group optionally having one or more halogen atoms, a hydrogen atom, a halogen atom, or a C1-C3 alkoxy group optionally having one or more halogen atoms, Q is Q1, $R^{10}$ is a hydrogen atom, and $X^1$ is an oxygen atom in formula (2).
An aromatic compound in which $R^1$ is a C1-C4 alkyl group optionally having one or more halogen atoms, $R^3$ is a hydrogen atom, and $R^4$ is a hydrogen atom or an alkyl group optionally having one or more halogen atoms in formula (2).
An aromatic compound in which $R^1$ is a C1-C4 alkyl group optionally having one or more halogen atoms, or a halogen atom, $R^3$ is a hydrogen atom or a methyl group, $R^4$ is a C1-C3 alkyl group optionally having one or more halogen atoms, hydrogen atom, a halogen atom, a C1-C3 alkoxy group optionally having one or more halogen atoms, or a C3-C4 cycloalkyl group optionally having one or more halogen atoms, Q is Q1 or Q2, $R^{10}$ is a hydrogen atom, and $X^1$ is an oxygen atom in formula (2).

An aromatic compound in which $R^1$ is a C1-C4 alkyl group optionally having one or more halogen atoms, $R^3$ is a hydrogen atom or a methyl group, $R^4$ is a C1-C3 alkyl group optionally having one or more halogen atoms, a hydrogen atom, a halogen atom, a C1-C3 alkoxy group optionally having one or more halogen atoms, or a C3-C4 cycloalkyl group optionally having one or more halogen atoms, Q is Q1, $R^{10}$ is a hydrogen atom, and $X^1$ is an oxygen atom in formula (2).

An aromatic compound in which $R^1$ is a C1-C4 alkyl group optionally having one or more halogen atoms, $R^3$ is a hydrogen atom or a methyl group, $R^4$ is a C1-C3 alkyl group optionally having one or more halogen atoms, a hydrogen atom, or a C1-C3 alkoxy group optionally having one or more halogen atoms, Q is Q1, $R^{10}$ is a hydrogen atom, and $X^1$ is an oxygen atom in formula (2).

An aromatic compound in which $X^1$ is an oxygen atom in formula (3).

An aromatic compound in which $X^1$ is a sulfur atom in formula (3).

An aromatic compound in which $X^1$ is an oxygen atom and $R^5$ is a methyl group in formula (3).

An aromatic compound in which $X^1$ is a sulfur atom and $R^5$ is a methyl group in formula (3).

An aromatic compound in which $X^1$ is an oxygen atom and $R^5$ is an ethyl group in formula (3).

An aromatic compound in which $X^1$ is a sulfur atom and $R^5$ is an ethyl group in formula (3).

An aromatic compound in which Q is Q1 in formula (3).
An aromatic compound in which Q is Q2 in formula (3).
An aromatic compound in which Q is Q3 in formula (3).
An aromatic compound in which T is $T_1$ in formula (3).
An aromatic compound in which T is T2 in formula (3).
An aromatic compound in which T is T3 in formula (3).
An aromatic compound in which $Z^2$ is a halogen atom in formula (3).
An aromatic compound in which $Z^2$ is a C1-C3 alkoxy group in formula (3).
An aromatic compound in which $Z^3$ is a halogen atom in formula (3).
An aromatic compound in which $Z^3$ is a C1-C3 alkyl group in formula (3).
An aromatic compound in which $R^1$ is a halogen atom in formula (3).
An aromatic compound in which $R^1$ is a C1-C4 alkyl group optionally having one or more halogen atoms in formula (3).
An aromatic compound in which $R^3$ is a hydrogen atom in formula (3).
An aromatic compound in which $R^3$ is a C1-C4 alkyl group optionally having one or more halogen atoms in formula (3).
An aromatic compound in which $R^6$ is a C1-C3 alkyl group optionally having one or more halogen atoms, a hydrogen atom, a halogen atom, or a C1-C3 alkoxy group optionally having one or more halogen atoms in formula (3).
An aromatic compound in which $R^6$ is a C1-C3 alkyl group optionally having one or more halogen atoms in formula (3).
An aromatic compound in which $R^6$ is a halogen atom in formula (3).
An aromatic compound in which $R^6$ is a C1-C3 alkoxy group optionally having one or more halogen atoms in formula (3).

An aromatic compound in which $R^6$ is a C3-C4 cycloalkyl group optionally having one or more halogen atoms in formula (3).

An aromatic compound in which Q is Q1, $R^{10}$ is a hydrogen atom, and $X^1$ is an oxygen atom in formula (3).

An aromatic compound in which Q is Q1, $R^{10}$ is a hydrogen atom, $X^1$ is an oxygen atom, and $X^2$ is an oxygen atom in formula (3).

An aromatic compound in which Q is Q1, $R^{10}$ is a hydrogen atom, and $X^1$ is a sulfur atom in formula (3).

An aromatic compound in which Q is Q1, $R^{10}$ is a hydroxyl group, and $X^1$ is an oxygen atom in formula (3).

An aromatic compound in which Q is Q1, $R^{10}$ is a hydroxyl group, and $X^1$ is a sulfur atom in formula (3).

An aromatic compound in which Q is Q1, $R^{10}$ is a methyl group, and $X^1$ is an oxygen atom in formula (3).

An aromatic compound in which Q is Q1, $R^{10}$ is a methyl group, and $X^1$ is a sulfur atom in formula (3).

An aromatic compound in which Q is Q2, $R^{11}$ is a hydrogen atom, and $X^1$ is an oxygen atom in formula (3).

An aromatic compound in which Q is Q2, $R^{11}$ is a hydrogen atom, and $X^1$ is a sulfur atom in formula (3).

An aromatic compound in which Q is Q2, $R^{11}$ is a hydroxyl group, and $X^1$ is an oxygen atom in formula (3).

An aromatic compound in which Q is Q2, $R^{11}$ is a hydroxyl group, and $X^1$ is a sulfur atom in formula (3).

An aromatic compound in which Q is Q2, $R^{11}$ is a methyl group, and $X^1$ is an oxygen atom in formula (3).

An aromatic compound in which Q is Q2, $R^{11}$ is a methyl group, and $X^1$ is a sulfur atom in formula (3).

An aromatic compound in which Q is Q2, $R^{11}$ is a methoxy group, and $X^1$ is an oxygen atom in formula (3).

An aromatic compound in which Q is Q2, $R^{11}$ is a methoxy group, and $X^1$ is a sulfur atom in formula (3).

An aromatic compound in which Q is Q3 and $X^2$ is an oxygen atom in formula (3).

An aromatic compound in which Q is Q3 and $X^2$ is $NR^{12}$ in formula (3).

An aromatic compound in which Q is Q3 and $X^2$ is a direct bond in formula (3).

An aromatic compound in which $R^1$ is a C1-C4 alkyl group optionally having one or more halogen atoms, $R^3$ is a hydrogen atom, and $R^6$ is a hydrogen atom or an alkyl group optionally having one or more halogen atoms in formula (3).

An aromatic compound in which $R^1$ is a C1-C4 alkyl group optionally having one or more halogen atoms, $R^3$ is a hydrogen atom or a methyl group, $R^6$ is a C1-C3 alkyl group optionally having one or more halogen atoms, a hydrogen atom, or a C1-C3 alkoxy group optionally having one or more halogen atoms, Q is Q1, $R^{10}$ is a hydrogen atom, and $X^1$ is an oxygen atom in formula (2).

Next, a process for producing the present compound will be described.

The present compound can be produced, for example, by the following Production Processes.

(Production Process A)

The present compound can be produced by reacting a compound represented by formula (A) (hereinafter referred to as the compound (A)) with a compound represented by formula (B) (hereinafter referred to as the compound (B)) in the presence of a base:

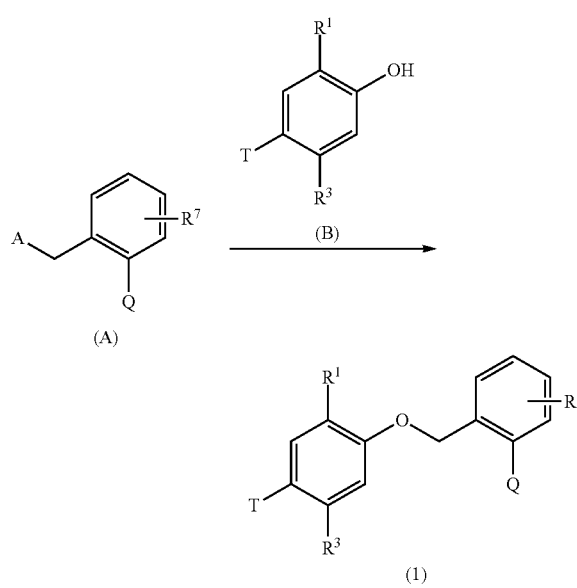

(1)

wherein $R^1$, $R^3$, $R^7$, Q, and T are the same as defined above, and A represents a leaving group such as a chlorine atom or a bromine atom]

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; acid amides such as dimethylformamide (hereinafter referred to as DMF), 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water and mixtures thereof.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate and potassium hydrogen carbonate, and these compounds are usually used in the proportion within a range of 0.05 to 5 mols based on 1 mol of the compound (A).

In the reaction, the compound (B) is usually used in the proportion within a range of 1 to 10 mols based on 1 mol of the compound (A).

The reaction temperature of the reaction is usually within a range of −20 to 150° C. The reaction time of the reaction is usually within a range of 0.1 to 24 hours.

After completion of the reaction, the present compound can be isolated by performing post-treatment operations such as extraction of the reaction mixture with an organic solvent, and drying and concentration of the organic layer. The isolated present compound may be further purified by operations such as distillation, chromatography, and recrystallization.

(Production Process B)

Among the present compounds, a compound in which Q is Q1 (hereinafter referred to as the compound (1-1)) can be produced by reacting a compound represented by formula (C) (hereinafter referred to as the compound (C)) with a compound represented by formula (D) (hereinafter referred to as the compound (D)):

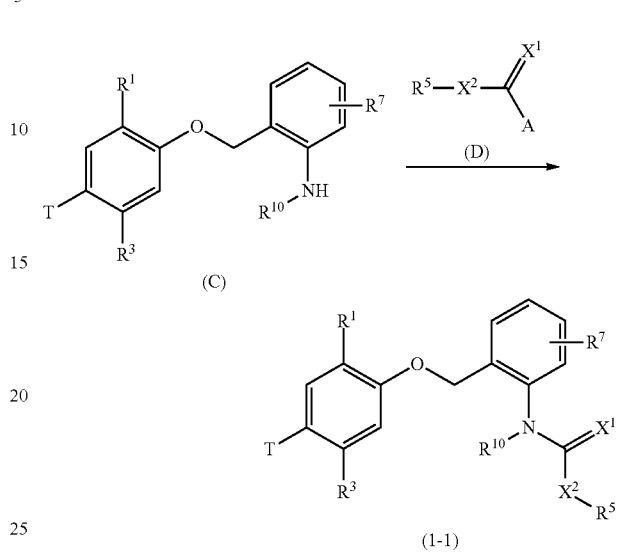

(1-1)

wherein symbols are the same as defined above.

Examples of the compound (D) to be used in the reaction include methyl chlorocarbonate, ethyl chlorocarbonate, acetyl chloride, propionyl chloride, dimethylcarbamoyl chloride, and the like, and commercially available products can be used.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; acid amides such as DMF, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water and mixtures thereof.

In the reaction, the compound (D) is usually used in the proportion within a range of 1 to 10 mols based on 1 mol of the compound (C).

The reaction temperature of the reaction is usually within a range of −20 to 150° C. The reaction time of the reaction is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate and potassium hydrogen carbonate may be added, and these compounds are usually used in the proportion within a range of 0.05 to 5 mols based on 1 mol of the compound (C).

After completion of the reaction, the compound (1-1) can be isolated by performing post-treatment operations such as extraction of the reaction mixture with an organic solvent, and drying and concentration of the organic layer. The isolated compound may be further purified by operations such as distillation, chromatography, and recrystallization.

(Production Process C)

Among the present compounds, a compound represented by formula (1-S) in which Q is Q1 or Q2, and $X^1$ is a sulfur atom (hereinafter referred to as the compound (1-S)) can be produced by reacting a compound in which Q is Q1 or Q2, and $X^1$ is an oxygen atom (hereinafter referred to as the compound (1-O)) among the present compounds with a sulfurizing agent:

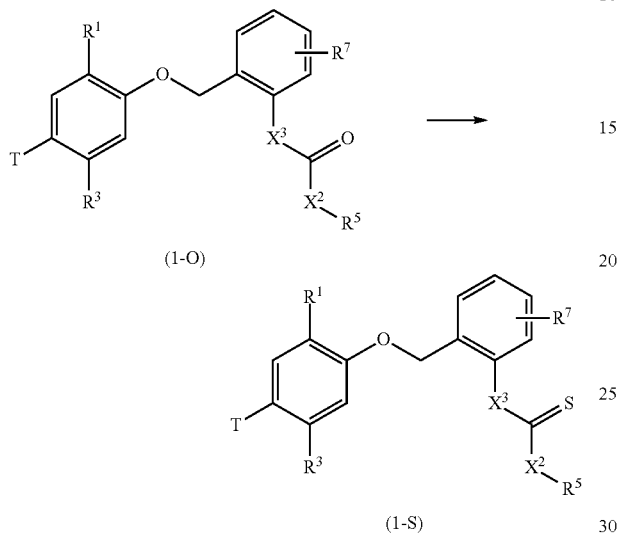

(1-O)

(1-S)

$X^3 = NR^{10}$ or $CHR^{11}$ wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether;

halogenated hydrocarbons such as chloroform, 1,2-dichloroetane, and chlorobenzene; nitriles such as acetonitrile; and mixtures thereof.

Examples of the sulfurizing agent to be used in the reaction include phosphorous pentasulfide and Lawesson's reagent (2,4-bis(4-methoxyphenyl)-1,3,2,4-dithiadiphosphetane 2,4-disulfide).

In the reaction, the sulfurizing agent is usually used in the proportion within a range of 0.5 to 1.5 mols based on 1 mol of the compound (1-O).

The reaction temperature of the reaction is usually within a range of −20 to 150° C. The reaction time of the reaction is usually within a range of 0.1 to 24 hours.

In the reaction, if necessary, organic bases such as pyridine and triethylamine; and inorganic bases such as alkali metal hydroxides and alkali metal carbonates may be added, and the amount of the base to be added is within a range of 0.5 to 1.5 mols based on the compound (1-O).

After completion of the reaction, the compound (1-S) can be isolated by performing post-treatment operations such as extraction of the reaction mixture with an organic solvent, and drying and concentration of the organic layer. The isolated compound (1-S) can also be purified by chromatography, recrystallization, and the like.

(Production Process D)

Among the present compounds, a compound represented by formula (1-3) in which Q is Q1 and $R^{10}$ is a methyl group (hereinafter referred to as the compound (1-3)) can be produced by reacting a compound represented by formula (1-2) in which Q is Q1 and $R^{10}$ is a hydrogen atom (hereinafter referred to as the compound (1-2)) in the present compounds with a methylating agent in the presence of a base:

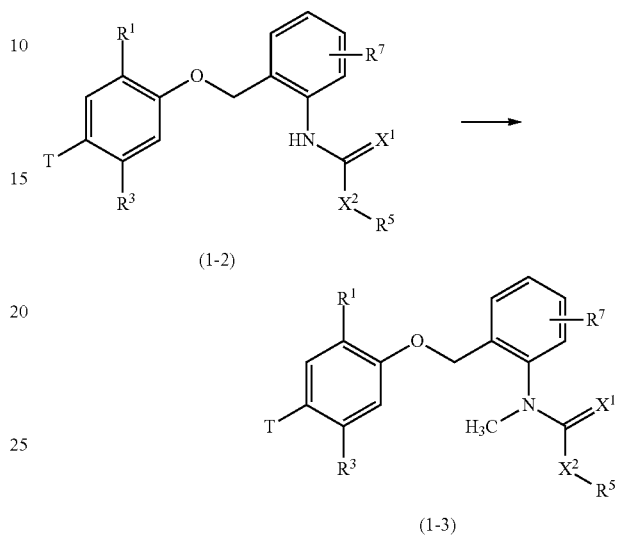

(1-2)

(1-3)

wherein symbols are the same as defined above.

The reaction is usually performed in a solvent.

Examples of the solvent to be used in the reaction include hydrocarbons such as n-hexane, cyclohexane, n-pentane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; sulfoxides such as methyl sulfoxide; nitriles such as acetonitrile; and mixtures thereof.

Commercially available products are usually used as the methylating agent to be used in the reaction, and examples thereof include methyl bromide, methyl iodide, dimethyl sulfate, methyl p-toluenesulfonate, methyl methanesulfonate, and the like.

Examples of the base to be used in the reaction include organic bases such as triethylamine, pyridine, N-methylmorpholine, 4-dimethyl amino pyridine, diisopropylethylamine, and diazabicycloundecene; alkali metal carbonates such as sodium carbonate and potassium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium tert-butoxide and potassium tert-butoxide.

In the reaction, the methylating agent is usually in the proportion within a range of 1 to 10 mols, and the base is usually used in the proportion within a range of 1 to 10 mols, based on 1 mol of the compound (1-2).

The reaction temperature of the reaction is usually within a range of −20 to 150° C. The reaction time of the reaction is usually within a range of 0.1 to 24 hours.

After completion of the reaction, the compound (1-3) can be isolated by performing post-treatment operations such as extraction of the reaction mixture with an organic solvent, and drying and concentration of the organic layer. The isolated compound (1-3) can also be purified by chromatography, recrystallization, and the like.

(Production Process E)

Among the present compounds, a compound represented by formula (1-4) in which Q is Q3 and $X^2$ is an oxygen atom (hereinafter referred to as the compound (1-4)) can be produced by reacting a compound represented by formula (E-1) (hereinafter referred to as the compound (E-1)) with a compound represented by formula (E-2) (hereinafter referred to as the compound (E-2)) in the presence of a Grignard reagent:

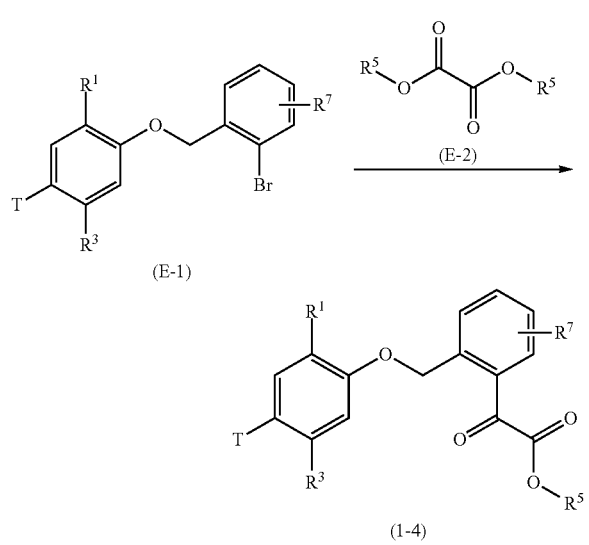

wherein symbols are the same as defined above.

The reaction is usually performed in a solvent. Examples of the solvent to be used in the reaction include hydrocarbons such as n-hexane, cyclohexane, n-pentane, toluene, and xylene; ethers such as tetrahydrofuran, 1, 4-dioxane, ethylene glycol dimethyl ether, methyl tert-butyl ether, and diisopropyl ether; and mixtures thereof.

Commercially available products are usually used as the Grignard reagent, and examples thereof include methyl magnesium chloride, methyl magnesium bromide, isopropyl magnesium chloride, and isopropyl magnesium bromide.

In the reaction, the Grignard reagent is usually used in the proportion within a range of 1 to 2 mols, and the compound (E-2) is usually used in the proportion within a range of 1 to 10 mols, based on 1 mol of the compound (E-1).

The reaction temperature of the reaction is usually within a range of –90 to 100° C. The reaction time of the reaction is usually within a range of 0.1 to 24 hours.

After completion of the reaction, the compound (1-4) can be isolated by performing post-treatment operations such as extraction of the reaction mixture with an organic solvent, and drying and concentration of the organic layer. The isolated compound (1-4) can also be purified by chromatography, recrystallization, and the like.

(Production Process F)

Among the present compounds, a compound represented by formula (1-6) in which Q is Q3 and $X^2$ is $NR^{12}$ (hereinafter referred to as the compound (1-6)) can be produced by reacting the compound (1-4) with a compound represented by formula (F-1) (hereinafter referred to as the compound (F-1)):

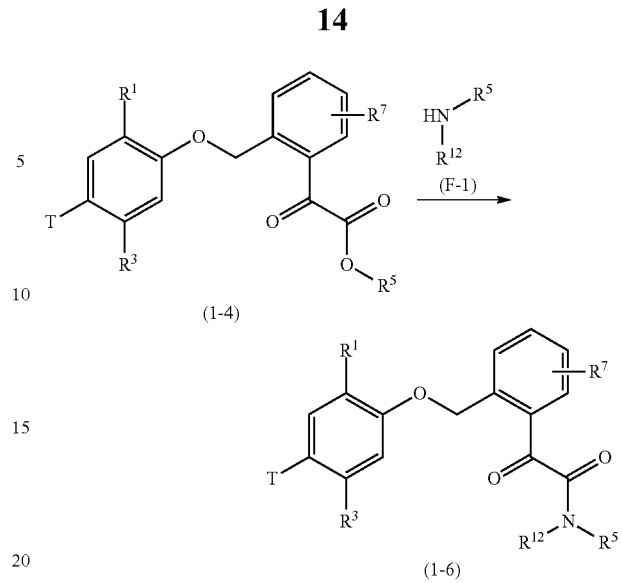

wherein symbols are the same as defined above.

The reaction is usually performed in a solvent.

Examples of the solvent to be used in the reaction include hydrocarbons such as n-hexane, cyclohexane, n-pentane, toluene, and xylene; ethers such as tetrahydrofuran, 1,4-dioxane, ethylene glycol dimethyl ether, methyl tert-butyl ether, and diisopropyl ether; alcohols such as methanol and ethanol; halogenated hydrocarbons such as chloroform, 1,2-dichloroethane, and chlorobenzene; sulfoxides such as methyl sulfoxide; nitriles such as acetonitrile; and mixtures thereof.

Commercially available products are usually used as the compound (F-1) to be used in the reaction, and examples thereof include methylamine, ethyl amine, and dimethylamine.

In the reaction, the compound (F-1) is usually used in the proportion within a range of 1 to 10 mols based on 1 mol of the compound (1-4).

The reaction temperature of the reaction is usually within a range of –20 to 150° C. The reaction time of the reaction is usually within a range of 0.1 to 24 hours.

After completion of the reaction, the compound (1-6) can be isolated by performing post-treatment operations such as extraction of the reaction mixture with an organic solvent, and drying and concentration of the organic layer. The isolated compound (1-6) can also be purified by chromatography, recrystallization, and the like.

(Production Process G)

Among the present compounds, a compound represented by formula (1-7) in which Q is Q2, $R^{11}$ is a hydroxyl group, and $X^1$ is an oxygen atom (hereinafter referred to as the compound (1-7)) can be produced by mixing a compound represented by formula (1-5) in which Q is Q3 (hereinafter referred to as the compound (1-5)) with a reducing agent:

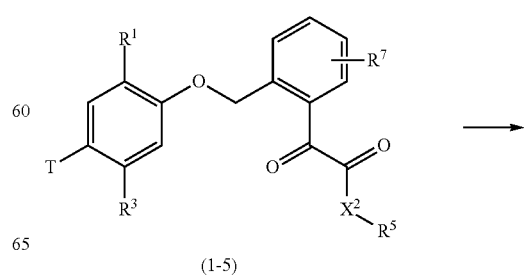

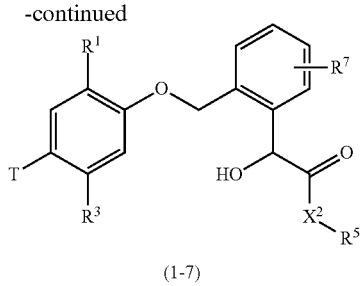

(1-7)

wherein symbols are the same as defined above.

The reaction is usually performed in a solvent. Examples of the solvent to be used in the reaction include hydrocarbons such as n-hexane, cyclohexane, n-pentane, toluene, and xylene; ethers such as tetrahydrofuran, 1, 4-dioxane, ethylene glycol dimethyl ether, methyl tert-butyl ether, and diisopropyl ether; alcohols such as methanol and ethanol; halogenated hydrocarbons such as chloroform, 1,2-dichloroetane, and chlorobenzene; sulfoxides such as methyl sulfoxide; nitriles such as acetonitrile; and mixtures thereof.

Examples of the reducing agent to be used in the reaction include sodium borohydride, sodium cyanoborohydride, and sodium triacetoxyborohydride.

In the reaction, the reducing agent is usually used in the proportion within a range of 1 to 10 mols based on 1 mol of the compound (1-5).

The reaction temperature of the reaction is usually within a range of −20 to 150° C. The reaction time of the reaction is usually within a range of 0.1 to 24 hours.

After completion of the reaction, the compound (1-7) can be isolated by performing post-treatment operations such as extraction of the reaction mixture with an organic solvent, and drying and concentration of the organic layer. The isolated compound (1-7) can also be purified by chromatography, recrystallization, and the like.

The present compound can be produced in accordance with reactions mentioned in aforementioned Production Processes A to G.

A method for synthesizing intermediate compounds will be shown below.

(Reference Production Process A)

The compound (A) can be produced by reacting a compound represented by formula (A1) (hereinafter referred to as the compound (A1)) with a halogenating agent:

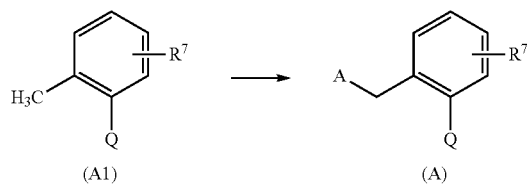

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the halogenating agent to be used in the reaction include a chlorinating agent, a brominating agent, and an iodinating agent, for example, a chlorinating agent such as chlorine, sulfuryl chloride, N-chlorosuccinimide, or N-bromosuccinimide; a brominating agent such as bromine, 1,3-dibromo-5,5-dimethylhydantoin, or N-bromophthalimide; and an iodinating agent such as iodine or iodosuccinimide.

In the reaction, a radical initiator can also be used.

Examples of the radical initiator to be used in the reaction include benzoyl peroxide, azobisisobutyronitrile (AIBN), diacyl peroxide, dialkyl peroxydicarbonate, tert-alkyl peroxy ester, monoperoxy carbonate, di(tert-alkylperoxy)ketal, and ketone peroxide.

In the reaction, the halogenating agent is usually used in the proportion within a range of 1 to 10 mols, and the radical initiator is usually used in the proportion within a range of 0.01 to 5 mols, based on 1 mol of the compound (A1).

The reaction temperature of the reaction is usually within a range of −20 to 150° C. The reaction time of the reaction is usually within a range of 0.1 to 24 hours.

After completion of the reaction, the compound (A) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process B)

The compound (B) can be produced by reacting a compound represented by formula (YA1) (hereinafter referred to as the compound (YA1)) with an acid:

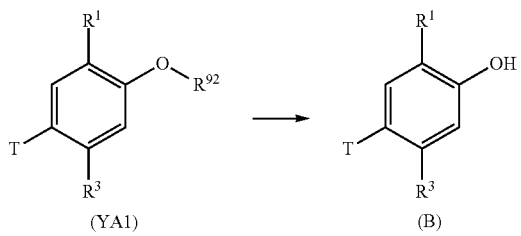

wherein $R^1$, $R^3$, and T are the same as defined above, and $R^{92}$ represents a C1-C3 alkyl group optionally having one or more halogens.

The reaction is usually performed in a solvent.

Examples of the solvent to be used in the reaction include alcohols such as methanol, ethanol, propanol, and butanol; water, acetic acid, and mixtures thereof.

Examples of the acid to be used in the reaction include hydrochloric acid and hydrobromic acid, and aqueous solutions thereof can also be used as the solvent.

In the reaction, the acid is usually used in the proportion of large excess based on 1 mol of the compound (YA1).

The reaction temperature of the reaction is usually within a range of −20 to 150° C. The reaction time of the reaction is usually within a range of 0.1 to 100 hours.

After completion of the reaction, the compound (B) can be isolated by performing post-treatment operations such as extraction of the reaction mixture with an organic solvent, and drying and concentration of the organic layer. Alternatively, the compound (B) can be isolated by performing post-treatment operations such concentration of the reaction mixture. The isolated compound can also be purified by chromatography, recrystallization, and the like.

(Reference Production Process C)

In the compound (YA1), a compound represented by formula (YC2) in which T is T1 (hereinafter referred to as the compound (YC2)) can be produced by reacting a compound represented by formula (YC1) (hereinafter referred to as the compound (YC1)) in the presence of an acid:

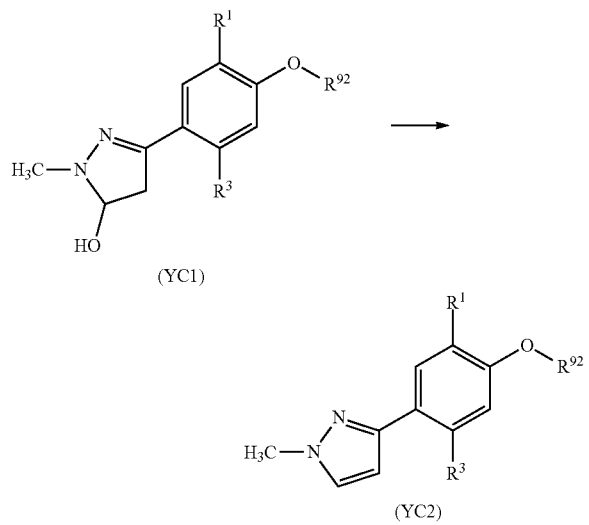

(YC1)

(YC2)

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; esters such as ethyl acetate and methyl acetate; sulfoxides such as dimethyl sulfoxide; ketones such as acetone, methyl ethyl ketone, and methyl isobutyl ketone; nitriles such as acetonitrile; alcohols such as methanol, ethanol, and isopropanol; water and mixtures thereof.

Examples of the acid to be used in the reaction include acetic acid, hydrochloric acid, hydrobromic acid, and the like, and aqueous solutions thereof can also be used as the solvent.

In the reaction, the acid is usually used in the proportion within a range of 1 to 10 mols based on 1 mol of the compound (YC1).

The reaction temperature of the reaction is usually within a range of −78 to 150° C. The reaction time of the reaction is usually within a range of 0.1 to 72 hours.

After completion of the reaction, the compound (YC2) can be isolated by performing post-treatment operations such as extraction of the reaction mixture with an organic solvent, and drying and concentration of the organic layer. The isolated compound can also be purified by chromatography, recrystallization, and the like.

(Reference Production Process C-1)

In the compound (YA1), a compound represented by formula (YC4) in which T is T2 and $Z^2$ is $R^{82}$ (hereinafter referred to as the compound (YC4)) can be produced by reacting a compound represented by formula (YC3) (hereinafter referred to as the compound (YC3)) in the presence of an acid:

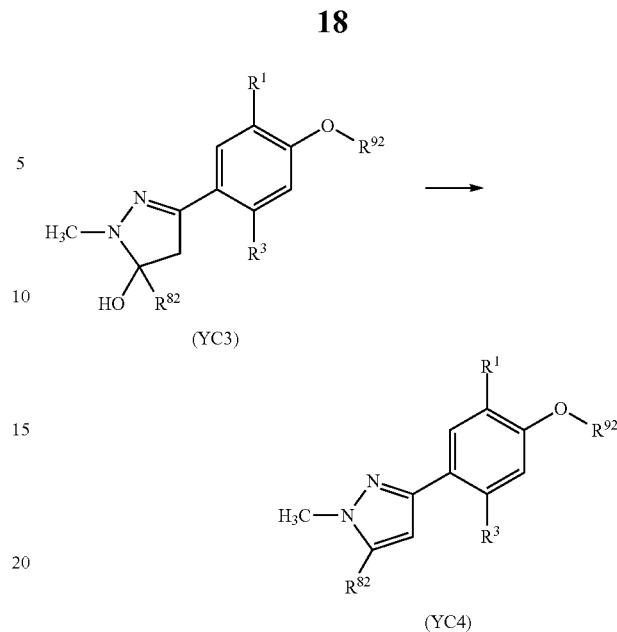

(YC3)

(YC4)

wherein $R^1$, $R^3$, and $R^{92}$ are the same as defined above, and $R^{82}$ represents a C1-C3 alkyl group optionally having one or more halogen atoms.

The reaction can be carried out in accordance with the reaction mentioned in Reference Production Process C.

(Reference Production Process C-2)

In the compound (YA1), a compound represented by formula (YC6) in which T is T3 and $Z^2$ is $R^{83}$ (hereinafter referred to as the compound (YC6)) can be produced by reacting a compound represented by formula (YC5) (hereinafter referred to as the compound (YC5)) in the presence of an acid:

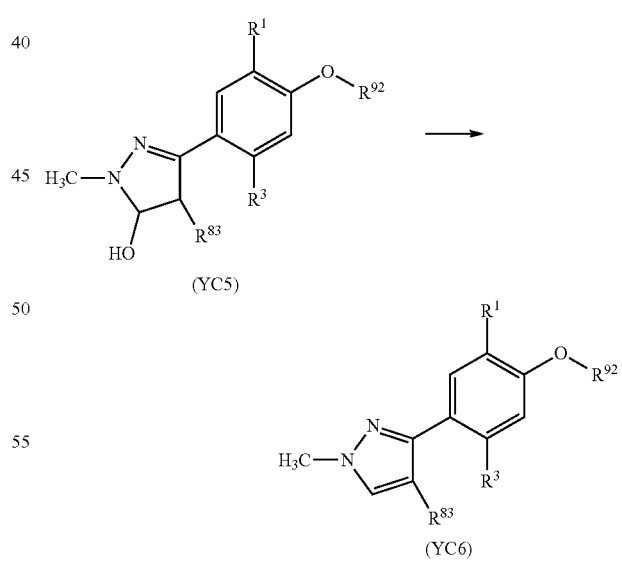

(YC5)

(YC6)

wherein $R^1$, $R^3$, and $R^{92}$ are the same as defined above, $R^{83}$ represents a C1-C3 alkyl group optionally having one or more halogen atoms, or a C1-C3 alkoxy group optionally having one or more halogen atoms.

The reaction can be carried out in accordance with the reaction mentioned in Reference Production Process C.

(Reference Production Process D)

The compound (YC1) can be produced by reacting a compound represented by formula (YD1) (hereinafter referred to as the compound (YD1)) with the compound (YD2):

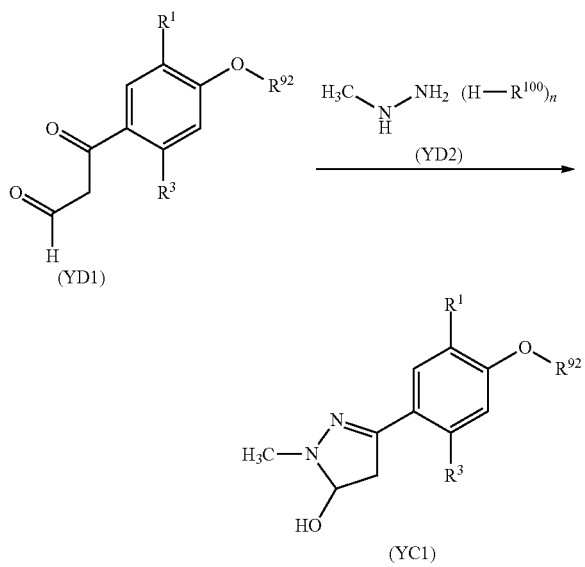

(YD1)

(YC1)

wherein $R^1$, $R^3$, and $R^{92}$ are the same as defined above, $R^{100}$ represents a halogen atom, and n represents 0 or 1.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroetane, tetrachloroethane, and chlorobenzene; acid amides such as DMF, 1,3-dimethyl-2-imidazolidinone, and N-methylpyrrolidone; esters such as ethyl acetate and methyl acetate; sulfoxides such as dimethyl sulfoxide; nitriles such as acetonitrile and propionitrile; alcohols such as methanol, ethanol, and isopropanol; water and mixtures thereof.

In the reaction, the compound (YD2) is usually used in the proportion within a range of 1 to 10 mols based on 1 mol of the compound (YD1).

The reaction temperature of the reaction is usually within a range of −78 to 150° C. The reaction time of the reaction is usually within a range of 0.1 to 72 hours.

After completion of the reaction, the compound (YC1) can be isolated by performing post-treatment operations such as extraction of the reaction mixture with an organic solvent, and drying and concentration of the organic layer. The isolated compound can also be purified by chromatography, recrystallization, and the like.

(Reference Production Process D-1)

The compound (YC3) can be produced by reacting a compound represented by formula (YD3) (hereinafter referred to as the compound (YD3)) with the compound (YD2):

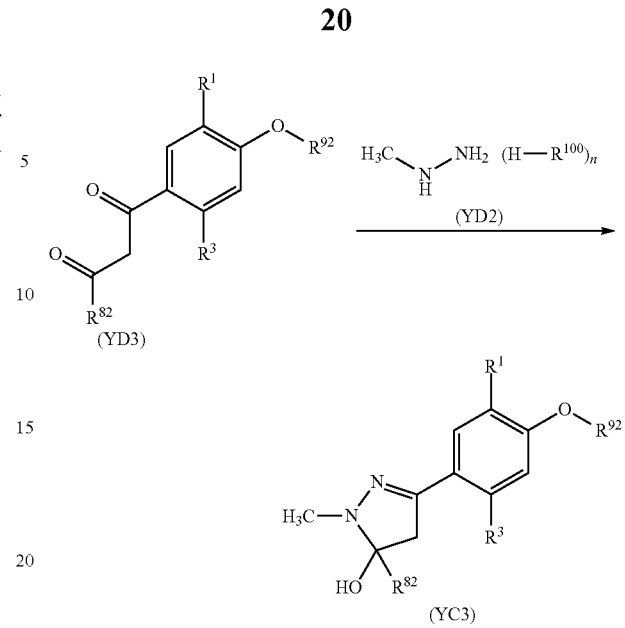

(YD3)

(YC3)

wherein symbols are the same as defined above.

The reaction can be carried out in accordance with the reaction mentioned in Reference Production Process D.

(Reference Production Process D-2)

The compound (YC5) can be produced by reacting a compound represented by formula (YD4) (hereinafter referred to as the compound (YD4)) with the compound (YD2):

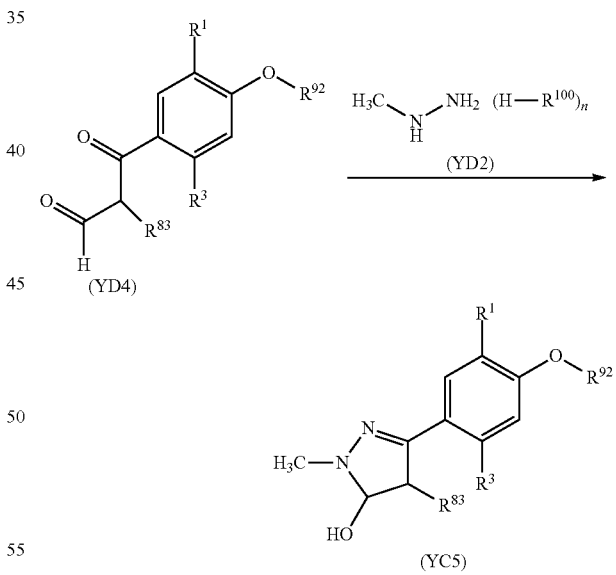

(YD4)

(YC5)

wherein symbols are the same as defined above.

The reaction can be carried out in accordance with the reaction mentioned in Reference Production Process D.

(Reference Production Process E)

The compound (YD1) can be produced by reacting a compound represented by formula (YE1) (hereinafter referred to as the compound (YE1)) with a compound represented by formula (YE2) (hereinafter referred to as the compound (YE2)) in the presence of a base:

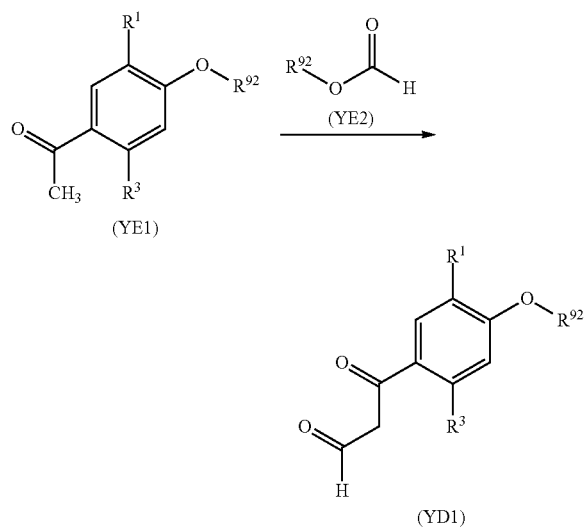

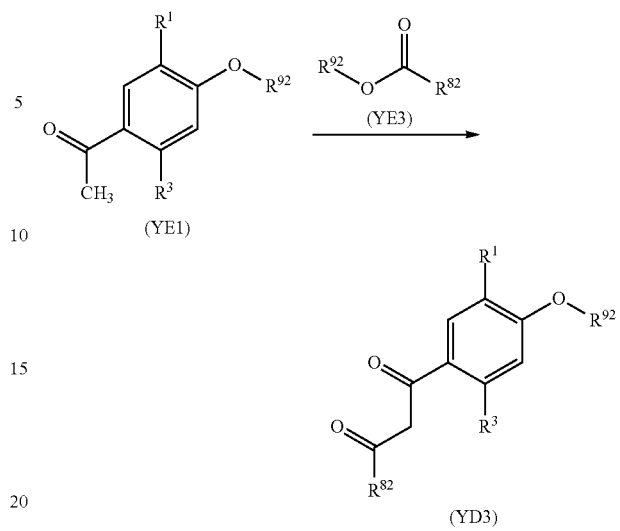

wherein symbols are the same as defined above.

The reaction is usually performed in a solvent.

Examples of the solvent to be used in the reaction include hydrocarbons such as n-hexane, cyclohexane, n-pentane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; esters such as ethyl acetate and methyl acetate; ketones such as acetone, methyl ethyl ketone, and methyl isobutyl ketone; sulfoxides such as methyl sulfoxide; nitriles such as acetonitrile; and mixtures thereof.

Examples of the base to be used in the reaction include alkali metal hydroxides such as sodium hydroxide; and alkali metal alkoxides such as potassium tert-butoxide.

In the reaction, the compound (YE2) is usually used in the proportion within a range of 1 to 10 mols, and the base is usually used in the proportion within a range of 1 to 10 mols, based on 1 mol of the compound (YE1).

The reaction temperature of the reaction is usually within a range of −20 to 150° C. The reaction time of the reaction is usually within a range of 0.1 to 24 hours.

In the reaction, if necessary, additives may be added, and examples thereof include 18-crown-6-ether and dibenzo-18-crown-6-ether. These additives are usually used in the proportion within a range of 0.001 to 1.2 mols based on 1 mol of the compound (YE1).

After completion of the reaction, the compound (YD1) can be isolated by performing post-treatment operations such as extraction of the reaction mixture with an organic solvent, and drying and concentration of the organic layer. The isolated compound (YD1) can also be purified by chromatography, recrystallization, and the like.

(Reference Production Process E-1)

The compound (YD3) can be produced by reacting the compound (YE1) with a compound represented by formula (YE3) (hereinafter referred to as the compound (YE3)) in the presence of a base:

wherein symbols are the same as defined above.

The reaction can be carried out in accordance with the reaction mentioned in Reference Production Process E.

(Reference Production Process E-2)

The compound (YD5) can be produced by reacting a compound represented by formula (YE4) (hereinafter referred to as the compound (YE4)) with the compound (YE2) in the presence of abase:

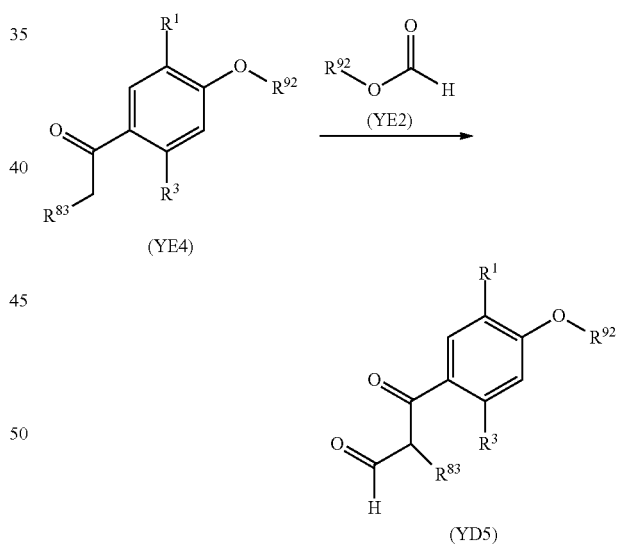

wherein symbols are the same as defined above.

The reaction can be carried out in accordance with the reaction mentioned in Reference Production Process E.

(Reference Production Process F)

A compound represented by formula (YF3) (hereinafter referred to as the compound (YF3)) can be produced by reacting a compound represented by formula (YF1) (hereinafter referred to as the compound (YF1)) with a compound represented by formula (YF2) (hereinafter referred to as the compound (YF2)) in the presence of a base:

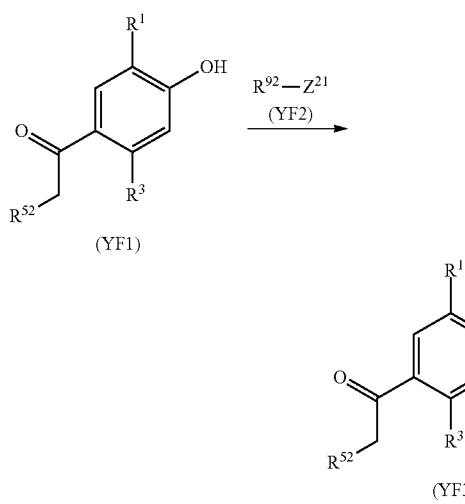

(Reference Production Process G)

The compound (YF1) can be produced by mixing a compound represented by formula (YG1) (hereinafter referred to as the compound (YG1)) in the presence of an acid catalyst:

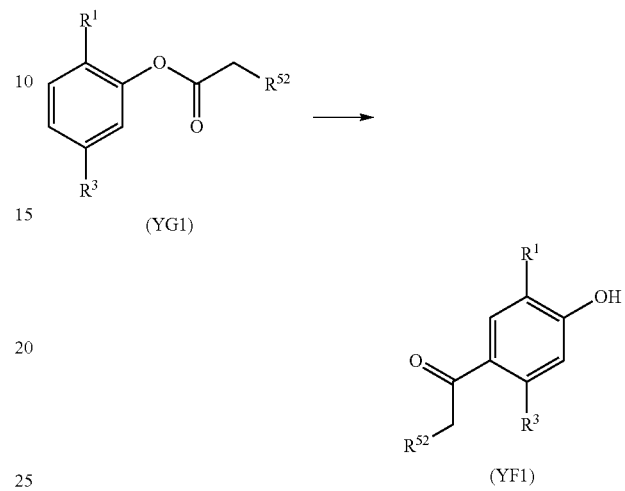

wherein $R^1$, $R^3$, and $R^{92}$ are the same as defined above, $Z^{21}$ represents a leaving group such as a chlorine atom, a bromine atom, an iodine atom, a methanesulfonyloxy group, a trifluoromethanesulfonyloxy group, or a p-toluenesulfonyloxy group, and $R^{52}$ represents a hydrogen atom, a C1-C3 alkyl group optionally having one or more halogen atoms, or a C1-C3 alkoxy group optionally having one or more halogen atoms.

The reaction is usually performed in a solvent.

Examples of the solvent to be used in the reaction include hydrocarbons such as n-hexane, cyclohexane, n-pentane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; esters such as ethyl acetate and methyl acetate; ketones such as acetone, methyl ethyl ketone, and methyl isobutyl ketone; sulfoxides such as methyl sulfoxide; nitriles such as acetonitrile; and mixtures thereof.

Examples of the base to be used in the reaction include organic bases such as triethylamine, pyridine, N-methylmorpholine, 4-dimethyl amino pyridine, diisopropylethylamine, and diazabicycloundecene; alkali metal carbonates such as lithium carbonate, sodium carbonate, and potassium carbonate; alkali metal hydrogen carbonates such as sodium hydrogen carbonate and potassium hydrogen carbonate; alkali metal hydroxides such as lithium hydroxide, sodium hydroxide, potassium hydroxide, and cesium hydroxide; and alkali metal alkoxides such as sodium tert-butoxide and potassium tert-butoxide.

In the reaction, the compound (YF2) is usually used in the proportion within a range of 1 to 10 mols, and the base is usually used in the proportion within a range of 1 to 10 mols, based on 1 mol of the compound (YF1).

The reaction temperature of the reaction is usually within a range of −20 to 150° C. The reaction time of the reaction is usually within a range of 0.1 to 24 hours.

After completion of the reaction, the compound (YF3) can be isolated by performing post-treatment operations such as extraction of the reaction mixture with an organic solvent, and drying and concentration of the organic layer. The isolated compound (YF3) can also be purified by chromatography, recrystallization, and the like.

wherein symbols are the same as defined above.

The reaction is usually performed in a solvent.

Examples of the solvent to be used in the reaction include hydrocarbons such as n-hexane, cyclohexane, and n-pentane; halogenated hydrocarbons such as chloroform, dichloromethane, 1,2-dichloroetane, and chlorobenzene; nitriles such as nitromethane, acetonitrile, and propionitrile; and mixtures thereof.

Examples of the acid catalyst to be used in the reaction include aluminum trichloride, titanium tetrachloride, iron trichloride, hydrogen fluoride, hypochlorous acid, and polyphosphoric acid.

In the reaction, a rearrangement agent is usually used in the proportion within a range of 1 to 10 mols based on 1 mol of the compound (YG1).

The reaction temperature of the reaction is usually within a range of −20 to 150° C. The reaction time of the reaction is usually within a range of 0.1 to 72 hours.

After completion of the reaction, the compound (YF1) can be isolated by performing post-treatment operations such as extraction of the reaction mixture with an organic solvent, and drying and concentration of the organic layer. The isolated compound (YF1) can also be purified by chromatography, recrystallization, and the like.

(Reference Production Process H)

The compound (YG1) can be produced by reacting a compound represented by formula (YH1) (hereinafter referred to as the compound (YH1)) with a compound represented by formula (YH2) (hereinafter referred to as the compound (YH2)) in the presence of a base:

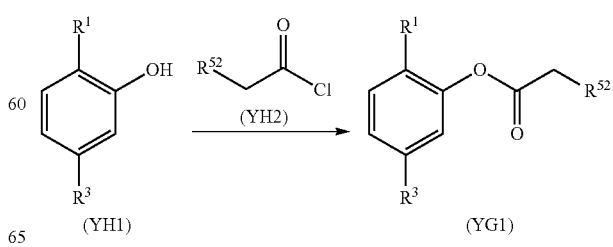

wherein symbols are the same as defined above.

The reaction is usually performed in a solvent.

Examples of the solvent to be used in the reaction include hydrocarbons such as n-hexane, cyclohexane, n-pentane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; esters such as ethyl acetate and methyl acetate; ketones such as acetone, methyl ethyl ketone, and methyl isobutyl ketone; sulfoxides such as methyl sulfoxide; nitriles such as acetonitrile; and mixtures thereof.

Examples of the base to be used in the reaction include organic bases such as triethylamine, pyridine, N-methylmorpholine, 4-dimethyl amino pyridine, diisopropylethylamine, and diazabicycloundecene; alkali metal carbonates such as sodium carbonate and potassium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium tert-butoxide and potassium tert-butoxide.

Commercially available products are usually used as the compound (YH1) to be used in the reaction, and examples thereof include 2-methylphenol, 2-chlorophenol, and 2,5-dimethylphenol.

Commercially available products are usually used as the compound (YH2) to be used the reaction, and examples thereof include acetyl chloride, 3,3,3-trifluoropropionic acid chloride, and methoxyacetyl chloride.

In the reaction, the compound (YH2) is usually used in the proportion within a range of 1 to 10 mols, and the base is usually used in the proportion within a range of 1 to 10 mols, based on 1 mol of the compound (YH1).

The reaction temperature of the reaction is usually within a range of −78 to 150° C. The reaction time of the reaction is usually within a range of 0.1 to 72 hours.

After completion of the reaction, the compound (YG1) can be isolated by performing post-treatment operations such as extraction of the reaction mixture with an organic solvent, and drying and concentration of the organic layer. The isolated compound (YG1) can also be purified by chromatography, recrystallization, and the like.

(Reference Production Process K)

In the compound (YA1), a compound represented by formula (YK1) in which T is T3 and $Z^3$ is $R^{100}$ (hereinafter referred to as the compound (YK1)) can be produced by reacting the compound (YC2) with a halogenating agent:

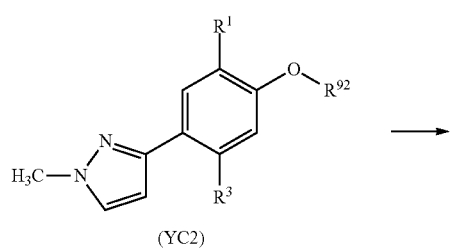

(YC2)

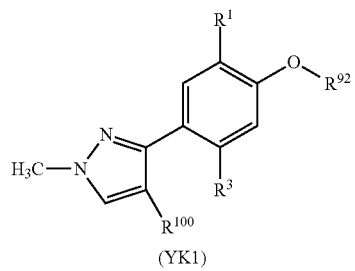

(YK1)

wherein symbols are the same as defined above.

The reaction is usually performed in a solvent.

Examples of the solvent to be used in the reaction include hydrocarbons such as n-hexane, cyclohexane, n-pentane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; esters such as ethyl acetate and methyl acetate; ketones such as acetone, methyl ethyl ketone, and methyl isobutyl ketone; sulfoxides such as methyl sulfoxide; nitriles such as acetonitrile; and mixtures thereof.

Examples of the halogenating agent to be used in the reaction include fluorine, chlorine, bromine, iodine, 1-chloromethyl-4-fluoro-1,4-diazoniabicyclo[2,2,2]octane-bistetrafluoroborate, N-chlorosuccinimide, N-bromosuccinimide, N-iodosuccinimide, and sulfuryl chloride.

In the reaction, the halogenating agent is usually used in the proportion within a range of 1 to 10 mols based on 1 mol of the compound (YC2).

The reaction temperature of the reaction is usually within a range of −20 to 150° C. The reaction time of the reaction is usually within a range of 0.1 to 24 hours.

After completion of the reaction, the compound (YK1) can be isolated by performing post-treatment operations such as extraction of the reaction mixture with an organic solvent, and drying and concentration of the organic layer. The isolated compound (YK1) can also be purified by chromatography, recrystallization, and the like.

(Reference Production Process L)

In the compound (YA1), a compound represented by formula (YL2) in which T is T2 and $Z^2$ is a C1-C3 alkoxy group optionally having one or more halogen atoms (hereinafter referred to as the compound (YL2)) can be produced by reacting the compound (YL1) with an alkylating agent in the presence of a base:

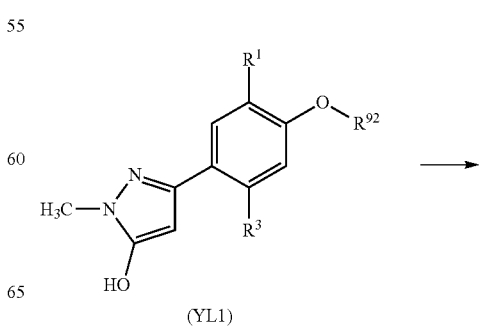

(YL1)

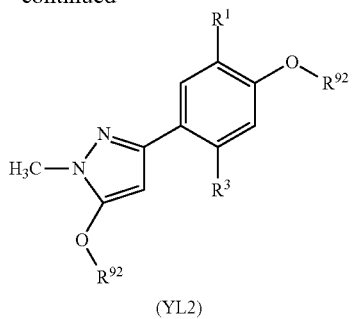

(YL2)

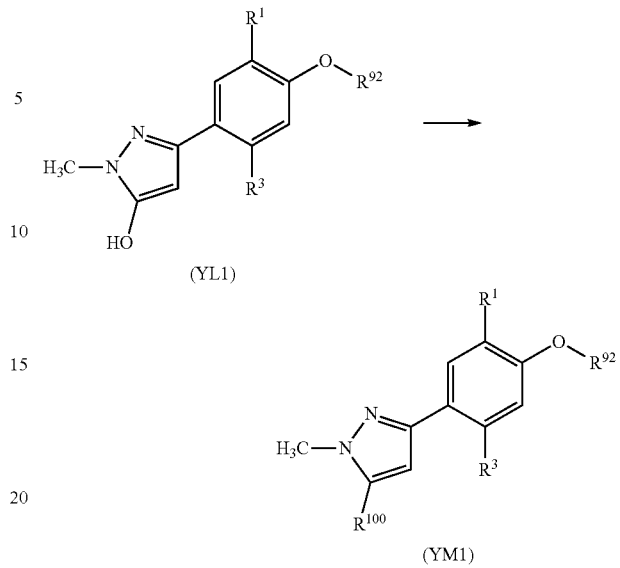

wherein symbols are the same as defined above.

The reaction is usually performed in a solvent.

Examples of the solvent to be used in the reaction include hydrocarbons such as n-hexane, cyclohexane, n-pentane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; sulfoxides such as methyl sulfoxide; nitriles such as acetonitrile; and mixtures thereof.

Commercially available products are usually used as the alkylating agent to be used in the reaction, and examples thereof include methyl bromide, ethyl bromide, propyl bromide, methyl iodide, ethyl iodide, propyl iodide, isopropyl iodide, dimethyl sulfate, methyl p-toluenesulfonate, ethyl p-toluenesulfonate, propyl p-toluenesulfonate, methyl methanesulfonate, ethyl methanesulfonate, propyl methanesulfonate, and the like.

Examples of the base to be used in the reaction include organic bases such as triethylamine, pyridine, N-methylmorpholine, 4-dimethyl amino pyridine, diisopropylethylamine, and diazabicycloundecene; alkali metal carbonates such as sodium carbonate and potassium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium tert-butoxide and potassium tert-butoxide.

In the reaction, the alkylating agent is usually in the proportion within a range of 1 to 10 mols, and the base is usually used in the proportion within a range of 1 to 10 mols, based on 1 mol of the compound (YL1).

The reaction temperature of the reaction is usually within a range of −20 to 150° C. The reaction time of the reaction is usually within a range of 0.1 to 24 hours.

After completion of the reaction, the compound (YL2) can be isolated by performing post-treatment operations such as extraction of the reaction mixture with an organic solvent, and drying and concentration of the organic layer. The isolated compound (YL2) can also be purified by chromatography, recrystallization, and the like.

(Reference Production Process M)

In the compound (YA1), a compound represented by formula (YM1) in which T is T2 and $Z^2$ is a halogen atom (hereinafter referred to as the compound (YM1)) can be produced by reacting the compound (YL1) with a halogenating agent:

wherein symbols are the same as defined above.

The reaction is usually performed in a solvent.

Examples of the solvent to be used in the reaction include hydrocarbons such as n-hexane, cyclohexane, n-pentane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; esters such as ethyl acetate and methyl acetate; ketones such as acetone, methyl ethyl ketone, and methyl isobutyl ketone; sulfoxides such as methyl sulfoxide; nitriles such as acetonitrile; and mixtures thereof.

Examples of the halogenating agent to be used in the reaction include diethylaminosulfur trifluoride, phosphorus oxychloride, and phosphorus oxybromide.

In the reaction, the halogenating agent is used in the proportion within a range of 1 to 10 mols based on 1 mol of the compound (YL1).

The reaction temperature of the reaction is usually within a range of −20 to 150° C. The reaction time of the reaction is usually within a range of 0.1 to 24 hours.

After completion of the reaction, the compound (YM1) can be isolated by usually performing post-treatment operations such as addition of water, extraction of the reaction mixture with an organic solvent, and drying and concentration of the organic layer. The isolated compound (YM1) can also be purified by chromatography, recrystallization, and the like.

(Reference Production Process N)

The compound (E-1) can be produced by reacting a compound represented by formula (YAM-1) (hereinafter referred to as the compound (YAM-1)) with the compound (B) in the presence of a base.

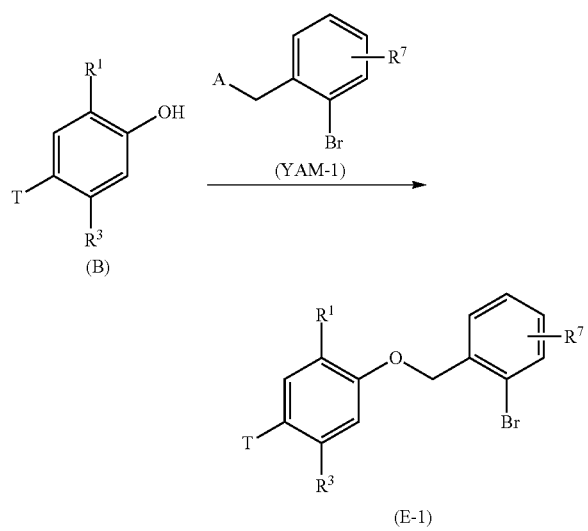

(B)　(YAM-1)　(E-1)

The reaction can be carried out in accordance with the reaction mentioned in Production Process A.

(Reference Production Process O)

The compound (YAM-1) can be produced by reacting a compound represented by formula (YAN-1) (hereinafter referred to as the compound (YAN-1)) with a halogenating agent.

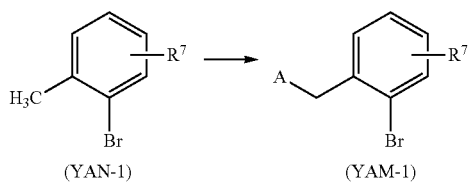

(YAN-1)　(YAM-1)

The reaction can be carried out in accordance with the reaction mentioned in Production Process A.

Commercially available products are usually used as the compound (YAN-1).

(Reference Production Process P)

In the compound (C), a compound represented by formula (YAO-2) in which $R^{10}$ is a methyl group (hereinafter referred to as the compound (YAO-2)) can be produced by reacting a compound represented by formula (YAO-1) which can be produced in accordance with Reference Production Process Q (hereinafter referred to as the compound (YAO-1)) with a methylating agent in the presence of a base:

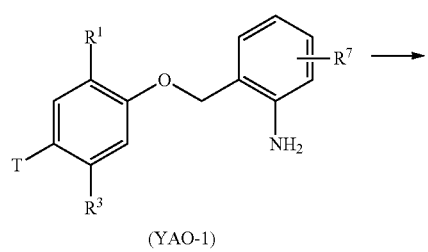

(YAO-1)

-continued

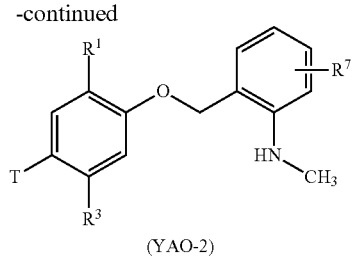

(YAO-2)

wherein symbols are the same as defined above.

The reaction is usually performed in a solvent.

Examples of the solvent to be used in the reaction include hydrocarbons such as n-hexane, cyclohexane, n-pentane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; sulfoxides such as methyl sulfoxide; nitriles such as acetonitrile; and mixtures thereof.

Commercially available products are usually used as the methylating agent to be used in the reaction, and examples thereof include methyl bromide, methyl iodide, dimethyl sulfate, methyl p-toluenesulfonate, methyl methanesulfonate, and the like.

Examples of the base to be used in the reaction include organic bases such as triethylamine, pyridine, N-methylmorpholine, 4-dimethyl amino pyridine, diisopropylethylamine, and diazabicycloundecene; alkali metal carbonates such as sodium carbonate and potassium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium tert-butoxide and potassium tert-butoxide.

In the reaction, the methylating agent is usually used in the proportion within a range of 1 to 10 mols, and the base is usually used in the proportion within a range of 1 to 10 mols, based on 1 mol of the compound (YAO-1).

The reaction temperature of the reaction is usually within a range of −20 to 150° C. The reaction time of the reaction is usually within a range of 0.1 to 24 hours.

After completion of the reaction, the compound (YAO-2) can be isolated by performing post-treatment operations such as extraction of the reaction mixture with an organic solvent, and drying and concentration of the organic layer. The isolated compound (YAO-2) can also be purified by chromatography, recrystallization, and the like.

(Reference Production Process Q)

In the compound (C), a compound represented by formula (YAP-2) in which $R^{10}$ is a hydrogen atom or a hydroxyl group (hereinafter referred to as the compound (YAP-2)) can be produced by reacting a compound represented by formula (YAP-1) (hereinafter referred to as the compound (YAP-1)) with hydrogen in the presence of a catalyst:

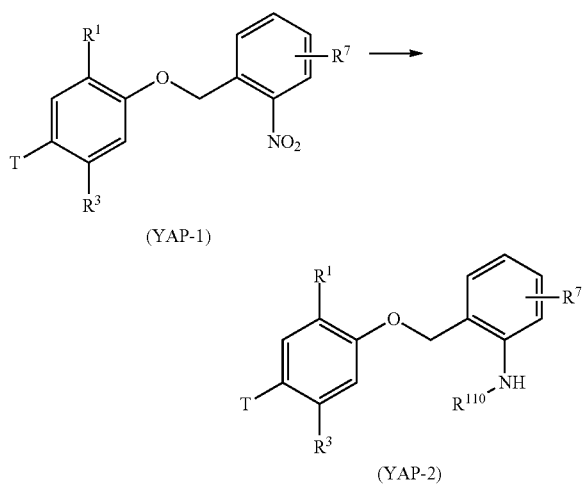

(YAP-1)

(YAP-2)

wherein R¹, R³, R⁶, and T are the same as defined above, and R¹¹⁰ represents a hydrogen atom or a hydroxyl group.

The reaction is usually performed in a solvent.

Examples of the solvent to be used in the reaction include alcohols such as methanol, ethanol, propanol, and butanol; esters such as ethyl acetate and butyl acetate; halogenated hydrocarbons such as carbon tetrachloride, chloroform, dichloromethane, 1,2-dichloroetane, tetrachloroethane, and chlorobenzene; ethers such as diethyl ether, tetrahydrofuran, 1,4-dioxane, ethylene glycol dimethyl ether, anisole, methyl tert-butyl ether, and diisopropyl ether; hydrocarbons such as n-heptane, n-hexane, cyclohexane, n-pentane, toluene, and xylene; water and mixtures thereof.

Examples of the catalyst to be used in the reaction include palladium-supported carbon (Pd/C), platinum-supported carbon (Pt/C), osmium-supported carbon (Os/C), ruthenium-supported carbon (Ru/C), rhodium-supported carbon (Rh/C), and Raney nickel.

The reaction temperature of the reaction is usually within a range of −20 to 150° C. The reaction time of the reaction is usually within a range of 0.1 to 24 hours.

After completion of the reaction, the compound (YAP-2) can be isolated by performing post-treatment operations such as filtration of the catalyst, followed by concentration of the filtrate. The isolated compound (YAP-2) can also be purified by chromatography, recrystallization, and the like.

(Reference Production Process R)

The compound (YAP-1) can be produced by reacting a compound represented by formula (YAQ-1) (hereinafter referred to as the compound (YAQ-1)) with the compound (B) in the presence of a base.

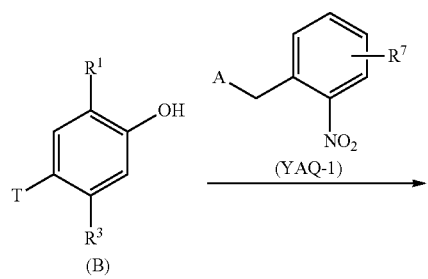

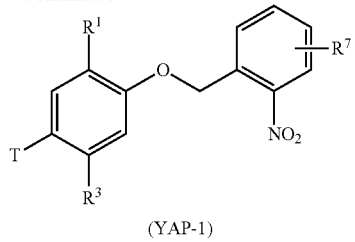

(YAP-1)

The reaction can be carried out in accordance with the reaction mentioned in Production Process A.

(Reference Production Process S)

The compound (YAQ-1) can be produced by reacting a compound represented by formula (YAR-1) (hereinafter referred to as the compound (YAQ-1)) with a halogenating agent.

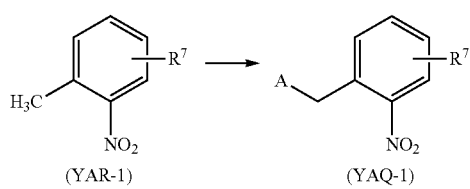

The reaction can be carried out in accordance with the method mentioned in Production Process H of WO 2013/162072 A.

(Reference Production Process T)

A compound represented by formula (YAS-2) (hereinafter referred to as the compound (YAS-2)) can be produced by reacting the compound (YAE-1) with a potassium fluoride:

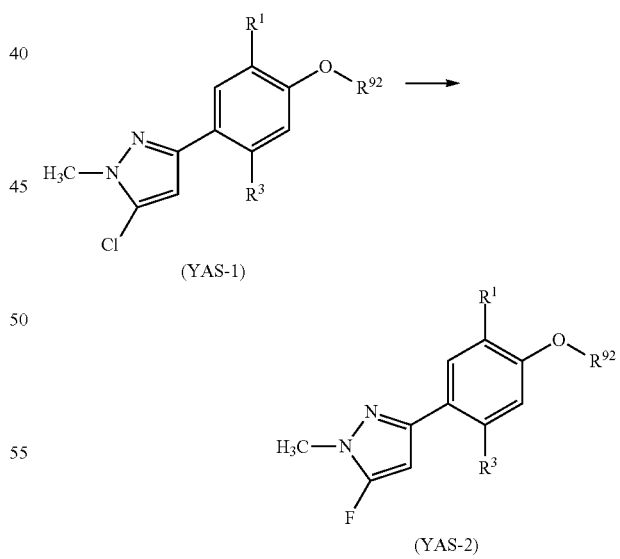

wherein symbols are the same as defined above.

The reaction is usually performed in a solvent.

Examples of the solvent to be used in the reaction include hydrocarbons such as n-hexane, cyclohexane, n-pentane, toluene, and xylene; sulfoxides such as sulfolane and methyl sulfoxide;

and mixtures thereof.

In the reaction, potassium fluoride is used in the proportion within a range of 1 to 10 mols based on 1 mol of the compound (YAS-1).

The reaction temperature of the reaction is usually within a range of 0° C. to 300° C. The reaction time of the reaction is usually within a range of 0.1 to 24 hours.

After completion of the reaction, the compound (YAS-2) can be obtained by usually performing post-treatment operations such as addition of 1 mol or more of water, extraction of the reaction mixture with an organic solvent, and drying and concentration of the organic layer. The isolated compound (YAS-2) can also be purified by chromatography, recrystallization, and the like.

(Reference Production Process U)

The compound (YL1) can be produced by reacting a compound represented by formula (YU1) (hereinafter referred to as the compound (YU1)) with the compound (YD2):

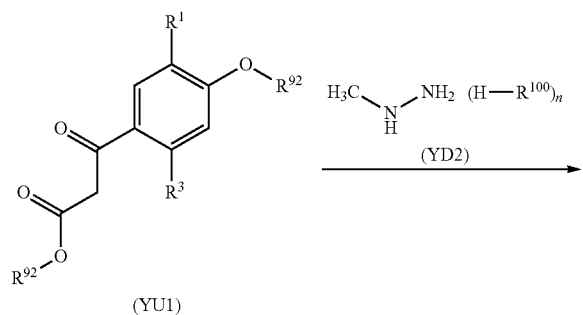

(YU1)

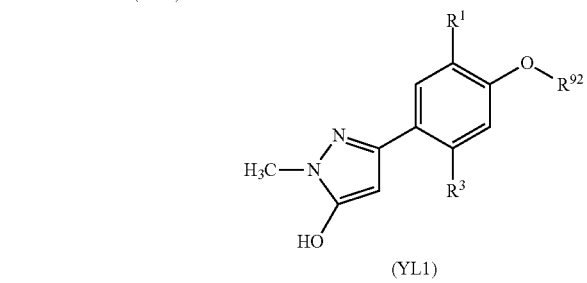

(YL1)

wherein symbols are the same as defined above.

The reaction can be carried out in accordance with the reaction mentioned in Reference Production Process D.

(Reference Production Process V)

The compound (YU1) can be produced by reacting the compound (YE1) with a compound represented by formula (YV2) (hereinafter referred to as the compound (YV2)) in the presence of a base:

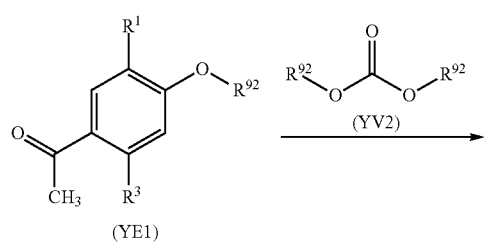

(YE1)

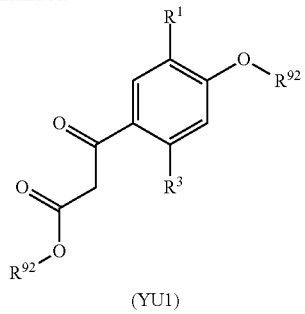

(YU1)

wherein symbols are the same as defined above.

The reaction can be carried out in accordance with the reaction mentioned in Reference Production Process E.

Regarding a form of the present control agent, the present compound is usually used after mixing with solid carriers, liquid carriers, surfactants, and the like, and optionally adding auxiliary agents for formulation, such as stickers, dispersers, and stabilizers to formulate into wettable powders, water dispersible granules, flowables, granules, dry flowables, emulsifiable concentrates, aqueous solutions, oil solutions, smoking agents, aerosols, microcapsules, and the like. In these formulations, the present compound is usually contained within a range of 0.1 to 99%, and preferably 0.2 to 90% by weight.

Examples of the solid carriers include clays (for example, kaolin, diatomaceous earth, synthetic hydrated silicon dioxide, Fubasami clay, bentonite, and acid clay), talcs or other inorganic minerals (for example, sericite, quartz powder, sulfur powder, activated charcoal, calcium carbonate, and hydrated silica) in the form of fine powders or particulates, and examples of the liquid carries include water, alcohols (for example, methanol and ethanol), ketones (for example, acetone and methyl ethyl ketone), aromatic hydrocarbons (for example, benzene, toluene, xylene, ethylbenzene, and methyl naphthalene), aliphatic hydrocarbons (for example, n-hexane, cyclohexanone, and kerosene), esters (for example, ethyl acetate and butyl acetate), nitriles (for example, acetonitrile and isobutyronitrile), ethers (for example, dioxane and diisopropylether), acid amides (for example, DMF and dimethylacetamide), and halogenated hydrocarbons (for example, dichloroethane, trichloroethylene, and carbon tetrachloride).

Examples of the surfactants include alkyl sulfates, alkyl sulfonates, alkyl aryl sulfonates, alkyl aryl ethers, and polyoxyethylenated compounds thereof, polyoxyethylene glycol ethers, polyhydric alcohol esters, and sugar alcohol derivatives.

Examples of other auxiliary agents for formulation include stickers and dispersers, specifically casein, gelatin, polysaccharides (for example, starch, gum arabic, cellulose derivatives, and alginic acid), lignin derivatives, bentonite, sugars, water-soluble synthetic polymers (for example, polyvinyl alcohol, polyvinylpyrrolidone, and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or esters thereof, and the like.

The method for applying the present compound is not particularly limited, as long as the applying form is a form by which the present compound may be applied substantially, and includes, for example, an application to plants such as a foliage application; an application to area for cultivating plants such as a submerged treatment; and an application to seed such as seed disinfection.

The present compound may be used as a mixture with various oil such as mineral oils or vegetable oils, or surfactants. Specific examples of oils or surfactants, which can be used as a mixture with various oils or surfactants, include Nimbus (registered trademark), Assist (registered trademark), Aureo (registered trademark), Iharol (registered trademark), Silwet L-77 (registered trademark), BreakThru (registered trademark), Sundancell (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7 (registered trademark), Emulad (registered trademark), TRITONX 45 (registered trademark), AGRAL 90 (registered trademark), AGROTIN (registered trademark), ARPON (registered trademark), EnSpray N (registered trademark), BANOLE (registered trademark), and the like.

The present compound can also be used as a mixture with or together with known fungicides, insecticides, acaricides, nematicides, and plant growth regulators.

The application dose of the present compound varies depending on weather conditions, dosage forms, timing of application, methods of application, areas to be applied, target diseases, target plants, and the like, and the amount of the present compound is usually within a range of 1 to 500 g, and preferably 2 to 200 g, per 1,000 $m^2$ of the area to be applied. The emulsifiable concentrate, the wettable powder, or the suspension concentrate is usually applied by diluting with water. In this case, the concentration of the present compound after dilution is usually within a range of 0.0005 to 2% by weight, and preferably 0.005 to 1% by weight. The dust formulation or the granular formulation is usually applied, as itself without dilution. In the application to seeds, the amount of the present compound in the present control agent is usually within a range of 0.001 to 100 g, and preferably 0.01 to 50 g, per 1 kg of the seeds.

Also, in another embodiment, for example, the present compound or the present control agent can be administered to the inside (inside of the body) or the outside (body surface) of the below-mentioned vertebrate to thereby exterminate systemically or unsystemically the living things or parasites which are parasitic on the vertebrate. Examples of a method of the internal administration include oral administration, anal administration, transplantation, or administration via injection subcutaneously, intramuscularly, or intravenously. Examples of a method of the external administration include transdermal administration. Also, the present compound can be ingested to a livestock animal so as to exterminate sanitary insects which occur in the excrement of the animal.

When the present compound or the present control agent is applied to the animals such as the livestock animal and pets on which pests are parasitic, the dose varies depending on the administration method etc., and it is desirable to administer the present compound so that a dose of the present compound is generally within a range of 0.1 mg to 2,000 mg, and preferably 0.5 mg to 1,000 mg, per 1 kg of body weight of the animal.

The present compound or the present control agent can be used as an agent for controlling plant diseases in agricultural lands such as fields, paddy fields, lawns, and orchards. The present compound or the present control agent can control diseases occurred in the agricultural lands for cultivating the following plants.

Crops: corn, rice, wheat, barley, rye, triticale, oat, sorghum, cotton, soybean, peanut, French bean (kidneybean), lima bean, adzuki bean, cowpea, mung bean, black gram, scarlet runner bean, rice bean, moth bean, tepary bean, broad bean, pea, chickpea, lentil, lupine, gandule bean, buckwheat, beet, rapeseed, sunflower, sugar cane, tobacco, and the like; Vegetables: solanaceous vegetables (for example, eggplant, tomato, pimento, pepper, bell pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), umbelliferous vegetables (for example, carrot, parsley, celery, and parsnip), chenopodiaceous vegetables (for example, spinach and Swiss chard), lamiaceous vegetables (for example, *Perilla frutescens*, mint, basil, and lavender), strawberry, sweet potato, *Dioscorea japonica, colocasia*, and the like; Flowers; Ornamental foliage plants;

Fruits: pomaceous fruits (for example, apple, pear, Japanese pear, Chinese quince, and quince), stone fruits (for example, peach, plum, nectarine, *Prunus* mume, cherry fruit, apricot, and prune), citrus fruits (for example, Citrus unshiu, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, kaki persimmon, olive, Japanese plum, banana, coffee, date palm, coconuts, and the like;

Trees other than fruit trees: tea, mulberry, flowering plant, roadside trees (for example, ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir wood, hemlock, juniper, *Pinus, Picea*, and *Taxus cuspidate*); and the like.

Lawn: lawn grasses (zoysiagrass, Korean lawn grass, etc.), Bermuda glasses (*cynodon dactylon*, etc.), bentgrasses (redtop grass, creeping bentgrass, colonial bentgrass, etc.), bluegrasses (Kentucky bluegrass, rough bluegrass, etc.), fescue grasses (tall fescue, chewings fescue, creeping red fescue, etc.), perennial ryegrasses, (Italian ryegrass, perennial flax, etc.), orchard grass, timothy, etc.

The above-mentioned plants include genetically modified crops.

The pests which can be controlled by the present compound or the present control agent include plant pathogens such as filamentous fungus, as well as harmful arthropods such as harmful insects and harmful mites, and nemathelminth such as nematodes, and specifically include the following examples, but are not limited thereto.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*); Wheat diseases: powdery mildew (*Erysiphe graminis*), fusarium blight (*Fusarium gaminearum, F. avenaceum, F. culmorum, Microdochium nivale*), rust (*Puccinia striiformis, P. graminis, P. recondita*), snow mould (*Micronectriella nivale*), typhula snow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), tan spot (*Pyrenophora tritici-repentis*), damping-off by *Rhizoctonia* (*Rhizoctonia solani*), and take all disease (*Gaeumannomyces graminis*); Barley diseases: powdery mildew (*Erysiphe* graminis), *fusarium* blight (*Fusarium gaminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia leaf spot (*Ramularia collo-cygni*), and damping-off by *Rhizoctonia* (*Rhizoctonia solani*); Corn diseases: rust (*Puccinia sorghi*), southern rust (*Puccinia polysora*), northern leaf blight (*Setosphaeriaturcica*), southern leaf blight (*Cochliobolus heterostrophus*), anthracnose (*Colletotrichum graminicola*), gray leaf spot (*Cercospora zeae-maydis*), eyespot (*Kabatiella zeae*), and *phaeosphaeria* leaf spot (*Phaeosphaeria maydis*); Cotton diseases: anthracnose (*Colletotrichum gossypii*), grey mildew (*Ramularia areola*), and *alternaria* leaf spot (*Alternaria macrospora, A. gossypii*);

Coffee diseases: rust (*Hemileia vastatrix*); Rape seed diseases: *sclerotinia* rot (*Sclerotinia sclerotiorum*), black spot (*Alternaria brassicae*), and black leg (*Phoma lingam*); Citrus diseases: melanose (*Diaporthe citri*), scab (*Elsinoe fawcetti*), and fruit rot (*Penicillium digitatum, P. italicum*); Apple diseases: blossom blight (*Monilinia mali*), canker (*Valsa ceratosperma*), powdery mildew (*Podosphaera leucotricha*), *alternaria* leaf spot (*Alternaria alternata* apple pathotype), scab (*Venturia inaequalis*), and bitter rot (*Glomerella cingulata, Colletotrichum acutatum*); Pear diseases: scab (*Venturia nashicola, V. pirina*), black spot (*Alternaria alternata* Japanese pear pathotype), and rust (*Gymnosporangium haraeanum*); Peach diseases: brown rot (*Monilinia fructicola*), scab (*Cladosporium carpophilum*), and *Phomopsis* rot (*Phomopsis* sp.); Grapes diseases: anthracnose (*Elsinoe ampelina*), ripe rot (*Glomerella cingulata, Colletotrichum acutatum*), powdery mildew (*Uncinula necator*), rust (*Phakopsora ampelopsidis*), black rot (*Guignardia bidwellii*), and downy mildew (*Plasmopara viticola*); Japanese persimmon diseases: anthracnose (*Gloeosporium kaki*) and leaf spot (*Cercospora kaki, Mycosphaerella nawae*); Diseases of gourd family: anthracnose (*Colletotrichum lagenarium*), powdery mildew (*Sphaerotheca fuliginea*), gummy stem blight (*Didymella bryoniae*), target spot (*Corynespora cassiicola*), *fusarium* wilt (*Fusarium oxysporum*), downy mildew (*Pseudoperonospora cubensis*), *phytophthora* rot (*Phytophthora* sp.), and damping-off (*Pythium* sp.); Tomato diseases: early blight (*Alternaria solani*), leaf mold (*Cladosporium fulvum*), leaf mold (*Pseudocercospora fuligena*), and late blight (*Phytophthora infestans*);

Eggplant diseases: brown spot (*Phomopsis vexans*) and powdery mildew (*Erysiphe cichoracearum*); Cruciferous vegetables diseases: *alternaria* leaf spot (*Alternaria japonica*), white spot (*Cercosporella brassicae*), clubroot (*Plasmodiophora parasitica*), and downy mildew (*Peronospora parasitica*); Welsh onion diseases: rust (*Puccinia allii*); Soybean diseases: purple stain (*Cercospora kikuchii*), *sphaceloma* scad (*Elsinoe glycines*), pod and stem blight (*Diaporthe phaseolorum* var. *sojae*), rust (*Phakopsora pachyrhizi*), target spot (*Corynespora cassiicola*), anthracnose (*Colletotrichum glycines, C. truncatum*), *Rhizoctonia* aerial blight (*Rhizoctonia solani*), *septoria* brown spot (*Septoria glycines*), and frog eye leaf spot (*Cercosporasojina*); Kidney bean diseases: anthracnose (*Colletotrichum lindemuthianum*); Peanut diseases: early leaf spot (*Cercospora personata*), late leaf spot (*Cercospora arachidicola*), and southern blight (*Sclerotium rolfsii*); Garden pea diseases: powdery mildew (*Erysiphe pisi*);

Potato diseases: early blight (*Alternaria solani*), late blight (*Phytophthora infestans*), and *verticillium* wilt (*Verticillium albo-atrum, V. dahliae, V. nigrescens*); Strawberry diseases: powdery mildew (*Sphaerotheca humuli*); Tea diseases: net blister blight (*Exobasidium reticulatum*), white scab (*Elsinoe leucospila*), gray blight (*Pestalotiopsis* sp.), and anthracnose (*Colletotrichum theae-sinensis*); Tobacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*); Sugar beet diseases: *cercospora* leaf spot (*Cercosporabeticola*), leaf blight (*Thanatephorus cucumeris*), root rot (*Thanatephorus cucumeris*), and *aphanomyces* root rot (*Aphanomyces cochlioides*); Rose diseases: black spot (*Diplocarpon rosae*) and powdery mildew (*Sphaerotheca pannosa*); Chrysanthemum diseases: leaf blight (*Septoria chrysanthemi-indici*) and white rust (*Puccinia horiana*);

Onion diseases: *botrytis* leaf blight (*Botrytis cinerea, B. byssoidea, B. squamosa*), gray-mold neck rot (*Botrytis alli*), and small sclerotial rot (*Botrytis squamosa*); various crops diseases: gray mold (*Botrytis cinerea*) and *sclerotinia* rot (*Sclerotinia sclerotiorum*); Japanese radish diseases: *alternaria* leaf spot (*Alternaria brassicicola*); Turfgrass diseases: dollar spot (*Sclerotinia homoeocarpa*) and brown patch and large patch (*Rhizoctonia solani*); and Banana diseases: Sigatoka disease (*Mycosphaerella fijiensis, Mycosphaerella musicola*).

Hemiptera: planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*) and green rice leafhopper (*Nephotettix virescens*); aphids (Aphididae) such as cotton aphid (*Aphis gossypii*), green peach aphid (*Myzuspersicae*), cabbage aphid (*Brevicoryne brassicae*), potato aphid (*Macrosiphum euphorbiae*), foxglove aphid (*Aulacorthum solani*), oat bird-cherry aphid (*Rhopalosiphum padi*), and tropical citrus aphid (*Toxoptera citricidus*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), stink bug (*Halyomorpha mista*), and tarnished plant bug (*Lygus lineolaris*); whiteflies (Aleyrodidae) such as greenhouse whitefly (*Trialeurodes vaporariorum*) and silverleaf whitefly (*Bemisia argentifolii*); scales (Coccidae) such as California red scale (*Aonidiella aurantii*), San Jose scale (*Comstockaspis perniciosa*), citrus north scale (*Unaspis citri*), red wax scale (*Ceroplastes rubens*), and cottony cushion scale (*Icerya purchasi*); lace bugs (Tingidae); jumping plant lices (Homoptera, Psylloidea).

Lepidoptera: pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit *tortrix* (*Adoxophyesoranafasciata*), smaller tea *tortrix* (*Adoxophyes* sp.), oriental tea *tortrix* (*Homona magnanima*), apple *tortrix*

(*Archips fuscocupreanus*), and codling moth (*Cydia pomonella*); leafblotch miners (*Gracillariidae*) such as tea leafroller (*Caloptilia theivora*), and apple leafminer (*Phyllonorycter ringoneella*); codling moths (*Carposimidae*) such as peach fruit moth (*Carposina niponensis*); lyonetiid moths (*Lyonetiidae*) such as *Lyonetia* spp.; tussock moths (*Lymantriidae*) such as *Lymantria* spp. and *Euproctis* spp.; yponomeutid moths (*Yponomeutidae*) such as diamondback (*Plutellaxylostella*); gelechildmoths (*Gelechiidae*) such as pink bollworm (*Pectinophora gossypiella*) and potato tubeworm (*Phthorimaea operculella*); tiger moths and allies (*Arctiidae*) such as fall webworm (*Hyphantria cunea*); and tineid moths (*Tineidae*) such as casemaking clothes moth (*Tinea translucens*), and webbing clothes moth (*Tineola bisselliella*).

Thysanoptera: yellow citrus thrips (*Frankliniella occidentalis*), melon thrips (*Thrips palmi*), yellow tea thrips (*Scirtothrips dorsalis*), onion thrips (*Thrips tabaci*), flower thrips (*Frankliniella intonsa*), and tobacco thrips (*Frankliniella fusca*).

Diptera: houseflies (*Musca domestica*), common mosquito (*Culex pipiens pallens*), horsefly (*Tabanus trigonus*), onion maggot (*Hylemya antiqua*), seedcorn maggot (*Hylemya platura*), *Anopheles sinensis*, rice leafminer (*Agromyza oryzae*), rice leafminer (*Hydrellia griseola*), rice stem maggot (*Chlorops oryzae*), melon fly (*Dacus cucurbitae*), Mediterranean fruit fly (*Ceratitis capitata*), and legume leafminer (*Liriomyza trifolii*).

Coleoptera: twenty-eight-spotted ladybirds (*Epilachna vigintioctopunctata*), cucurbit leaf beetle (*Aulacophora femoralis*), yellow striped flea beetle (*Phyllotreta striolata*), rice leaf beetle (*Oulema oryzae*), rice curculio (*Echinocnemus squameus*), riced water weevil (*Lissorhoptrus oryzophilus*), boll weevil (*Anthonomus grandis*), azuki bean weevil (*Callosobruchus chinensis*), hunting billbug (*Sphenophorus venatus*), Japanese beetle (*Popillia japonica*), cupreous chafer (*Anomala cuprea*), corn root worms (*Diabrotica* spp.), Colorado beetle (*Leptinotarsa decemlineata*), click beetles (*Agriotes* spp.), cigarette beetle (*Lasioderma serricorne*), varied carper beetle (*Anthrenus verbasci*), red flour beetle (*Tribolium castaneum*), powder post beetle (*Lyctus brunneus*), white-spotted longicorn beetle (*Anoplophora malasiaca*), and pine shoot beetle (*Tomicus piniperda*).

Orthoptera: asiatic locusts (*Locusta migratoria*), African mole cricket (*Gryllotalpa africana*), rice grasshopper (*Oxya yezoensis*), and rice grasshopper (*Oxya japonica*).

Hymenoptera: cabbage sawflies (*Athalia rosae*), leafcutting ant (*Acromyrmex* spp.), and fire ant (*Solenopsis* spp.).

Nematodes: white-tip nematode (*Aphelenchoides besseyi*), strawberry bud nematode (*Nothotylenchus acris*), soybean cyst nematode (*Heterodera glycines*), southern root-knot nematode (*Meloidogyne incognita*), cobb's rootlesion nematode (*Pratylenchuspenetrans*), and false rootknot nematode (*Nacobbus aberrans*).

Blattariae: German cockroach (*Blattella germanica*), smoky-brown cockroach (*Periplaneta fuliginosa*), American cockroach (*Periplaneta americana*), brown cockroach (*Periplaneta brunnea*), and oriental cockroach (*Blatta orientalis*).

Acarina: Tetranychidae (for example, two-spotted spider mite (*Tetranychus urticae*), citrus red mite (*Panonychus citri*), and *Oligonychus* spp.); Eriophyidae (for example, pink citrus rust mite (*Aculops pelekassi*)); Tarsonemidae (for example, broad mite (*Polyphagotarsonemus latus*)); Tenuipalpidae; Tuckerellidae; Tuckerellidae Acaridae (for example, common grain mite (*Tyrophagus putrescentiae*)); Pyroglyphidae (for example, Americal house dust mite (*Dermatophagoides farinae*) and house dust mite (*Dermatophagoides pteroenyssinus*)); Cheyletidae (for example, cheyletid mite (*Cheyletus eruditus*), *Cheyletus malaccensis*, and *Cheyletus moorei*; and Dermanyssidae.

The present control agent comprising the present compound can be used in the field relating to a treatment of livestock diseases or livestock industry, and can exterminate the living things or parasites which are parasitic on the inside and/or the outside of vertebrates such as human being, cow, sheep, goat, pig, poultry, dog, cat, and fish, so as to maintain public health. Examples of the pests include ticks (*Ixodes* spp.) (for example, *Ixodes scapularis*), *Boophilus* spp. (for example, cattle tick (*Boophilus microplus*)), *Amblyomma* spp., *Hyalomma* spp., *Rhipicephalus* spp. (for example, kennel tick (*Rhipicephalus sanguineus*)), *Haemaphysalis* spp. (for example, *Haemaphysalis longicornis*), *Dermacentor* spp., *Ornithodoros* spp. (for example, *Ornithodoros moubata*), red mite (*Dermanyssus gallinae*), ghost ant (*Ornithonyssus sylviarum*), *Sarcoptes* spp. (for example, *Sarcoptes scabiei*), *Psoroptes* spp., *Chorioptes* spp., *Demodex* spp., *Eutrombicula* spp., *Ades* spp. (for example, Asian tiger mosquito (*Aedes albopictus*)), *Anopheles* spp., *Culexspp.*, *Culicoides* spp., *Musca* spp., *Hypoderma* spp., *Gasterophilus* spp., *Haematobia* spp., *Tabanus* spp., *Simulium* spp., *Triatoma* spp., lice (*Phthiraptera*) (for example, *Damalinia* spp.), *Linognathus* spp., *Haematopinus* spp., *Ctenocephalides* spp. (for example, cat flea (*Ctenocephalides felis*)) *Xenopsylla* spp., Pharaoh's ant (*Monomoriumpharaonis*) and nematodes [for example, hairworm (for example, *Nippostrongylus brasiliensis, Trichostrongylus axei, Trichostrongylus colubriformis*), *Trichinella* spp. (for example, *Trichinella spiralis*), barber pole worm (*Haemonchus contortus*), *Nematodirus* spp. (for example, *Nematodirus battus*), *Ostertagia circumcincta, Cooperia* spp., *Hymenolepis nana*, and the like.

The present control agent containing at least one selected from the group consisting of the above-mentioned known fungicides, insecticide, acaricides, nematicides, and plant growth regulators may be directly applied to a plant body to be protected from pests, or may be applied to soil for fix planting of the plant body, and seeds.

At least one selected from the group consisting of the above-mentioned known fungicides, insecticide, acaricides, nematicides, and plant growth regulators may be applied to the plant body, simultaneously or separately, when using together with the present control agent. When applying separately, an application date may be different and a different dosage form may be used.

It is possible to combine an application of the present control agent to seeds of the plant with an application of at least one selected from the group consisting of the above-mentioned known fungicides, insecticide, acaricides, nematicides, and plant growth regulators to the plant, or soil for fix planting of the plant. It is also possible to combine an application of at least one selected from the group consisting of the above-mentioned known fungicides, insecticide, acaricides, nematicides, and plant growth regulators to seeds of the plant with an application of the present control agent to the plant, or soil for fix planting of the plant. An application to the plant, or soil for fix planting of the plant may be performed before, on, or after fix planting.

This application method is preferably applied to cultivation of corn, wheat, and rice.

It is possible to combine an application of the present control agent to a plant body, or soil on which the plant body is cultivated or to be cultivated (for example, soil of paddy fields, crop fields, orchards, or non-cultivated lands) with an application of at least one selected from known herbicides to the soil. The pest control agent of the present invention and herbicides can be applied simultaneously or separately. When applying separately, the application may be performed on the same or different day.

Examples of the herbicide, which can be used together with the present control agent, include glyphosate, salts of glyphosate, glufosinate, salts of glyphosate, 2,4-D, salts of 2,4-D, dicamba, salts of dicamba, and flumioxazin.

EXAMPLES

The present invention will be described in more detail below by way of Production Examples, Formulation Examples, and Test Examples, but the present invention is not limited to these Examples.

First, Production Examples of the present compound will be described.

Production Example 1

A mixture of 1.40 g of 5A mentioned in Reference Production Example 5 and 4 ml of tetrahydrofuran was cooled to −78° C., and 2.75 ml of an isopropyl magnesium chloride-lithium chloride complex tetrahydrofuran solution (1.3 mol/L) was added dropwise thereto, followed by stirring at 60° C. for 4 hours. This reaction solution was added dropwise to a mixture of 1.57 g of diethyl oxalate and 3 ml of tetrahydrofuran cooled to 0° C., and then the temperature was raised to room temperature while stirring. To the reaction solution, an aqueous saturation ammonium chloride solution was added, and the mixture was extracted with chloroform. The organic layer was washed with water, dried over anhydrous magnesium sulfate, and then concentrated under reduced pressure. The residue thus obtained was subjected to silica gel column chromatography to obtain 0.09 g of the present compound 1 shown below.

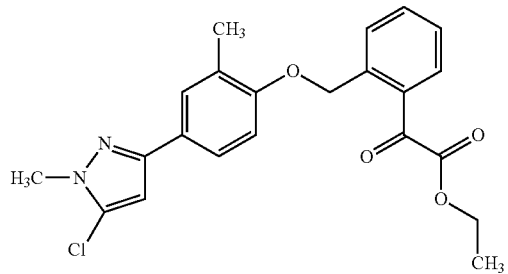 [SMILES: CCOC(=O)C(=O)c1ccccc1COc1ccc(-c2cc(Cl)n(C)n2)cc1C]

$^1$H-NMR (CDCl$_3$) δ: 7.84-7.78 (2H, m), 7.69-7.64 (1H, m), 7.58-7.41 (3H, m), 6.90 (1H, d, J=8.5 Hz), 6.44-6.43 (1H, m), 5.43 (2H, s), 4.30 (2H, q, J=7.2 Hz), 3.88 (3H, s), 2.34 (3H, s), 1.31 (3H, t, J=7.2 Hz).

Production Example 2

A mixed solution of 0.25 g of the intermediate (15A) mentioned in Reference Production Example 7, 0.24 ml of pyridine, and 4 ml of chloroform was ice-cooled and 0.08 ml of methyl chlorocarbonate was added, followed by stirring at room temperature for 30 minutes. The reaction solution was concentrated under reduced pressure. The residue thus obtained was subjected to silica gel column chromatography to obtain 0.22 g of the present compound shown below.

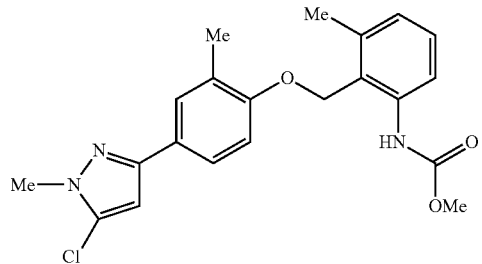 [SMILES: COC(=O)Nc1cccc(C)c1COc1ccc(-c2cc(Cl)n(C)n2)cc1C]

$^1$H-NMR (CDCl$_3$) δ: 7.77 (1H, s), 7.58-7.53 (3H, m), 7.27 (1H, dd, J=10.2, 5.7 Hz), 7.00-6.98 (2H, m), 6.44 (1H, s), 5.12 (2H, s), 3.88 (3H, s), 3.74 (3H, s), 2.40 (3H, s), 2.25 (3H, s).

Compounds produced in accordance with the method mentioned in Production Example 2 and physical properties thereof are shown below.

Compound Represented by Formula (a):

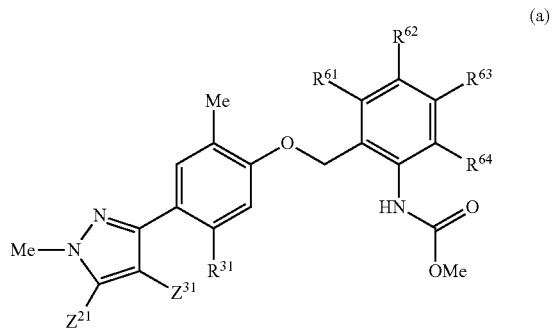

(a)

wherein $Z^{21}$, $Z^{31}$, $R^{31}$, $R^{61}$, $R^{62}$, $R^{63}$, and $R^{64}$ are shown in [Table 1].

TABLE 1

|  | $Z^{21}$ | $Z^{31}$ | $R^{31}$ | $R^{61}$ | $R^{62}$ | $R^{63}$ | $R^{64}$ |
| --- | --- | --- | --- | --- | --- | --- | --- |
| Present Compound 3 | Cl | H | Me | Me | H | H | H |
| Present Compound 4 | Cl | H | Me | H | H | H | Me |
| Present Compound 6 | H | Me | H | Me | H | H | H |
| Present Compound 7 | Me | H | H | Me | H | H | H |
| Present Compound 8 | Me | H | Me | Me | H | H | H |
| Present Compound 9 | Me | H | Me | OMe | H | H | H |
| Present Compound 10 | OMe | H | H | Me | H | H | H |

Present Compound 3

$^1$H-NMR (CDCl$_3$) δ: 7.78 (1H, s), 7.54 (1H, s), 7.34 (1H, s), 7.29-7.25 (1H, m), 6.98 (1H, d, J=7.6 Hz), 6.86 (1H, s), 6.32 (1H, s), 5.11 (2H, s), 3.89 (3H, s), 3.74 (3H, s), 2.45 (3H, s), 2.42 (3H, s), 2.20 (3H, s).

Present Compound 4

$^1$H-NMR (CDCl$_3$) δ: 7.32 (2H, s), 7.26-7.19 (3H, m), 6.78 (1H, s), 6.30 (1H, s), 5.06 (2H, s), 3.88 (3H, s), 3.75 (3H, s), 2.41 (3H, s), 2.32 (3H, s), 2.22 (3H, s).

Present Compound 6

$^1$H-NMR (CDCl$_3$) δ: 7.78 (1H, s), 7.59 (1H, s), 7.52-7.52 (1H, m), 7.47 (1H, dd, J=8.2, 1.8 Hz), 7.28-7.26 (1H, m), 7.19 (1H, s), 7.03 (1H, d, J=8.5 Hz), 6.98 (1H, d, J=7.6 Hz), 5.12 (2H, s), 3.88 (3H, s), 3.74 (3H, s), 2.41 (3H, s), 2.26 (3H, s), 2.22 (3H, s).

Present Compound 7

$^1$H-NMR (CDCl$_3$) δ: 7.78 (1H, s), 7.60-7.54 (3H, m), 7.29-7.25 (1H, m), 6.98 (2H, t, J=7.1 Hz), 6.26 (1H, s), 5.11 (2H, s), 3.82 (3H, s), 3.74 (3H, s), 2.40 (3H, s), 2.30 (3H, s), 2.25 (3H, s).

Present Compound 8

$^1$H-NMR (CDCl$_3$) δ: 7.79 (1H, s), 7.61 (1H, s), 7.37 (1H, s), 7.28-7.26 (1H, m), 6.98 (1H, d, J=7.7 Hz), 6.86 (1H, s), 6.13 (1H, s), 5.10 (2H, s), 3.83 (3H, s), 3.74 (3H, s), 2.46 (3H, s), 2.42 (3H, s), 2.32 (3H, s), 2.20 (3H, s).

Present Compound 9

$^1$H-NMR (CDCl$_3$) δ: 7.98 (1H, s), 7.65 (1H, d, J=8.4 Hz), 7.33-7.30 (2H, m), 6.92 (1H, s), 6.66 (1H, d, J=8.4 Hz), 6.10 (1H, s), 5.28 (2H, s), 3.88 (3H, s), 3.81 (3H, s), 3.75 (3H, s), 2.42 (3H, s), 2.31 (3H, s), 2.22 (3H, s).

Present Compound 10

$^1$H-NMR (CDCl$_3$) δ: 7.78 (1H, s), 7.47 (1H, s), 7.29-7.24 (3H, m), 7.05 (1H, d, J=8.2 Hz), 7.01 (1H, d, J=7.5 Hz), 5.67 (1H, s), 5.14 (2H, s), 3.91 (3H, s), 3.76 (3H, s), 3.73 (3H, s), 2.42 (3H, s), 2.26 (3H, s).

With respect to intermediates for the production of the above-mentioned present compounds, Reference Production Examples are shown below.

Reference Production Example 1

A mixture of 279 g of commercially available 1-(4-hydroxy-3-methylphenyl)-ethanone, 317 g of methyl iodide, 514 g of potassium carbonate, and 5,600 ml of acetone was stirred with heating under reflux for 5 hours. The reaction mixture was filtered and water was added to the filtrate, and the mixture was extracted with ethyl acetate. The organic layer was washed with water, dried over anhydrous magnesium sulfate, and then concentrated under reduced pressure to obtain 275 g of a compound represented by formula shown below (hereinafter referred to as the intermediate (1A)).

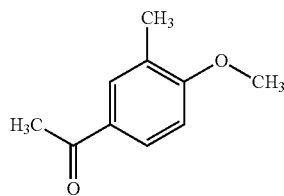

$^1$H-NMR (CDCl$_3$) δ: 7.82 (1H, dd, J=8.5, 1.7 Hz), 7.79-7.76 (1H, m), 6.85 (1H, d, J=8.5 Hz), 3.90 (3H, s), 2.55 (3H, s), 2.25 (3H, s).

Reference Production Example 2

To a mixture of 247 g of the intermediate (1A) and 4,900 ml of tetrahydrofuran, 356 g of diethyl carbonate, 136 g of 55% sodium hydride, 1.14 g of dibenzo-18-crown-6, and 74 ml of ethanol were added at room temperature, followed by stirring with heating under reflux for 6 hours. To the reaction mixture, water was added and 10% hydrochloric acid was added to thereby acidify the solution, which was extracted with ethyl acetate. The organic layer was washed with water, dried over anhydrous magnesium sulfate, and then concentrated under reduced pressure. The residue thus obtained was subjected to silica gel column chromatography to obtain 302 g of a compound represented by formula shown below (hereinafter referred to as the intermediate (2A)).

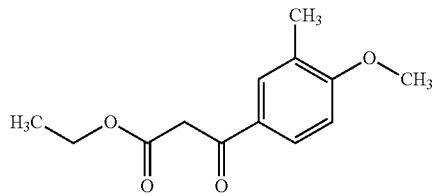 [SMILES: CCOC(=O)CC(=O)c1ccc(OC)c(C)c1]

$^1$H-NMR (CDCl$_3$) δ: 7.82-7.76 (2H, m), 6.86 (1H, d, J=8.5 Hz), 4.21 (2H, q, J=7.1 Hz), 3.94 (2H, s), 3.89 (3H, s), 2.24 (3H, s), 1.26 (3H, t, J=7.1 Hz).

Reference Production Example 3

To a mixture of 272 g of the intermediate (2A) and 2,800 ml of toluene, 533 g of methylhydrazine was added at room temperature, followed by stirring at room temperature for 10 hours. Toluene was distilled off under reduced pressure and 10% hydrochloric acid was added to thereby acidify the solution, followed by stirring for 3 hours. The precipitate formed by stirring was filtered and the filtrate was washed with water and ethyl acetate, and then dried under reduced pressure to obtain 226 g of a compound represented by formula shown below (hereinafter referred to as the intermediate (3A)).

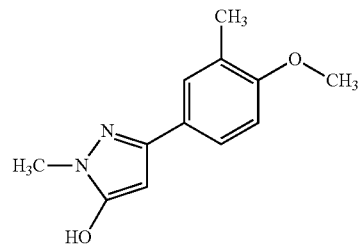

$^1$H-NMR (DMSO-D$_6$) δ: 7.49-7.46 (2H, m), 6.92-6.89 (1H, m), 5.70 (1H, s), 3.79 (3H, s), 3.53 (3H, s), 2.16 (3H, s).

Reference Production Example 4

A mixture of 5.00 g of the intermediate (3A) and 35.0 g of phosphorus oxychloride was stirred at 90° C. for 4 hours, and then concentrated under reduced pressure. To the reaction mixture, water was added and the mixture was extracted with ethyl acetate. The organic layer was washed with water, dried over anhydrous magnesium sulfate, and then concentrated under reduced pressure. The residue thus obtained was subjected to silica gel column chromatography to obtain 5.79 g of a compound represented by formula shown below (hereinafter referred to as the intermediate (4A)).

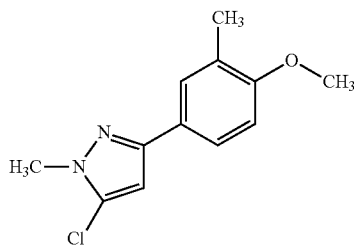

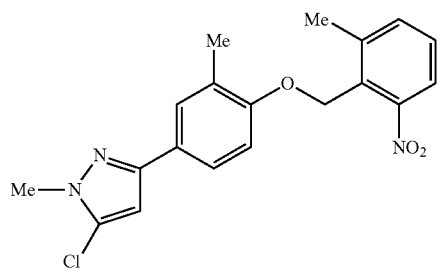 [SMILES: Cc1cc(-c2cc(Cl)n(C)n2)ccc1OCc1c(C)cccc1[N+](=O)[O-]]

$^1$H-NMR (CDCl$_3$) δ: 7.56-7.52 (2H, m), 6.85 (1H, d, J=9.3 Hz), 6.46 (1H, s), 3.92 (3H, s), 3.86 (3H, s), 2.26 (3H, s).

$^1$H-NMR (CDCl$_3$) δ: 7.66 (1H, d, J=7.1 Hz), 7.51-7.48 (3H, m), 7.40 (1H, t, J=7.8 Hz), 6.93 (1H, d, J=8.2 Hz), 6.43 (1H, s), 5.25 (2H, s), 3.87 (3H, s), 2.53 (3H, s), 2.17 (3H, s).

Compounds produced in accordance with Reference Production Example 6, and physical properties thereof are shown below. Compounds represented by formula (aA):

Reference Production Example 5

A mixture of 5.42 g of the intermediate (4A), 28.0 g of 47% hydrobromic acid, and 27.5 g of acetic acid was stirred with heating under reflux for 15 hours. The mixture was cooled to 0° C. and the precipitate thus formed was filtered, and the precipitate was washed with iced water and then filtered to obtain a solid.

(Operation 1) The filtrate was concentrated under reduced pressure and cooled to 0° C., and the precipitate thus obtained was filtered and the precipitate was washed with iced water and then filtered to obtain a solid.

The above-mentioned (operation 1) was performed three times and the entire solid thus obtained was dried under reduced pressure to obtain 3.80 of a compound represented by formula shown below (hereinafter referred to as the intermediate (5A)).

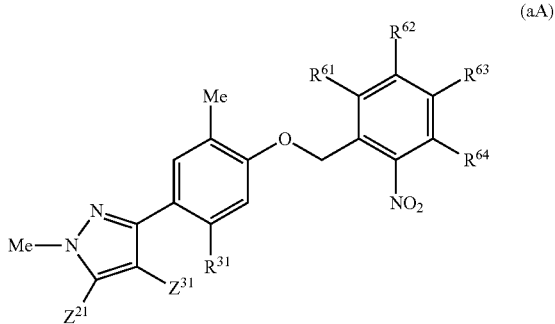

(aA)

wherein $Z^{21}$, $Z^{31}$, $R^{31}$, $R^{61}$, $R^{62}$, $R^{63}$, and $R^{64}$ are shown in [Table 2].

TABLE 2

| | $Z^{21}$ | $Z^{31}$ | $R^{31}$ | $R^{61}$ | $R^{62}$ | $R^{63}$ | $R^{64}$ |
|---|---|---|---|---|---|---|---|
| Intermediate (7A) | Cl | H | Me | Me | H | H | H |
| Intermediate (8A) | Cl | H | Me | H | H | H | Me |
| Intermediate (10A) | H | Me | H | Me | H | H | H |
| Intermediate (11A) | Me | H | H | Me | H | H | H |
| Intermediate (12A) | Me | H | Me | Me | H | H | H |
| Intermediate (13A) | Me | H | Me | OMe | H | H | H |
| Intermediate (14A) | OMe | H | H | Me | H | H | H |

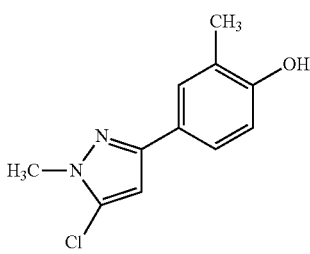

$^1$H-NMR (CDCl$_3$) δ: 7.57-7.54 (1H, m), 7.48-7.43 (1H, m), 6.80 (1H, d, J=8.4 Hz), 6.43 (1H, s), 3.90 (3H, s), 2.29 (3H, s).

Reference Production Example 6

A mixture of 0.22 g of the intermediate (5A), 0.24 g of 2-(bromomethyl)-3-methyl-1-nitrobenzene, 0.22 g of potassium carbonate, and 4 ml of acetonitrile was stirred with heating under reflux for 4 hours. After cooling, the reaction solution was filtered with Celite (registered trademark) and then the filtrate was concentrated under reduced pressure. The residue thus obtained was subjected to silica gel column chromatography to obtain 0.30 g of a compound represented by formula shown below (hereinafter referred to as the intermediate (6A)).

Intermediate (7A)

$^1$H-NMR (CDCl$_3$) δ: 7.66 (1H, d, J=7.2 Hz), 7.47 (1H, d, J=7.0 Hz), 7.40 (1H, t, J=7.8 Hz), 7.30 (1H, s), 6.78 (1H, s), 6.30 (1H, s), 5.24 (2H, s), 3.88 (3H, s), 2.53 (3H, s), 2.43 (3H, s), 2.12 (3H, s).

Intermediate (8A)

$^1$H-NMR (CDCl$_3$) δ: 7.52 (1H, d, J=7.7 Hz), 7.43 (1H, t, J=7.7 Hz), 7.31-7.29 (2H, m), 6.68 (1H, s), 6.30 (1H, s), 5.13 (2H, s), 3.88 (3H, s), 2.40 (3H, s), 2.39 (3H, s), 2.23 (3H, s).

Intermediate (10A)

$^1$H-NMR (CDCl$_3$) δ: 7.66 (1H, d, J=7.9 Hz), 7.48-7.38 (4H, m), 7.18 (1H, s), 6.95 (1H, d, J=8.4 Hz), 5.25 (2H, s), 3.88 (3H, s), 2.53 (3H, s), 2.21 (3H, s), 2.18 (3H, s).

Intermediate (11A)

$^1$H-NMR (CDCl$_3$) δ: 7.65 (1H, d, J=7.1 Hz), 7.56-7.52 (2H, m), 7.47 (1H, d, J=7.1 Hz), 7.40 (1H, d, J=7.8 Hz), 6.92 (1H, d, J=8.5 Hz), 6.25 (1H, s), 5.24 (2H, s), 3.81 (3H, s), 2.52 (3H, s), 2.30 (3H, s), 2.17 (3H, s).

Intermediate (12A)

¹H-NMR (CDCl₃) δ: 7.65 (1H, d, J=8.0 Hz), 7.46 (1H, d, J=7.1 Hz), 7.40 (1H, d, J=7.8 Hz), 7.32 (1H, s), 6.77 (1H, s), 6.11 (1H, s), 5.23 (2H, s), 3.82 (3H, s), 2.53 (3H, s), 2.44 (3H, s), 2.31 (3H, s), 2.12 (3H, s).

Intermediate (13A)

¹H-NMR (CDCl₃) δ: 7.45-7.38 (2H, m), 7.28 (1H, s), 7.14 (1H, dd, J=7.8, 1.6 Hz), 6.79 (1H, s), 6.10 (1H, s), 5.38 (2H, s), 3.94 (3H, s), 3.81 (3H, s), 2.42 (3H, s), 2.30 (3H, s), 2.09 (3H, s).

Intermediate (14A)

¹H-NMR (CDCl₃) δ: 7.68 (1H, d, J=8.0 Hz), 7.49 (1H, d, J=6.9 Hz), 7.42 (1H, t, J=7.9 Hz), 7.21 (1H, dd, J=8.2, 2.3 Hz), 7.19-7.16 (1H, m), 6.97 (1H, d, J=8.2 Hz), 5.66 (1H, s), 5.27 (2H, s), 3.91 (3H, s), 3.72 (3H, s), 2.54 (3H, s), 2.18 (3H, s).

Reference Production Example 7

To a mixture of 0.30 g of the intermediate (6A), 0.30 g of the copper (I) chloride, and 10 ml of methanol, 0.36 g of potassium borohydride was added under ice cooling, followed by stirring for 1 hour under ice cooling. The reaction solution was filtered with Celite (registered trademark) and then the filtrate was concentrated under reduced pressure. To the residue, ethyl acetate was added, followed by washing with an aqueous saturated sodium hydrogen carbonate solution. The organic layer was dried over anhydrous magnesium sulfate and then concentrated under reduced pressure to obtain 0.25 g of an intermediate (15A) shown below.

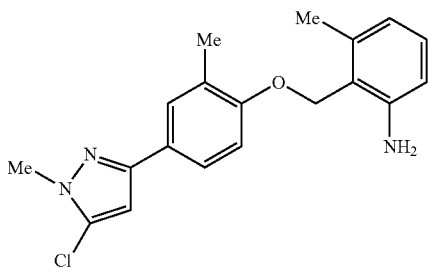 [SMILES: Cc1cc(-c2cc(Cl)n(C)n2)ccc1OCc1c(C)cccc1N]

¹H-NMR (CDCl₃) δ: 7.55-7.53 (2H, m), 7.08-7.04 (2H, m), 6.65-6.62 (2H, m), 6.44 (1H, s), 5.09 (2H, s), 4.03 (2H, s), 3.88 (3H, s), 2.36 (3H, s), 2.22 (3H, s).

Compounds produced in accordance with Reference Production Example 7, and physical properties thereof are shown below. Compounds represented by formula (bA):

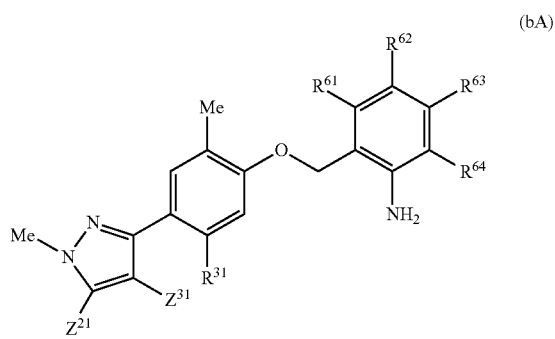

wherein $Z^{21}$, $Z^{31}$, $R^{31}$, $R^{61}$, $R^{62}$, $R^{63}$, and $R^{64}$ are shown in [Table 3].

TABLE 3

| | $Z^{21}$ | $Z^{31}$ | $R^{31}$ | $R^{61}$ | $R^{62}$ | $R^{63}$ | $R^{64}$ |
|---|---|---|---|---|---|---|---|
| Intermediate (16A) | Cl | H | Me | Me | H | H | H |
| Intermediate (17A) | Cl | H | Me | H | H | H | Me |
| Intermediate (19A) | H | Me | H | Me | H | H | H |
| Intermediate (20A) | Me | H | H | Me | H | H | H |
| Intermediate (21A) | Me | H | Me | Me | H | H | H |
| Intermediate (22A) | Me | H | Me | OMe | H | H | H |
| Intermediate (23A) | OMe | H | H | Me | H | H | H |

Intermediate (16A)

¹H-NMR (CDCl₃) δ: 7.32 (1H, s), 7.07 (1H, t, J=7.8 Hz), 6.90 (1H, s), 6.66 (1H, d, J=7.5 Hz), 6.62 (1H, d, J=7.9 Hz), 6.31 (1H, s), 5.08 (2H, s), 4.02 (2H, s), 3.89 (3H, s), 2.45 (3H, s), 2.38 (3H, s), 2.17 (3H, s).

Intermediate (17A)

¹H-NMR (CDCl₃) δ: 7.31 (1H, s), 7.11-7.09 (2H, m), 6.86 (1H, s), 6.71 (1H, t, J=7.5 Hz), 6.30 (1H, s), 5.06 (2H, s), 4.10 (2H, s), 3.88 (3H, s), 2.43 (3H, s), 2.22 (3H, s), 2.20 (3H, s).

Intermediate (19A)

¹H-NMR (CDCl₃) δ: 7.50-7.45 (2H, m), 7.18 (1H, s), 7.07-7.05 (2H, m), 6.66 (1H, d, J=7.5 Hz), 6.62 (1H, d, J=7.9 Hz), 5.09 (2H, s), 4.16 (2H, s), 3.88 (3H, s), 2.37 (3H, s), 2.23 (3H, s), 2.21 (3H, s).

Intermediate (20A)

¹H-NMR (CDCl₃) δ: 7.58-7.58 (1H, m), 7.56-7.54 (1H, m), 7.06 (1H, t, J=7.8 Hz), 7.02 (1H, d, J=8.5 Hz), 6.65 (1H, d, J=7.6 Hz), 6.61 (1H, d, J=8.0 Hz), 6.26 (1H, s), 5.08 (2H, s), 4.03 (2H, s), 3.81 (3H, s), 2.36 (3H, s), 2.30 (3H, s), 2.22 (3H, s).

Intermediate (21A)

¹H-NMR (CDCl₃) δ: 7.35 (1H, s), 7.06 (1H, t, J=7.7 Hz), 6.89 (1H, s), 6.65 (1H, d, J=7.5 Hz), 6.62 (1H, d, J=7.9 Hz), 6.13 (1H, s), 5.07 (2H, s), 4.03 (2H, s), 3.82 (3H, s), 2.46 (3H, s), 2.37 (3H, s), 2.31 (3H, s), 2.17 (3H, s).

Intermediate (22A)

¹H-NMR (CDCl₃) δ: 7.31 (1H, s), 7.09 (1H, t, J=8.2 Hz), 6.96 (1H, s), 6.37-6.35 (2H, m), 6.10 (1H, s), 5.24 (2H, s), 4.21 (2H, s), 3.85 (3H, s), 3.81 (3H, s), 2.42 (3H, s), 2.30 (3H, s), 2.18 (3H, s).

Intermediate (23A)

¹H-NMR (CDCl₃) δ: 7.24-7.22 (1H, m), 7.19 (1H, s), 7.11-7.07 (2H, m), 6.67 (1H, d, J=7.3 Hz), 6.63 (1H, d, J=8.0 Hz), 5.67 (1H, s), 5.11 (2H, s), 4.01 (2H, s), 3.91 (3H, s), 3.72 (3H, s), 2.38 (3H, s), 2.23 (3H, s).

Reference Production Example 8

A mixture of 4.0 g of 2-(bromomethyl)-3-methyl nitrobenzene, 2.4 g of 4-bromo-2-methylphenol, 4.8 g of potassium carbonate, and 40 ml of acetonitrile was heated under reflux for 5 hours. The reaction solution was filtered with Celite (registered trademark) and then the filtrate was concentrated under reduced pressure. The residue thus obtained was subjected to silica gel column chromatography to obtain 3.2 g of an intermediate (24A) shown below.

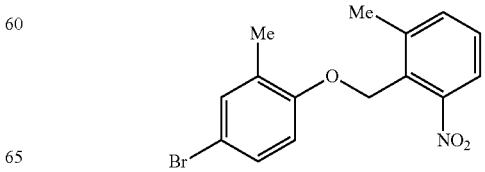

$^1$H-NMR (400 MHz, CDCl$_3$) δ: 7.74 (1H, d, J=8 Hz), 7.62 (1H, d, J=7.2 Hz), 7.53 (1H, t, J=7.8 Hz), 7.39-7.32 (2H, m), 7.04 (1H, d, J=8.4 Hz), 5.20 (2H, s), 2.50 (3H, s), 2.03 (3H, s).

Reference Production Example 9

Using the intermediate (24A) in place of the intermediate (6A), an intermediate (25A) shown below was obtained in accordance with the method mentioned in Reference Production Example 7.

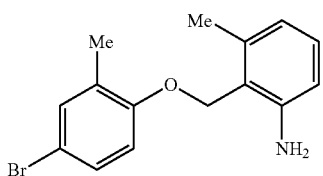 [SMILES: Cc1cc(Br)ccc1OCc1c(C)cccc1[N+](=O)[O-]]

$^1$H-NMR (400 MHz, DMSO-d$_6$) δ: 7.32-7.25 (2H, m), 7.07 (1H, t, J=7.8 Hz), 6.88 (1H, d, J=8.4 Hz), 6.68-6.56 (2H, m), 5.03 (2H, s), 3.96 (2H, brs), 2.34 (3H, s), 2.16 (3H, s).

Reference Production Example 10

Using the intermediate (25A) in place of the intermediate (15A), an intermediate (26A) shown below was obtained in accordance with the method mentioned in Reference Production Example 2.

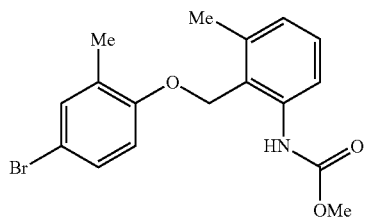 [SMILES: COC(=O)Nc1cccc(C)c1COc1ccc(Br)cc1C]

$^1$H NMR (400 MHz, DMSO-d$_6$) NMR (400 1H, brs), 7.30-7.38 (2H, m), 7.25 (2H, d, J=6.4 Hz), 7.12-6.96 (2H, m), 5.05 (2H, s), 3.60 (3H, s), 2.35 (3H, s), 2.06 (3H, s)

In accordance with the process mentioned above, it is possible to obtain compounds HA1001-0001 to HW1084-0023.

The compounds HA1001-0001 to HW1084-0023 (hereinafter referred to as the present compounds A) represent aromatic compounds shown below [wherein E represents any one of the following substituent numbers 0001 to 0023].

In [substituent number; E] mentioned below, F represents fluoro, Cl represents chloro, Br represents bromo, Me represents methyl, Et represents ethyl, OMe represents methoxy, OEt represents ethoxy, CHF2 represents difluoromethyl, CF3 represents trifluoromethyl, OCHF2 represents a difluoromethoxy group, OCF3 represents a trifluoromethoxy group, and PYR3 represents a pyrazol-3-yl group.

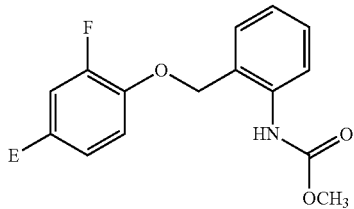
(HA1001)

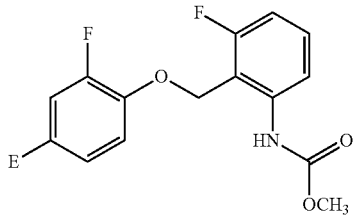
(HA1002)

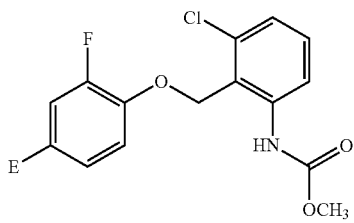
(HA1003)

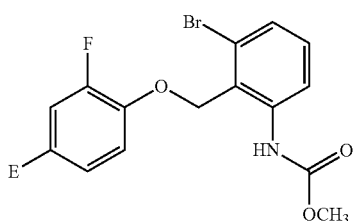
(HA1004)

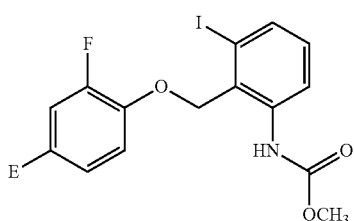
(HA1005)

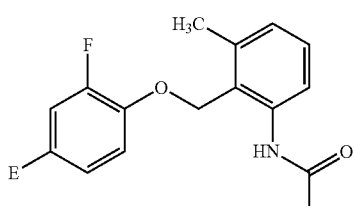
(HA1006)

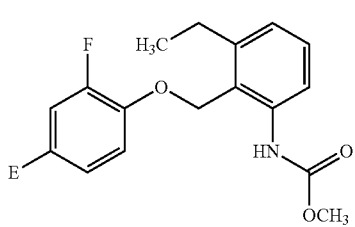
(HA1007)

-continued (HA1008)
(HA1009)
(HA1010)
(HA1011)
(HA1012)
(HA1025)

-continued (HA1026)
(HA1027)
(HA1028)
(HA1029)
(HA1030)
(HA1031)
(HA1032)

| | |
|---|---|
| (HA1033) | (HA1039) |
| (HA1034) | (HA1040) |
| | (HA1041) |
| (HA1035) | (HA1042) |
| (HA1036) | (HA1043) |
| (HA1037) | (HA1044) |
| (HA1038) | (HA1045) |

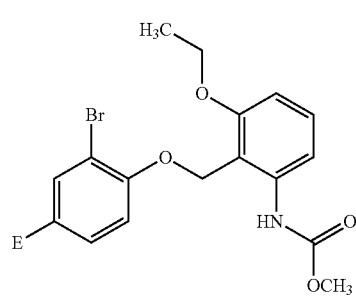
(HA1046)
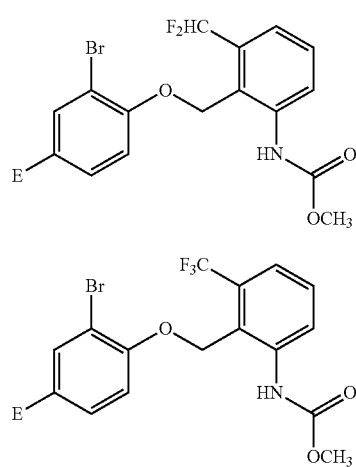
(HA1047)
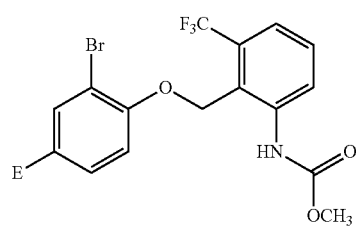
(HA1048)
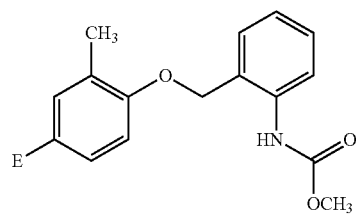
(HA1049)
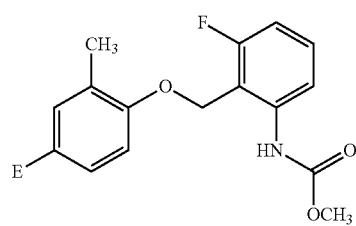
(HA1050)
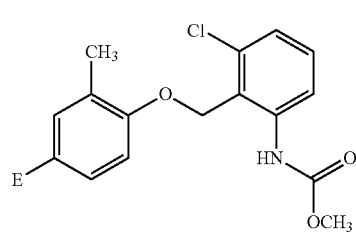
(HA1051)
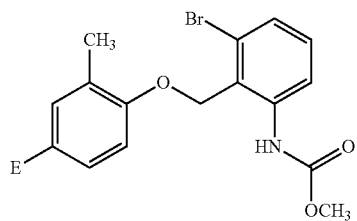
(HA1052)
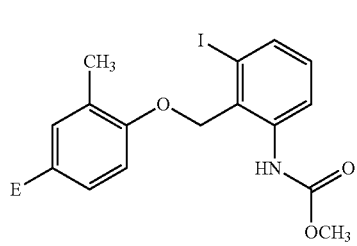
(HA1053)
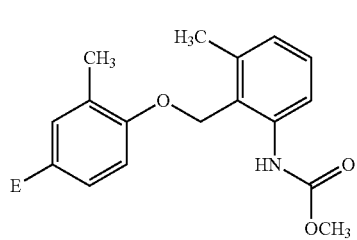
(HA1054)
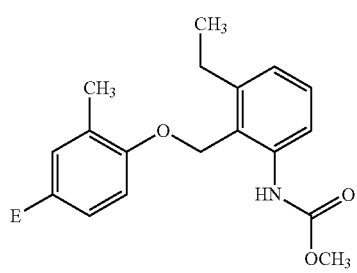
(HA1055)
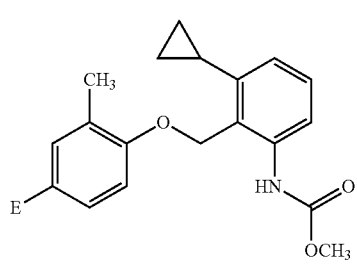
(HA1056)
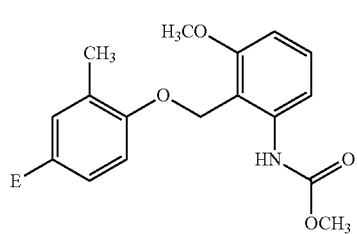
(HA1057)

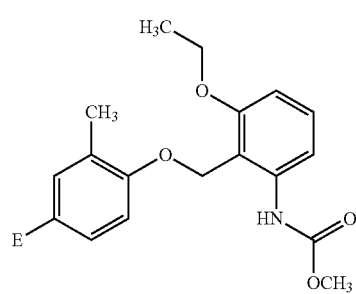
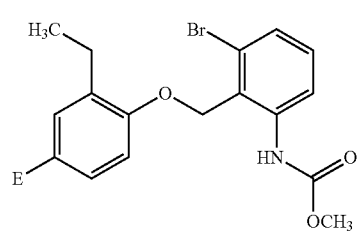

-continued (HA1070)
(HA1071)
(HA1072)
(HA1073)
(HA1074)
(HA1075)
(HA1076)
(HA1077)
(HA1078)
(HA1079)
(HA1080)
(HA1081)

-continued (HA1082)

(HA1083)

(HA1084)

(HA1085)

(HA1086)

(HA1087)

(HA1088)

(HA1089)

(HA1090)

(HA1091)

(HA1092)

(HA1093)

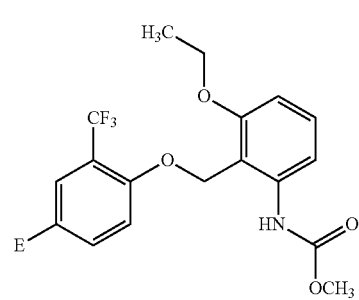
(HA1094)
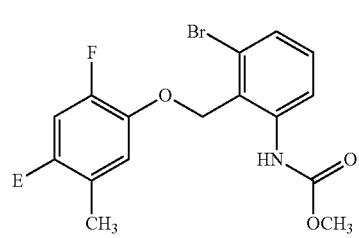
(HA4016)
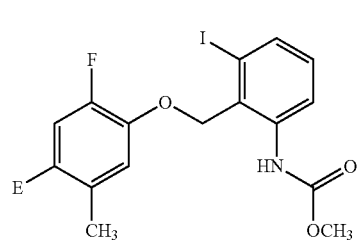
(HA4017)
(HA1095)
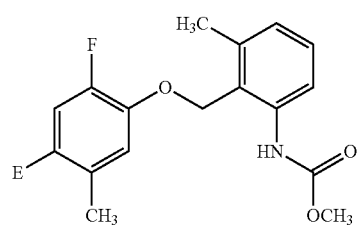
(HA4018)
(HA1096)
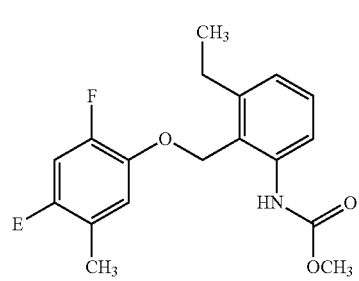
(HA4019)
(HA4013)
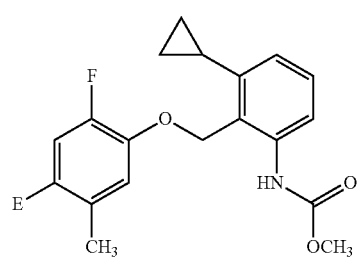
(HA4020)
(HA4014)
(HA4015)
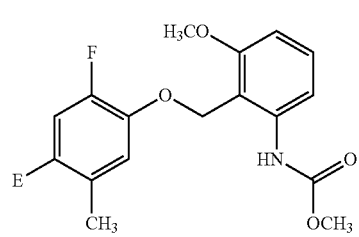
(HA4021)

(HA4022) 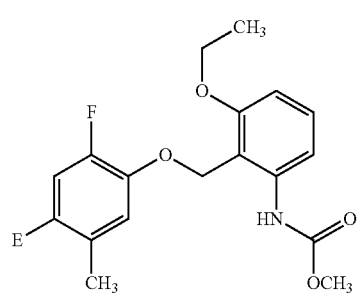
(HA4023) 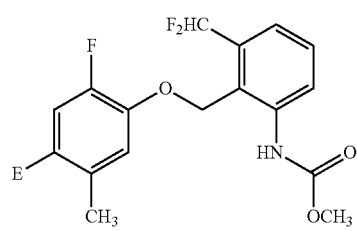
(HA4024) 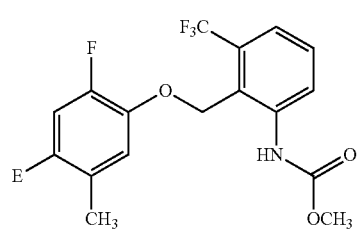
(HA4025) 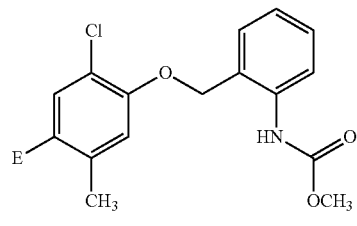
(HA4026) 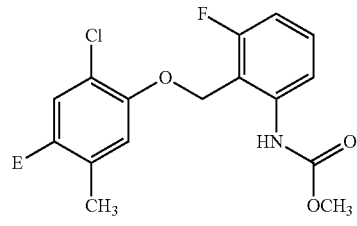
(HA4027) 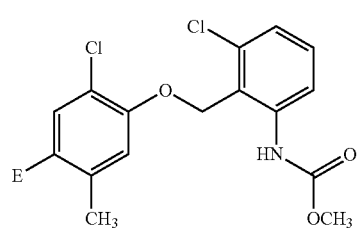
(HA4028) 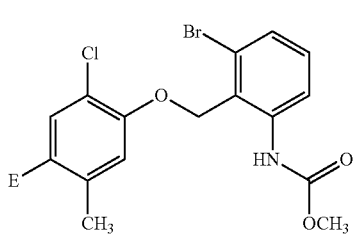
(HA4029) 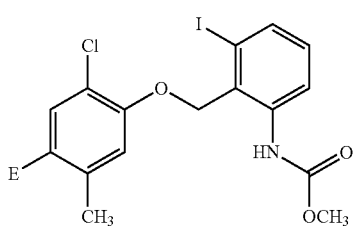
(HA4030) 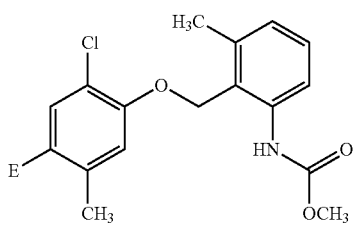
(HA4031) 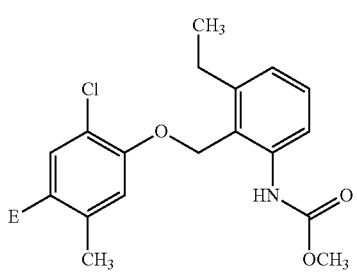
(HA4032) 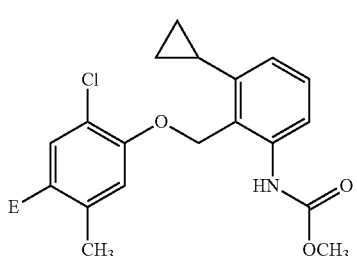
(HA4033) 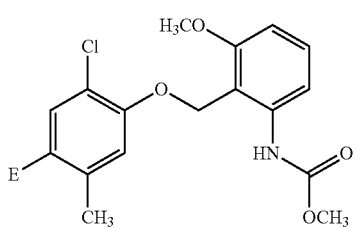

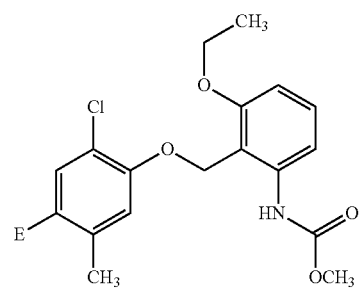 (HA4034)
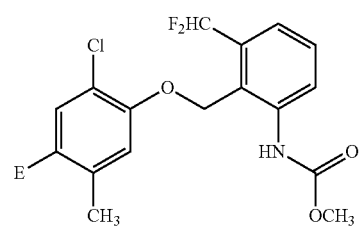 (HA4035)
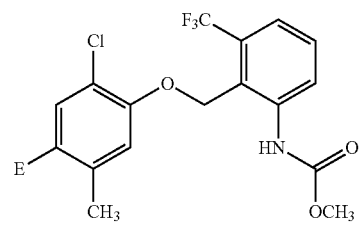 (HA4036)
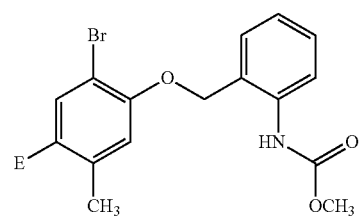 (HA4037)
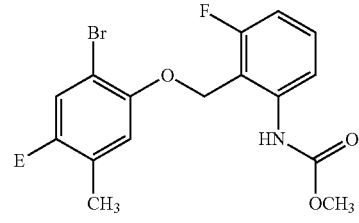 (HA4038)
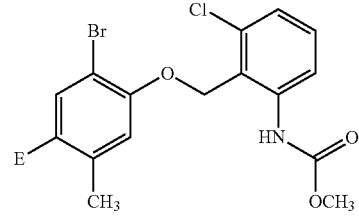 (HA4039)
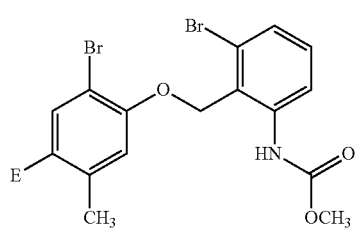 (HA4040)
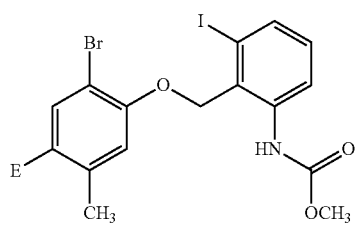 (HA4041)
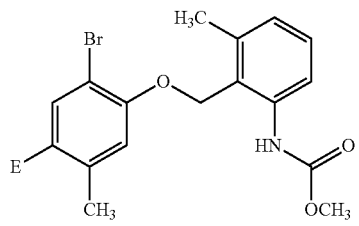 (HA4042)
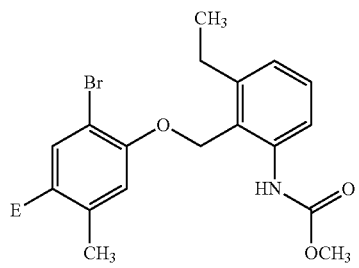 (HA4043)
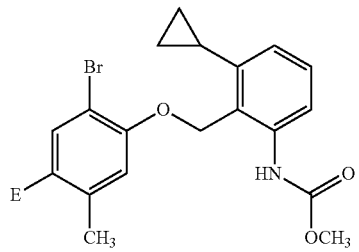 (HA4044)
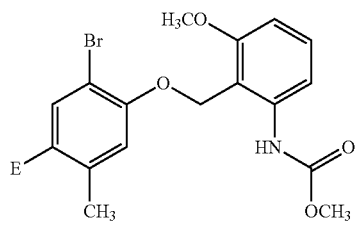 (HA4045)

(HA4046) 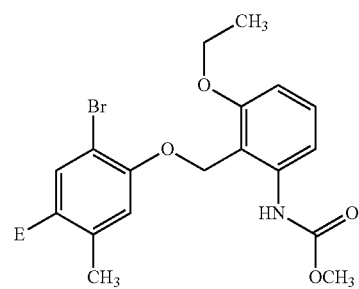
(HA4047) 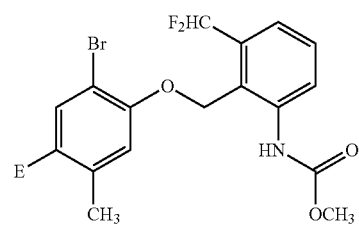
(HA4048) 
(HA4049) 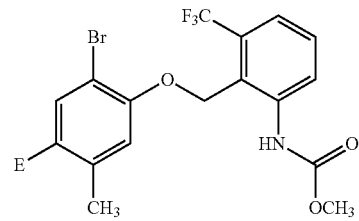
(HA4050) 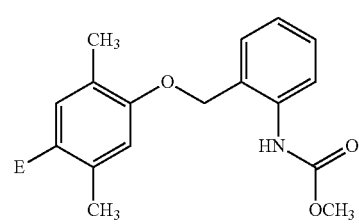
(HA4051) 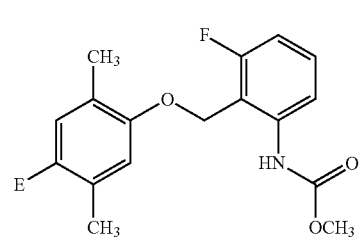
(HA4052) 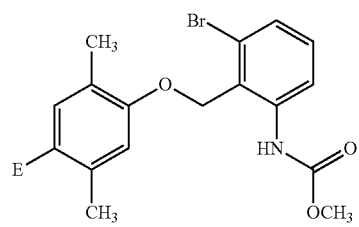
(HA4053) 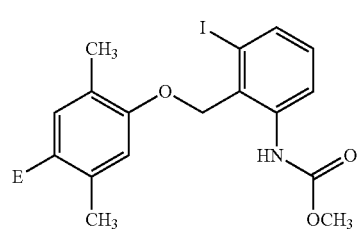
(HA4054) 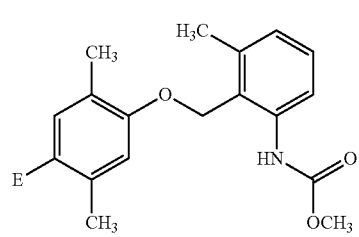
(HA4055) 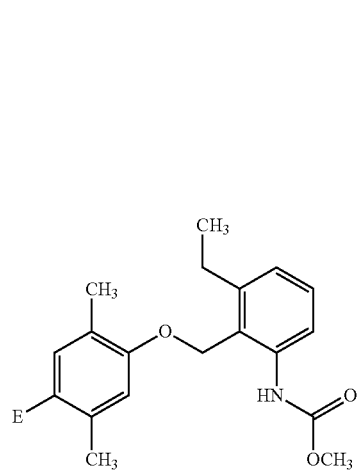
(HA4056) 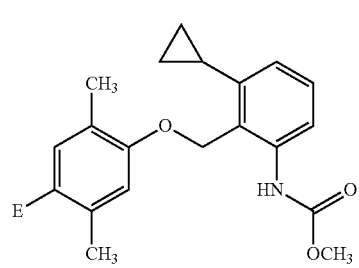
(HA4057) 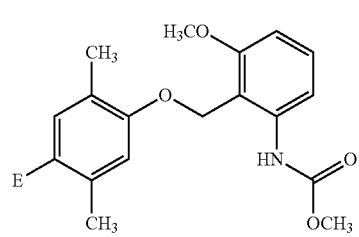

(HA4058)
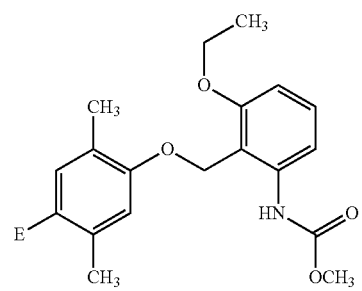
(HA4059)
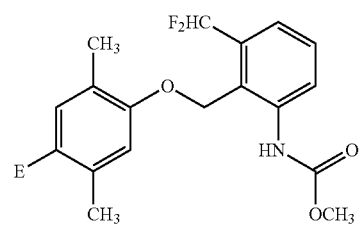
(HA4060)
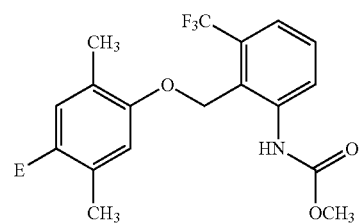
(HA4061)
(HA4062)
(HA4063)
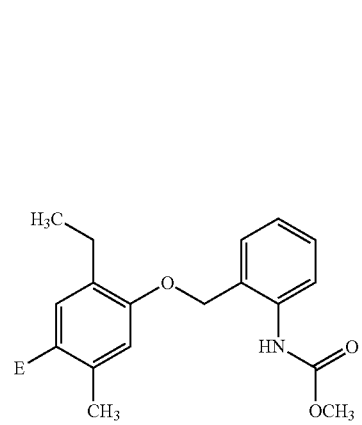
(HA4064)
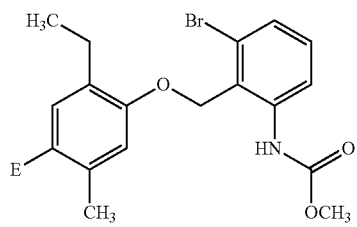
(HA4065)
(HA4066)
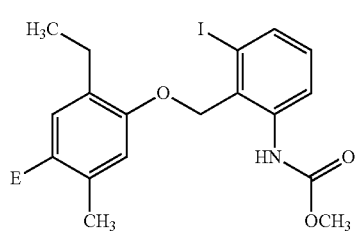
(HA4067)
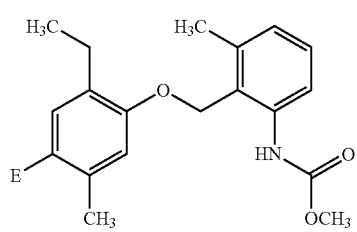
(HA4068)
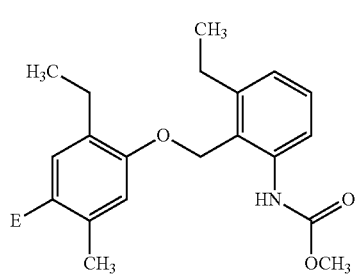
(HA4069)
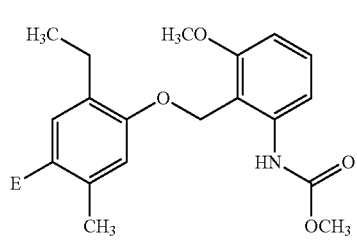

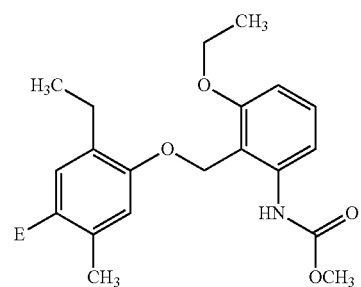 (HA4070)
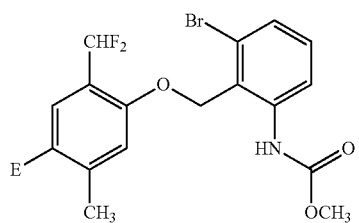 (HA4076)
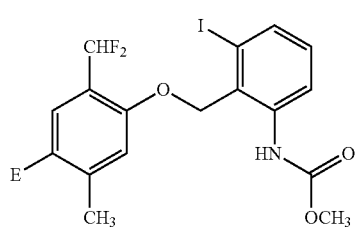 (HA4077)
(HA4071)
(HA4078) 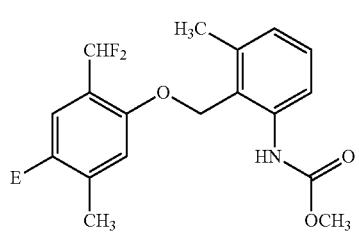
(HA4072)
(HA4079) 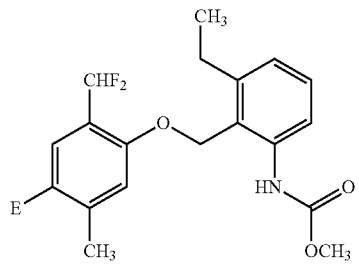
(HA4073)
(HA4080) 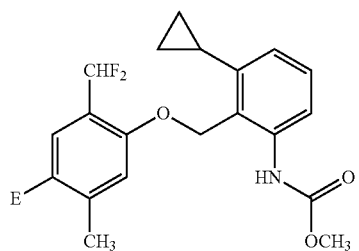
(HA4074)
(HA4075)
(HA4081) 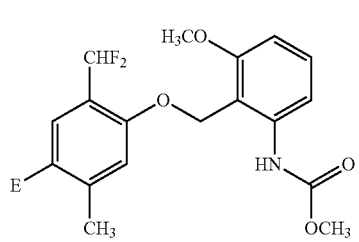

-continued
(HA4082)
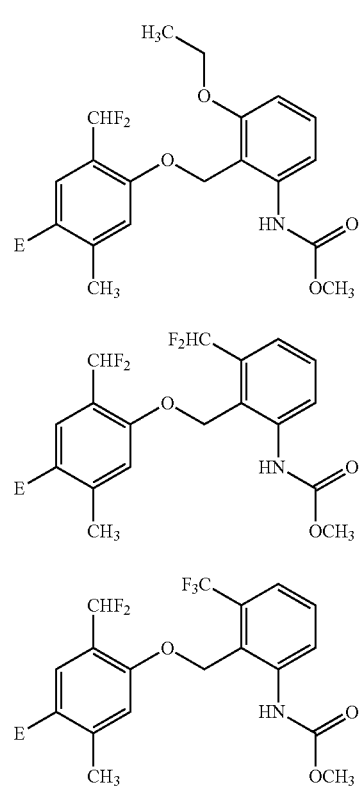
(HA4083)
(HA4084)
(HA4085)
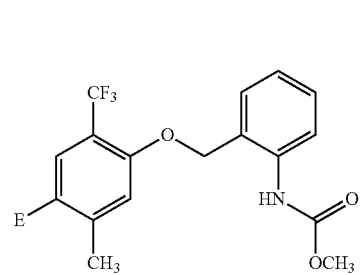
(HA4086)
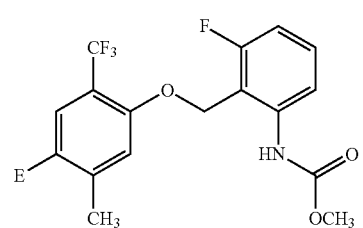
(HA4087)
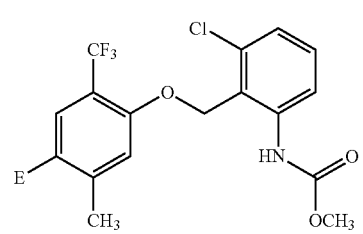
-continued
(HA4088)
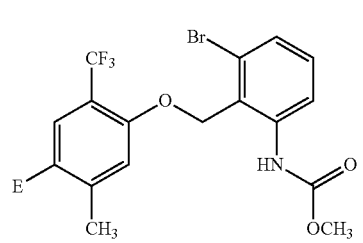
(HA4089)
(HA4090)
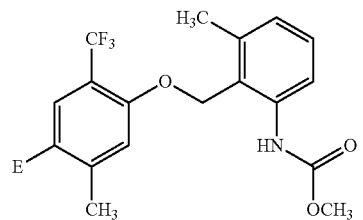
(HA4091)
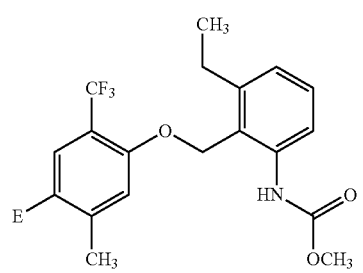
(HA4092)
(HA4093)
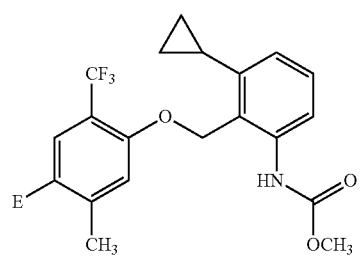

-continued

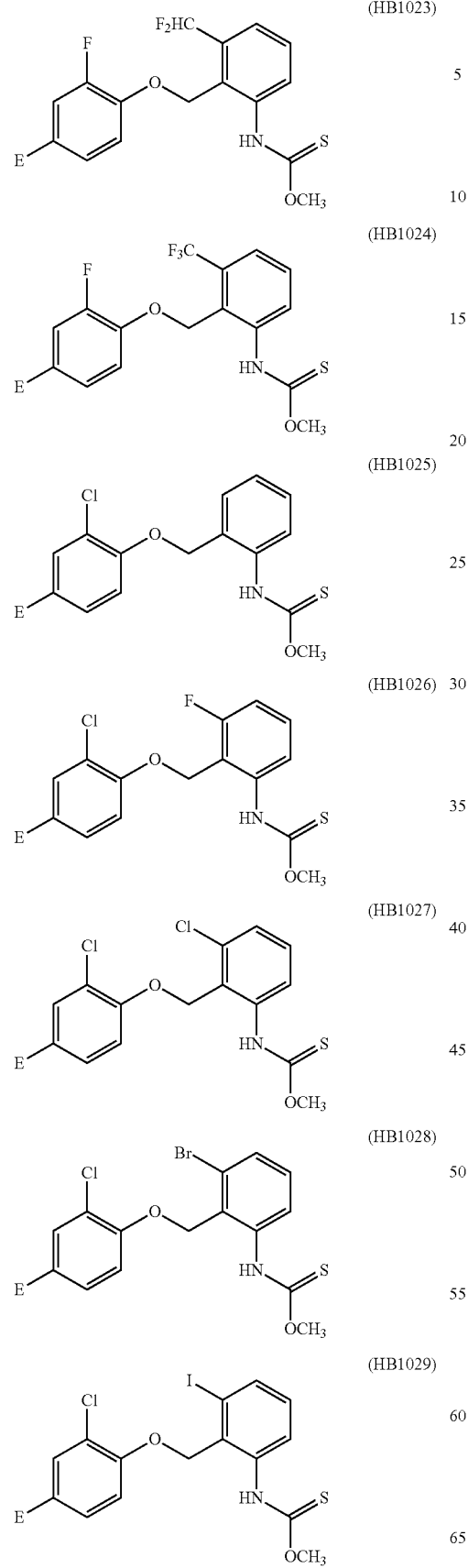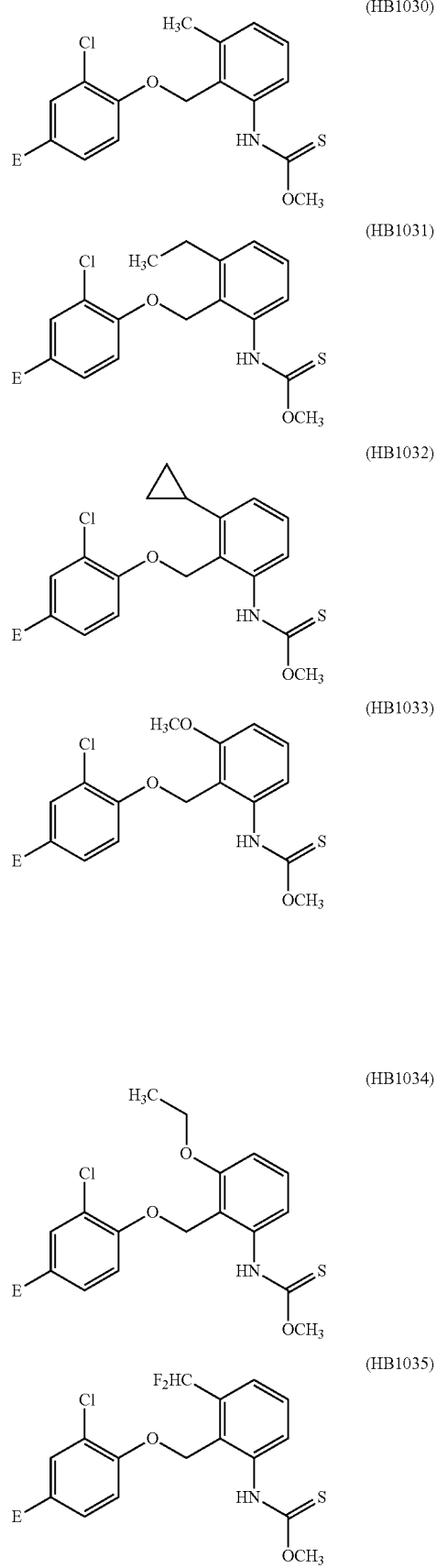

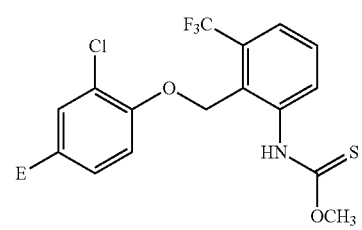
(HB1036)
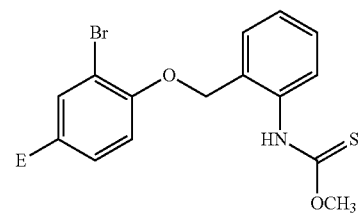
(HB1037)
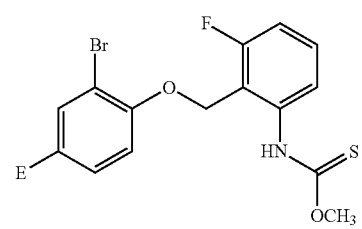
(HB1038)
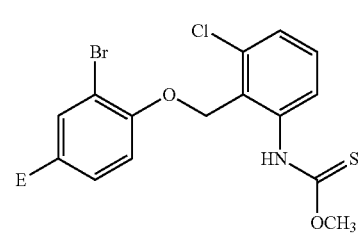
(HB1039)
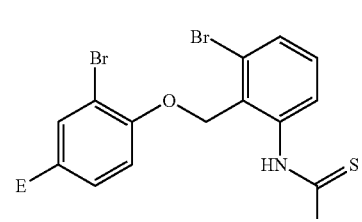
(HB1040)
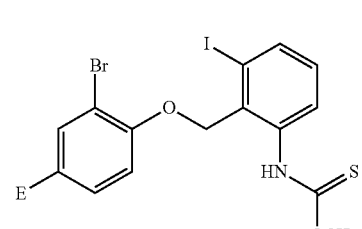
(HB1041)
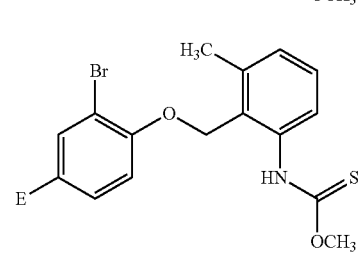
(HB1042)
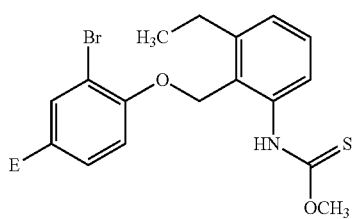
(HB1043)
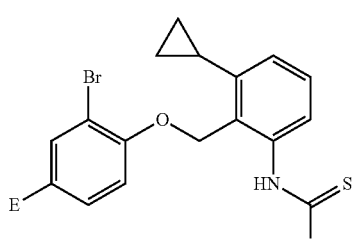
(HB1044)
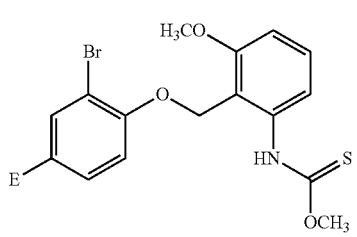
(HB1045)
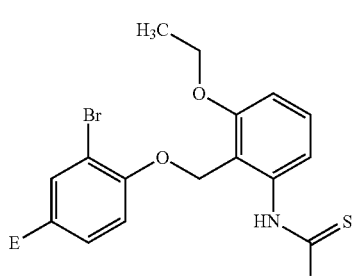
(HB1046)
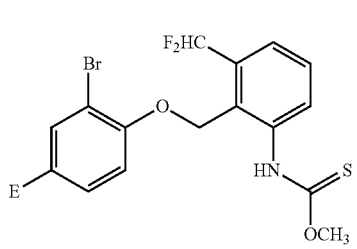
(HB1047)
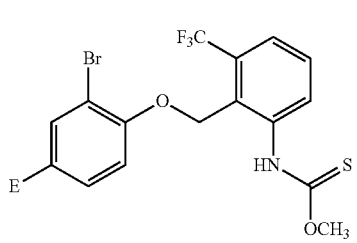
(HB1048)

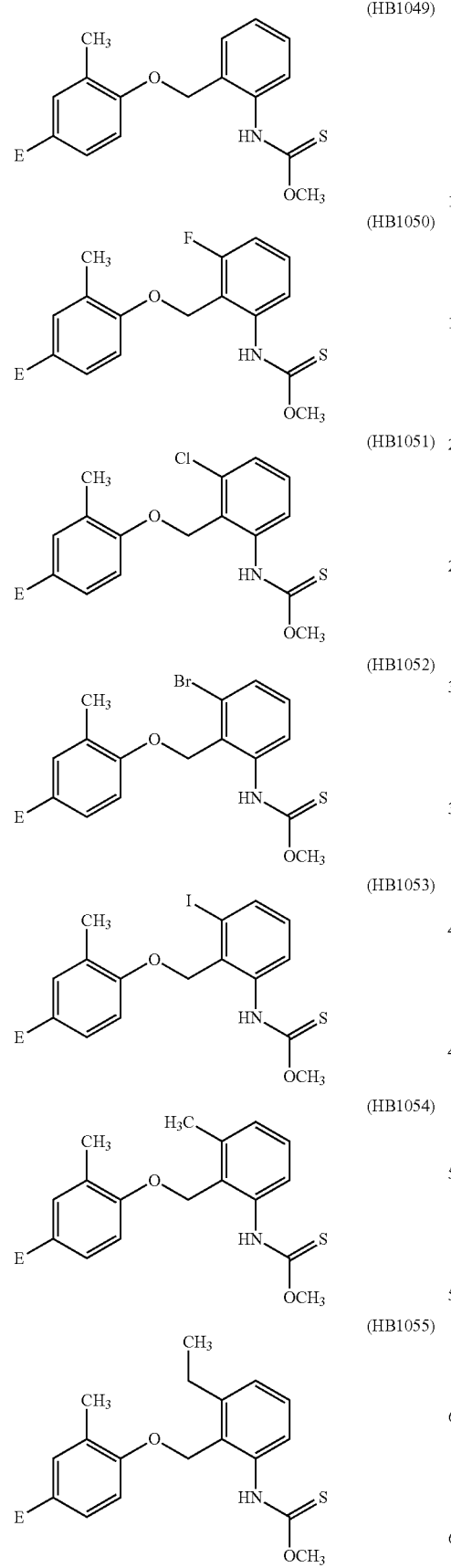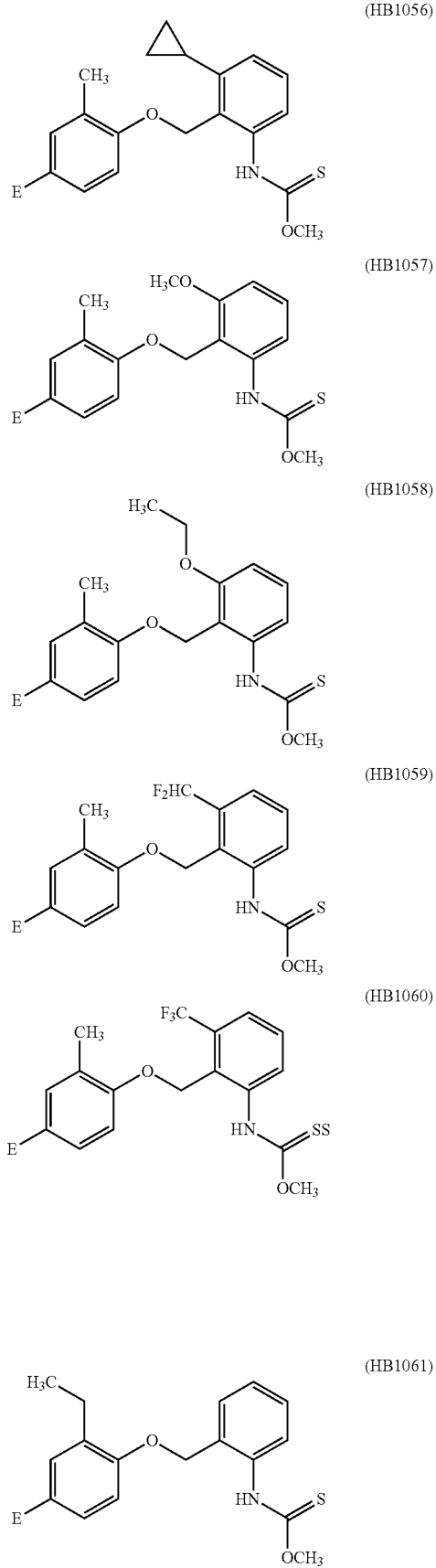

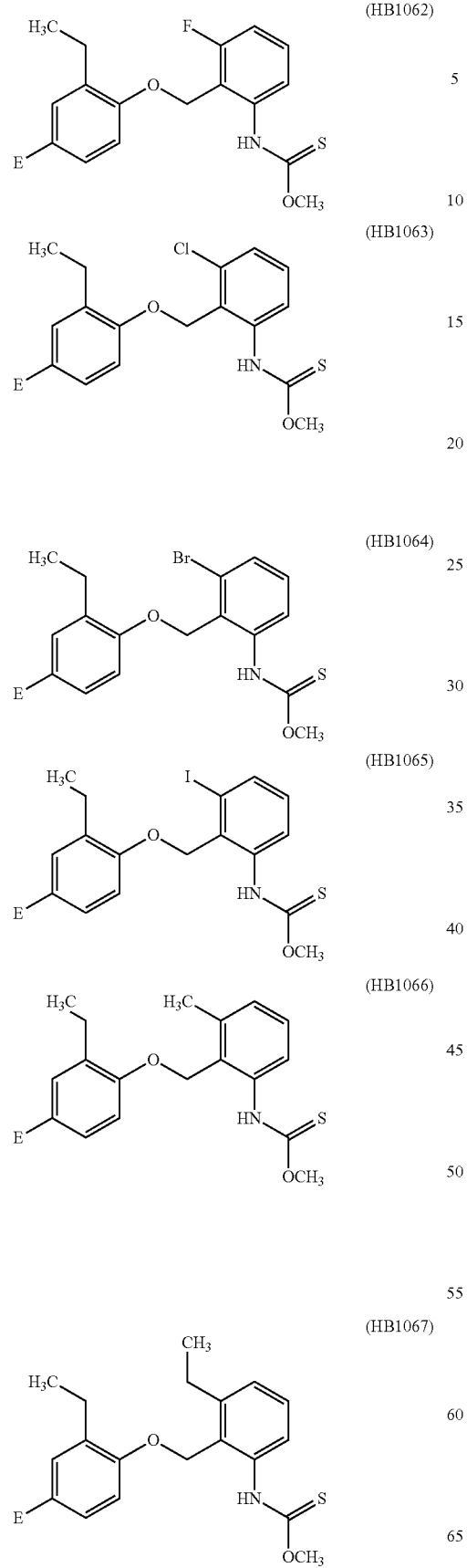
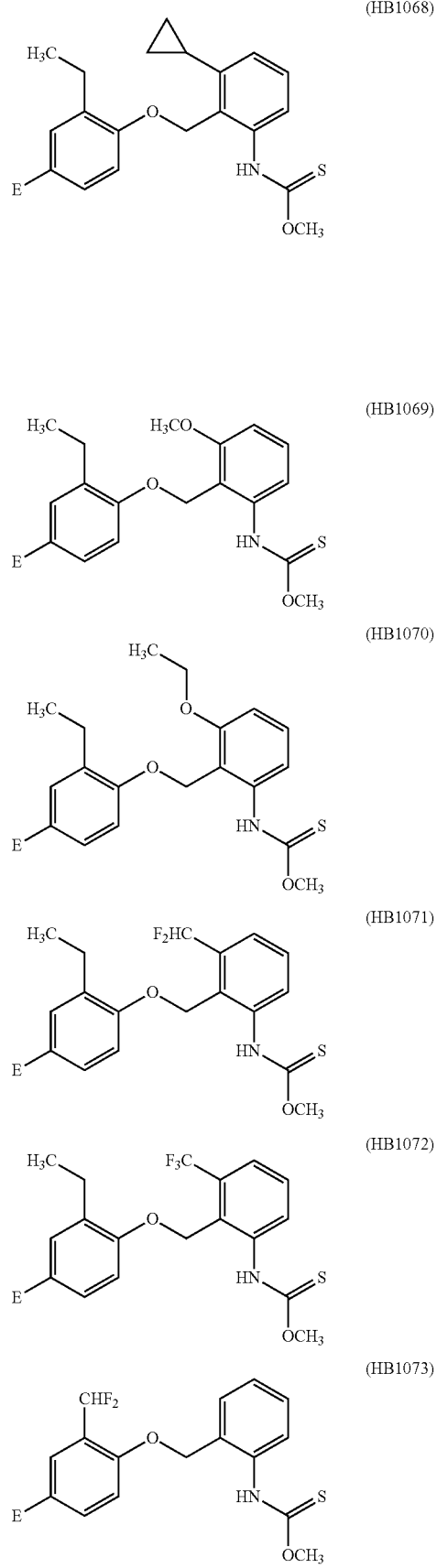

-continued (HB1074)

(HB1075)

(HB1076)

(HB1077)

(HB1078)

(HB1079)

-continued (HB1080)

(HB1081)

(HB1082)

(HB1083)

(HB1084)

(HB1085)

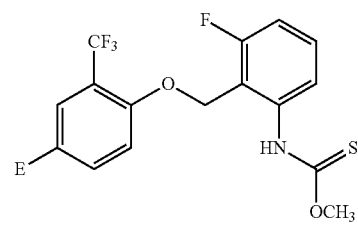
(HB1086)
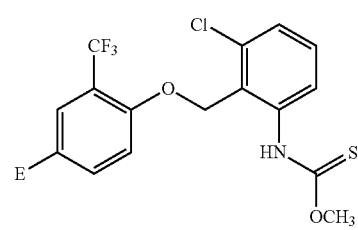
(HB1087)
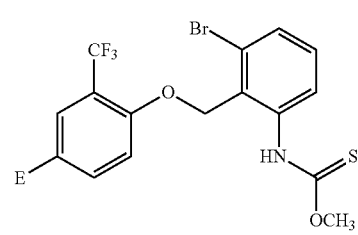
(HB1088)
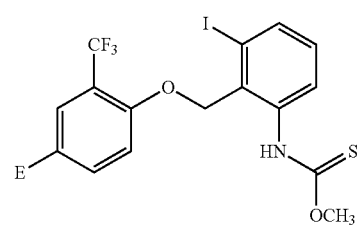
(HB1089)
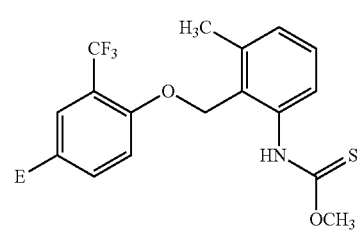
(HB1090)
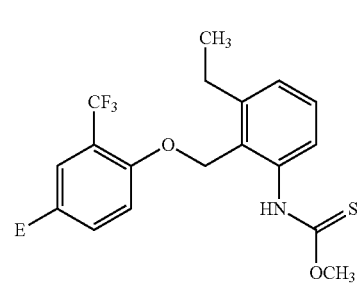
(HB1091)
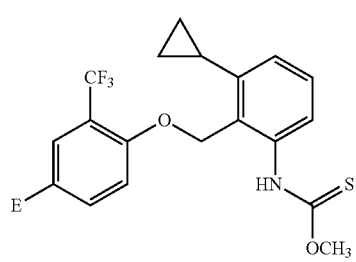
(HB1092)
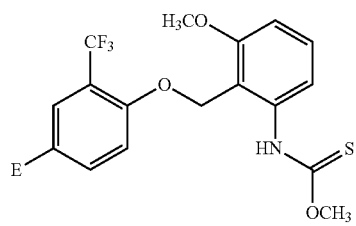
(HB1093)
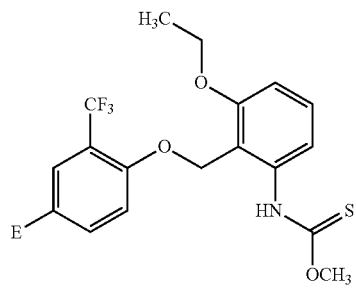
(HB1094)
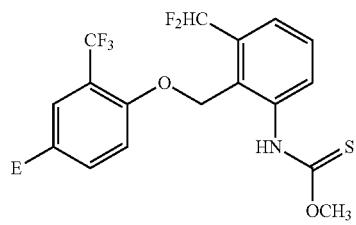
(HB1095)
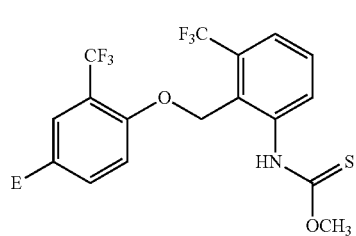
(HB1096)
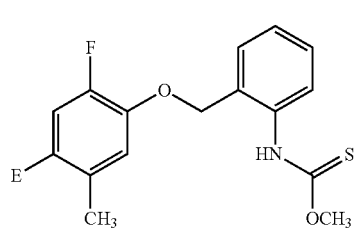
(HB4013)

-continued
(HB4014) 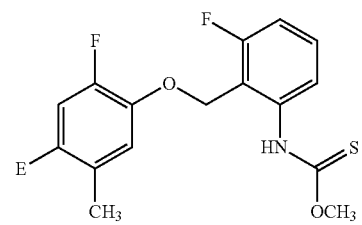
(HB4015) 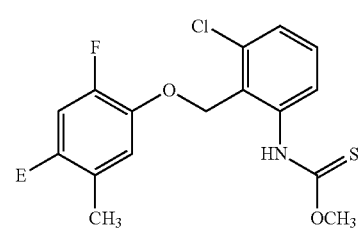
(HB4016) 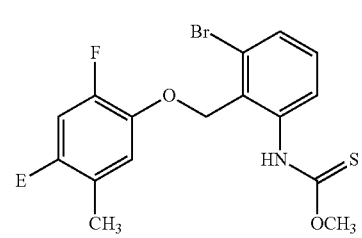
(HB4017) 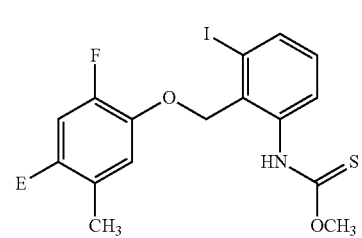
(HB4018) 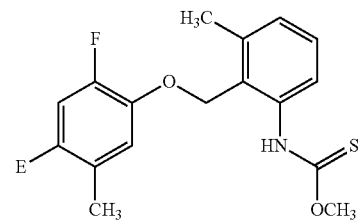
(HB4019) 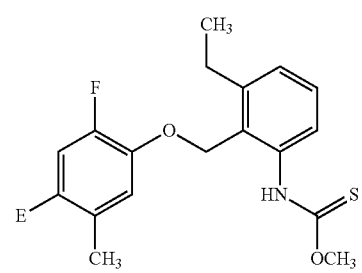
-continued
(HB4020) 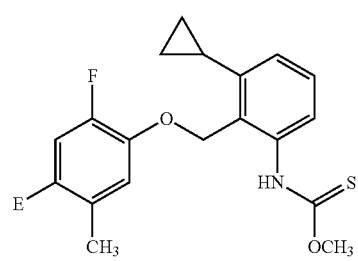
(HB4021) 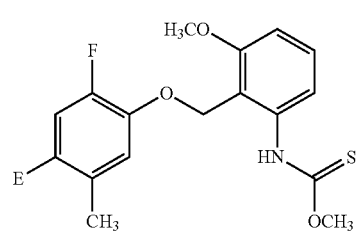
(HB4022) 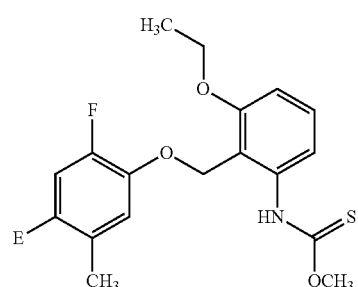
(HB4023) 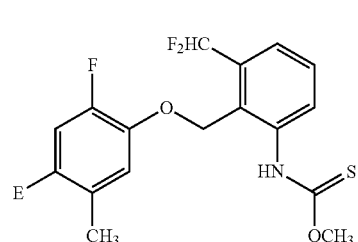
(HB4024) 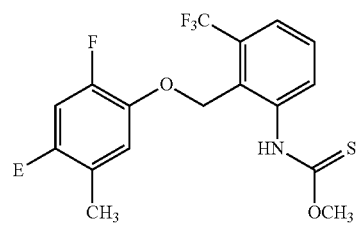
(HB4025) 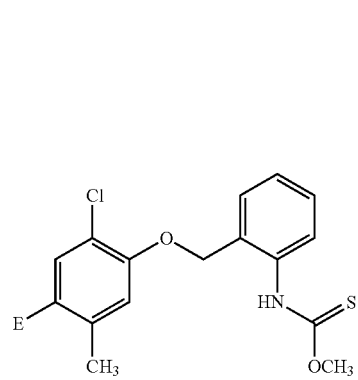

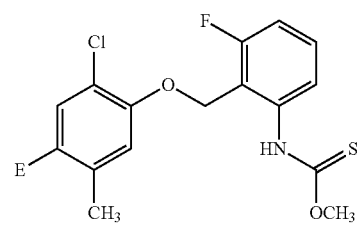
(HB4026)

(HB4027)
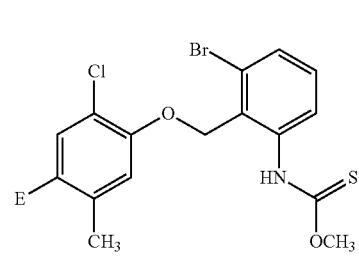
(HB4028)
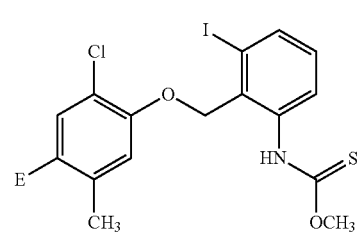
(HB4029)
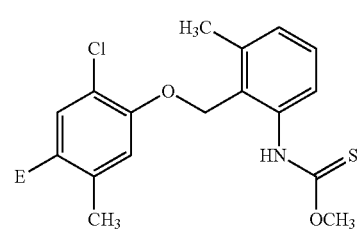
(HB4030)
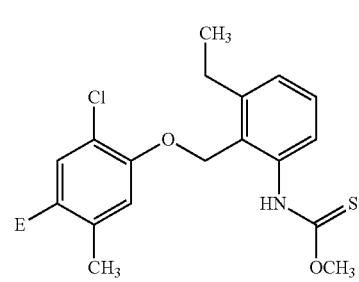
(HB4031)
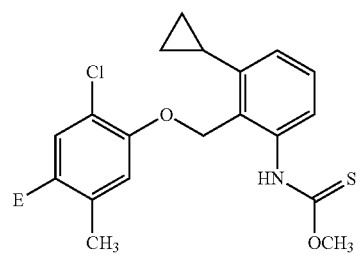
(HB4032)
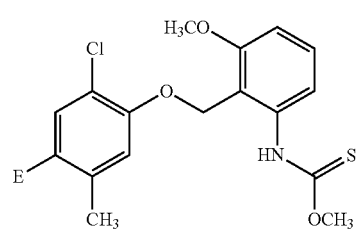
(HB4033)
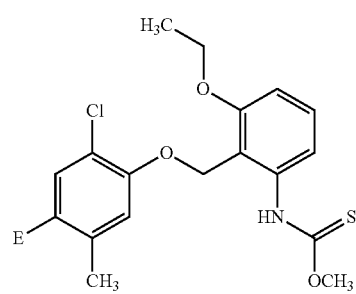
(HB4034)
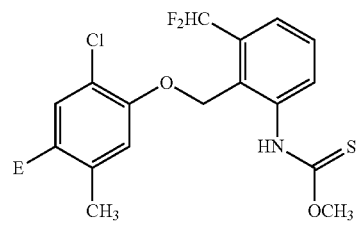
(HB4035)
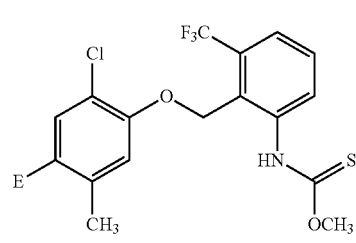
(HB4036)
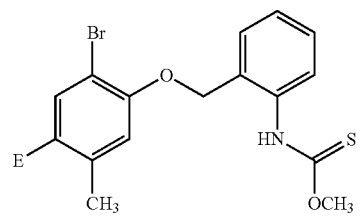
(HB4037)

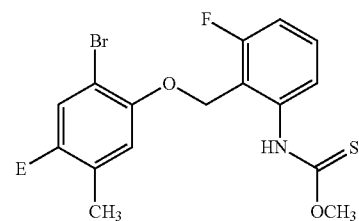
(HB4038)
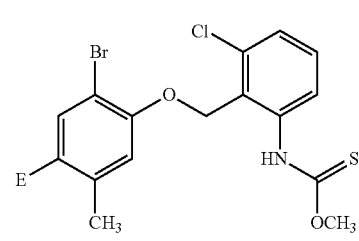
(HB4039)
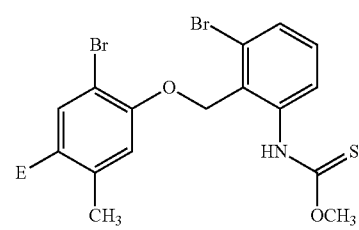
(HB4040)
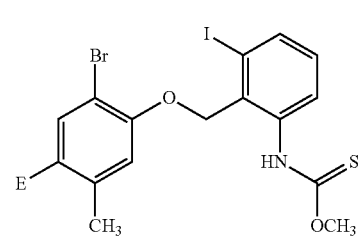
(HB4041)
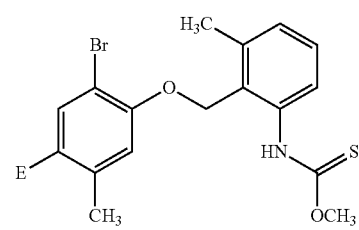
(HB4042)
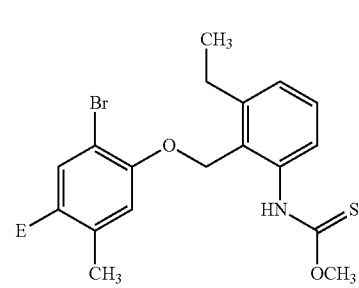
(HB4043)
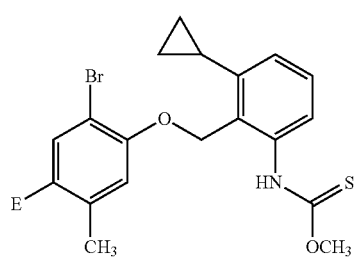
(HB4044)
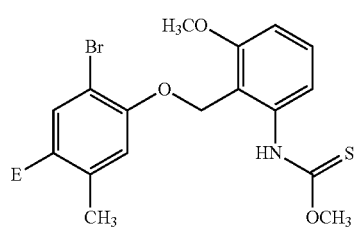
(HB4045)
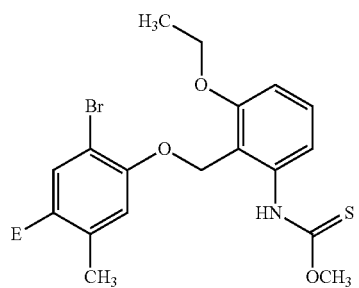
(HB4046)
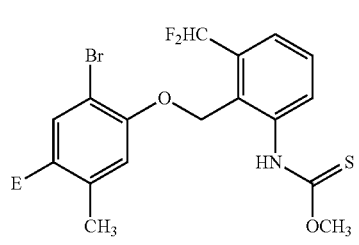
(HB4047)
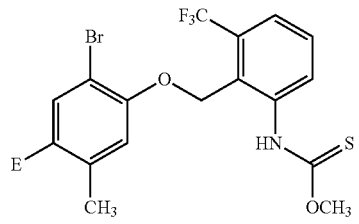
(HB4048)
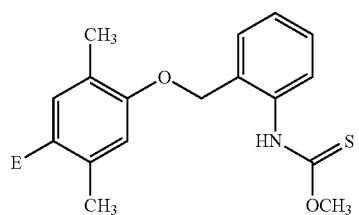
(HB4049)

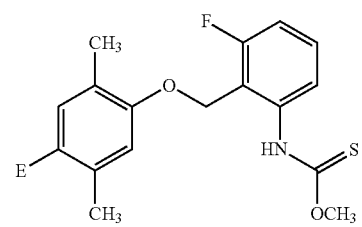
(HB4050)
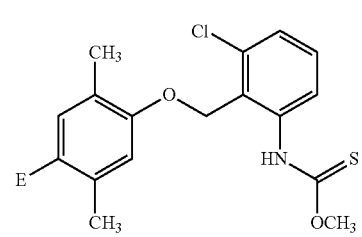
(HB4051)
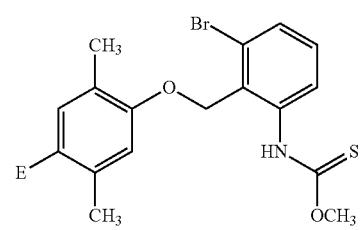
(HB4052)
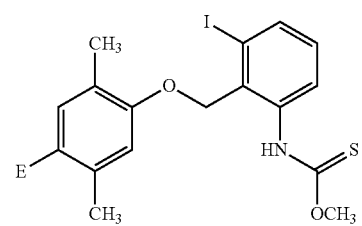
(HB4053)
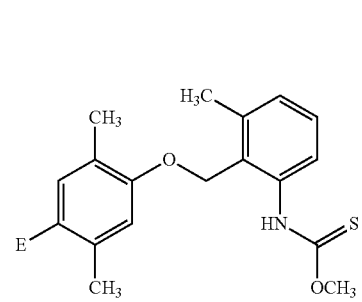
(HB4054)
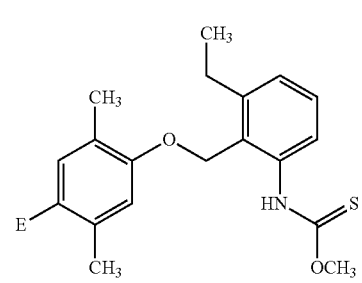
(HB4055)
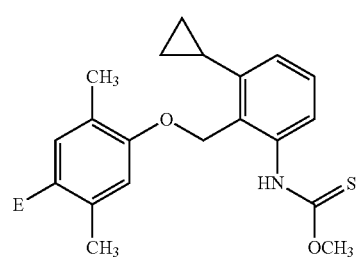
(HB4056)
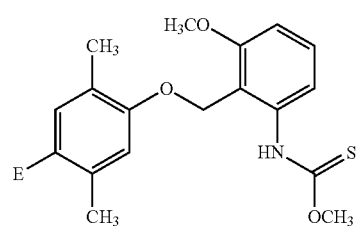
(HB4057)
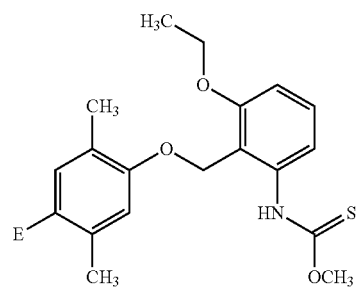
(HB4058)
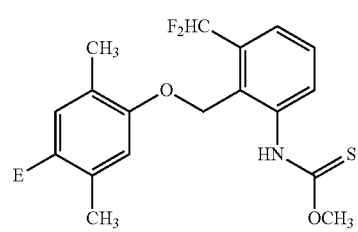
(HB4059)
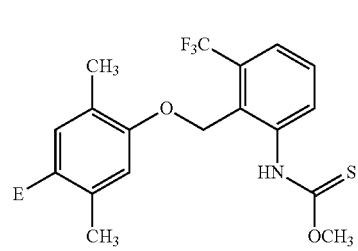
(HB4060)
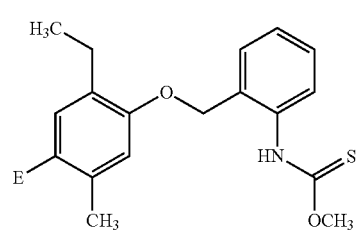
(HB4061)

99
-continued
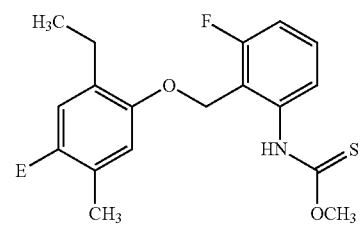
(HB4062)
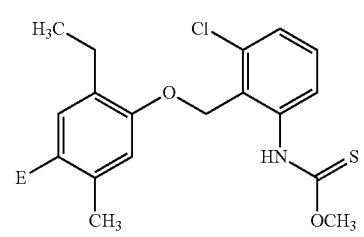
(HB4063)
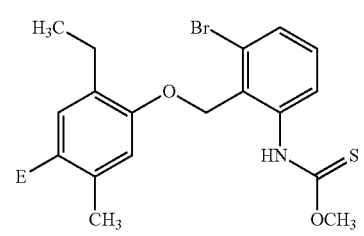
(HB4064)
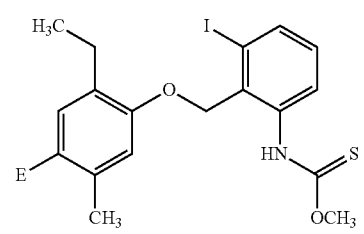
(HB4065)
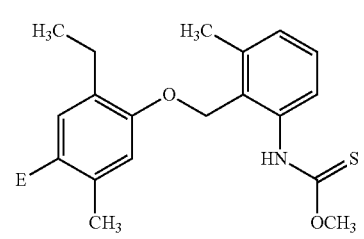
(HB4066)
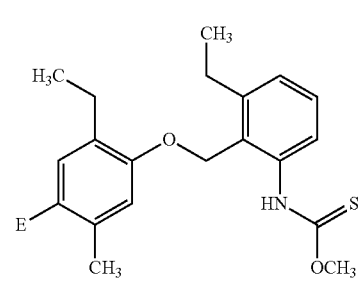
(HB4067)
100
-continued
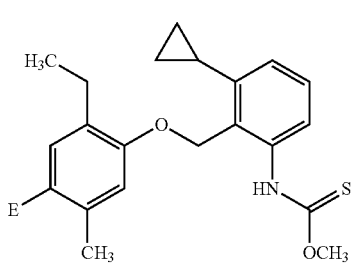
(HB4068)
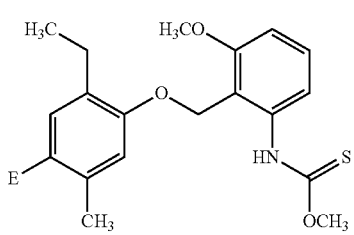
(HB4069)
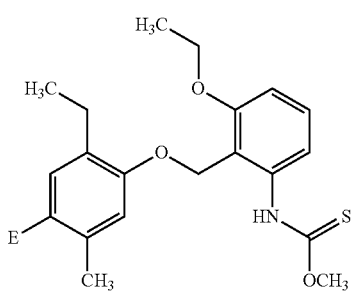
(HB4070)
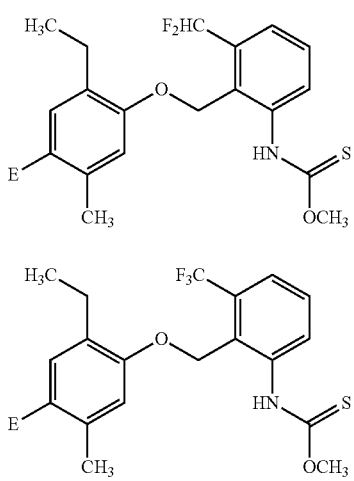
(HB4071)
(HB4072)
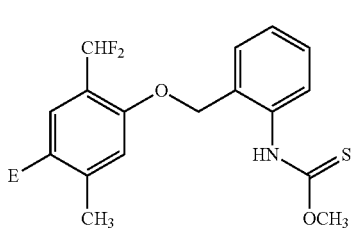
(HB4073)

(HB4074) 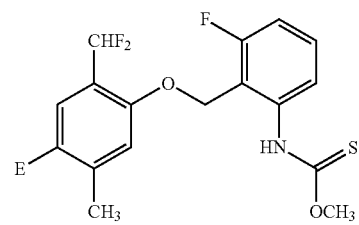
(HB4075) 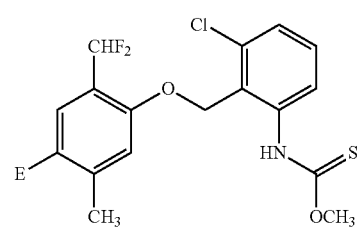
(HB4076) 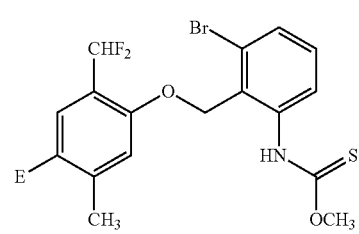
(HB4077) 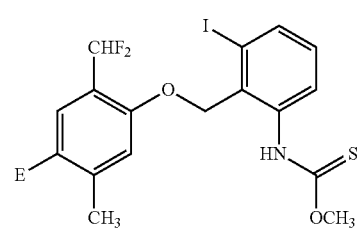
(HB4078) 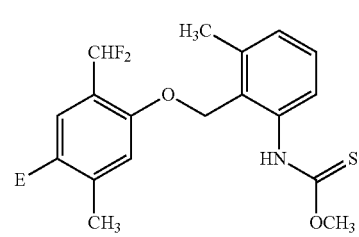
(HB4079) 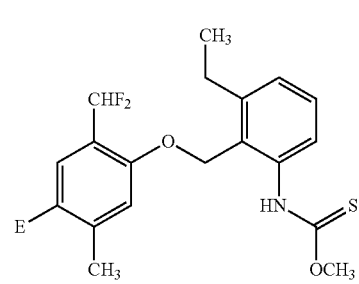
(HB4080) 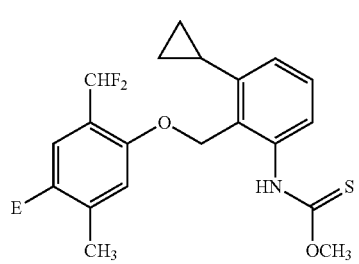
(HB4081) 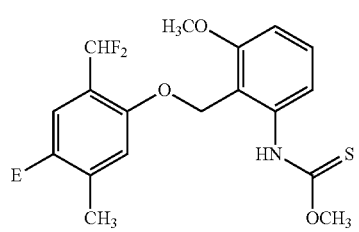
(HB4082) 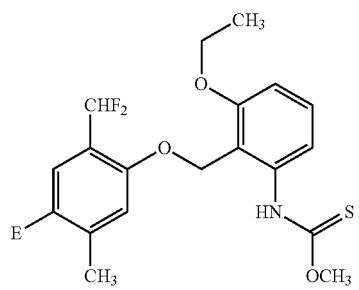
(HB4083) 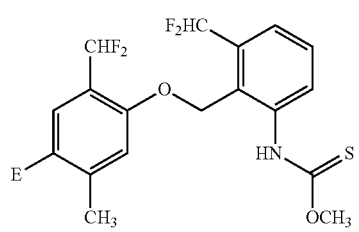
(HB4084) 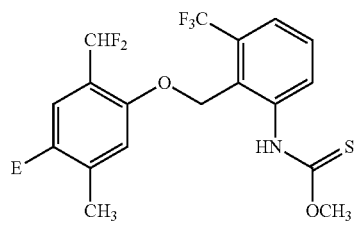
(HB4085) 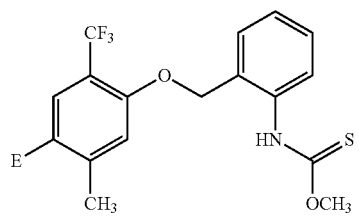

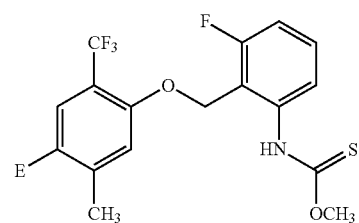
(HB4086)
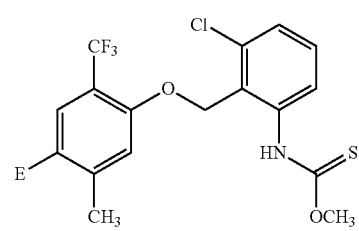
(HB4087)
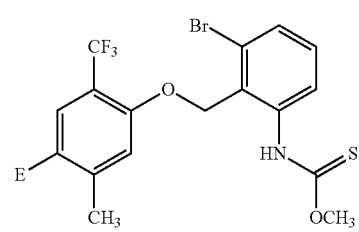
(HB4088)
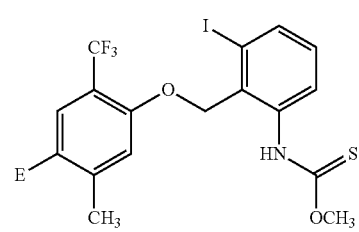
(HB4089)
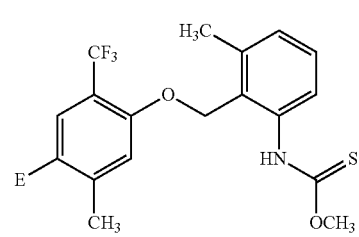
(HB4090)
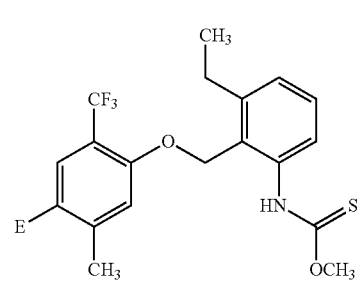
(HB4091)
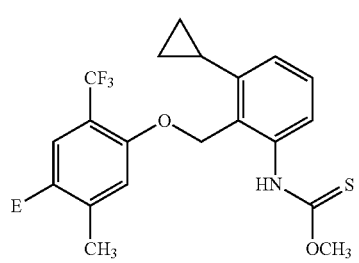
(HB4092)
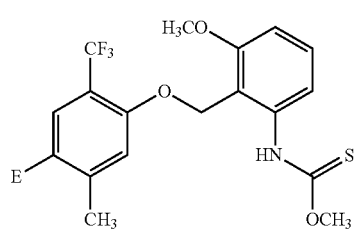
(HB4093)
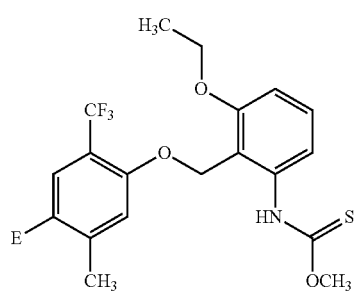
(HB4094)
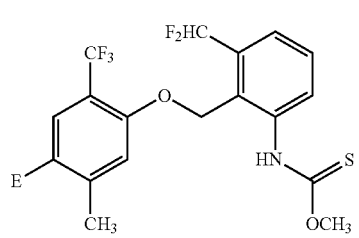
(HB4095)
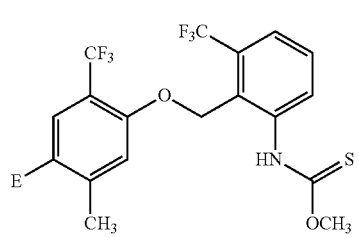
(HB4096)
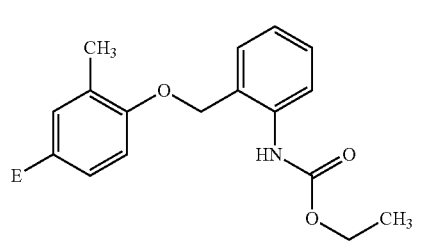
(HC1001)

(HC1002)
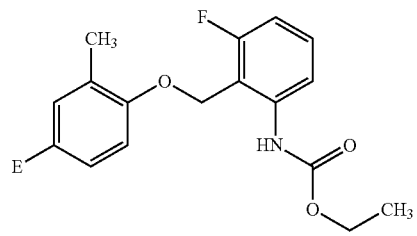
(HC1003)
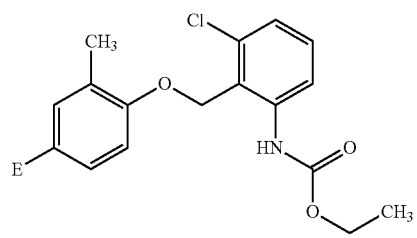
(HC1004)
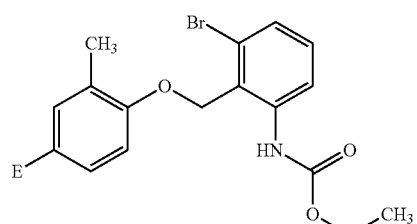
(HC1005)
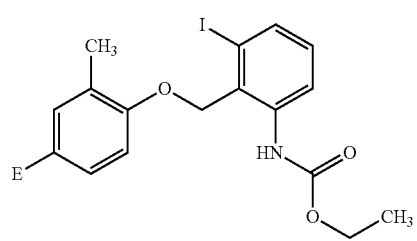
(HC1006)
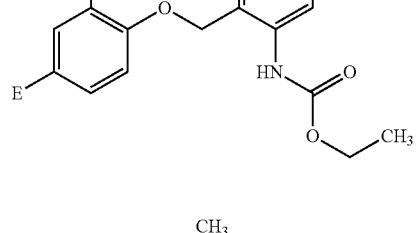
(HC1007)
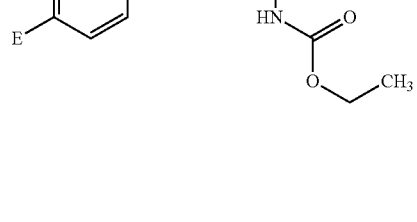
(HC1008)
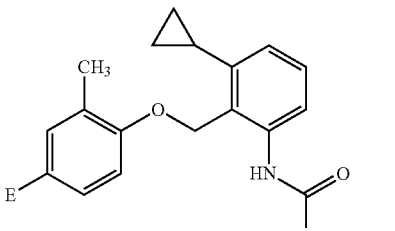
(HC1009)
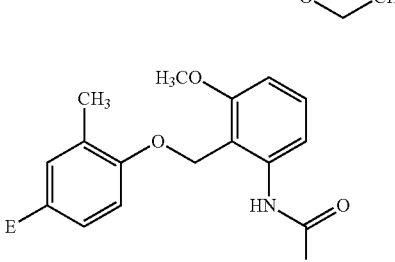
(HC1010)
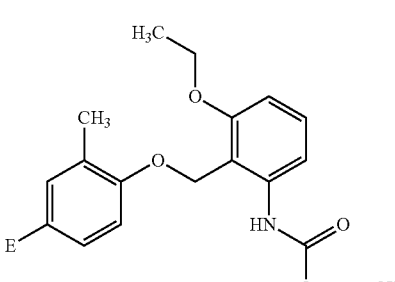
(HC1011)
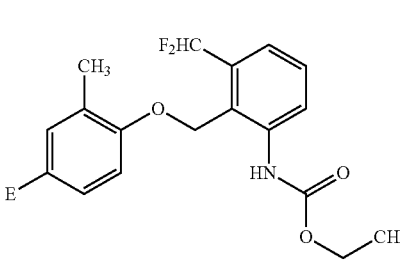
(HC1012)
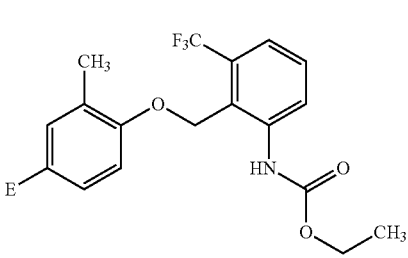
(HC1013)
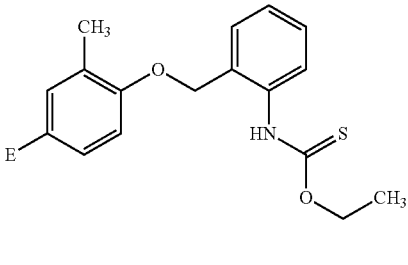

(HC1014)
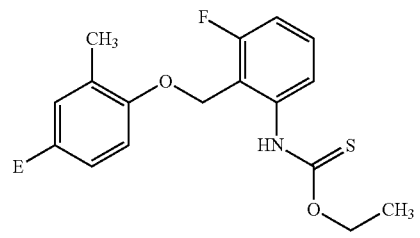
(HC1015)

(HC1016)
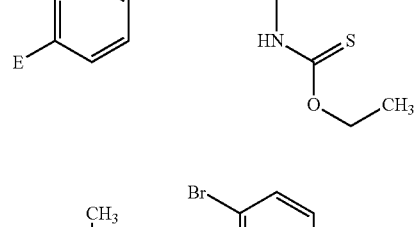
(HC1017)
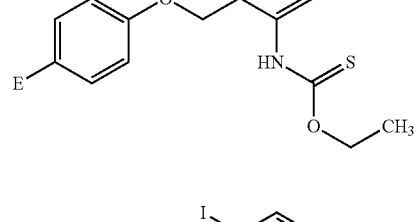
(HC1018)
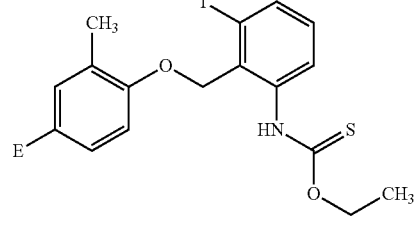
(HC1019)
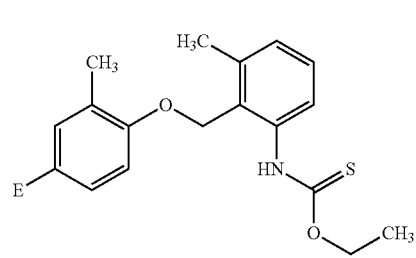
(HC1020)
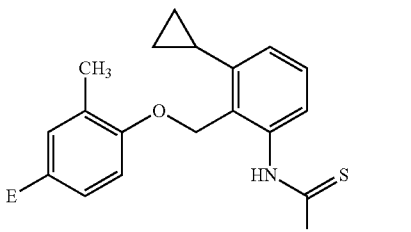
(HC1021)
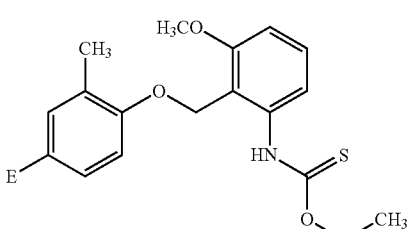
(HC1022)
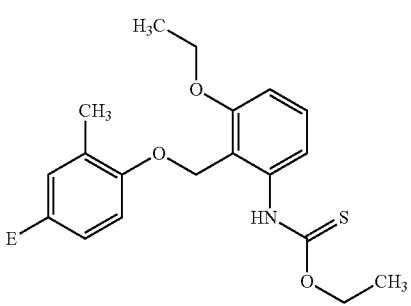
(HC1023)
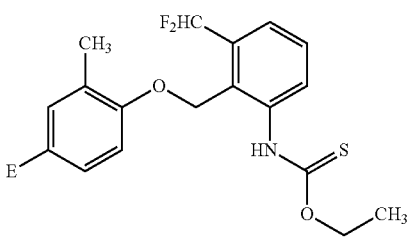
(HC1024)
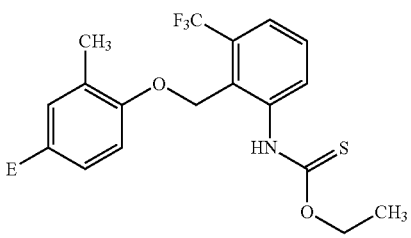
(HC1025)
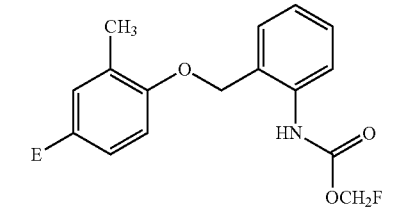

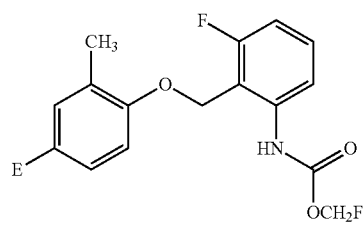 (HC1026)
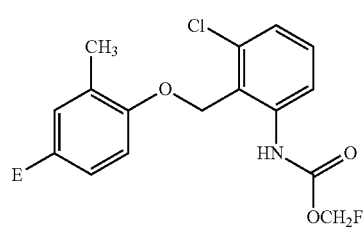 (HC1027)
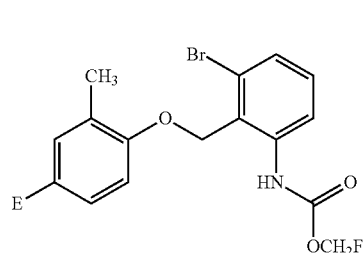 (HC1028)
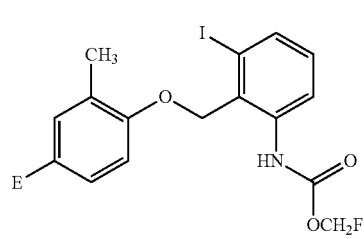 (HC1029)
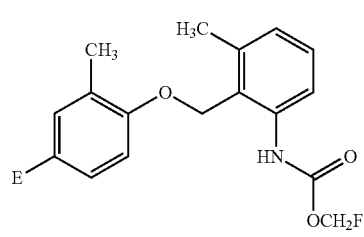 (HC1030)
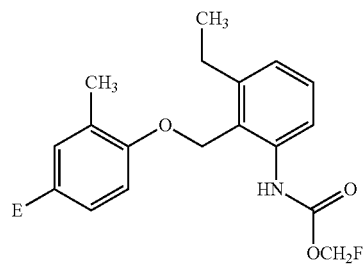 (HC1031)
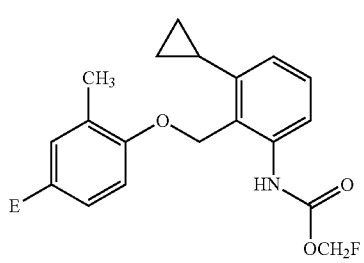 (HC1032)
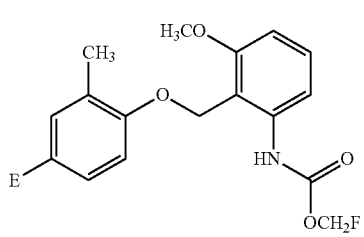 (HC1033)
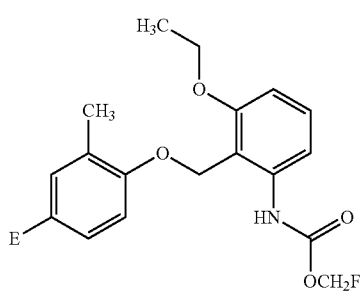 (HC1034)
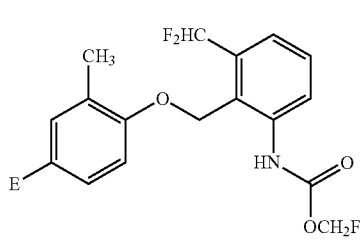 (HC1035)
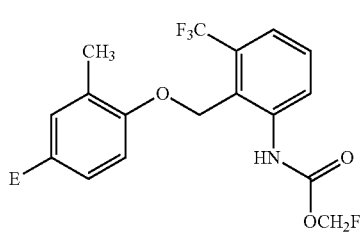 (HC1036)
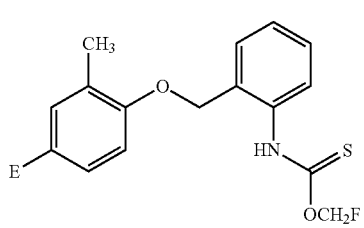 (HC1037)

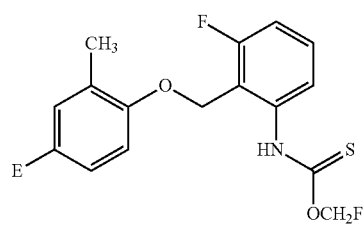
(HC1038)
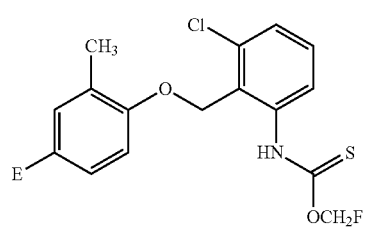
(HC1039)
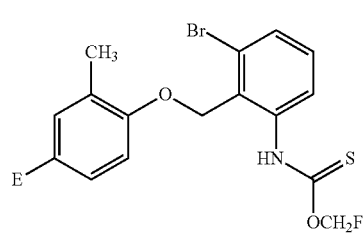
(HC1040)
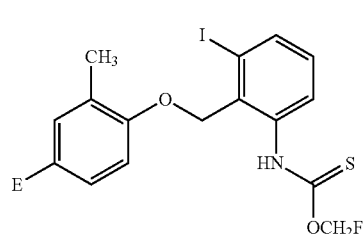
(HC1041)
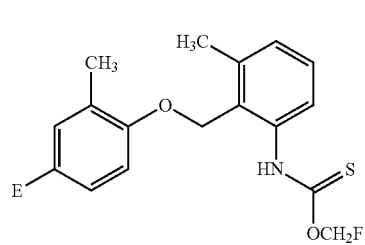
(HC1042)
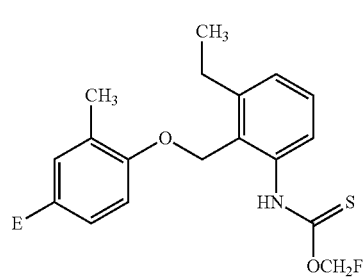
(HC1043)
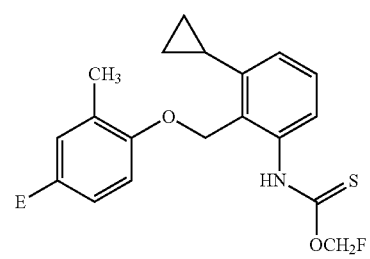
(HC1044)
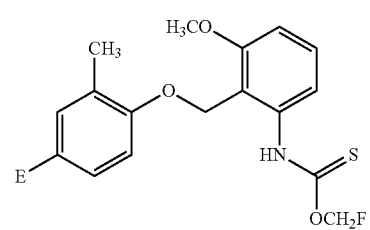
(HC1045)
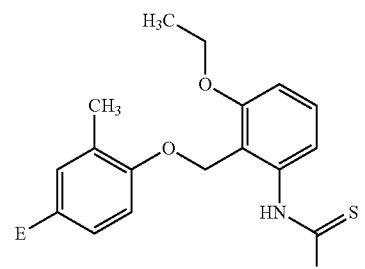
(HC1046)
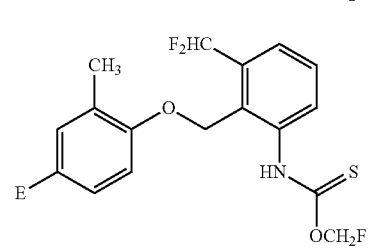
(HC1047)
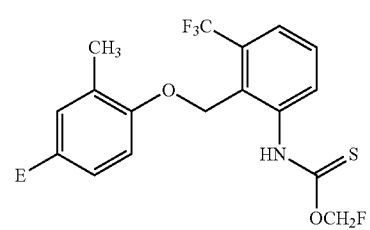
(HC1048)
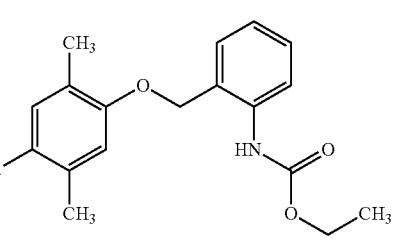
(HC2001)

(HC2002)
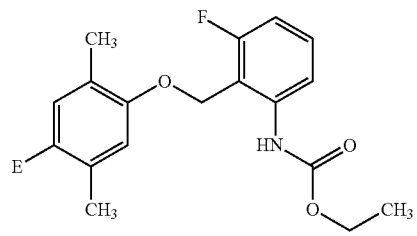
(HC2003)
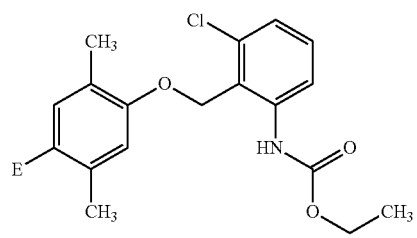
(HC2004)
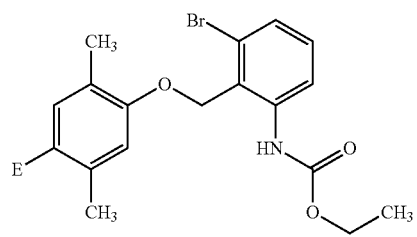
(HC2005)
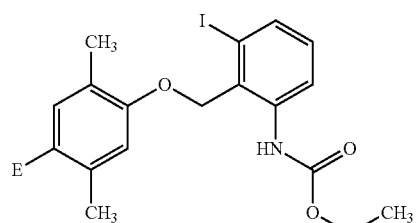
(HC2006)
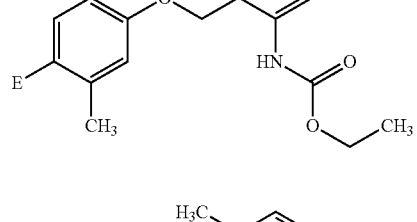
(HC2007)
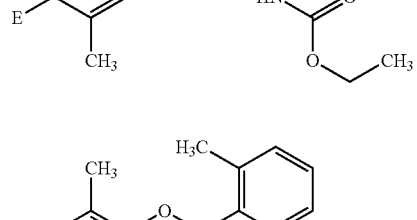
(HC2008)
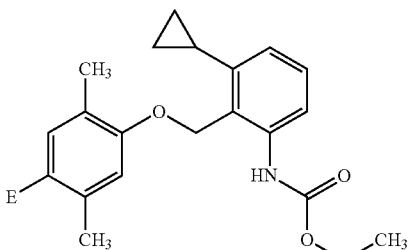
(HC2009)
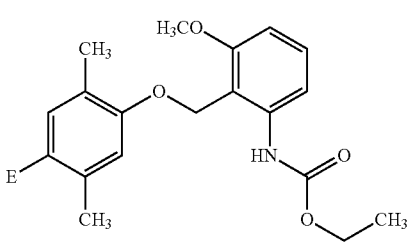
(HC2010)
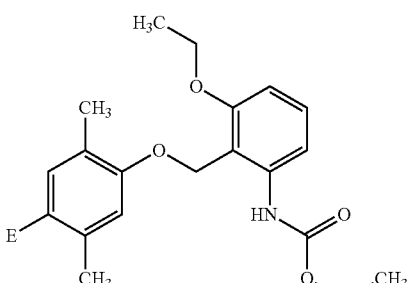
(HC2011)
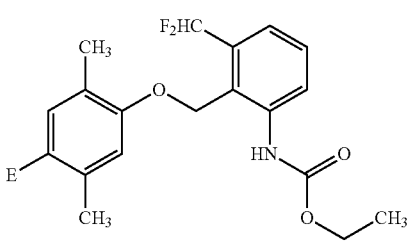
(HC2012)
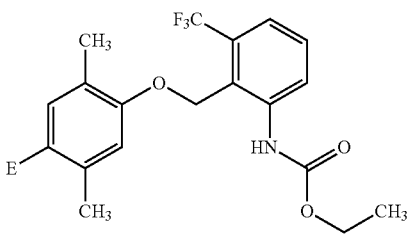
(HC2013)
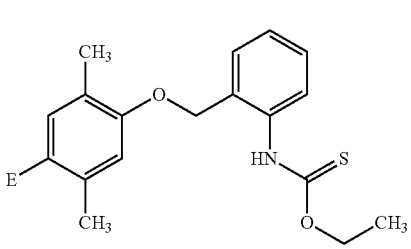

-continued
(HC2014)
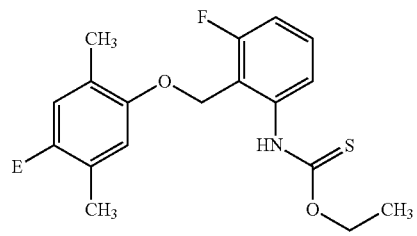
(HC2015)
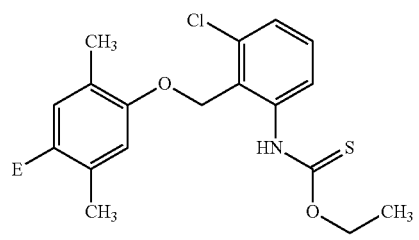
(HC2016)
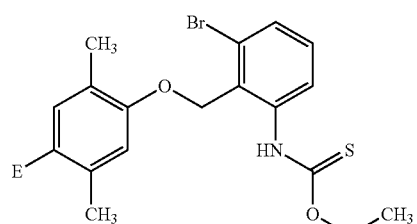
(HC2017)
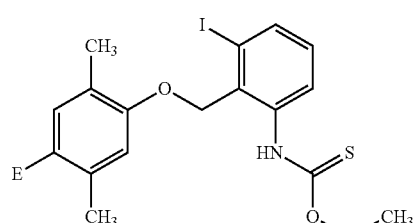
(HC2018)
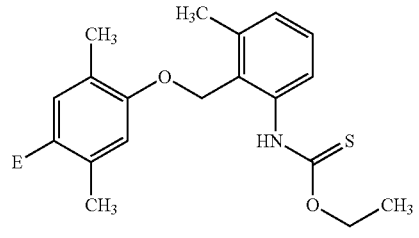
(HC2019)
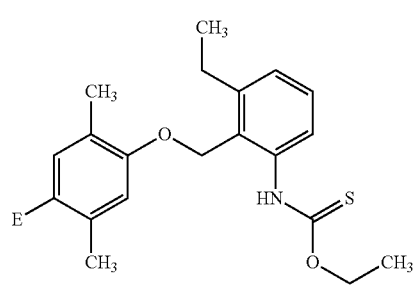
-continued
(HC2020)
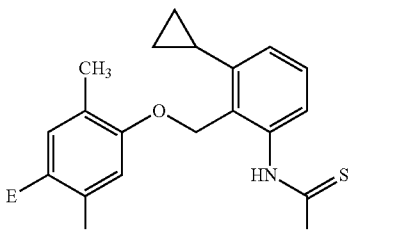
(HC2021)
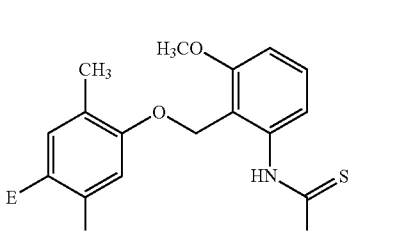
(HC2022)
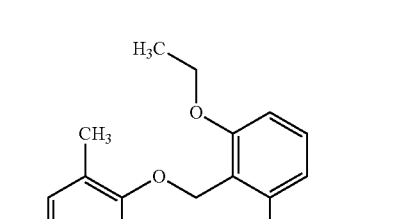
(HC2023)
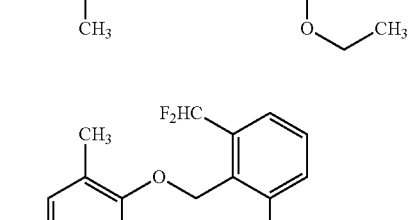
(HC2024)
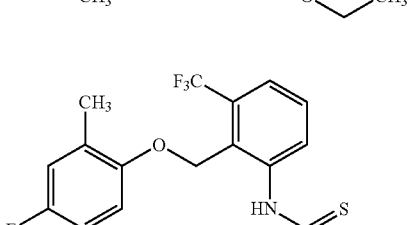
(HC2025)
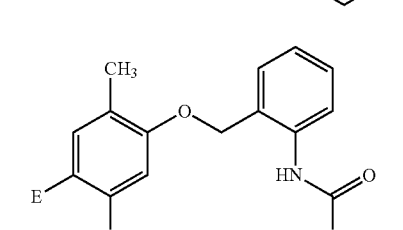

(HC2026) 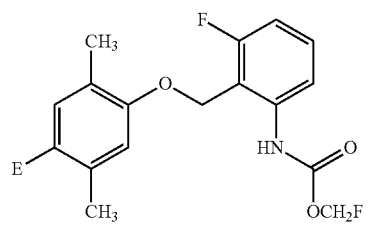
(HC2027) 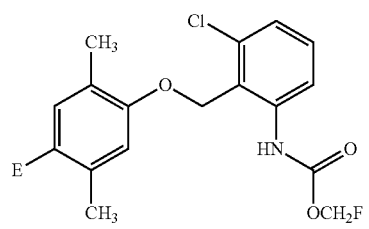
(HC2028) 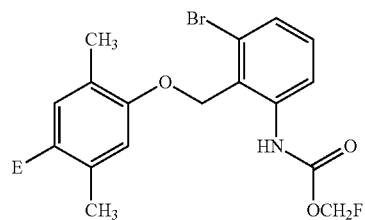
(HC2029) 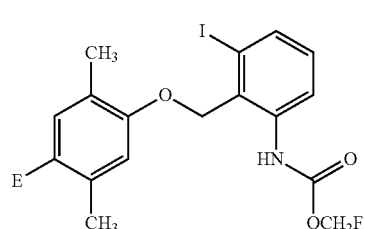
(HC2030) 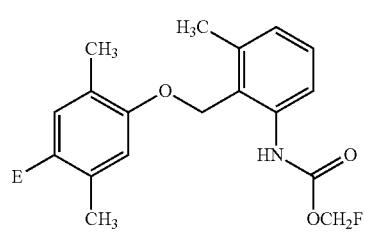
(HC2031) 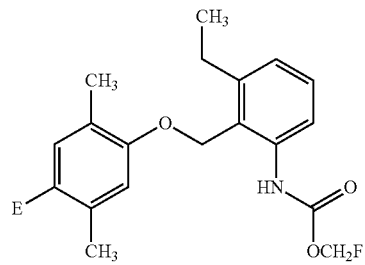
(HC2032) 
(HC2033) 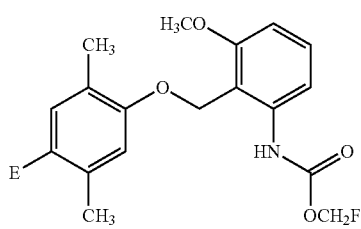
(HC2034) 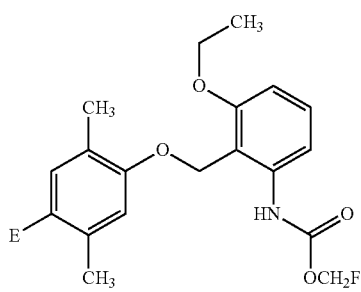
(HC2035) 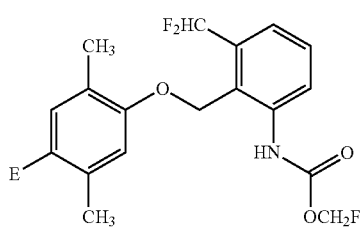
(HC2036) 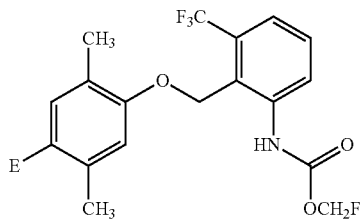
(HC2037) 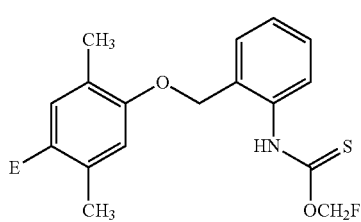

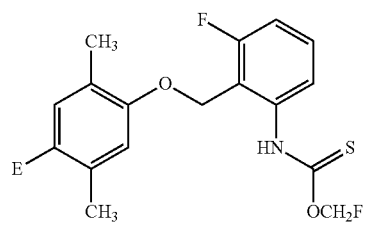 (HC2038)
 (HC2039)
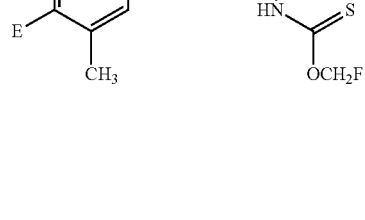 (HC2040)
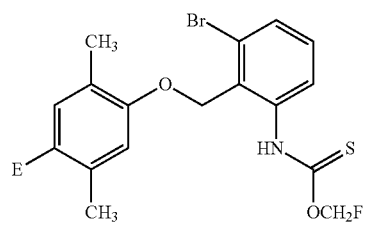 (HC2041)
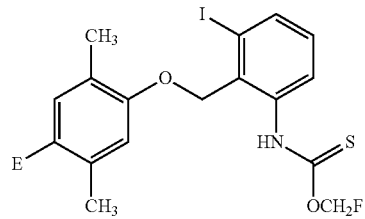 (HC2042)
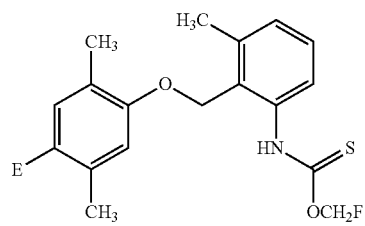 (HC2043)
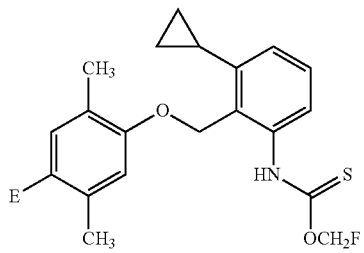 (HC2044)
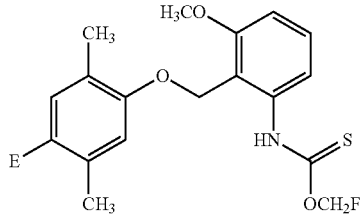 (HC2045)
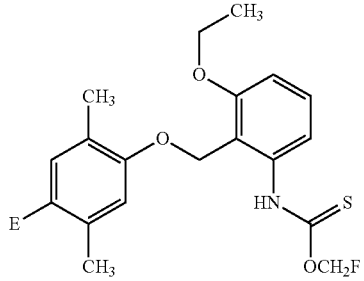 (HC2046)
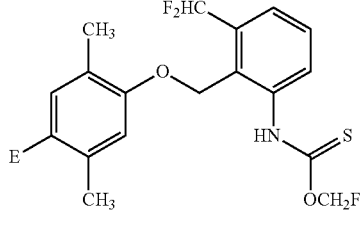 (HC2047)
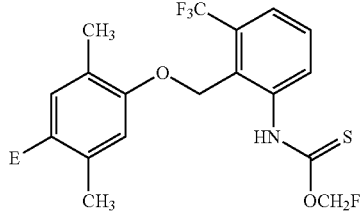 (HC2048)
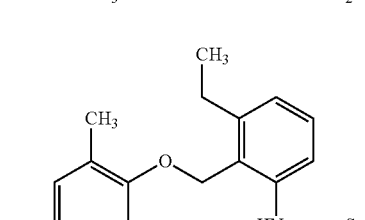 (HD1001)

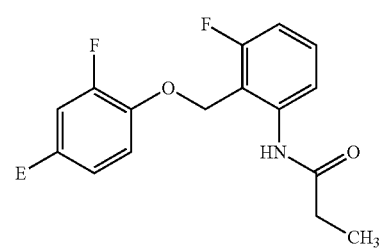
(HD1002)
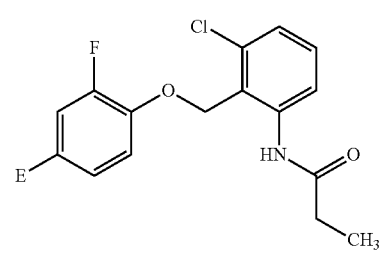
(HD1003)
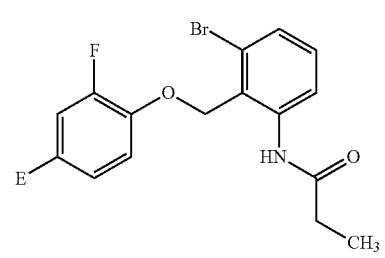
(HD1004)
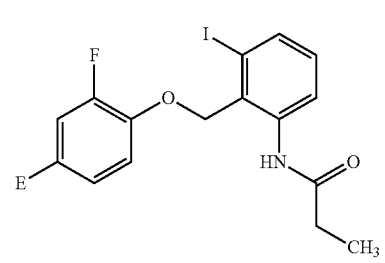
(HD1005)
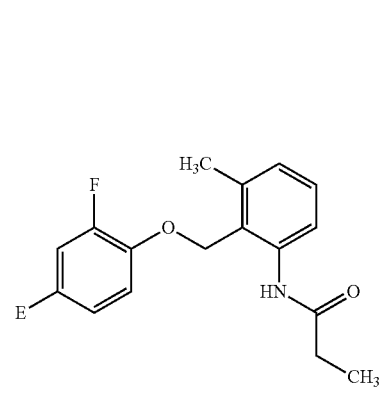
(HD1006)

(HD1007)
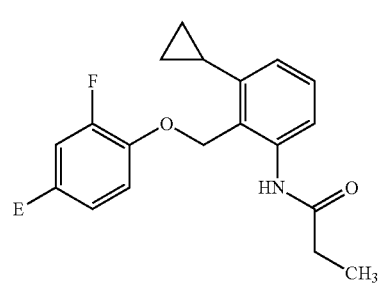
(HD1008)
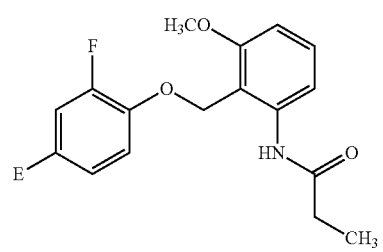
(HD1009)
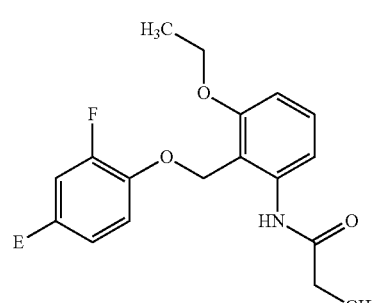
(HD1010)
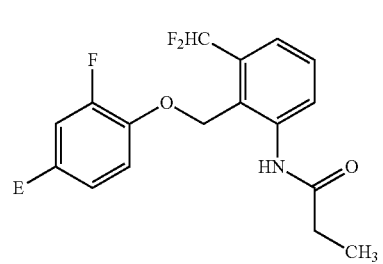
(HD1011)
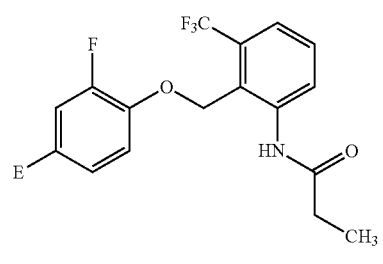
(HD1012)

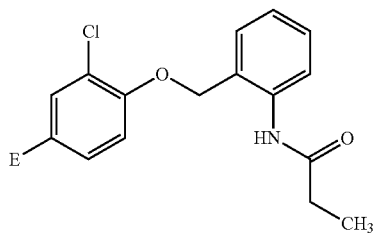
(HD1025)
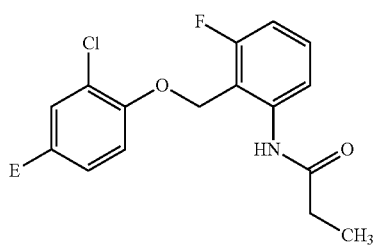
(HD1026)
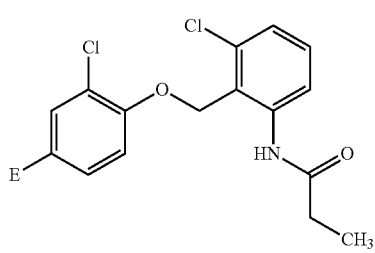
(HD1027)
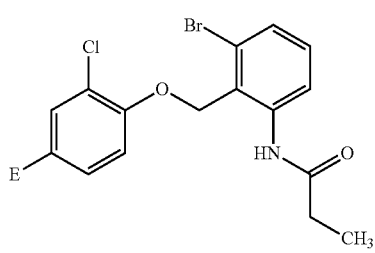
(HD1028)
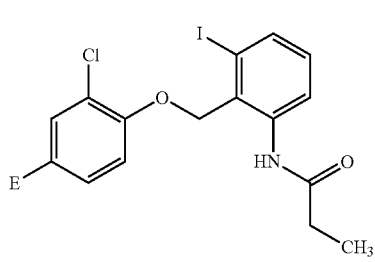
(HD1029)
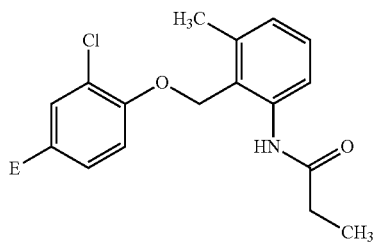
(HD1030)
-continued
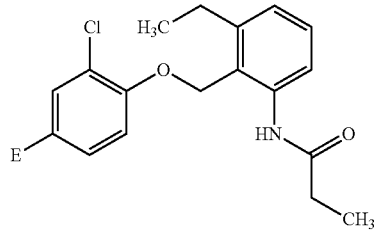
(HD1031)
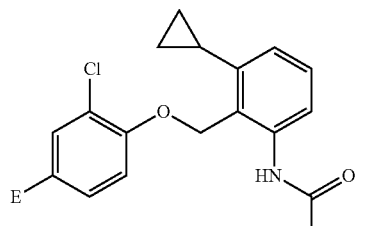
(HD1032)
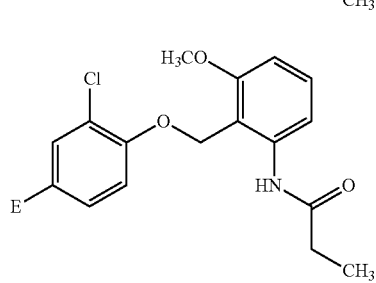
(HD1033)

(HD1034)
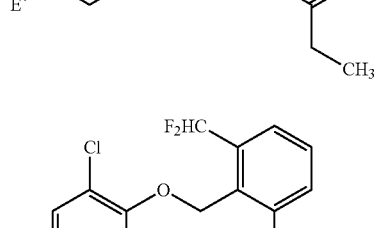
(HD1035)
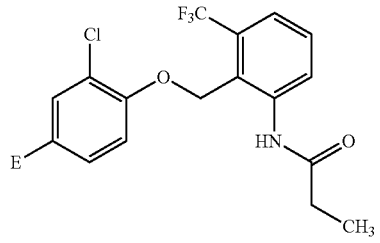
(HD1036)

(HD1037)
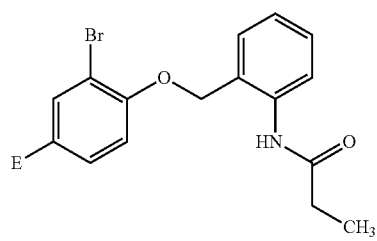
(HD1038)
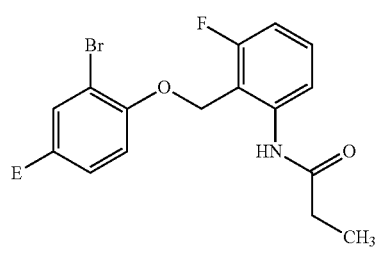
(HD1039)
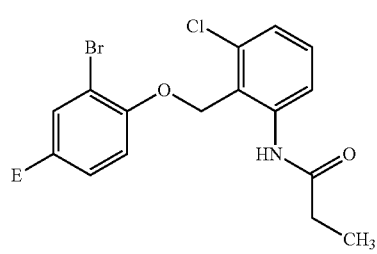
(HD1040)
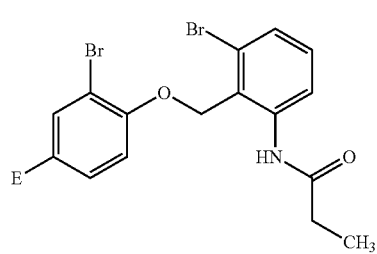
(HD1041)
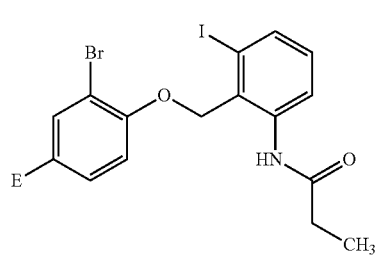
(HD1042)
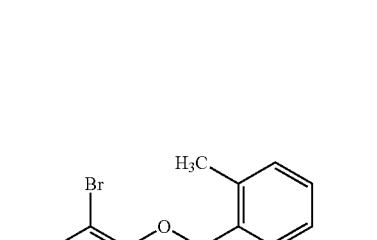
(HD1043)
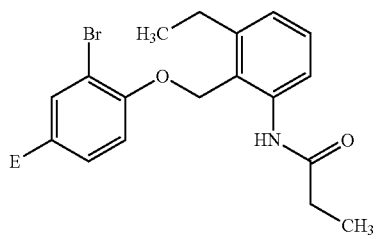
(HD1044)
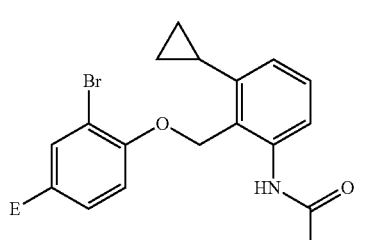
(HD1045)
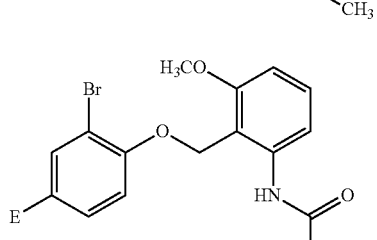
(HD1046)
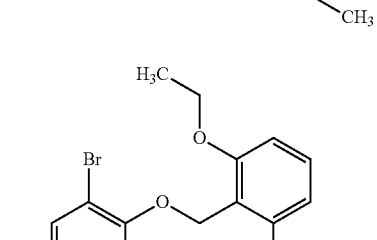
(HD1047)
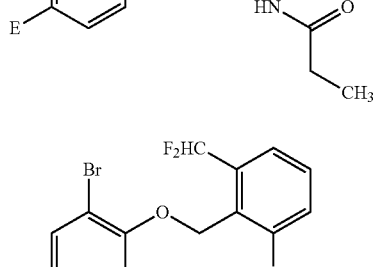
(HD1048)
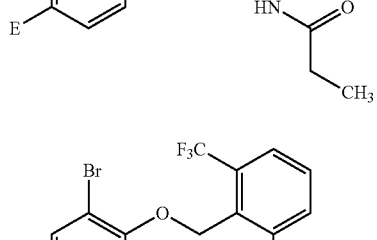

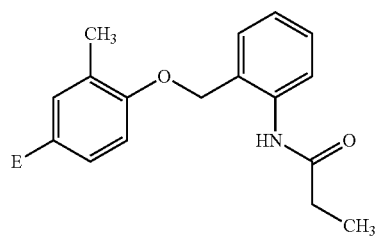 (HD1049)
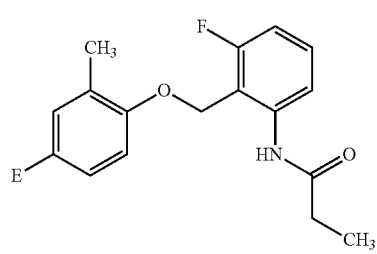 (HD1050)
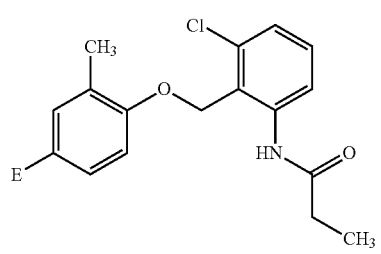 (HD1051)
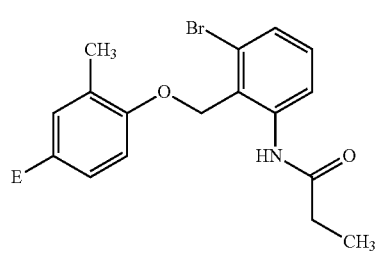 (HD1052)
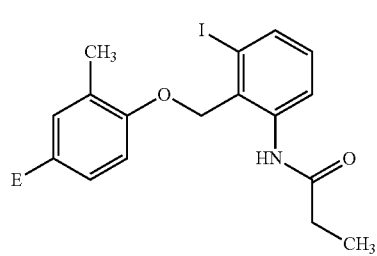 (HD1053)
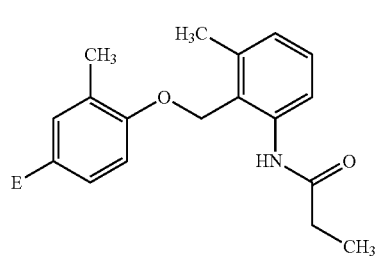 (HD1054)
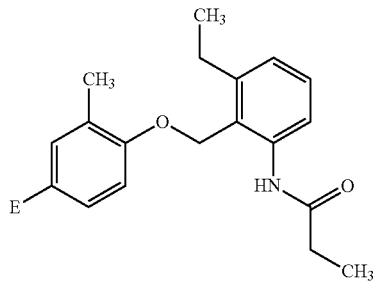 (HD1055)
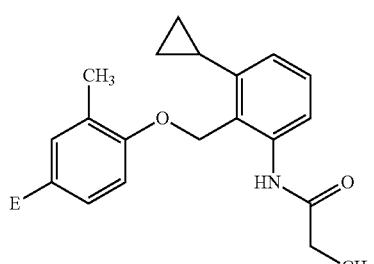 (HD1056)
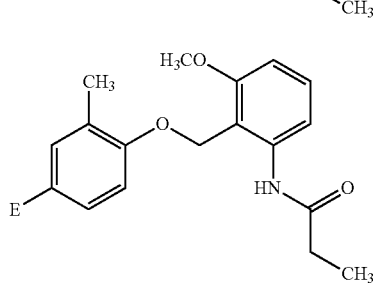 (HD1057)
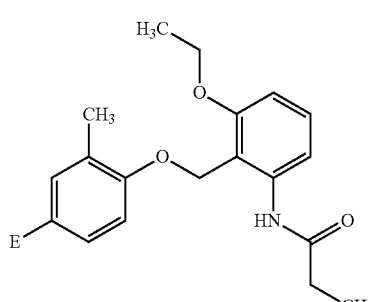 (HD1058)
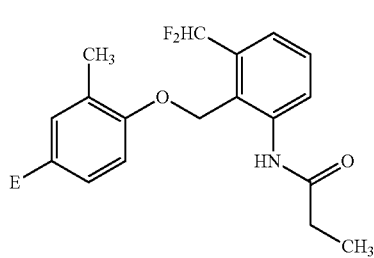 (HD1059)
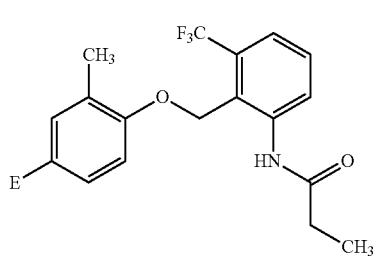 (HD1060)

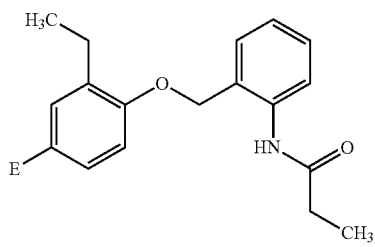 (HD1061)
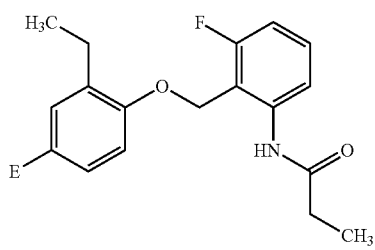 (HD1062)
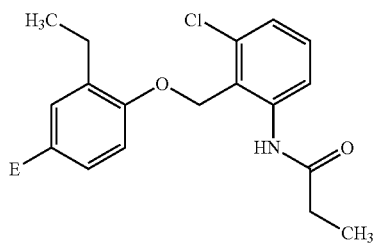 (HD1063)
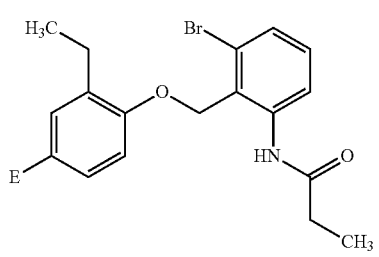 (HD1064)
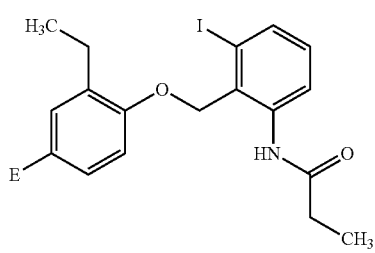 (HD1065)
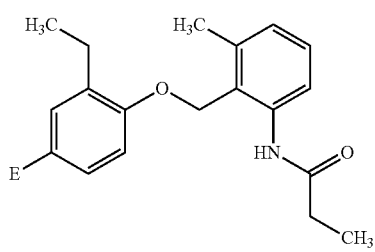 (HD1066)
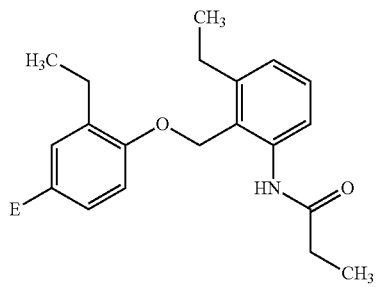 (HD1067)
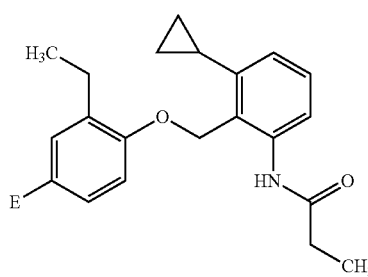 (HD1068)
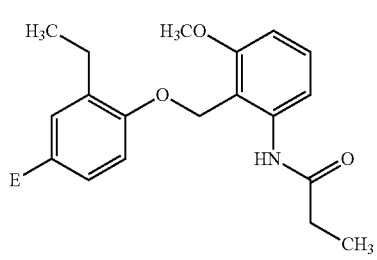 (HD1069)
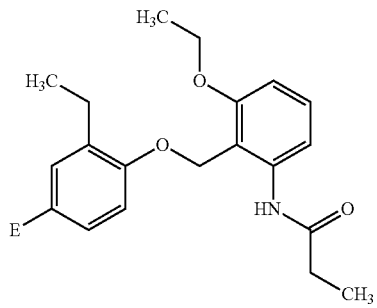 (HD1070)
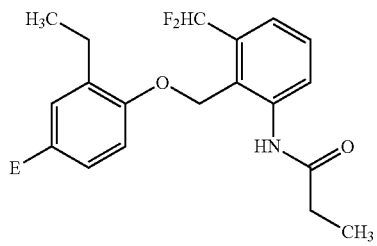 (HD1071)
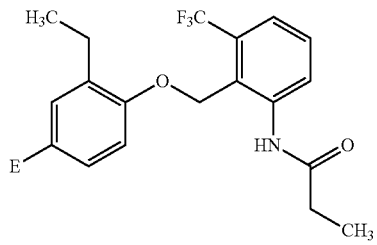 (HD1072)

(HD1073)
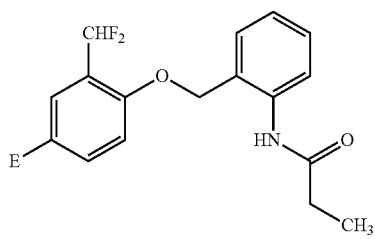
(HD1074)
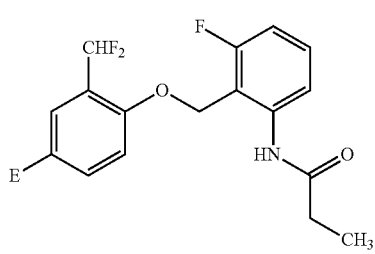
(HD1075)
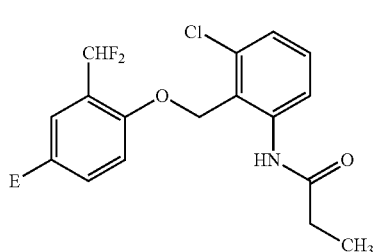
(HD1076)
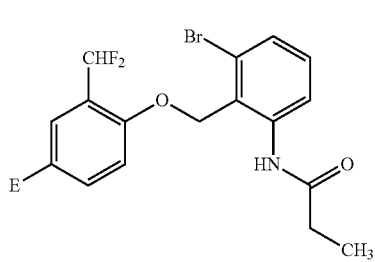
(HD1077)
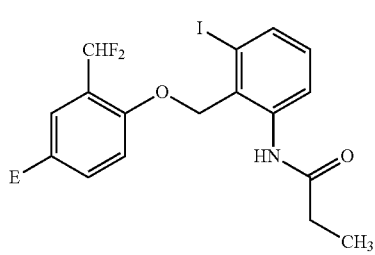
(HD1078)
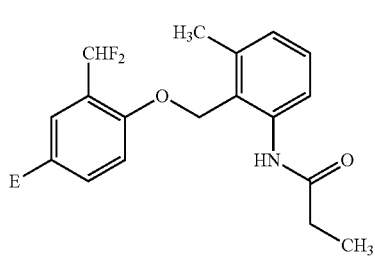
(HD1079)
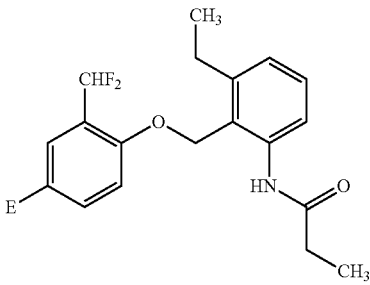
(HD1080)
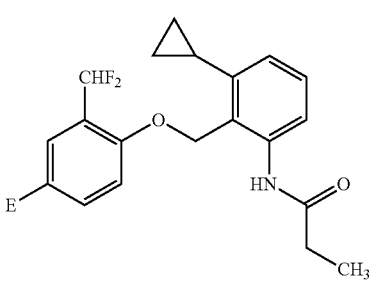
(HD1081)
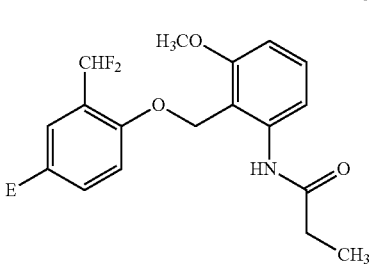
(HD1082)
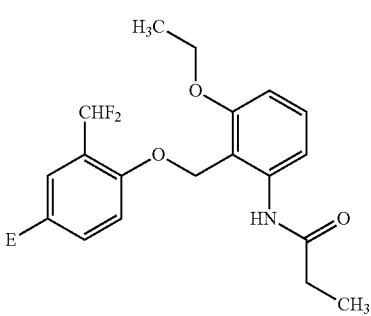
(HD1083)
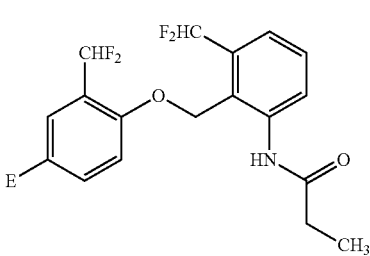
(HD1084)
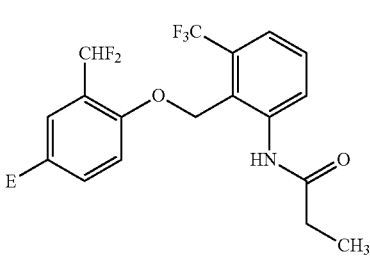

-continued
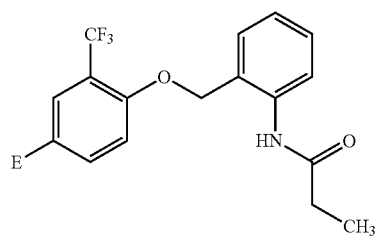
(HD1085)
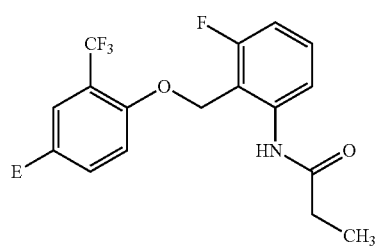
(HD1086)
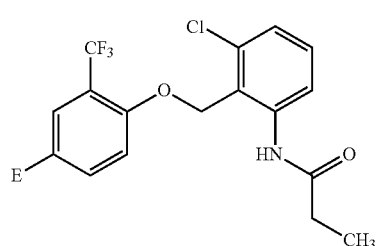
(HD1087)
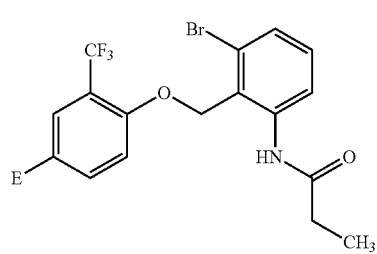
(HD1088)
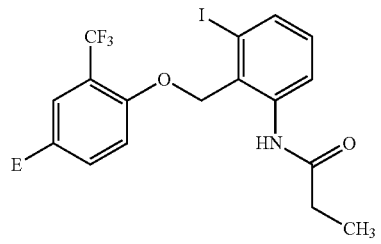
(HD1089)
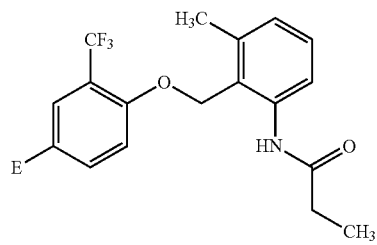
(HD1090)
-continued
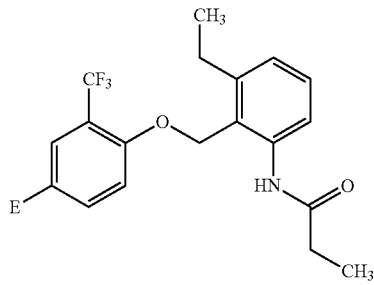
(HD1091)
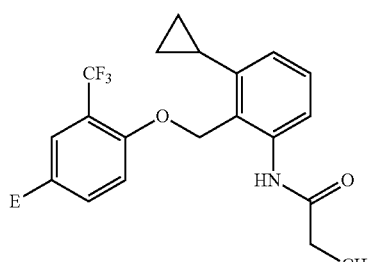
(HD1092)
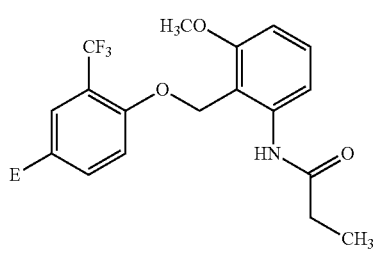
(HD1093)
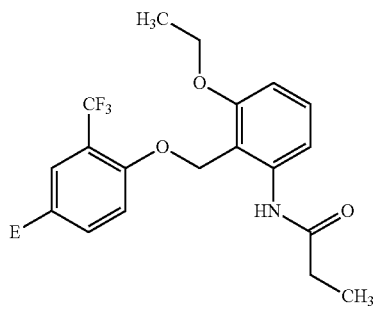
(HD1094)
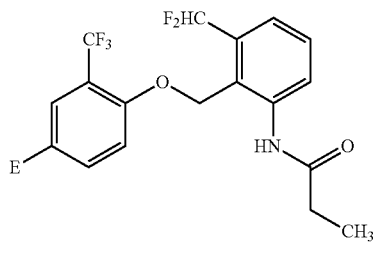
(HD1095)
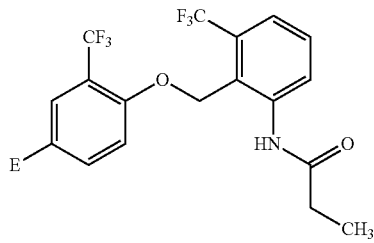
(HD1096)

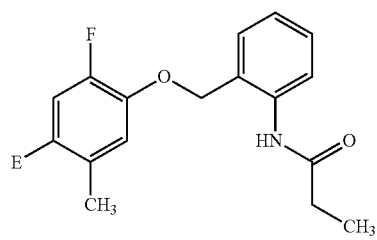
(HD4013)

(HD4014)
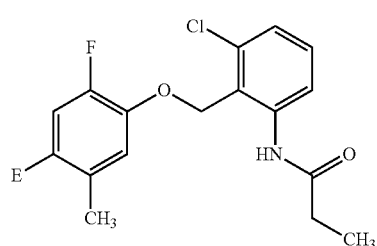
(HD4015)
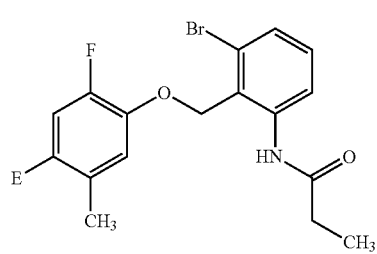
(HD4016)
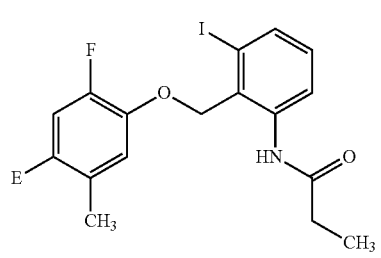
(HD4017)
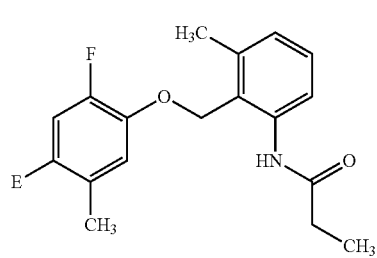
(HD4018)
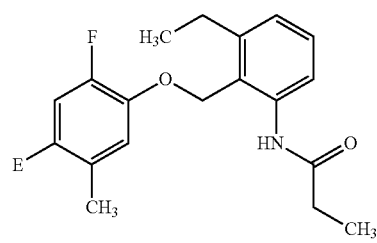
(HD4019)
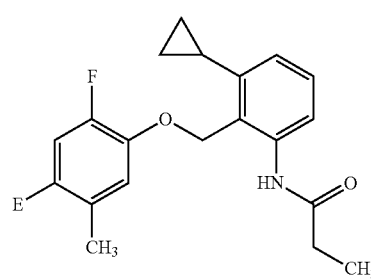
(HD4020)
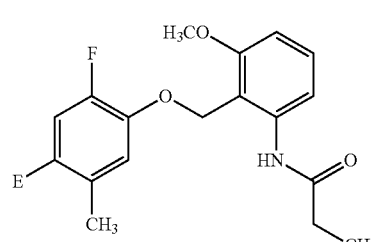
(HD4021)
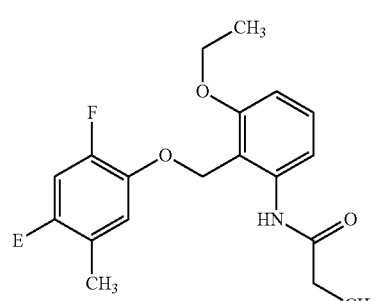
(HA4022)
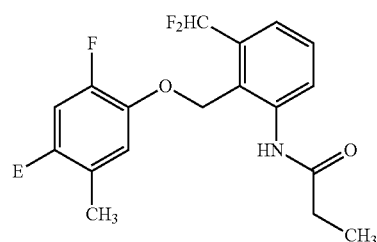
(HA4023)
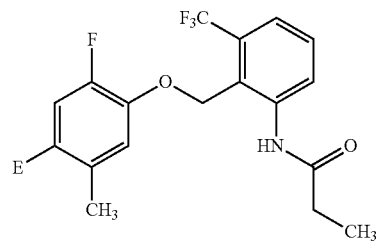
(HA4024)

-continued
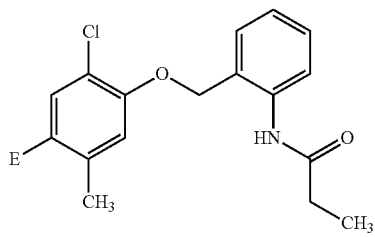 (HD4025)
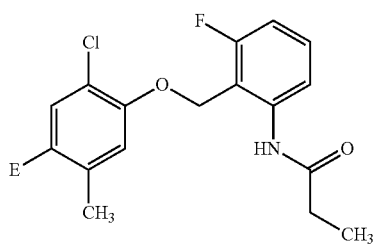 (HD4026)
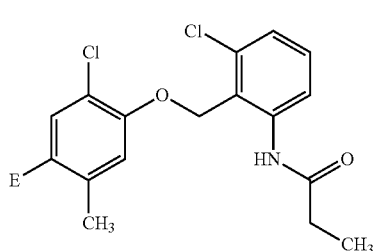 (HD4027)
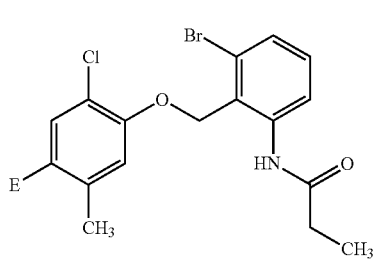 (HD4028)
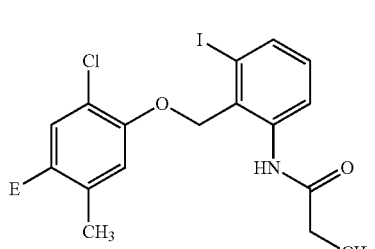 (HD4029)
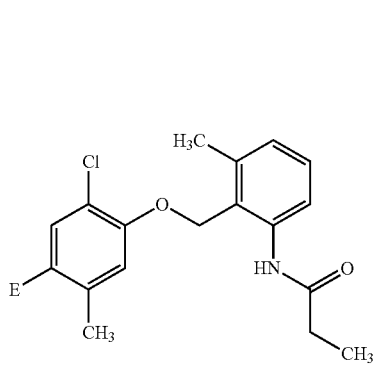 (HD4030)
-continued
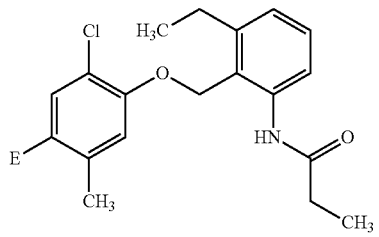 (HD4031)
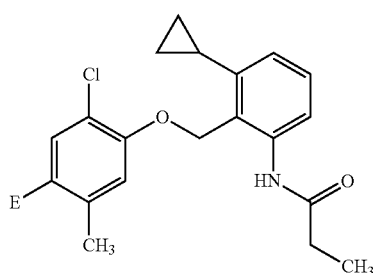 (HD4032)
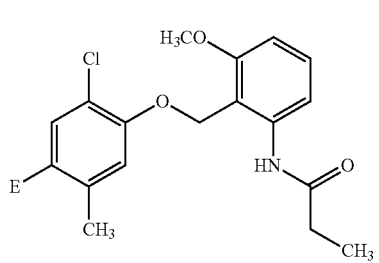 (HD4033)
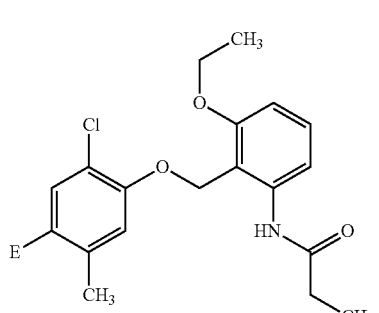 (HD4034)
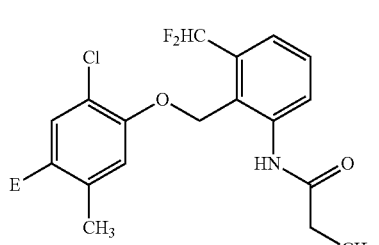 (HD4035)
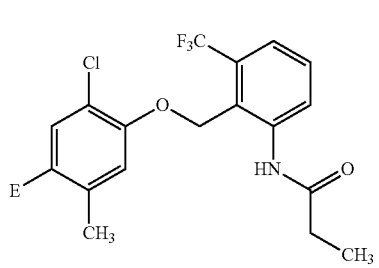 (HD4036)

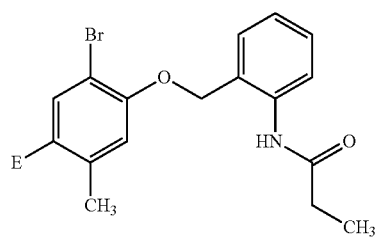
(HD4037)
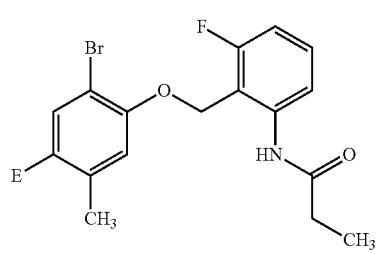
(HD4038)
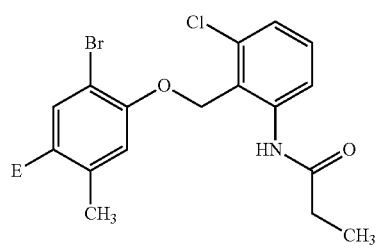
(HD4039)
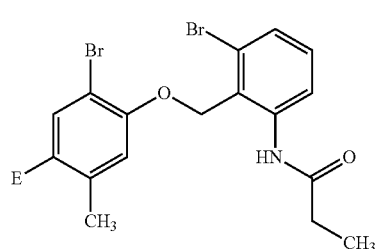
(HD4040)
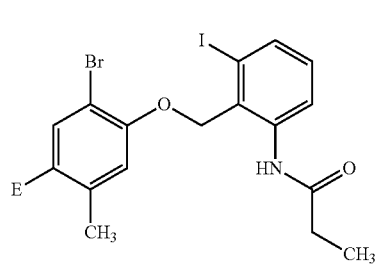
(HD4041)
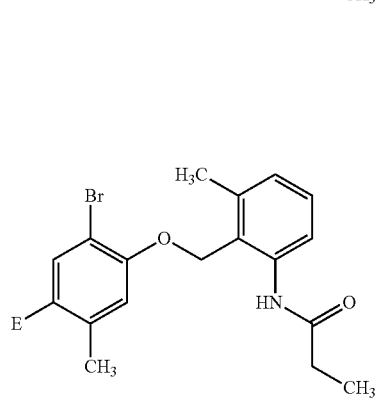
(HD4042)
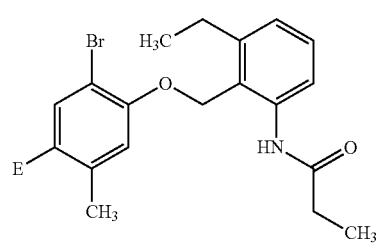
(HD4043)
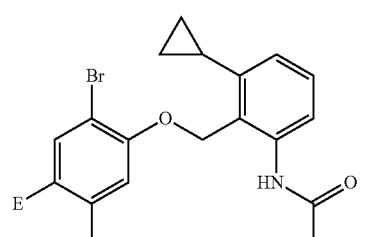
(HD4044)
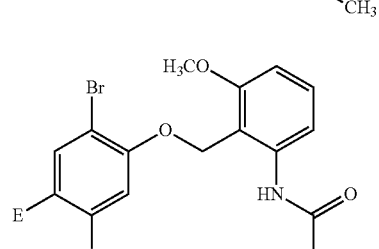
(HD4045)

(HD4046)
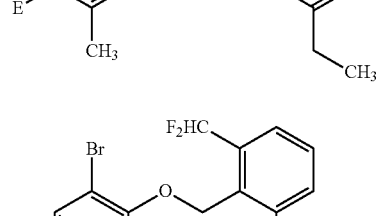
(HD4047)
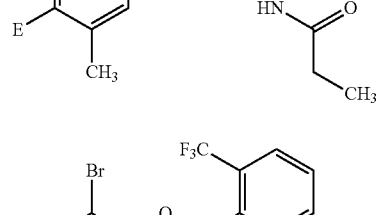
(HD4048)
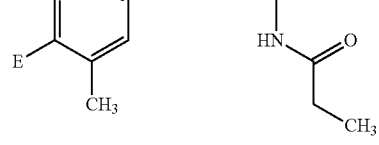

(HD4049) 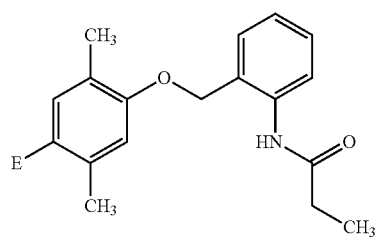
(HD4050) 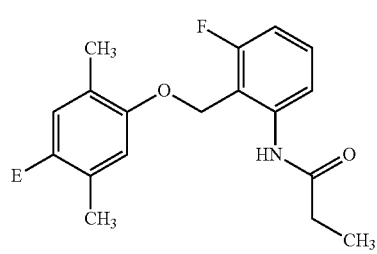
(HD4051) 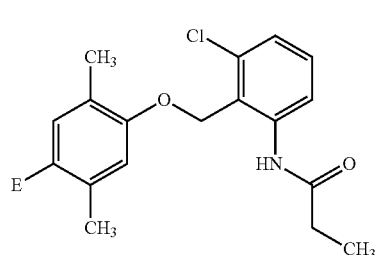
(HD4052) 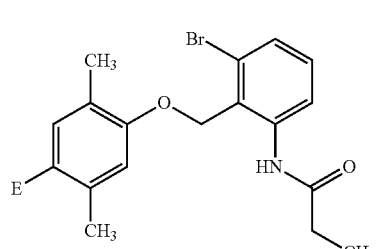
(HD4053) 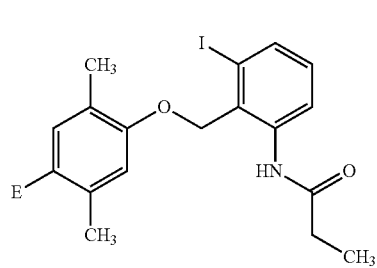
(HD4054) 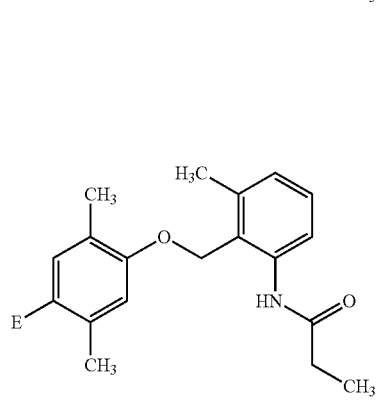
(HD4055) 
(HD4056) 
(HD4057) 
(HD4058) 
(HD4059) 
(HD4060) 

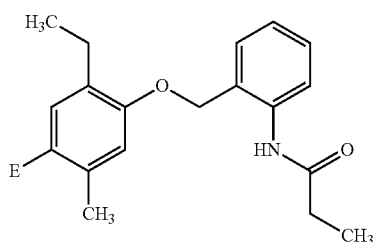
(HD4061)
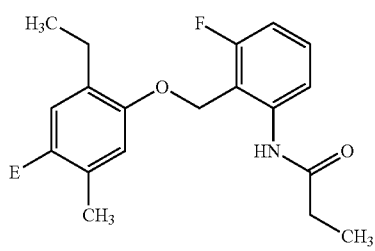
(HD4062)
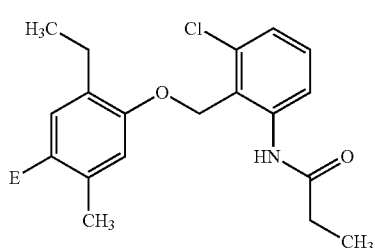
(HD4063)
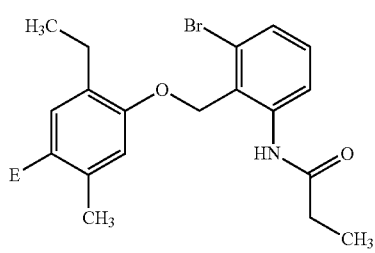
(HD4064)
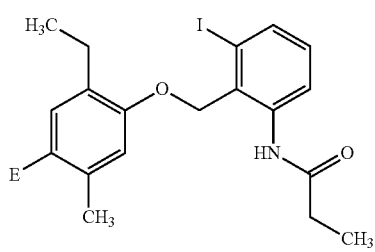
(HD4065)
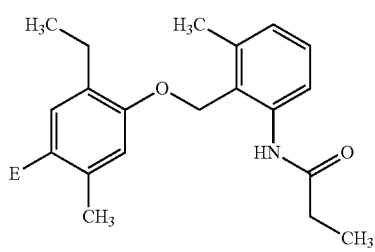
(HD4066)
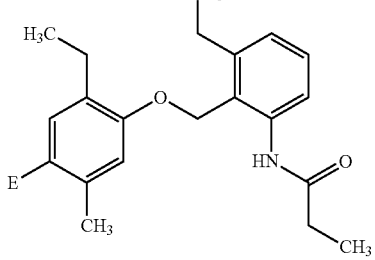
(HD4067)
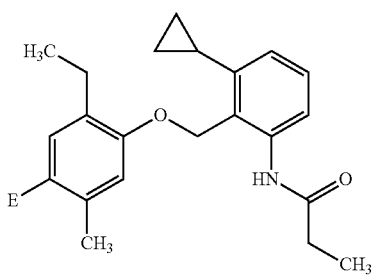
(HD4068)
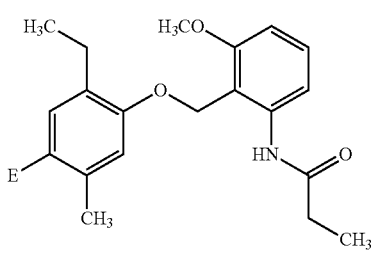
(HD4069)
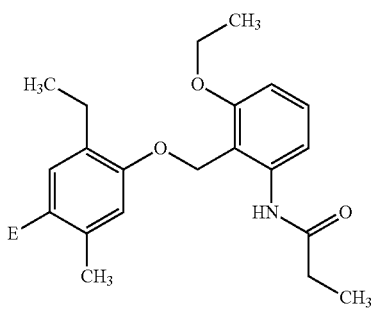
(HD4070)
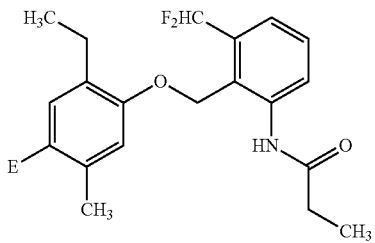
(HD4071)
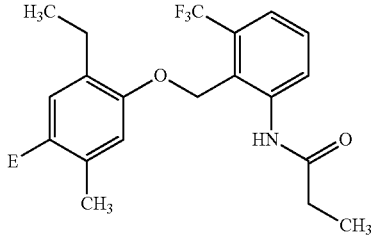
(HD4072)

(HD4073)
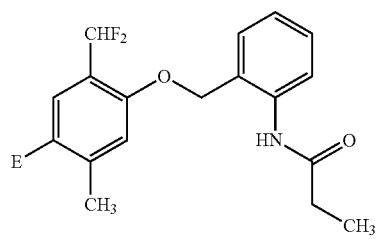
(HD4074)
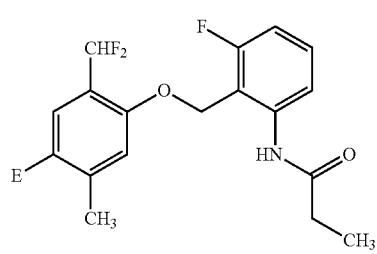
(HD4075)
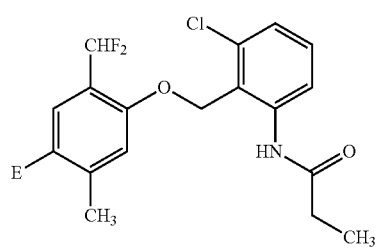
(HD4076)
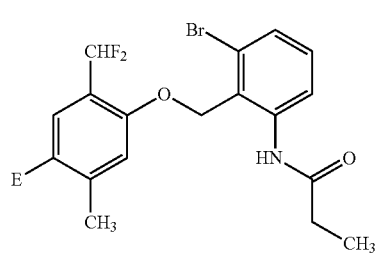
(HD4077)
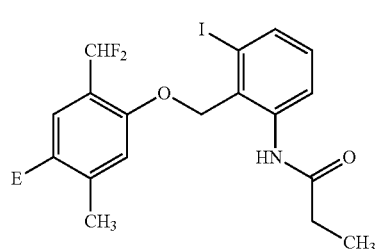
(HD4078)
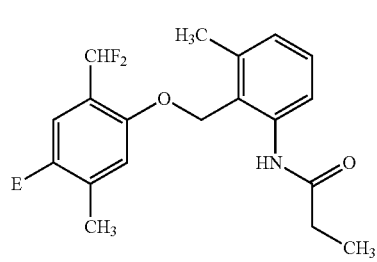
(HD4079)
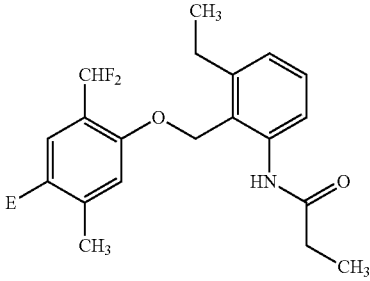
(HD4080)
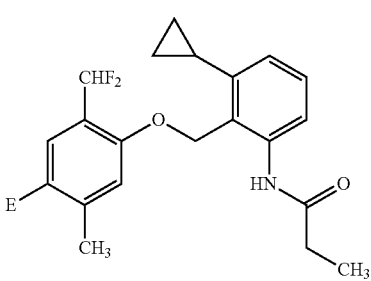
(HD4081)
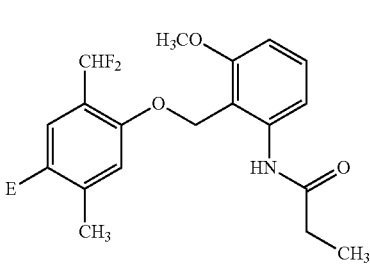
(HD4082)
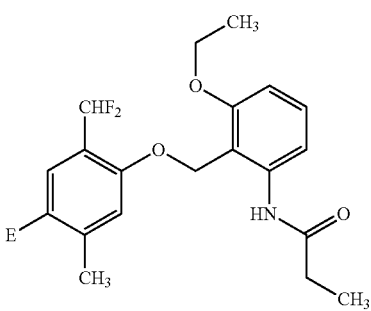
(HD4083)
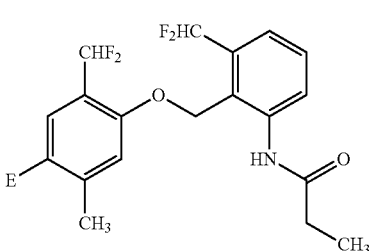
(HD4084)
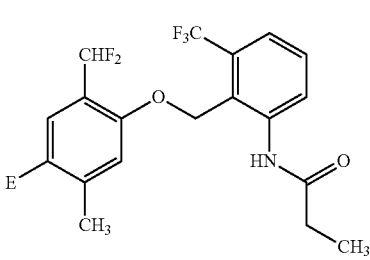

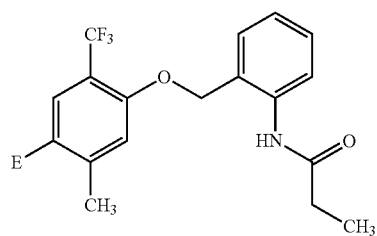 (HD4085)
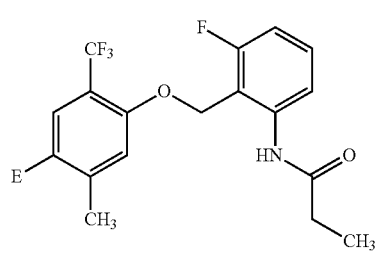 (HD4086)
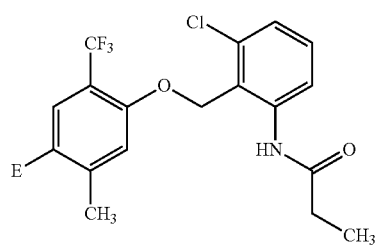 (HD4087)
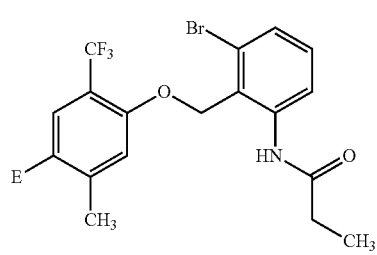 (HD4088)
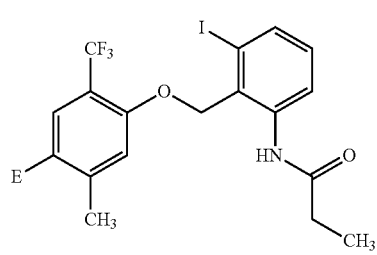 (HD4089)
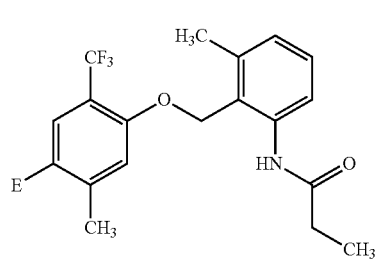 (HD4090)
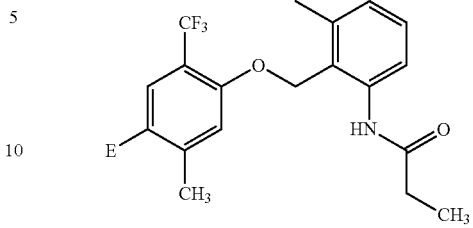 (HD4091)
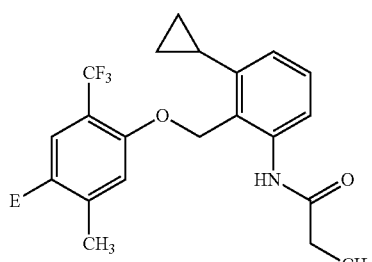 (HD4092)
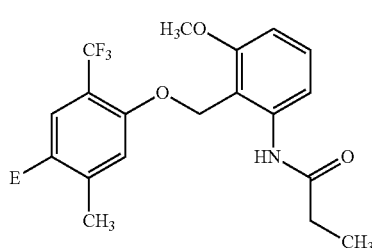 (HD4093)
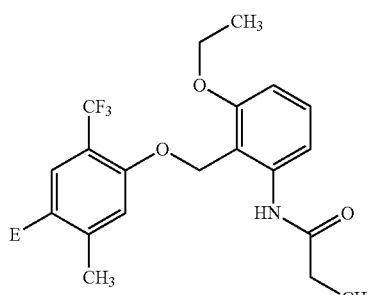 (HD4094)
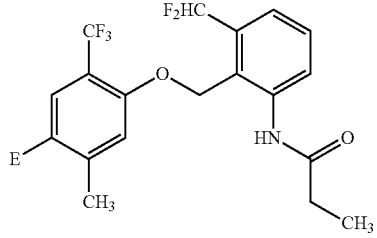 (HD4095)
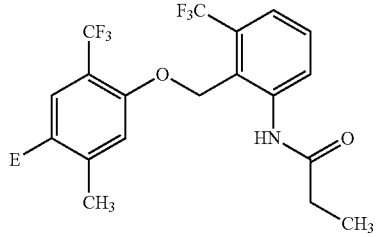 (HD4096)

-continued
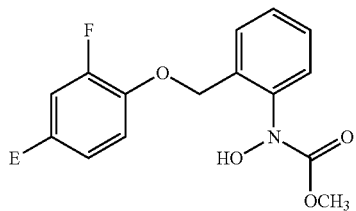 (HE1013)
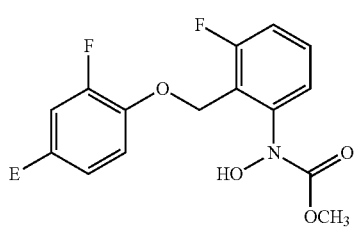 (HE1014)
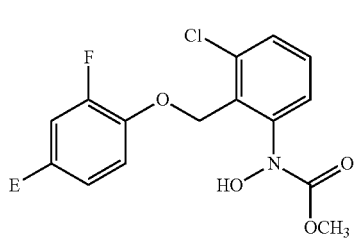 (HE1015)
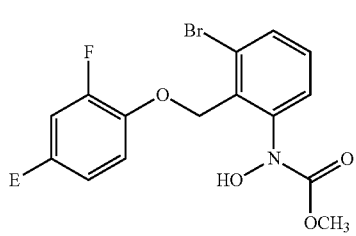 (HE1016)
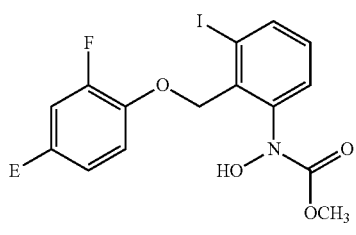 (HE1017)
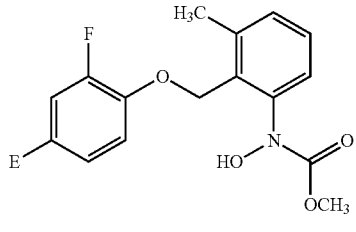 (HE1018)
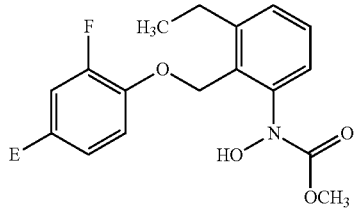 (HE1019)
-continued
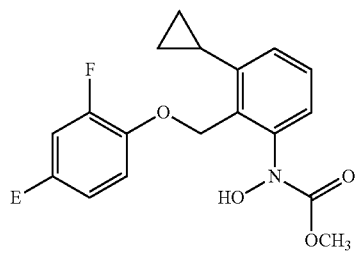 (HE1020)
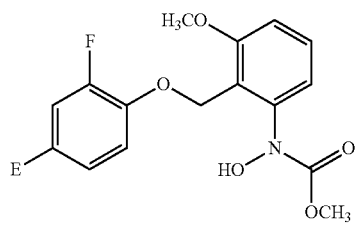 (HE1021)
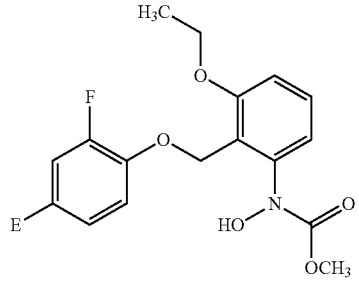 (HE1022)
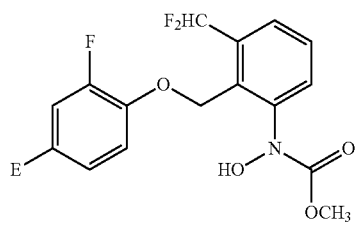 (HE1023)
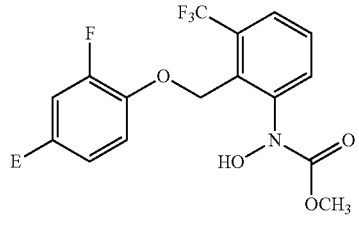 (HE1024)
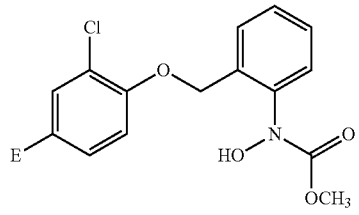 (HE1025)

-continued
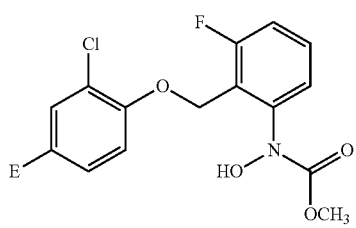 (HE1026)
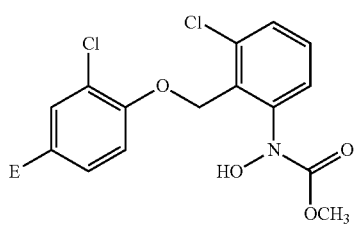 (HE1027)
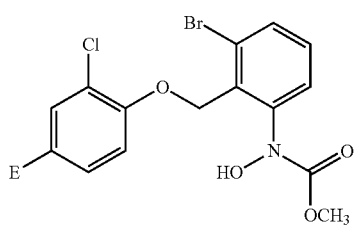 (HE1028)
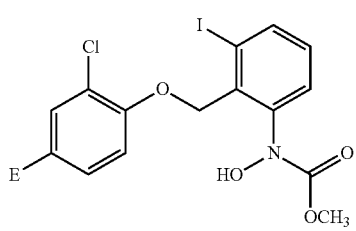 (HE1029)
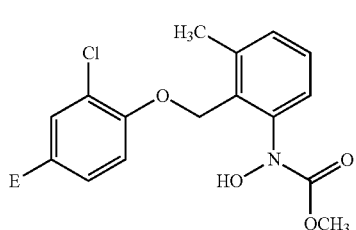 (HE1030)
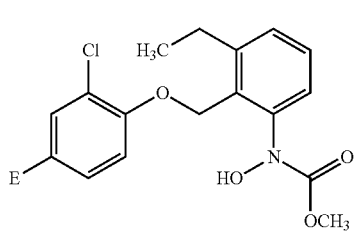 (HE1031)
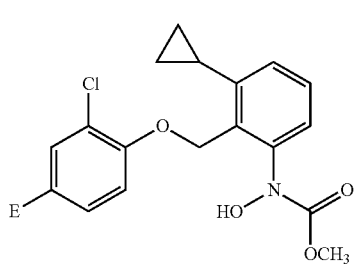 (HE1032)
-continued
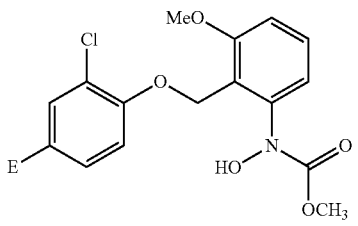 (HE1033)
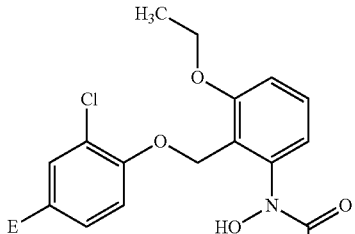 (HE1034)
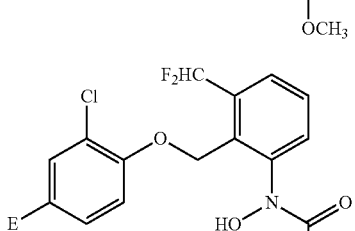 (HE1035)
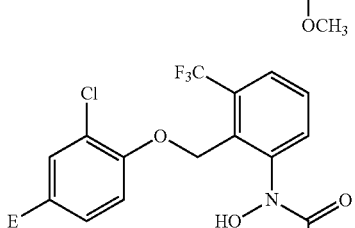 (HE1036)
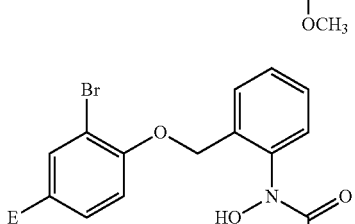 (HE1037)
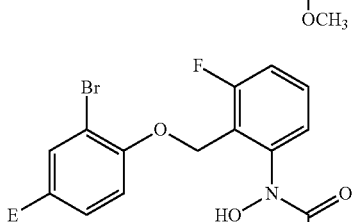 (HE1038)
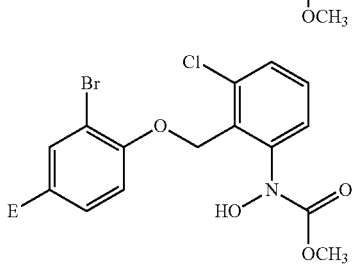 (HE1039)

153
-continued
(HE1040)
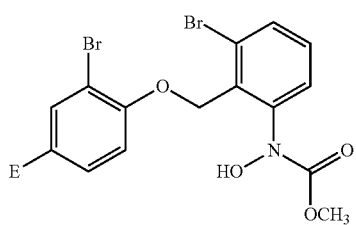
(HE1041)
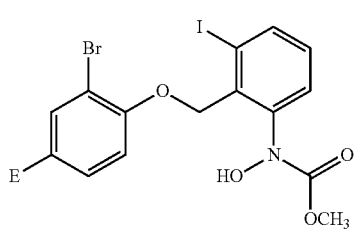
(HE1042)
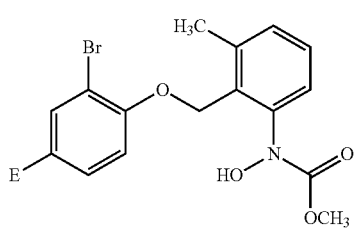
(HE1043)
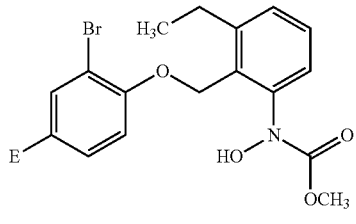
(HE1044)
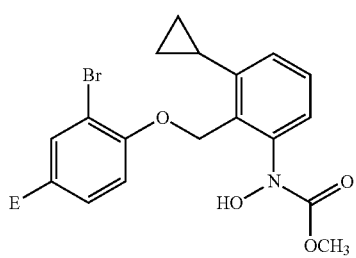
(HE1045)
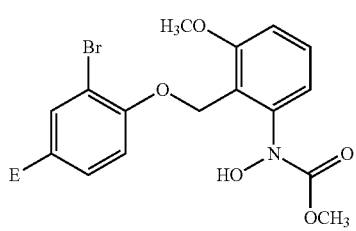
154
-continued
(HE1046)
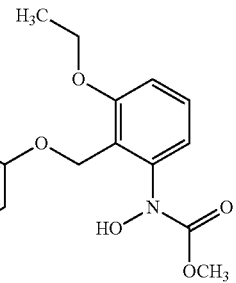
(HE1047)
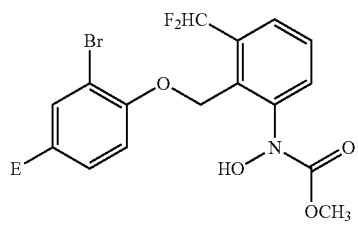
(HE1048)
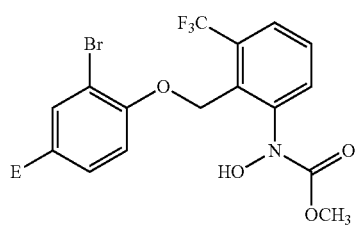
(HE1049)
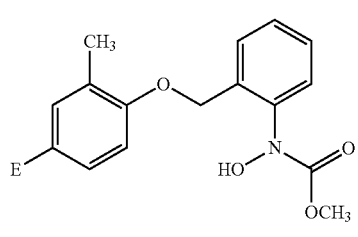
(HE1050)
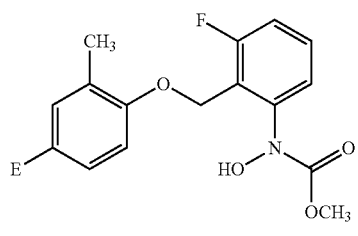
(HE1051)
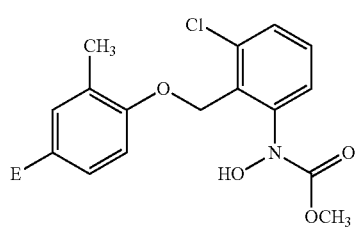
(HE1052)
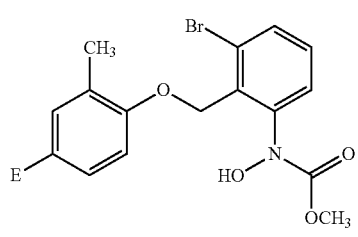

(HE1053)
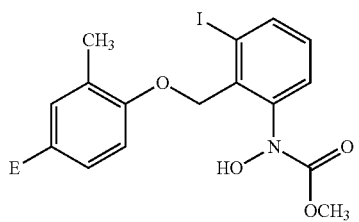
(HE1054)
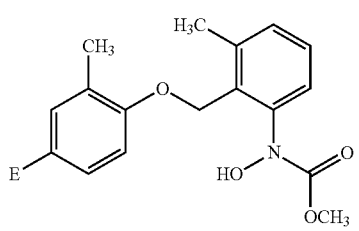
(HE1055)
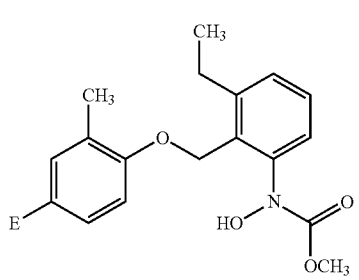
(HE1056)
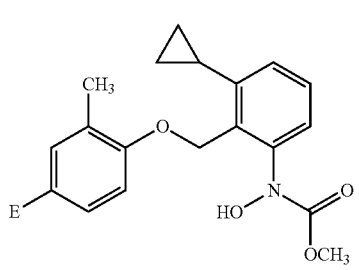
(HE1057)
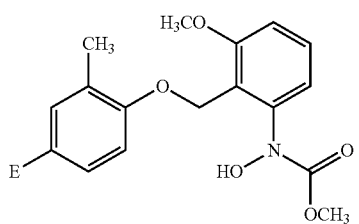
(HE1058)
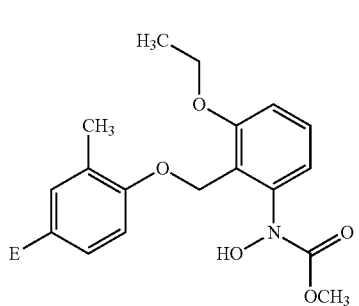
(HE1059)
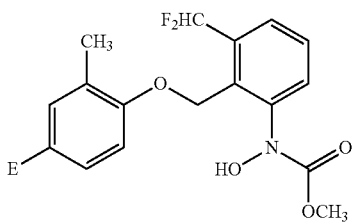
(HE1060)
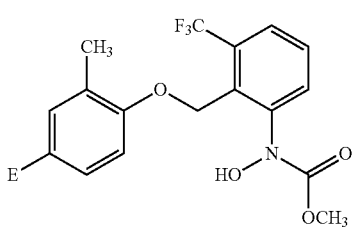
(HE1061)
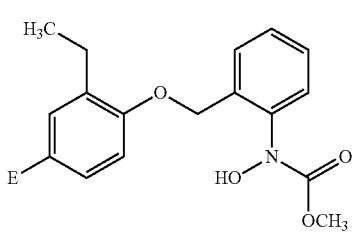
(HE1062)
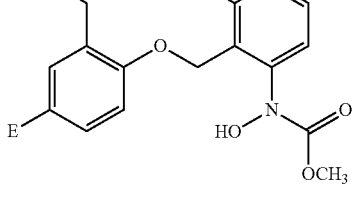
(HE1063)
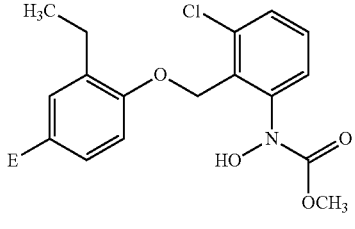
(HE1064)
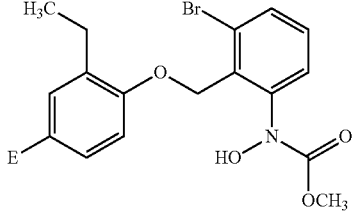
(HE1065)
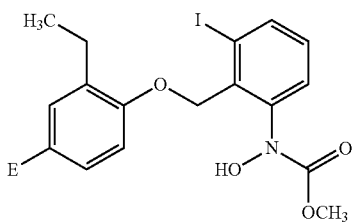

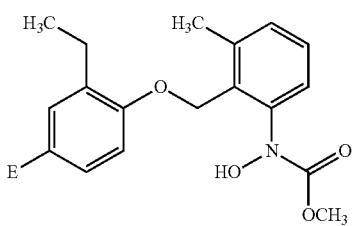
(HE1066)
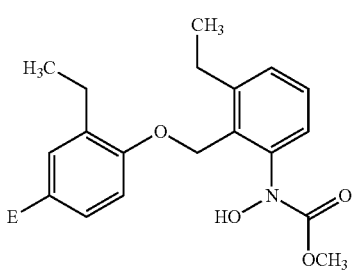
(HE1067)
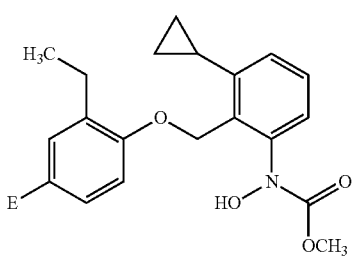
(HE1068)
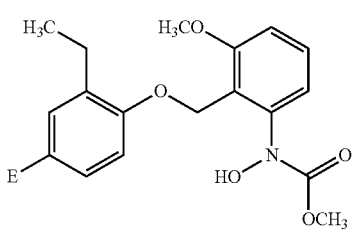
(HE1069)
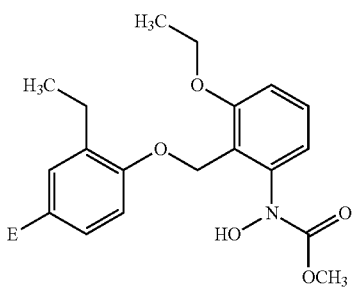
(HE1070)
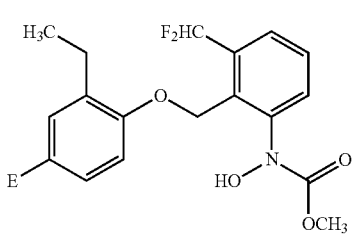
(HE1071)
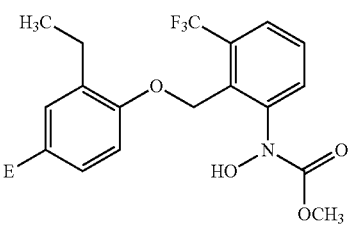
(HE1072)
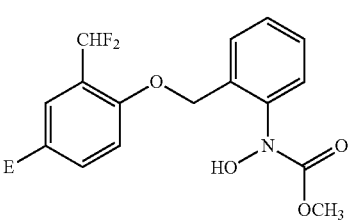
(HE1073)
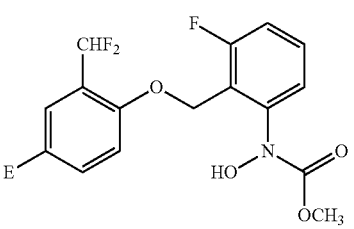
(HE1074)
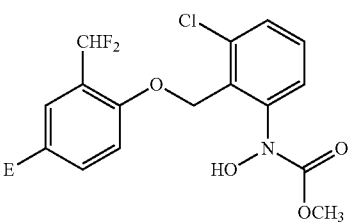
(HE1075)
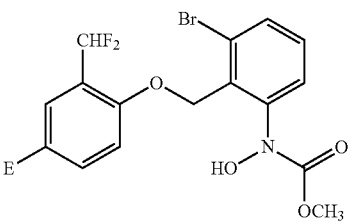
(HE1076)
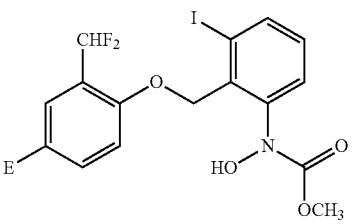
(HE1077)
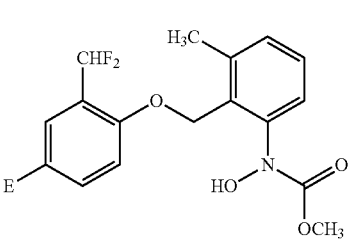
(HE1078)

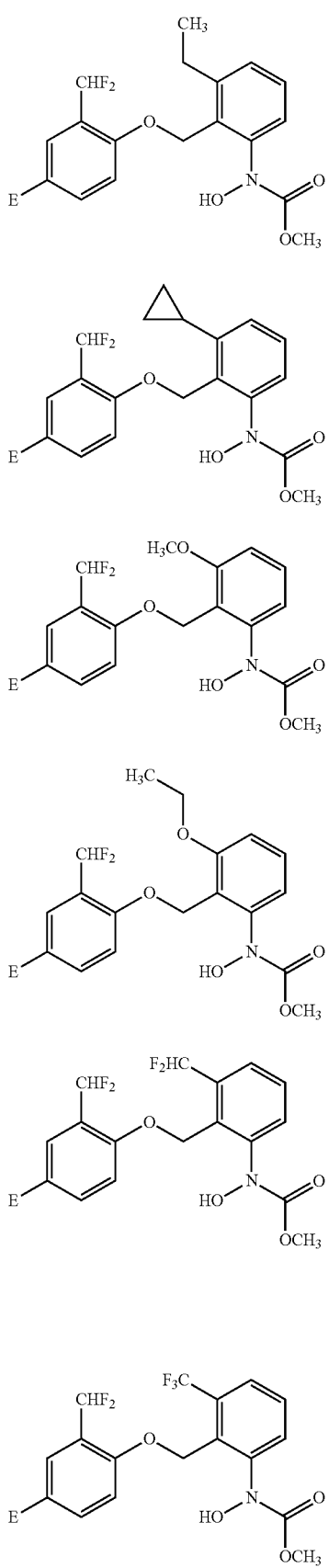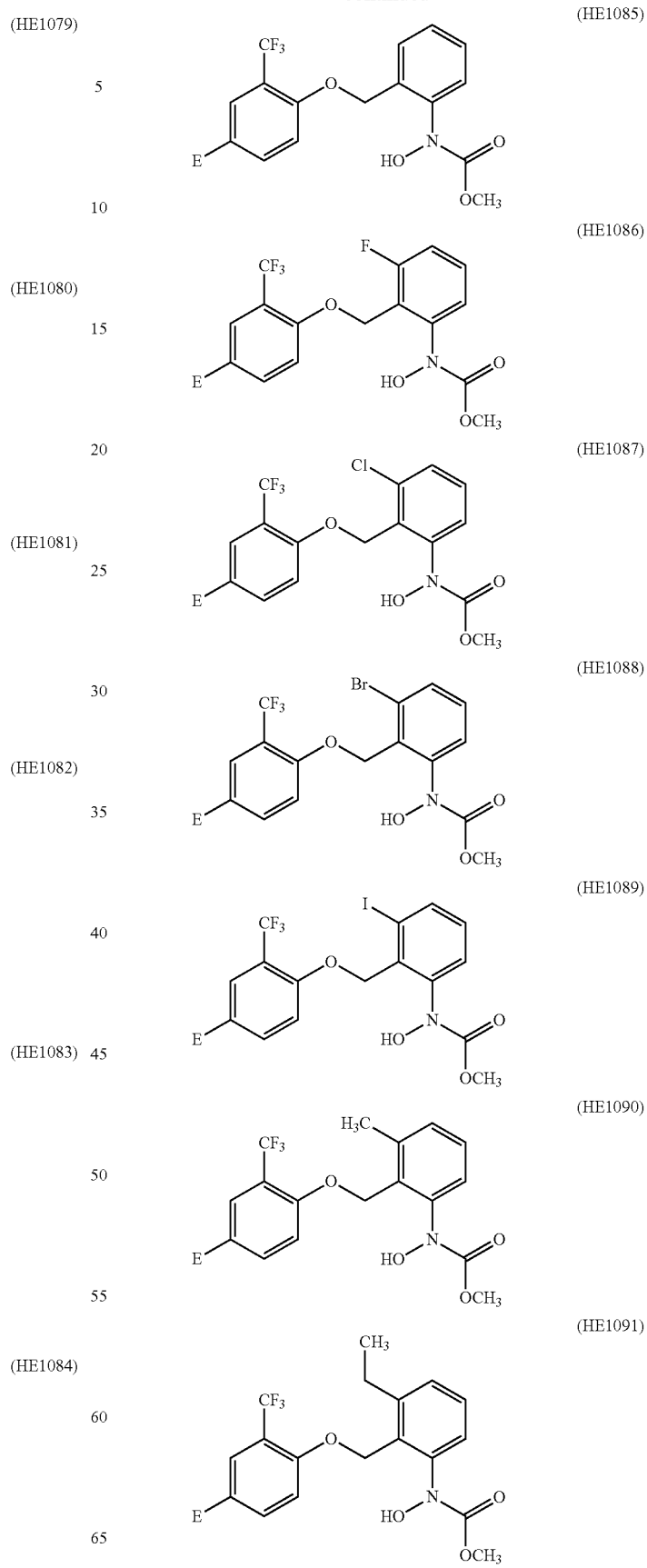

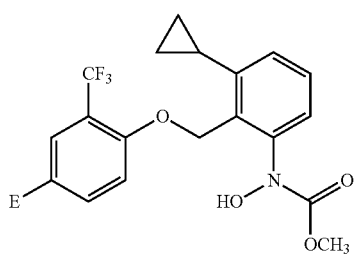
(HE1092)
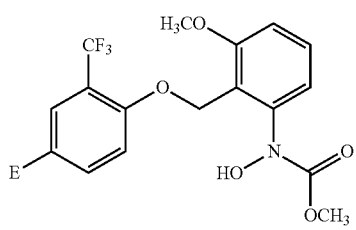
(HE1093)
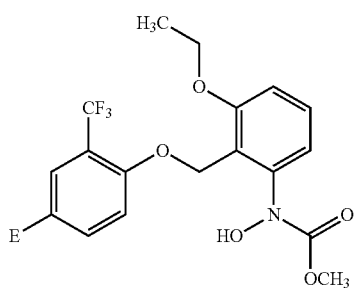
(HE1094)
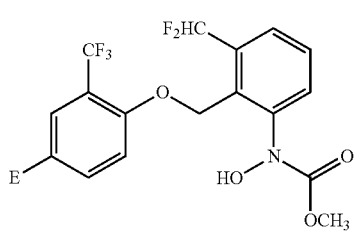
(HE1095)
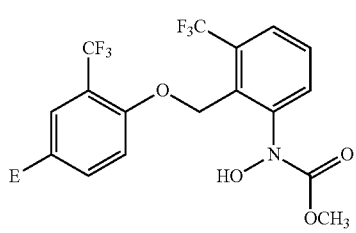
(HE1096)
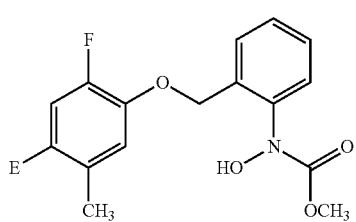
(HE4013)
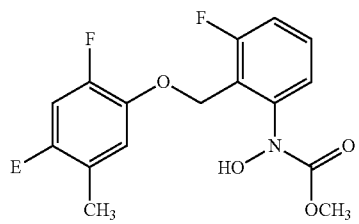
(HE4014)
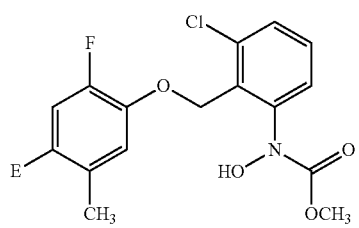
(HE4015)
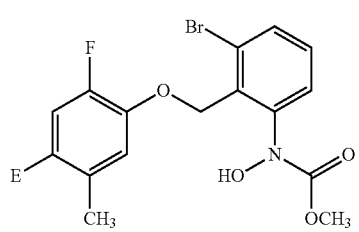
(HE4016)
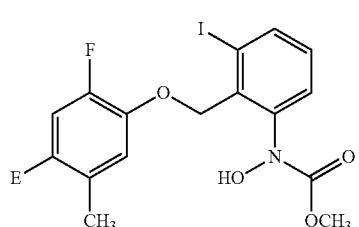
(HE4017)
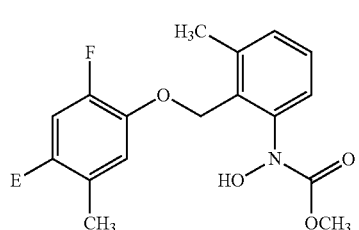
(HE4018)
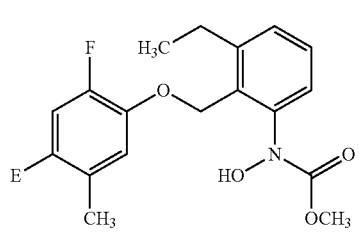
(HE4019)
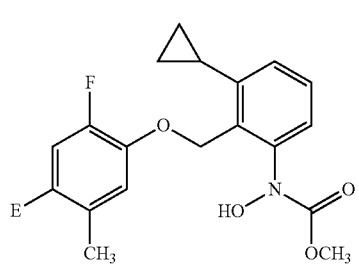
(HE4020)

(HE4021)
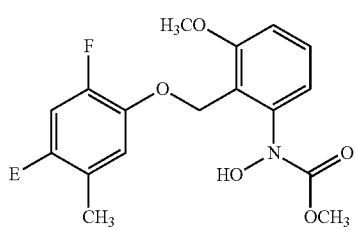
(HE4022)
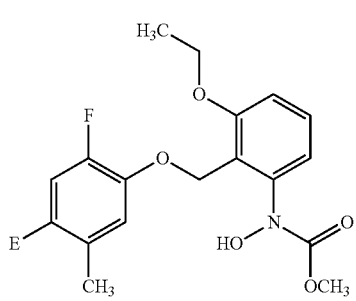
(HE4023)
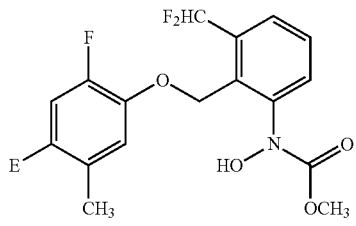
(HE4024)
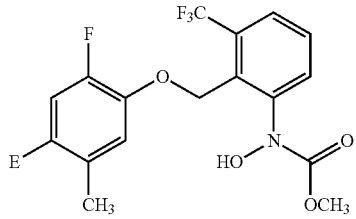
(HE4025)
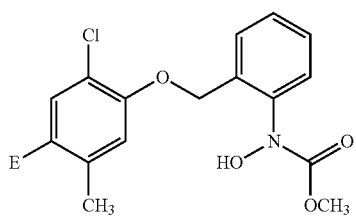
(HE4026)
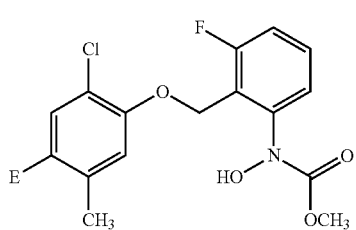
(HE4027)
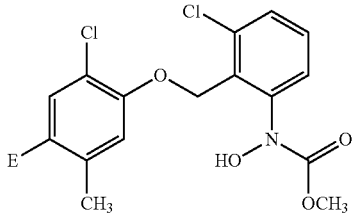
(HE4028)
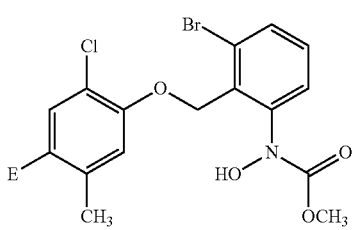
(HE4029)
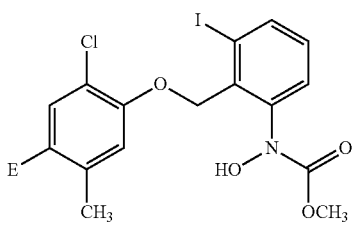
(HE4030)
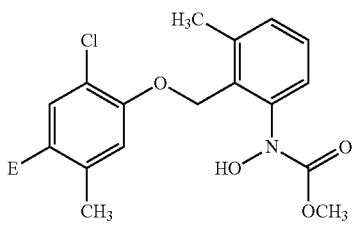
(HE4031)
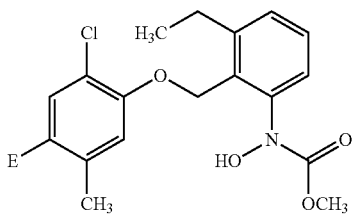
(HE4032)
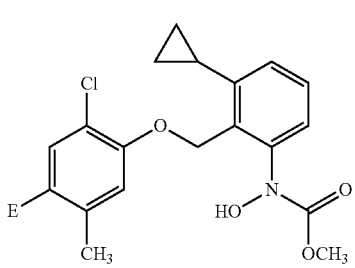
(HE4033)
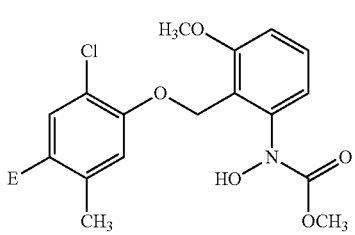

(HE4034)
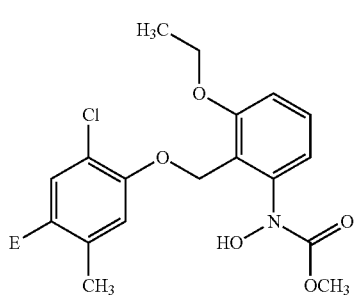
(HE4035)
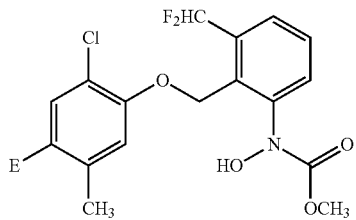
(HE4036)
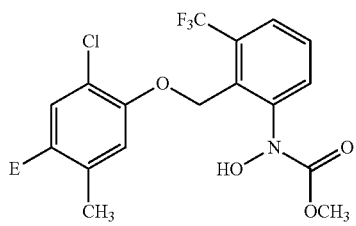
(HE4037)
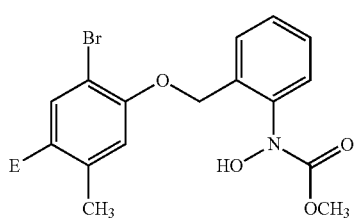
(HE4038)
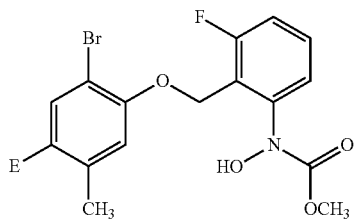
(HE4039)
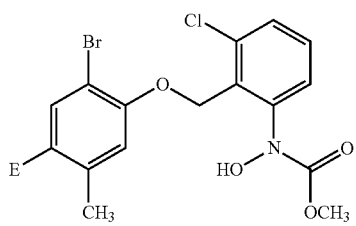
(HE4040)
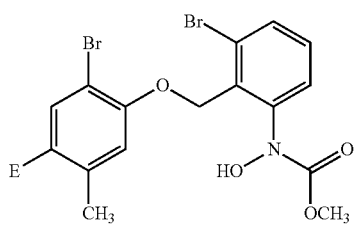
(HE4041)
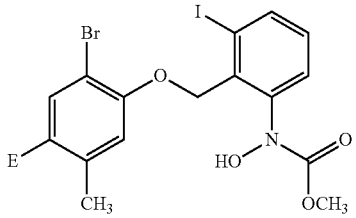
(HE4042)
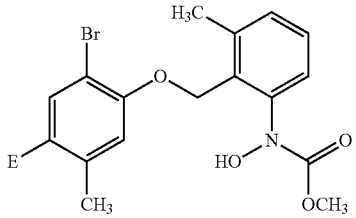
(HE4043)
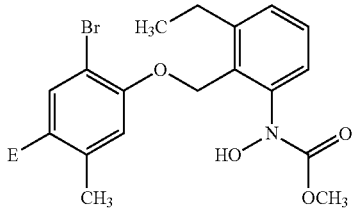
(HE4044)
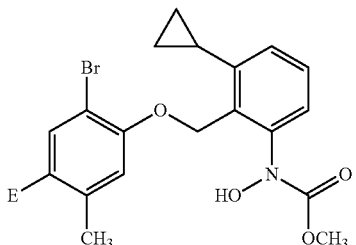
(HE4045)
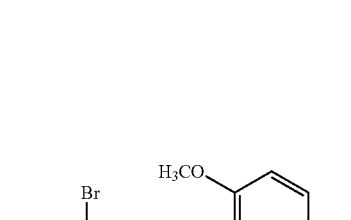
(HE4046)
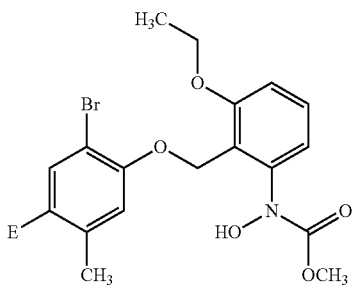

167
-continued
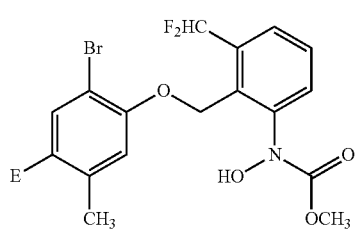
(HE4047)
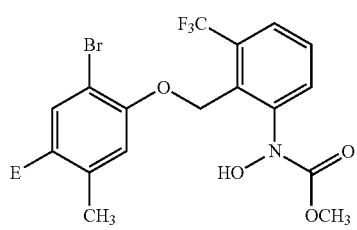
(HE4048)
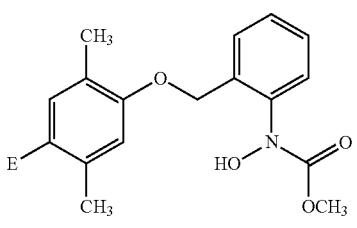
((HE4049)
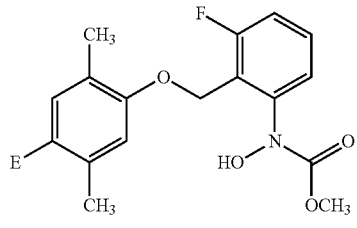
(HE4050)
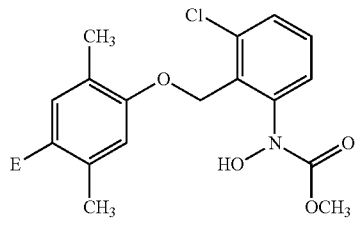
(HE4051)
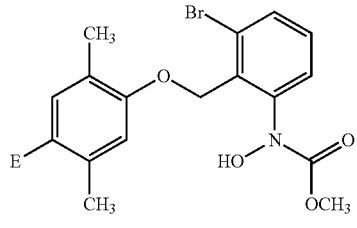
(HE4052)
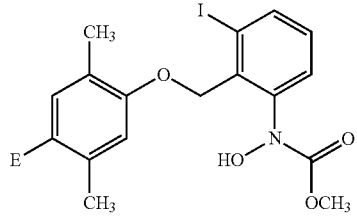
(HE4053)
168
-continued
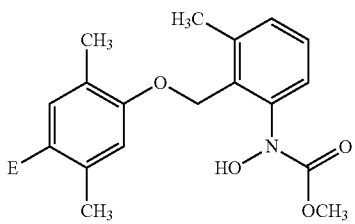
(HE4054)
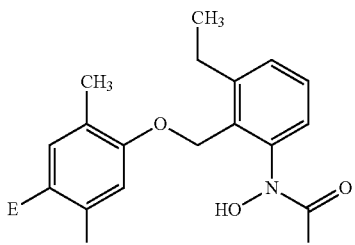
(HE4055)
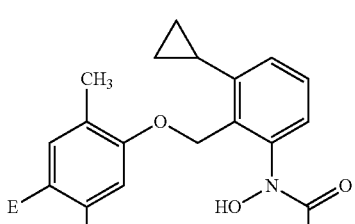
(HE4056)
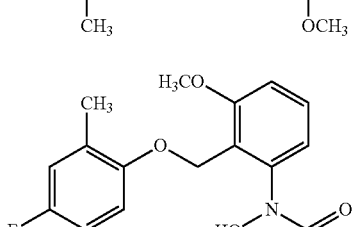
(HE4057)
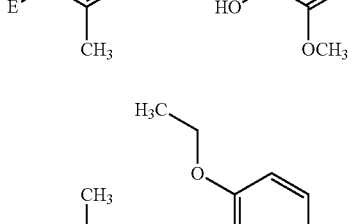
(HE4058)
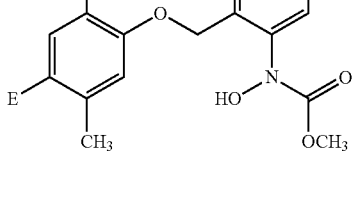
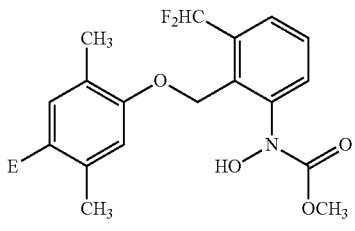
(HE4059)

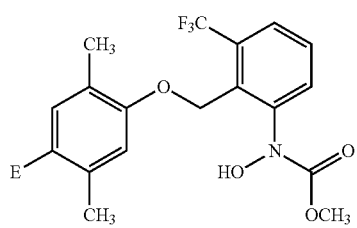
(HE4060)
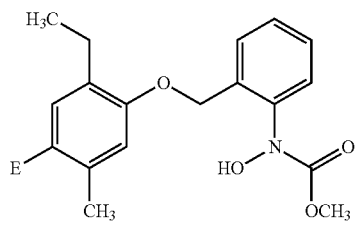
(HE4061)
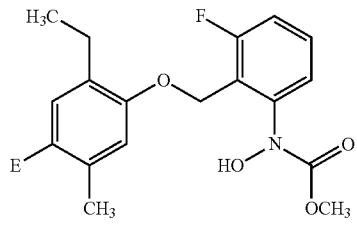
(HE4062)
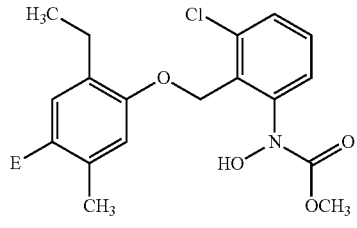
(HE4063)
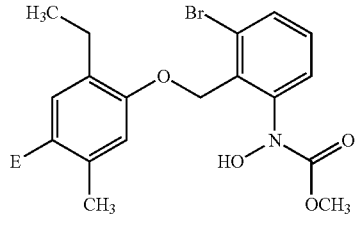
(HE4064)
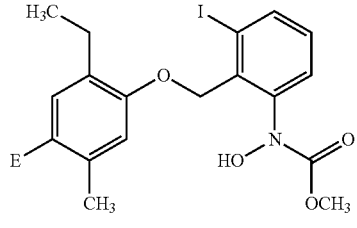
(HE4065)
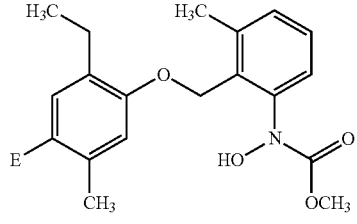
(HE4066)
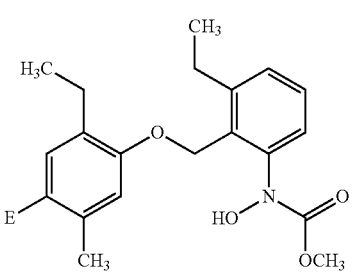
(HE4067)
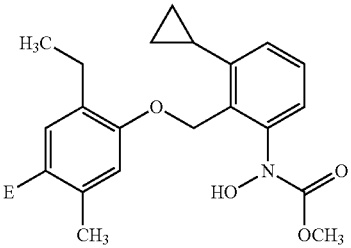
(HE4068)
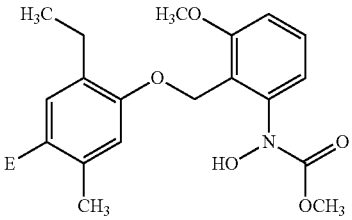
(HE4069)
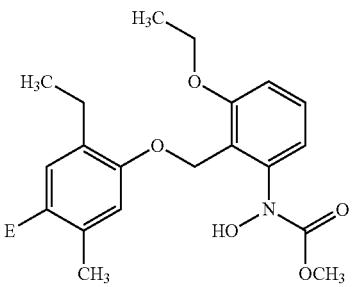
(HE4070)
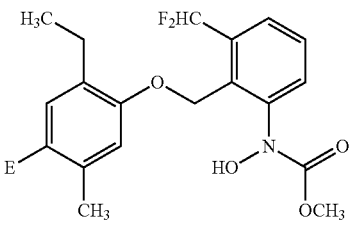
(HE4071)
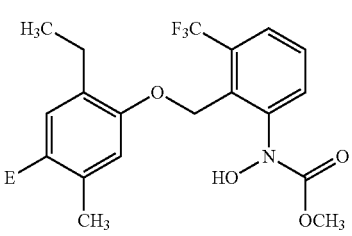
(HE4072)

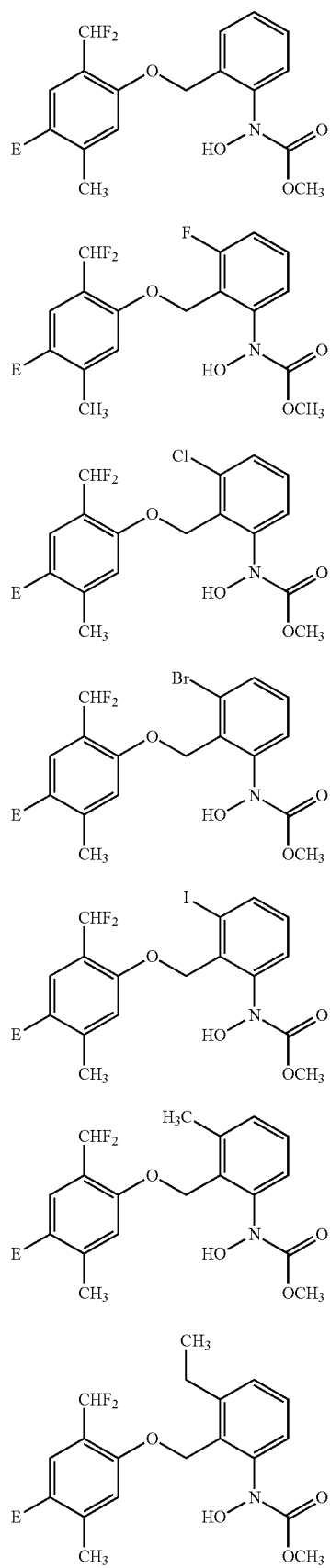
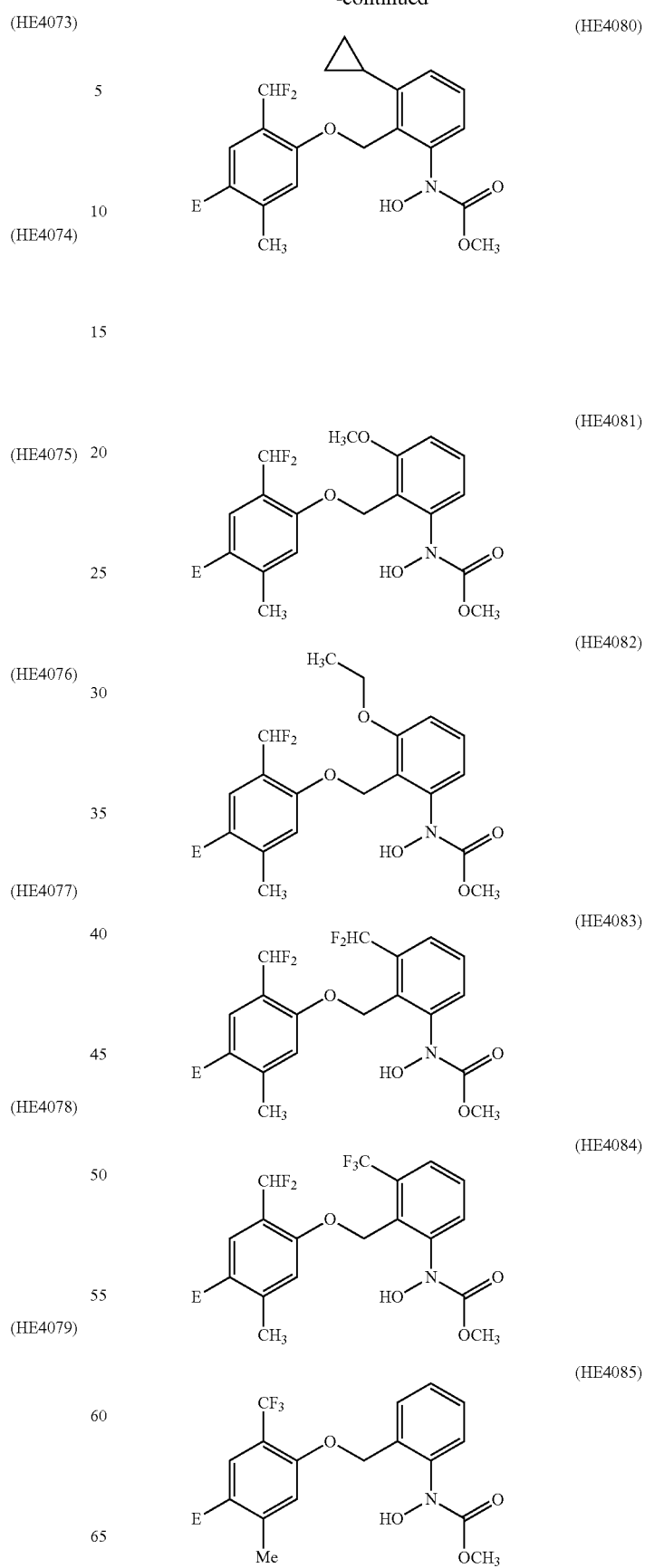

173
-continued
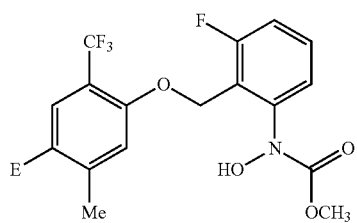
(HE4086)
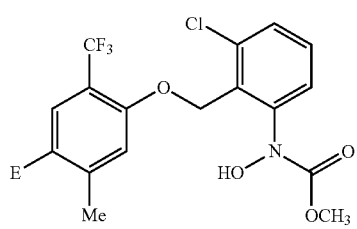
(HE4087)
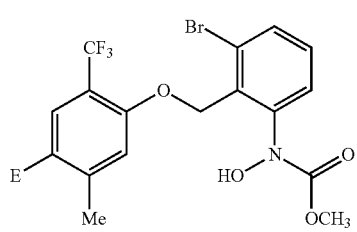
(HE4088)
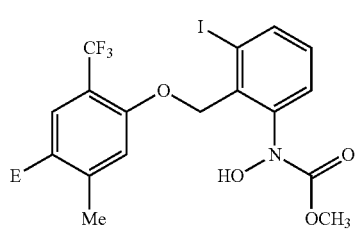
(HE4089)
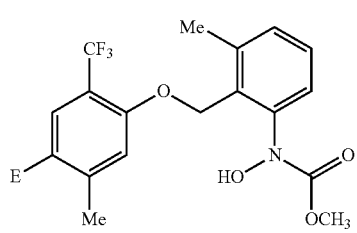
(HE4090)
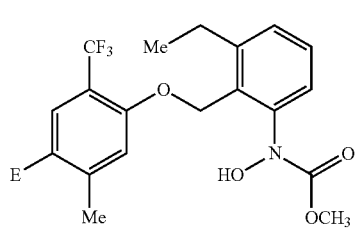
(HE4091)
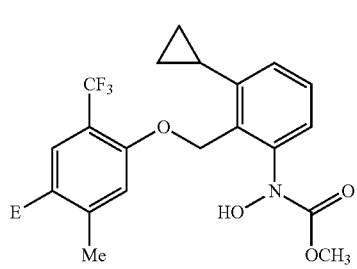
(HE4092)
174
-continued
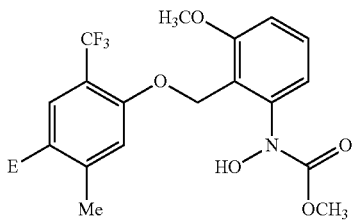
(HE4093)
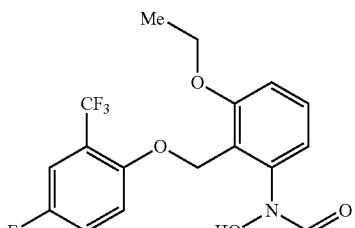
(HE4094)
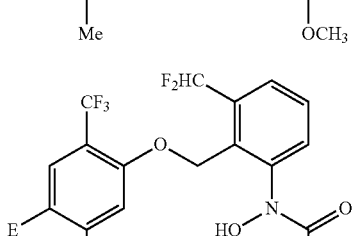
(HE4095)
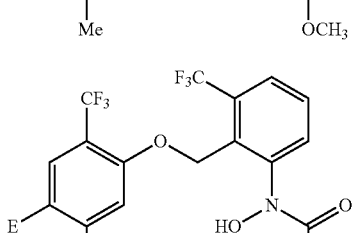
(HE4096)
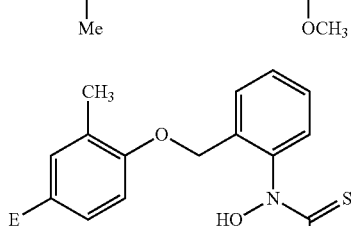
(HF1001)
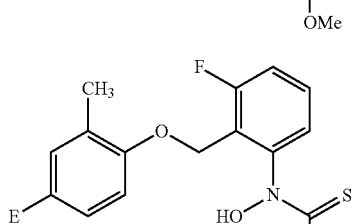
(HF1002)
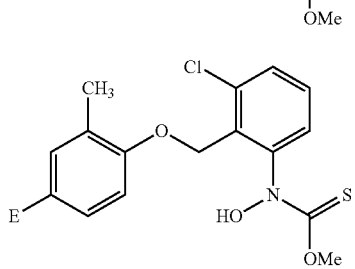
(HF1003)

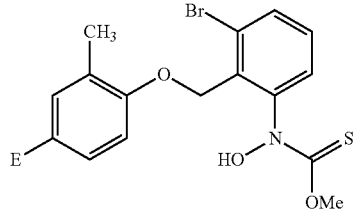 (HF1004)
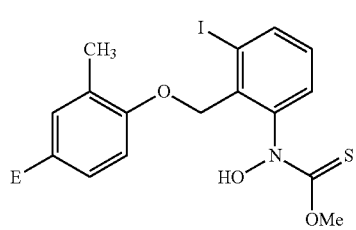 (HF1005)
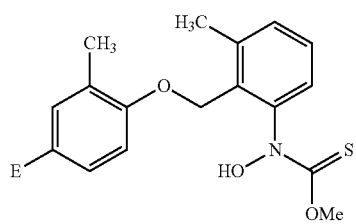 (HF1006)
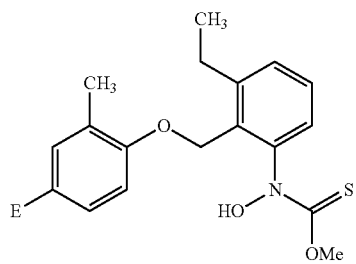 (HF1007)
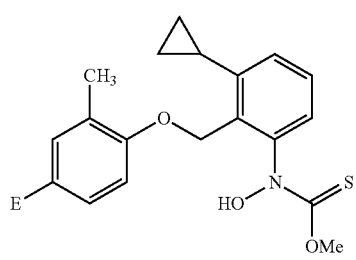 (HF1008)
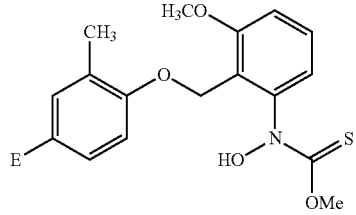 (HF1009)
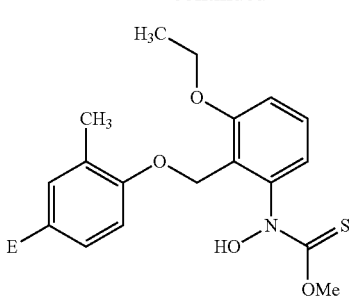 (HF1010)
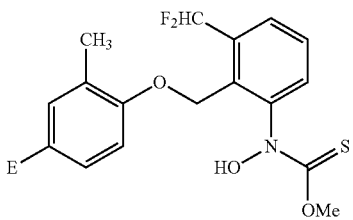 (HF1011)
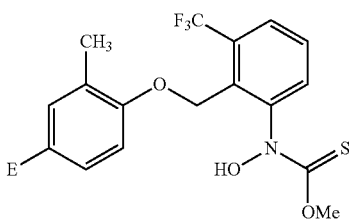 (HF1012)
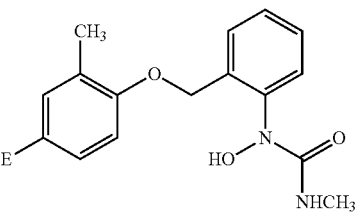 (HF1013)
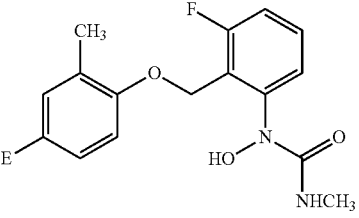 (HF1014)
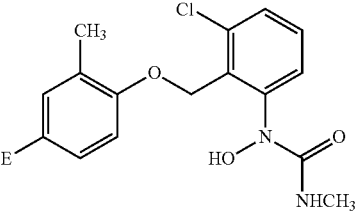 (HF1015)
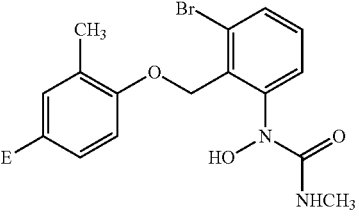 (HF1016)

-continued
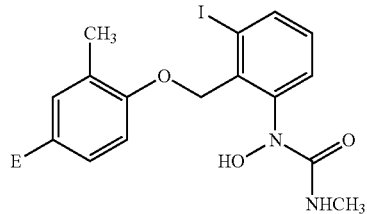
(HF1017)
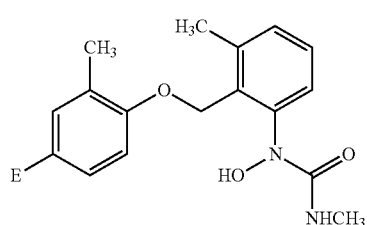
(HF1018)
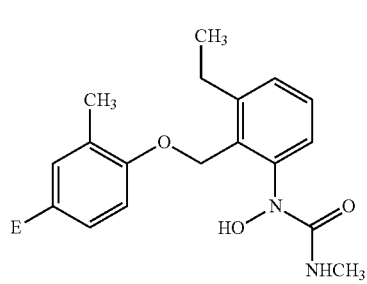
(HF1019)
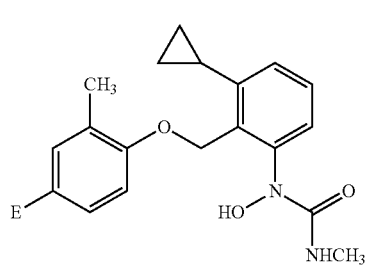
(HF1020)
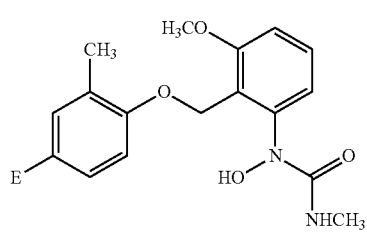
(HF1021)
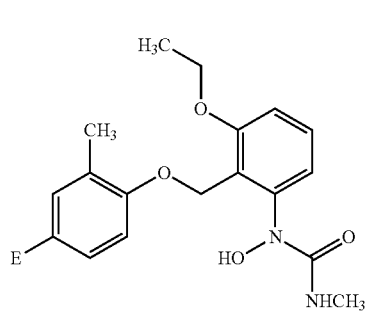
(HF1022)
-continued
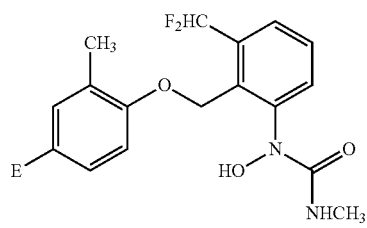
(HF1023)
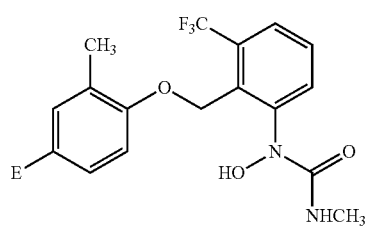
(HF1024)
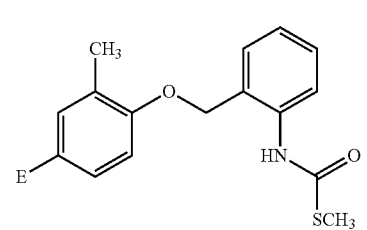
(HF1025)
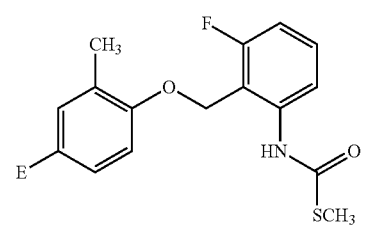
(HF1026)
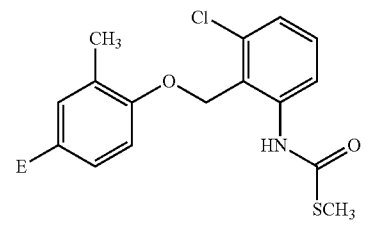
(HF1027)
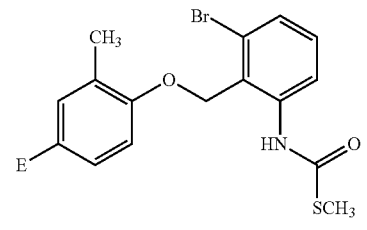
(HF1028)
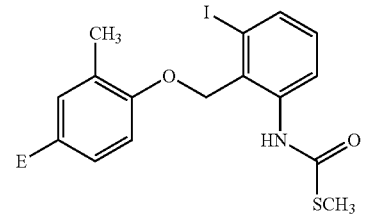
(HF1029)

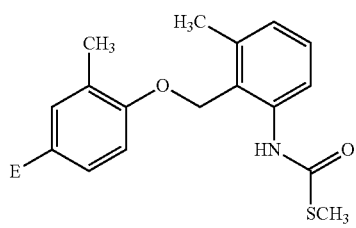
(HF1030)
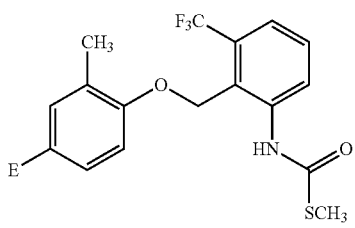
(HF1036)
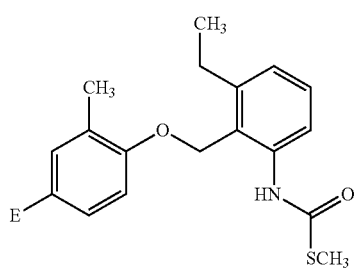
(HF1031)
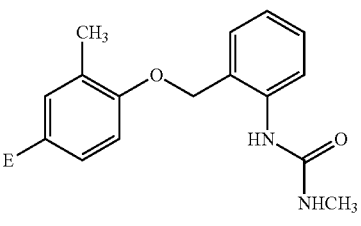
(HF1037)
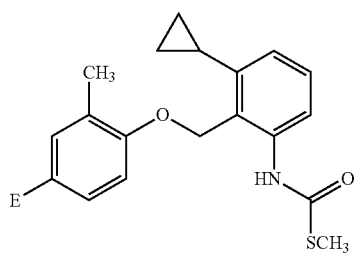
(HF1032)
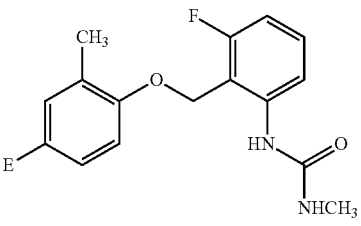
(HF1038)
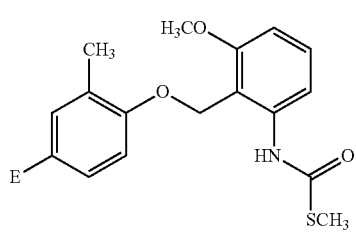
(HF1033)
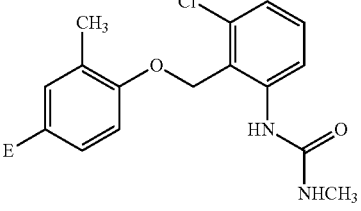
(HF1039)
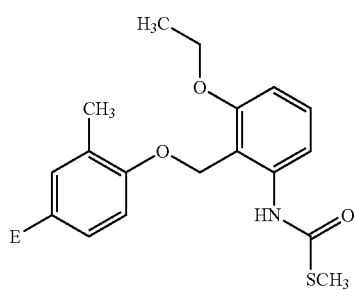
(HF1034)
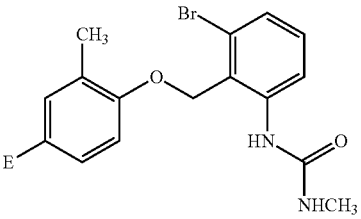
(HF1040)
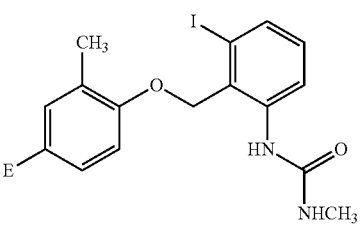
(HF1041)
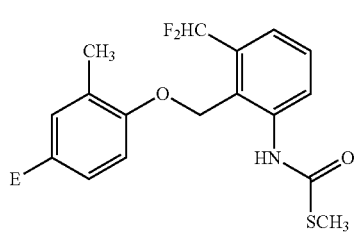
(HF1035)
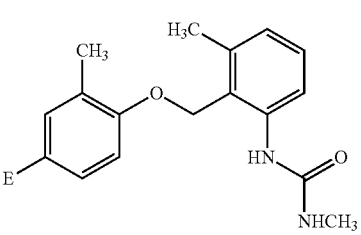
(HF1042)

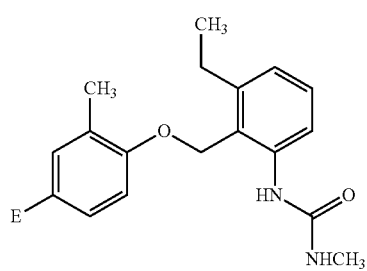 (HF1043)
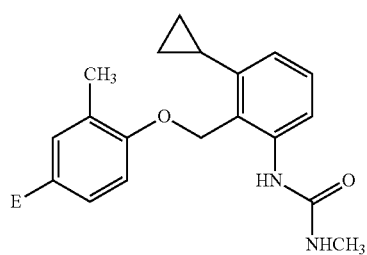 (HF1044)
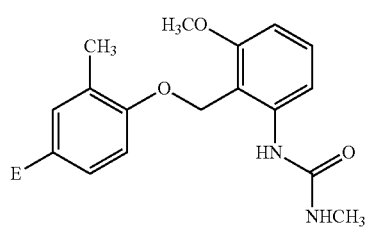 (HF1045)
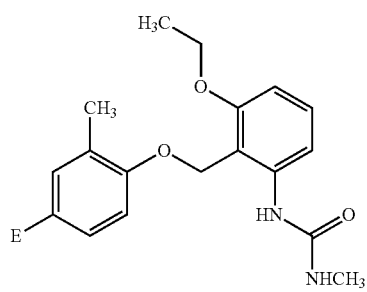 (HF1046)
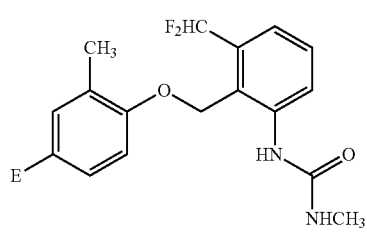 (HF1047)
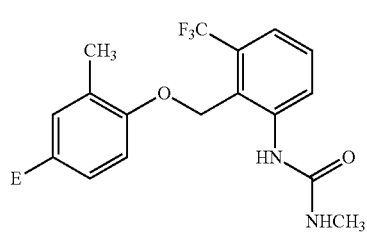 (HF1048)
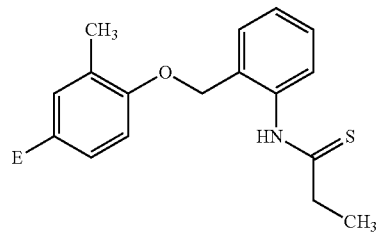 (HF1049)
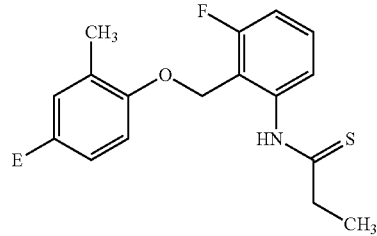 (HF1050)
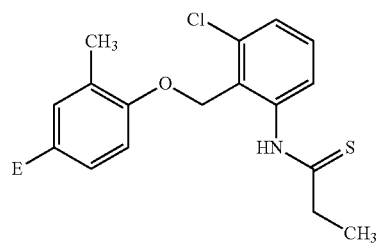 (HF1051)
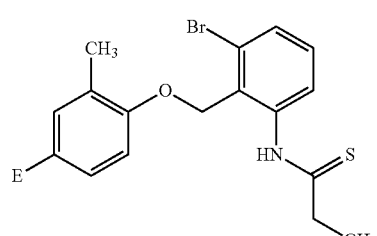 (HF1052)
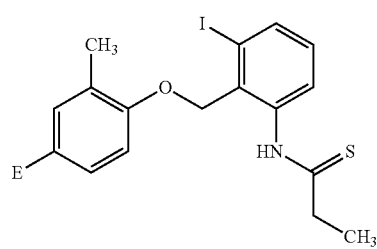 (HF1053)
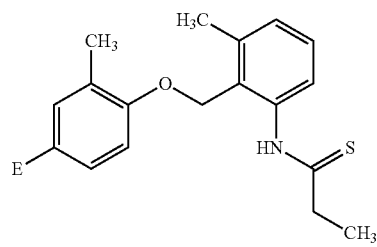 (HF1054)

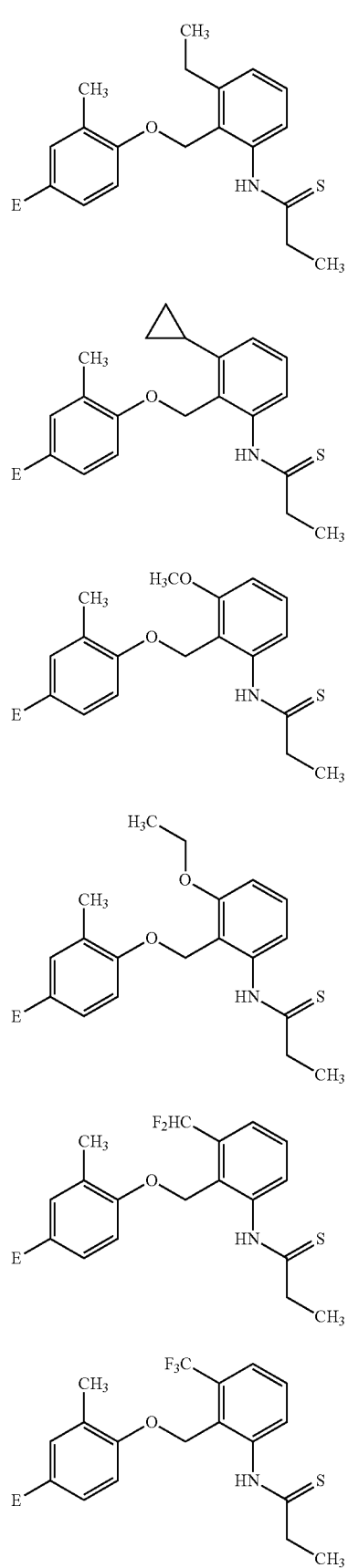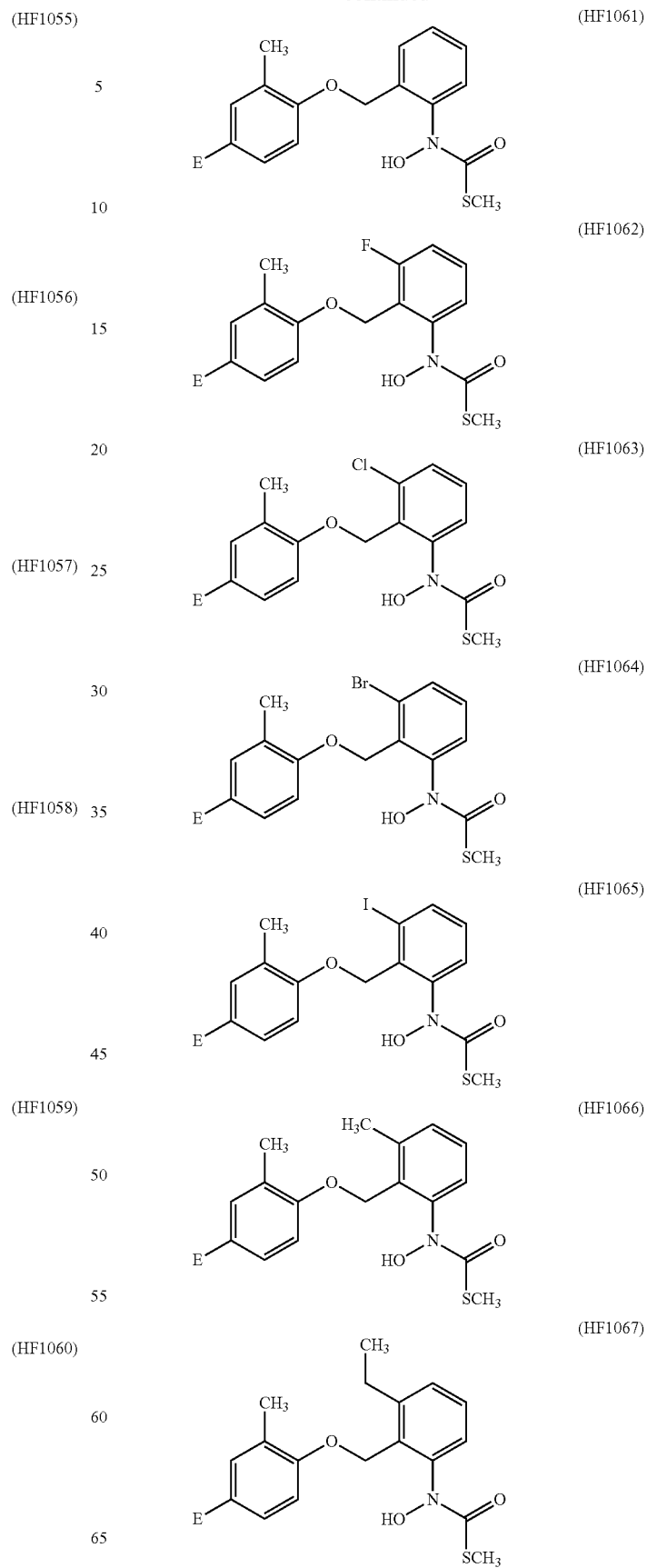

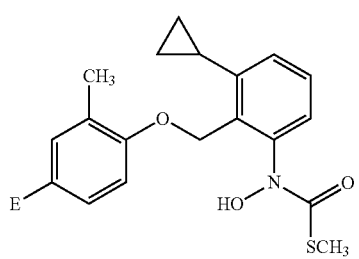
(HF1068)
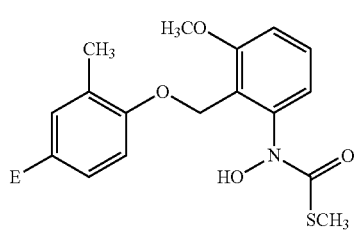
(HF1069)
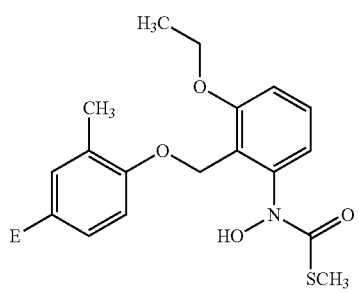
(HF1070)
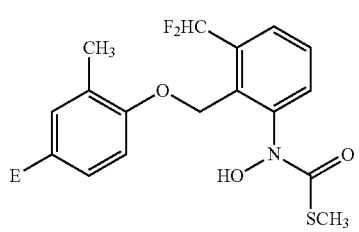
(HF1071)
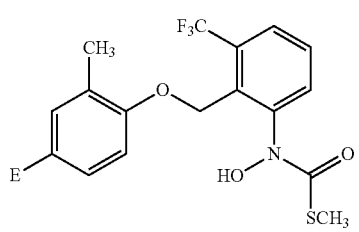
(HF1072)
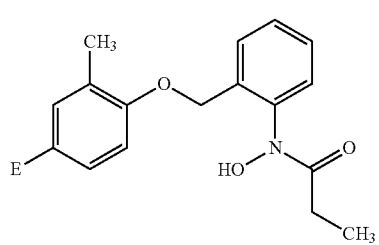
(HF1085)
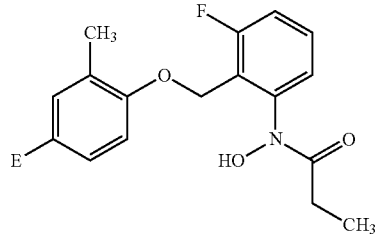
(HF1086)
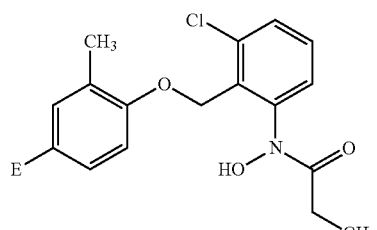
(HF1087)
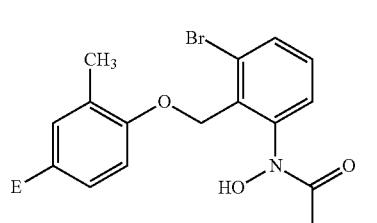
(HF1088)
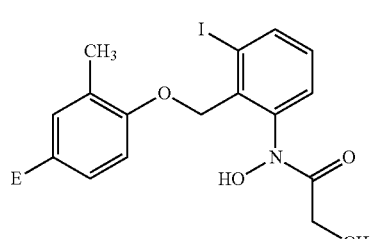
(HF1089)
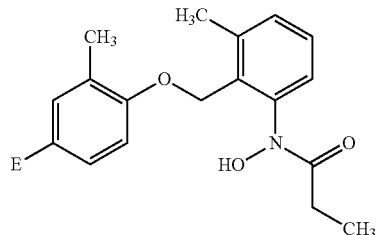
(HF1090)
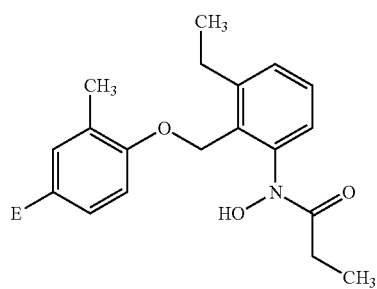
(HF1091)

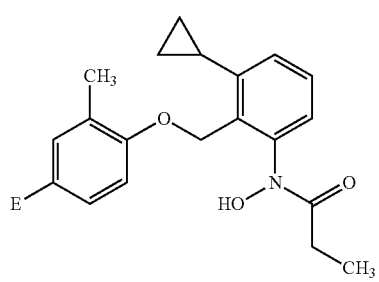
(HF1092)
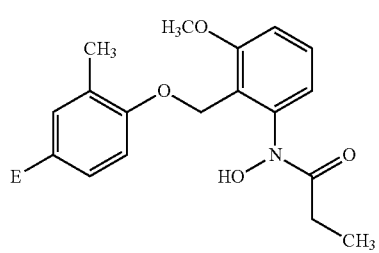
(HF1093)
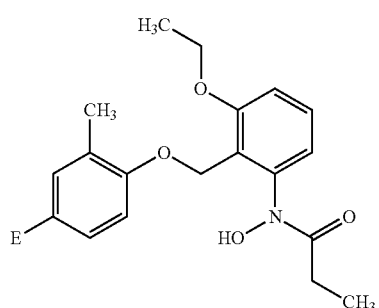
(HF1094)
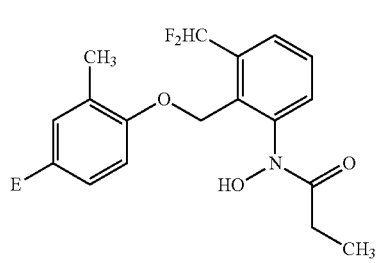
(HF1095)
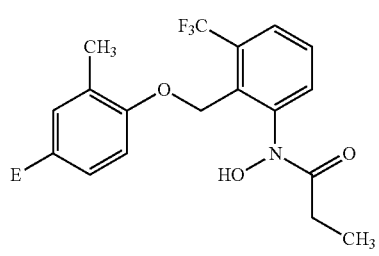
(HF1096)
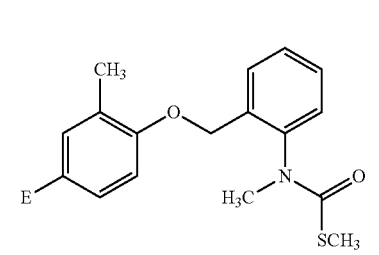
(HF1097)
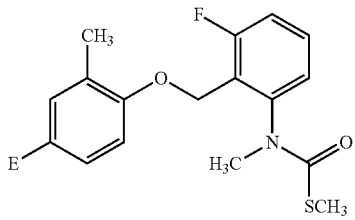
(HF1098)
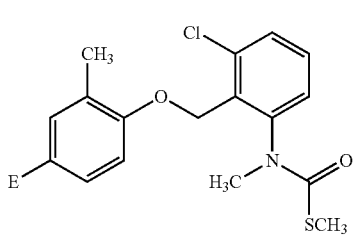
(HF1099)
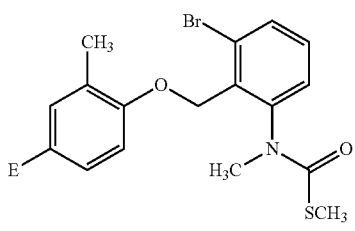
(HF1100)
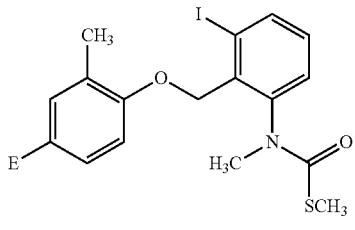
(HF1101)
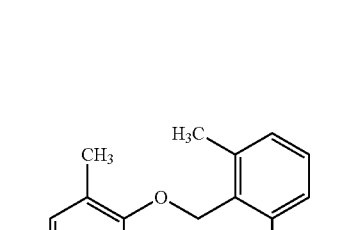
(HF1102)
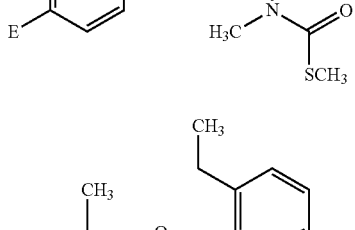
(HF1103)

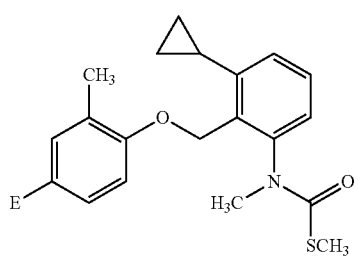
(HF1104)
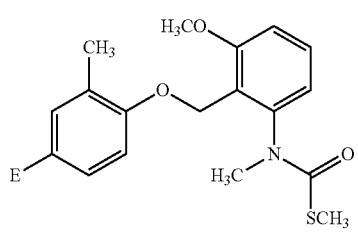
(HF1105)
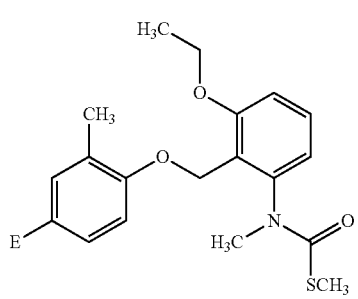
(HF1106)
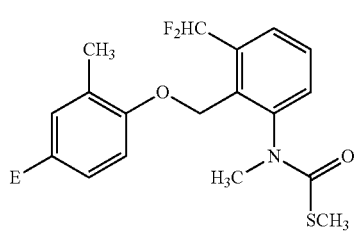
(HF1107)
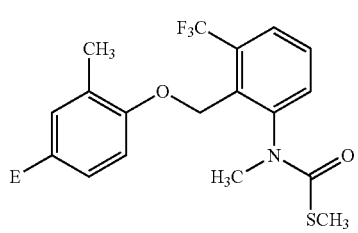
(HF1108)
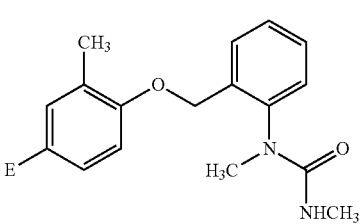
(HF1109)
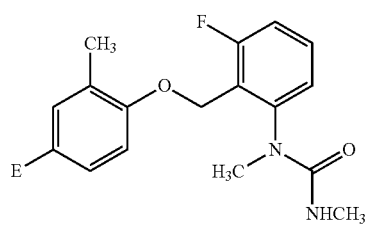
(HF1110)
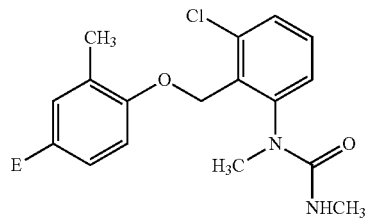
(HF1111)
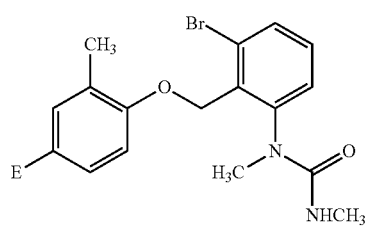
(HF1112)
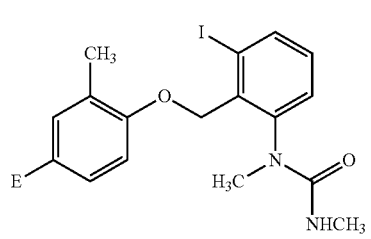
(HF1113)
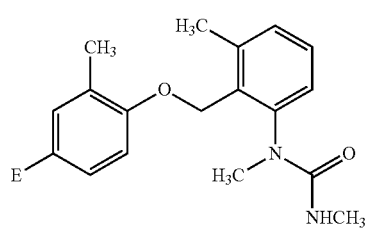
(HF1114)
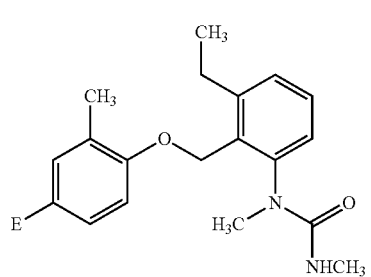
(HF1115)

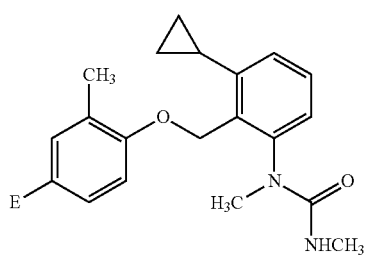
(HF1116)
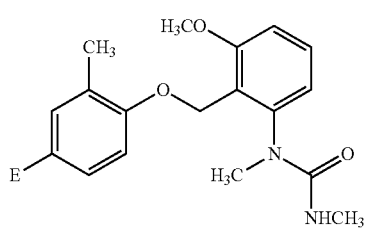
(HF1117)
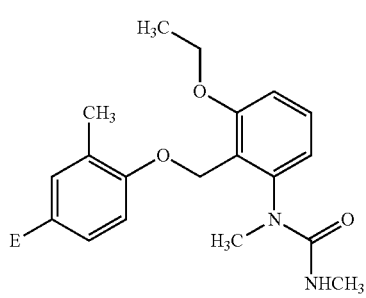
(HF1118)
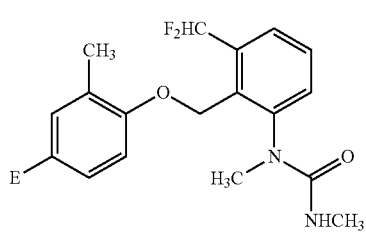
(HF1119)
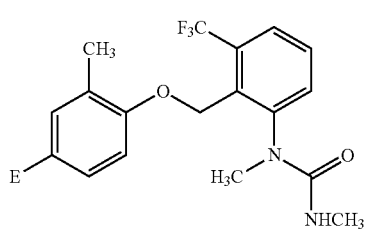
(HF1120)
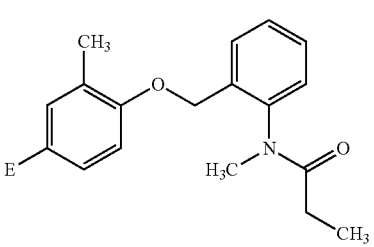
(HF1121)
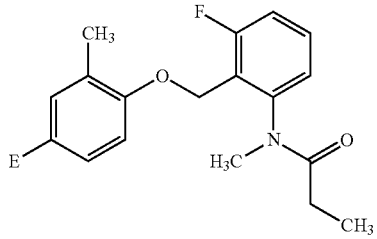
(HF1122)
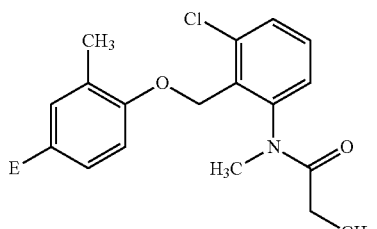
(HF1123)
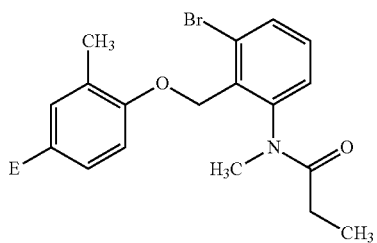
(HF1124)
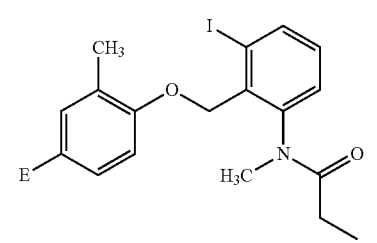
(HF1125)
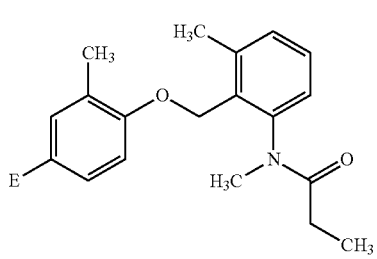
(HF1126)
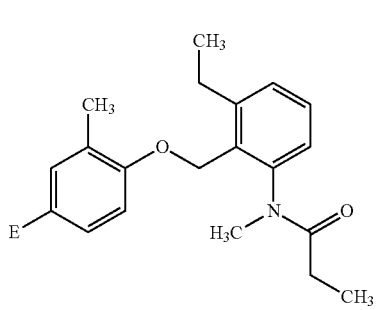
(HF1127)

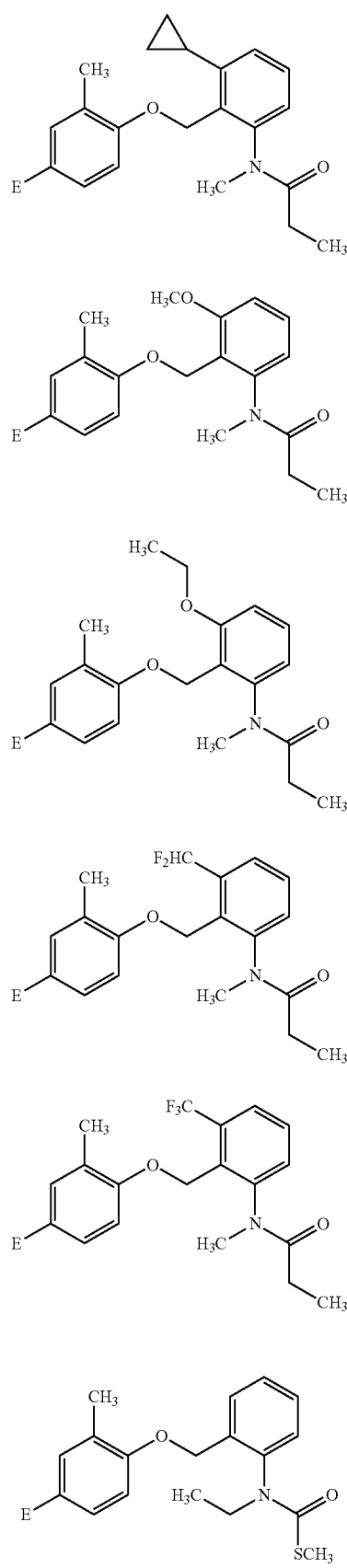
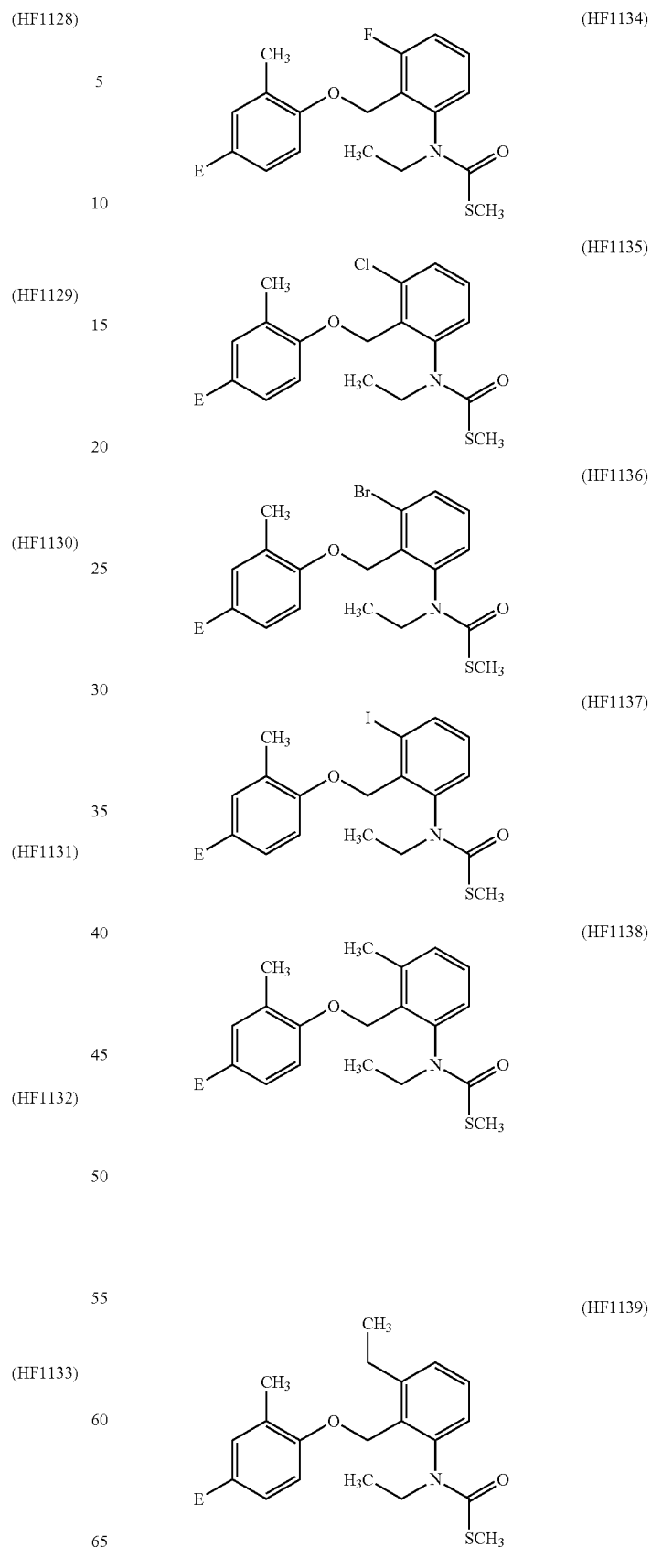

(HF1140)
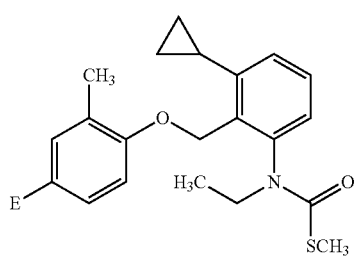
(HF1141)
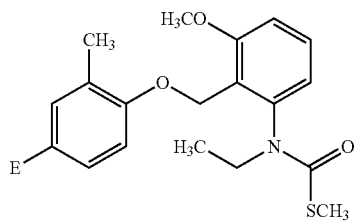
(HF1142)
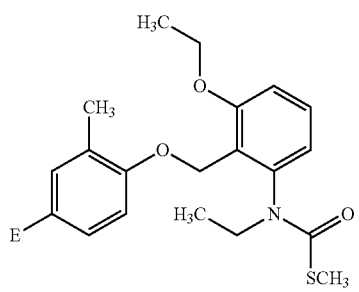
(HF1143)
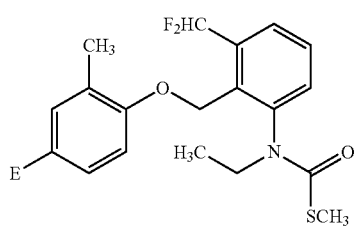
(HF1144)
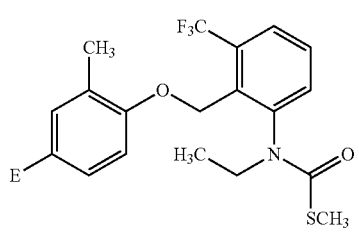
(HF1145)
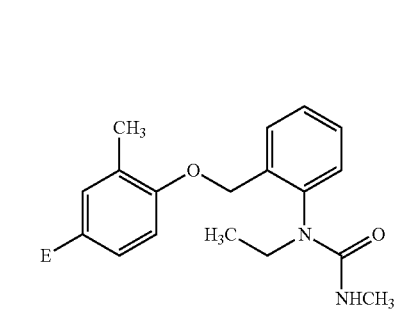
(HF1146)
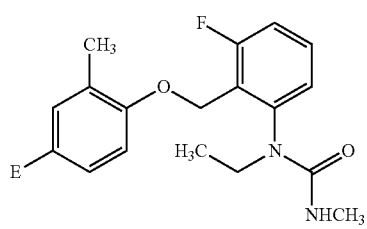
(HF1147)
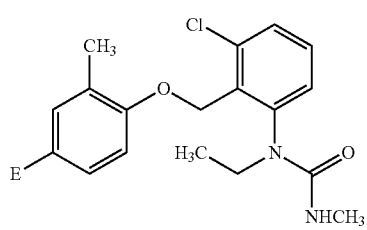
(HF1148)
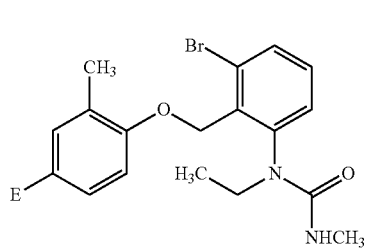
(HF1149)
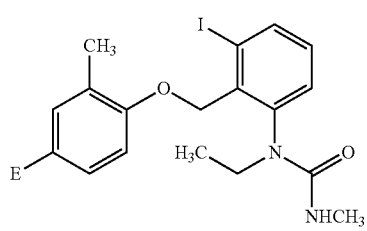
(HF1150)
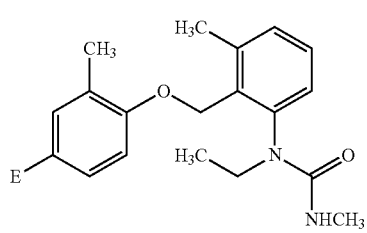
(HF1151)
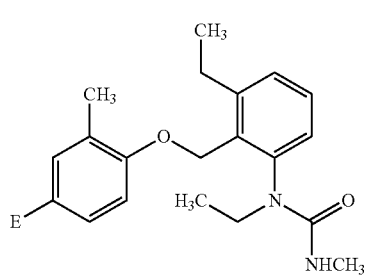

-continued
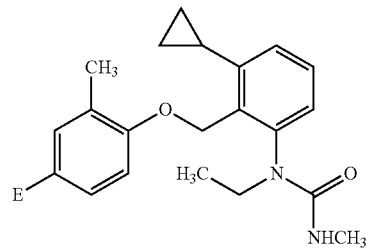 (HF1152)
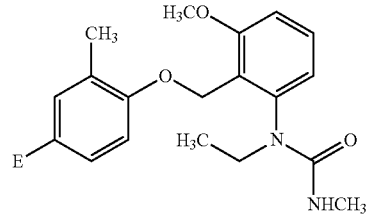 (HF1153)
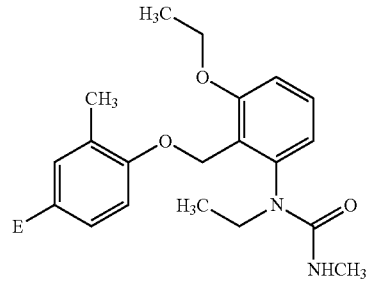 (HF1154)
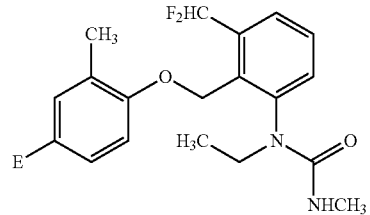 (HF1155)
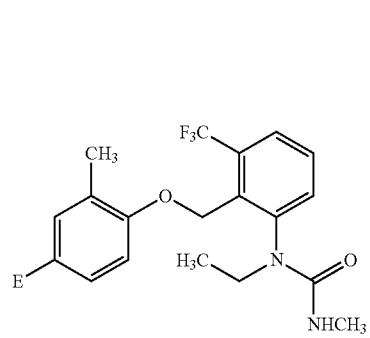 (HF1156)
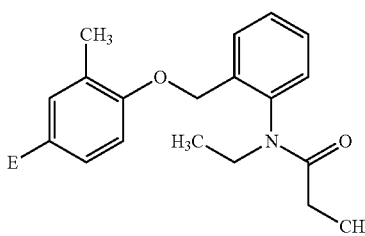 (HF1157)
-continued
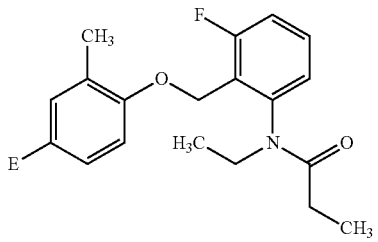 (HF1158)
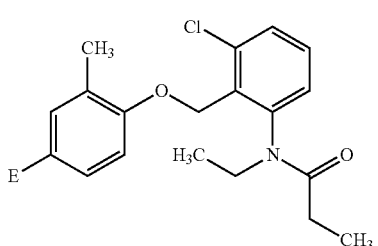 (HF1159)
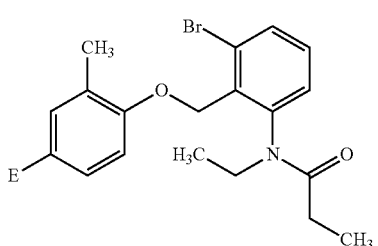 (HF1160)
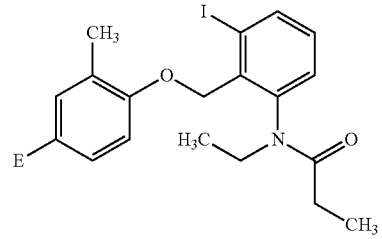 (HF1161)
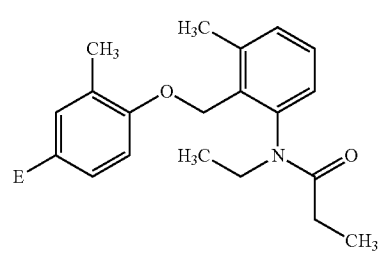 (HF1162)
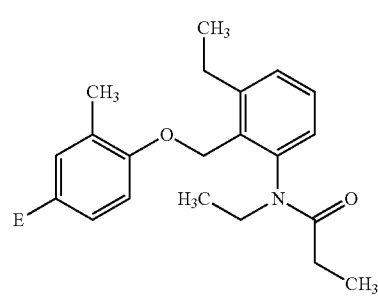 (HF1163)

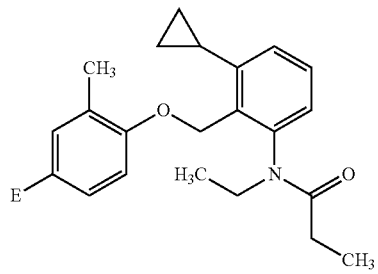
(HF1164)
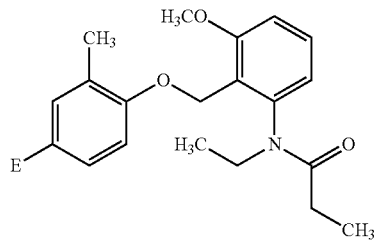
(HF1165)
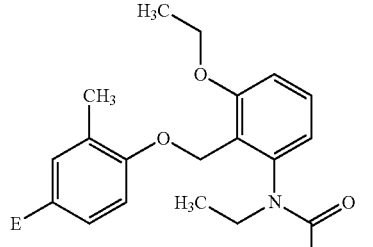
(HF1166)
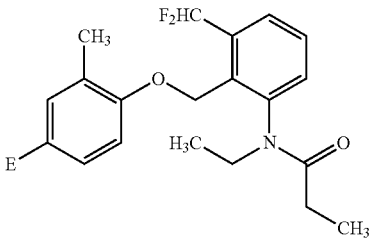
(HF1167)
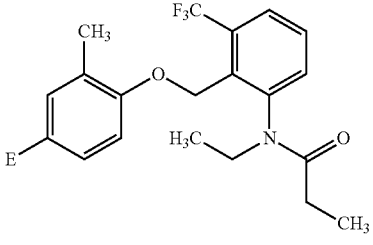
(HF1168)
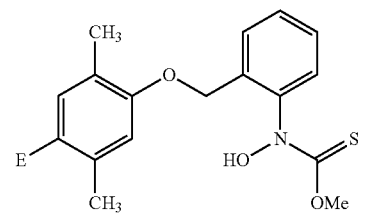
(HF2001)
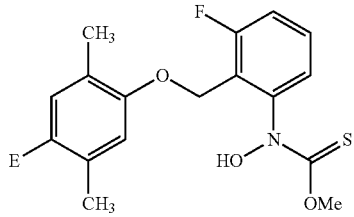
(HF2002)
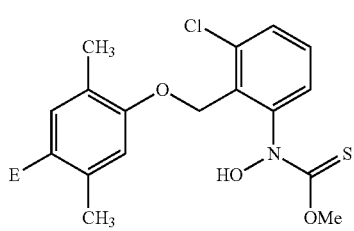
(HF2003)
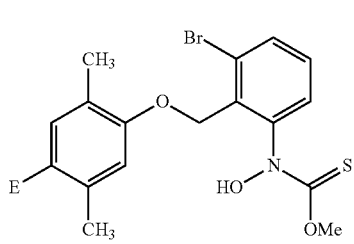
(HF2004)
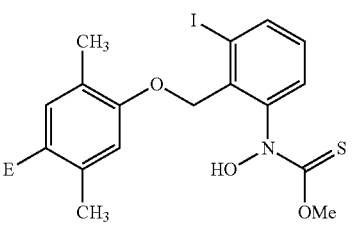
(HF2005)
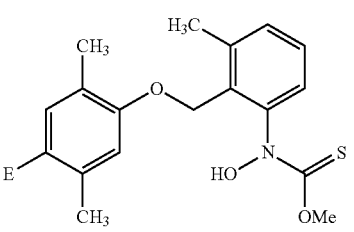
(HF2006)
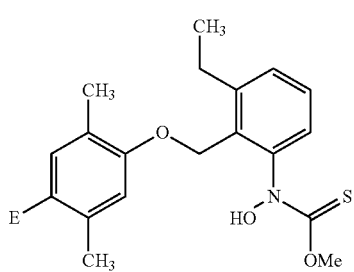
(HF2007)

201
-continued
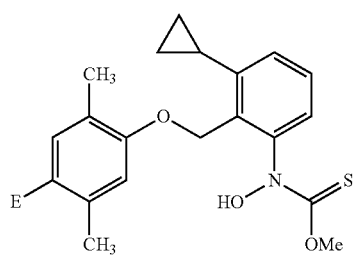
(HF2008)
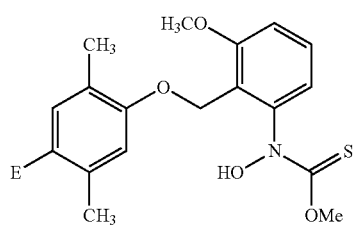
(HF2009)
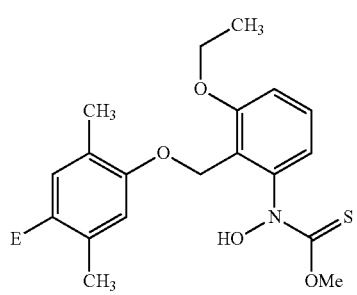
(HF2010)
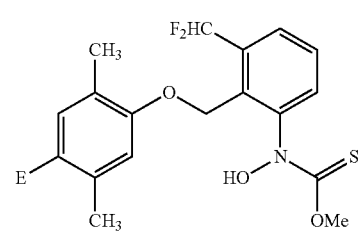
(HF2011)
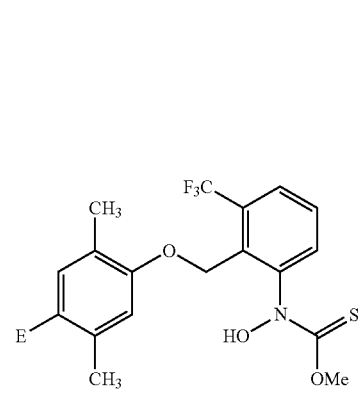
(HF2012)
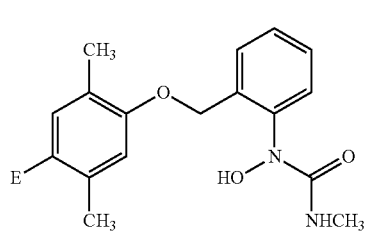
(HF2013)
202
-continued
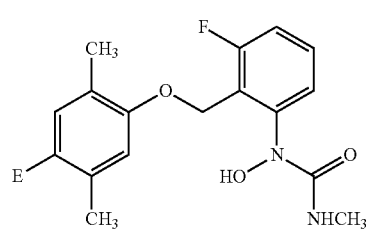
(HF2014)
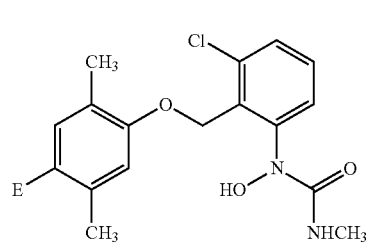
(HF2015)
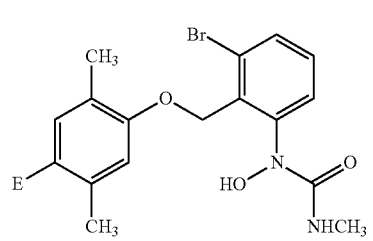
(HF2016)
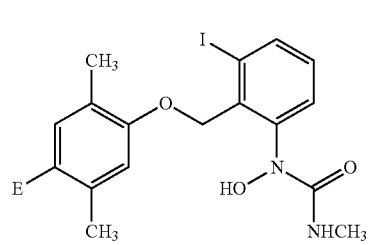
(HF2017)
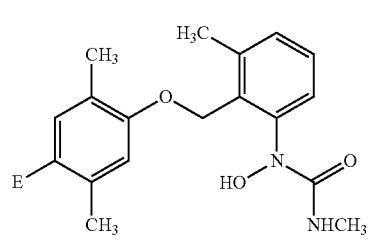
(HF2018)
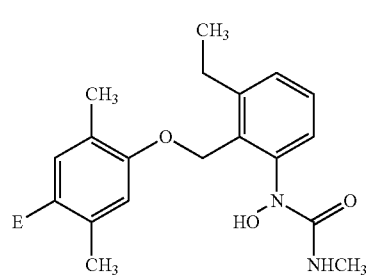
(HF2019)

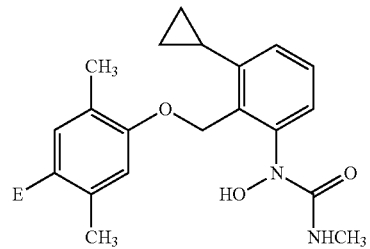
(HF2020)
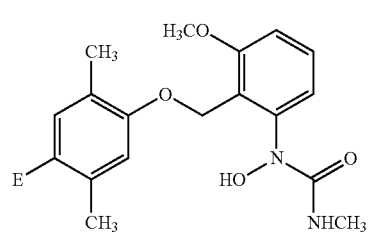
(HF2021)
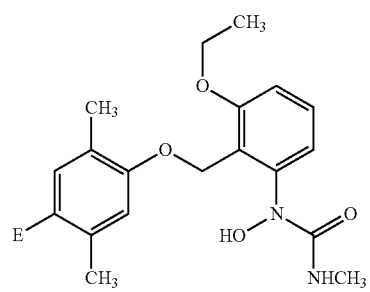
(HF2022)
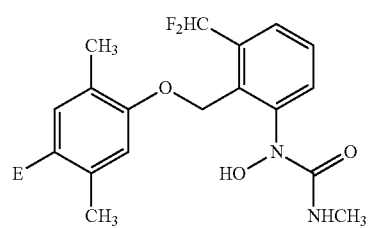
(HF2023)
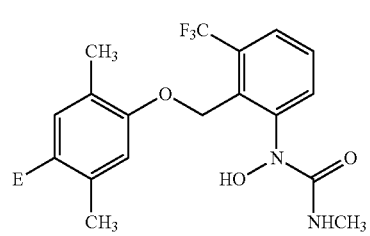
(HF2024)
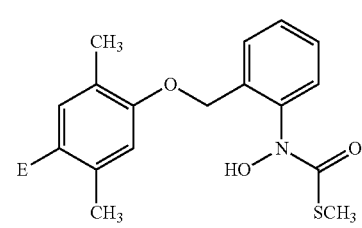
(HF2025)
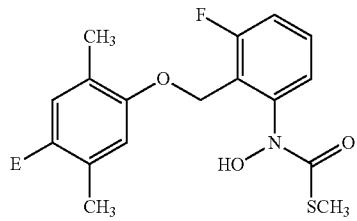
(HF2026)
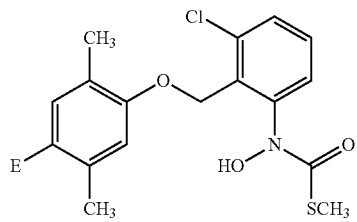
(HF2027)
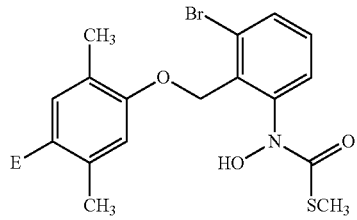
(HF2028)
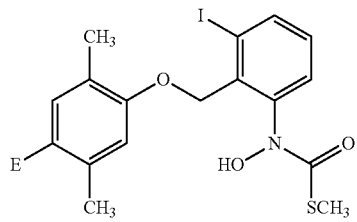
(HF2029)
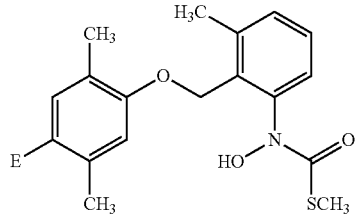
(HF2030)
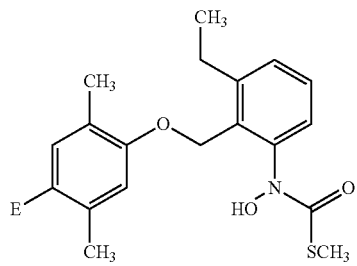
(HF2031)

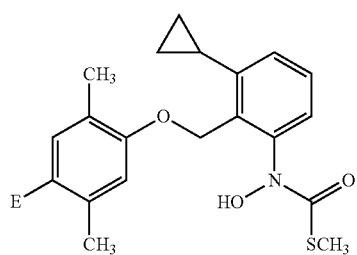
(HF2032)
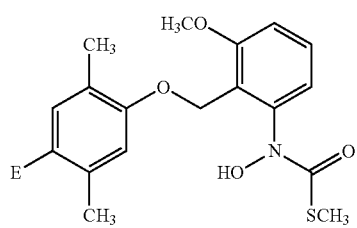
(HF2033)
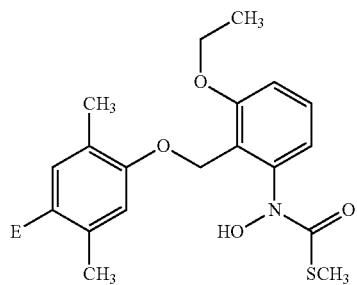
(HF2034)
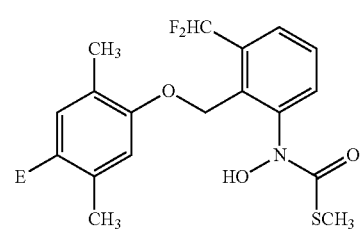
(HF2035)
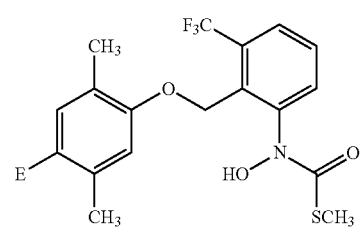
(HF2036)
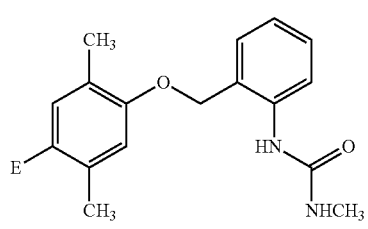
(HF2037)
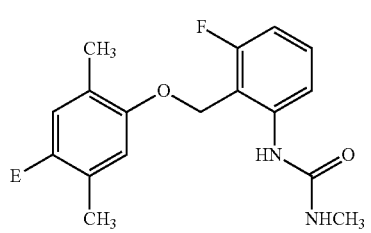
(HF2038)
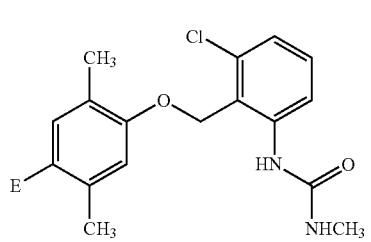
(HF2039)
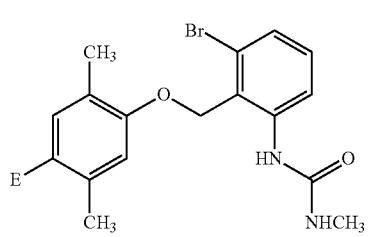
(HF2040)
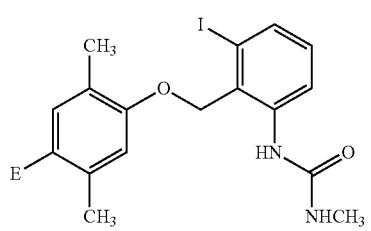
(HF2041)
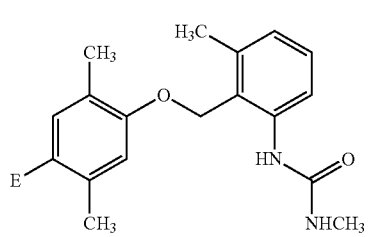
(HF2042)
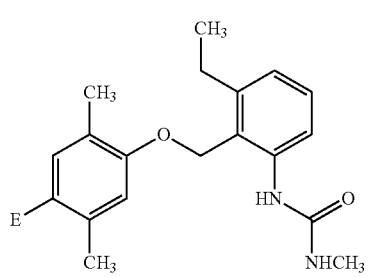
(HF2043)

207
-continued
(HF2044)
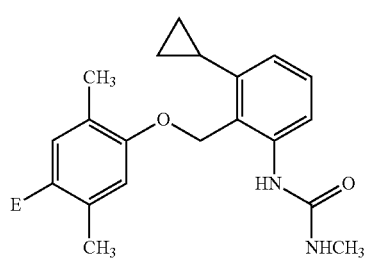
(HF2045)
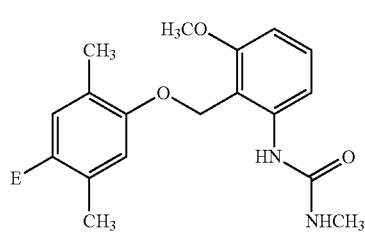
(HF2046)
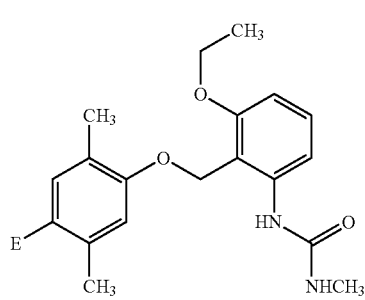
(HF2047)
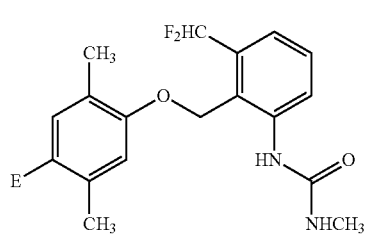
(HF2048)
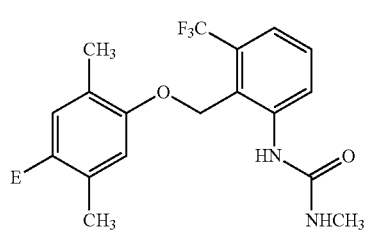
(HF2049)
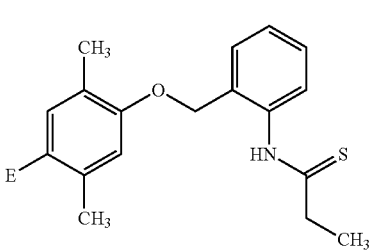
208
-continued
(HF2050)
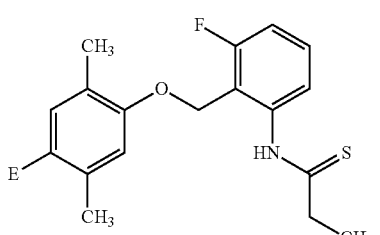
(HF2051)
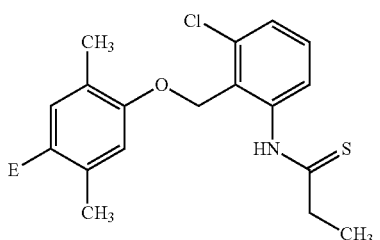
(HF2052)
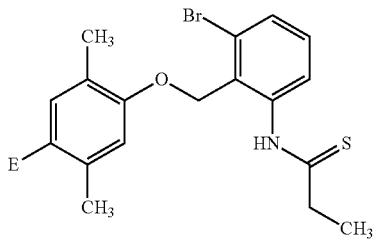
(HF2053)
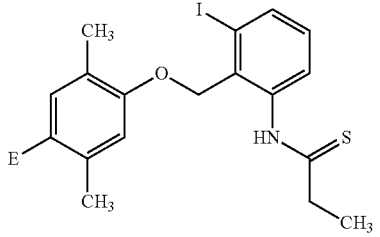
(HF2054)
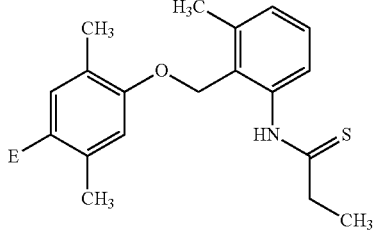
(HF2055)

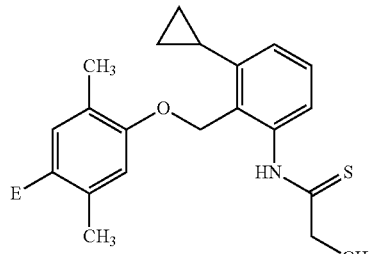 (HF2056)
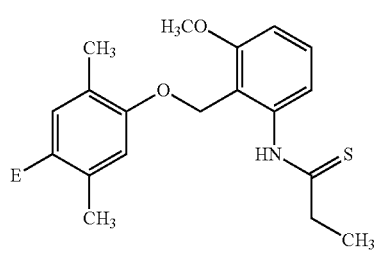 (HF2057)
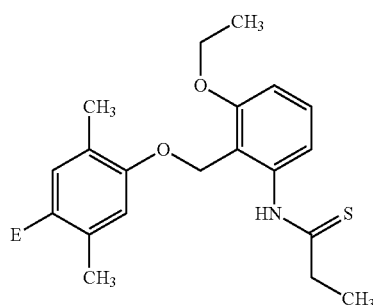 (HF2058)
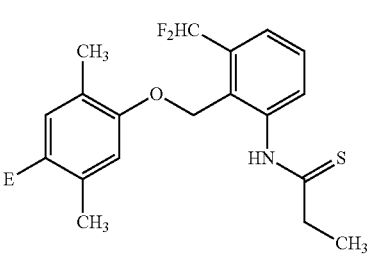 (HF2059)
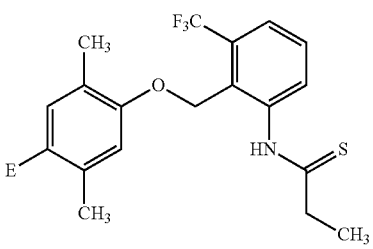 (HF2060)
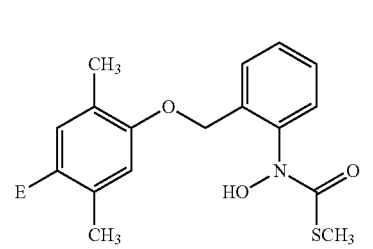 (HF2061)
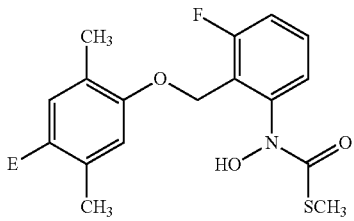 (HF2062)
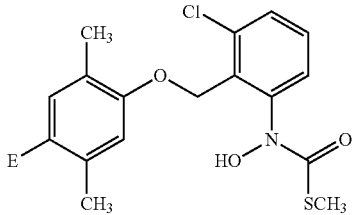 (HF2063)
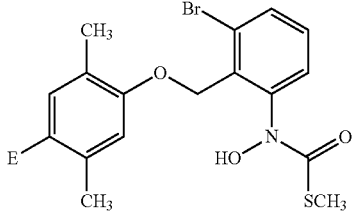 (HF2064)
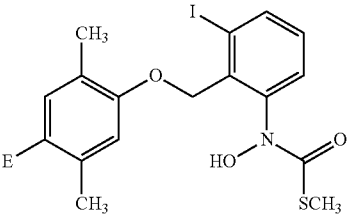 (HF2065)
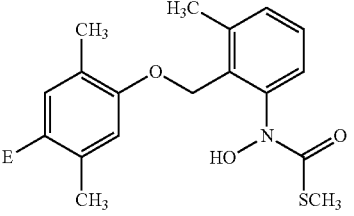 (HF2066)
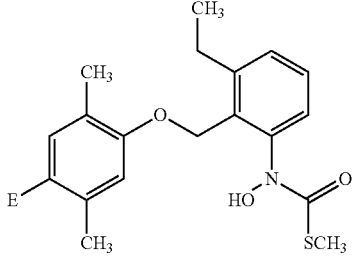 (HF1067)

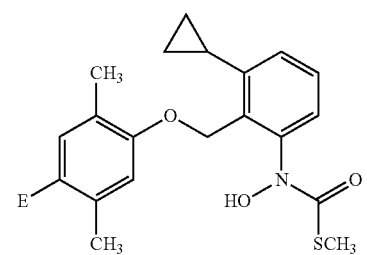
(HF1068)
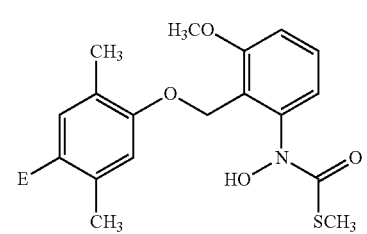
(HF2069)
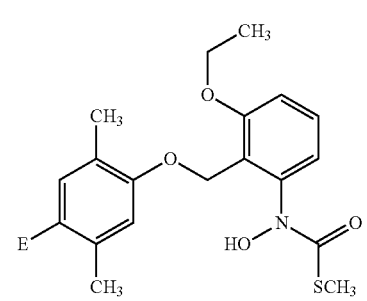
(HF1070)
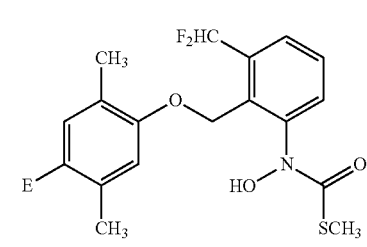
(HF1071)
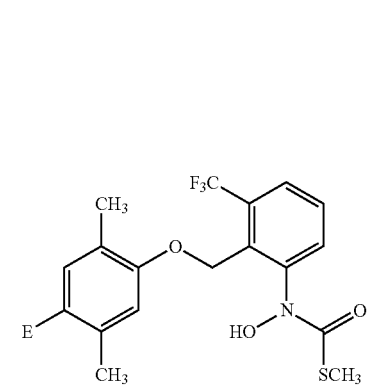
(HF2072)
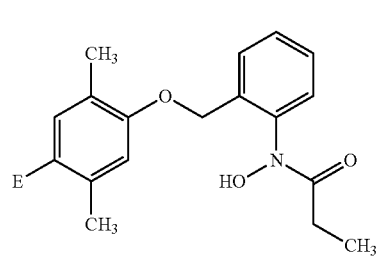
(HF2085)
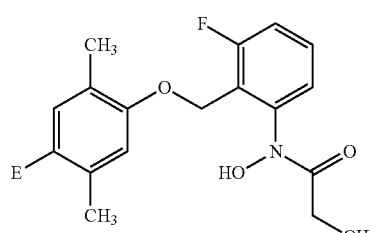
(HF2086)
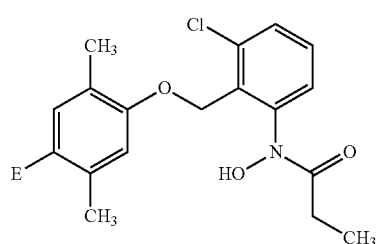
(HF2087)
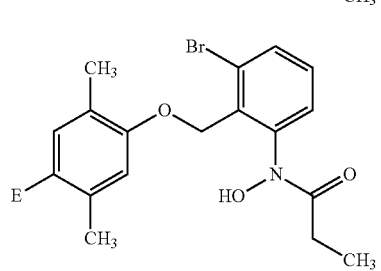
(HF2088)
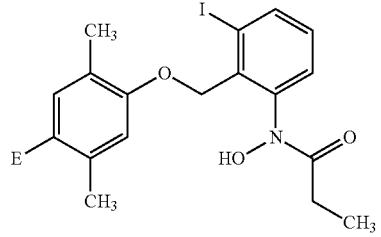
(HF2089)
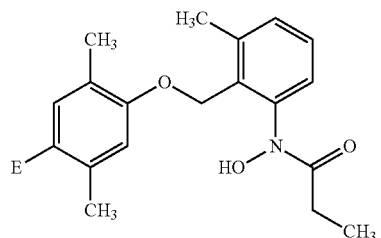
(HF2090)
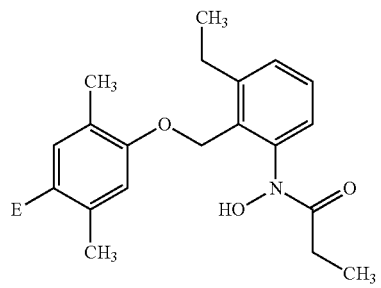
(HF2091)

(HF2092) 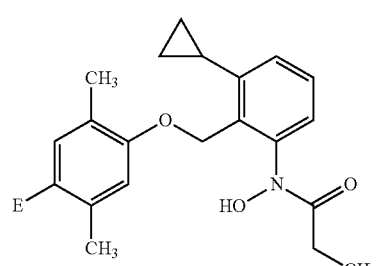
(HF2093) 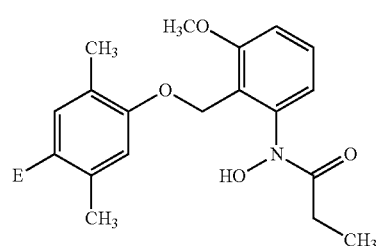
(HF2094) 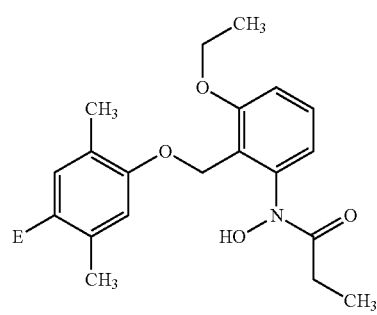
(HF2095) 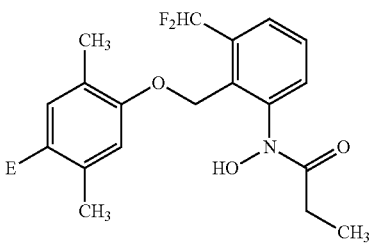
(HF2096) 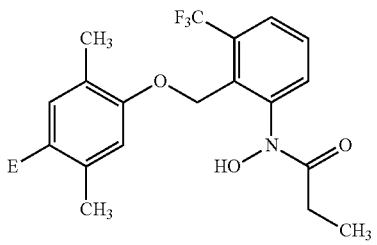
(HF2097) 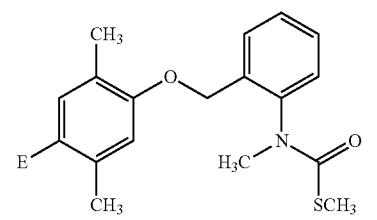
(HF2098) 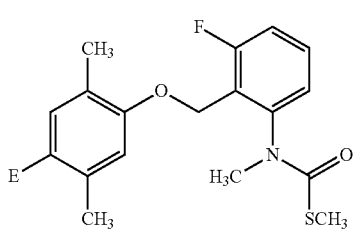
(HF2099) 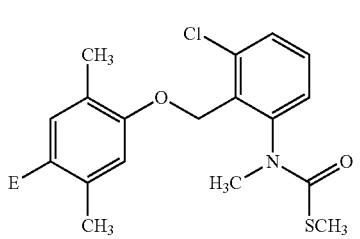
(HF2100) 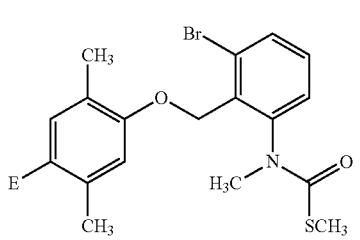
(HF2101) 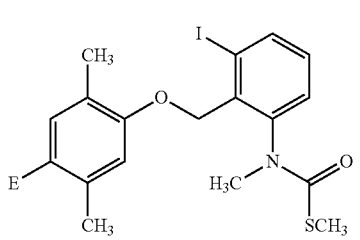
(HF2102) 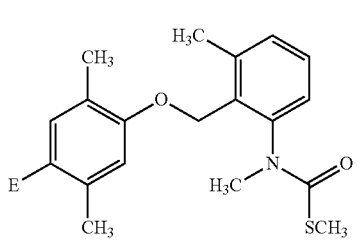
(HF2103) 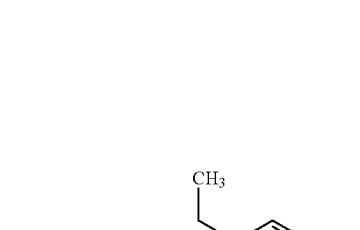

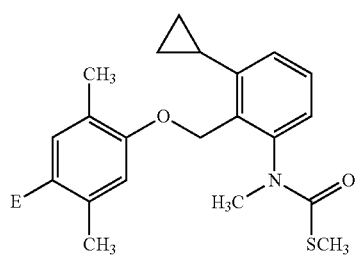
(HF2104)
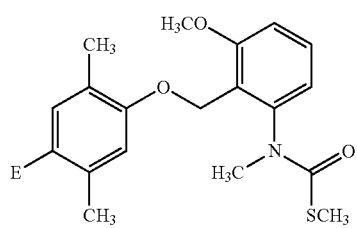
(HF2105)
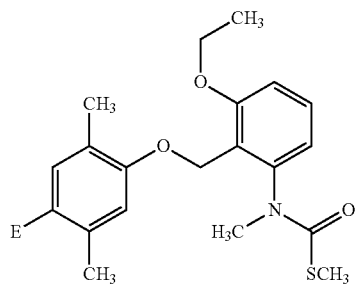
(HF2106)
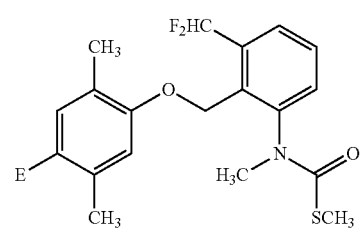
(HF2107)
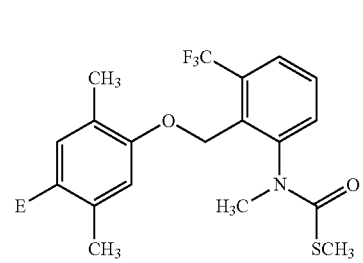
(HF2108)
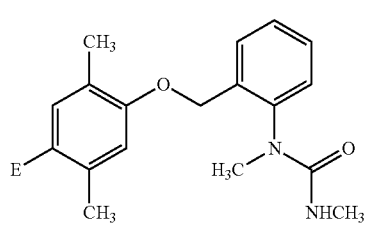
(HF2109)
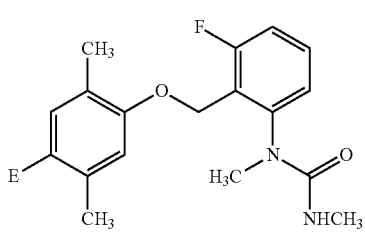
(HF2110)
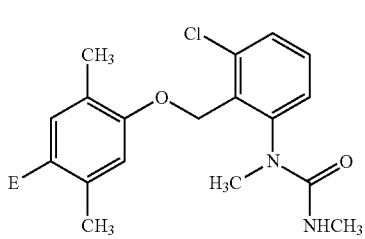
(HF2111)
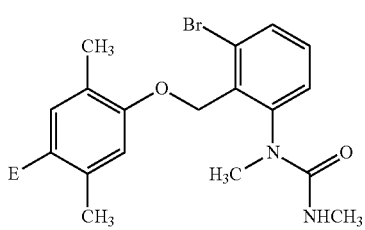
(HF2112)
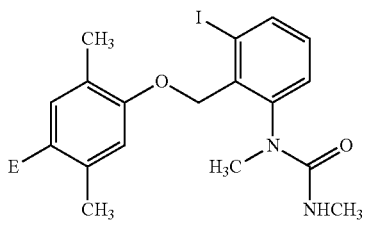
(HF2113)
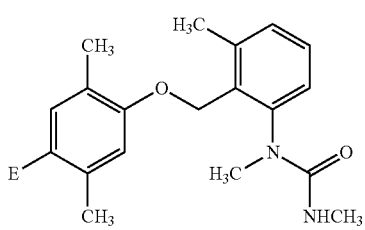
(HF2114)
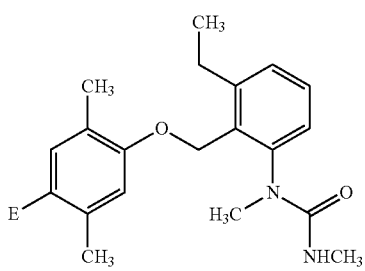
(HF2115)

217
-continued
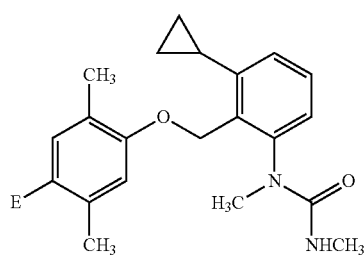 (HF2116)
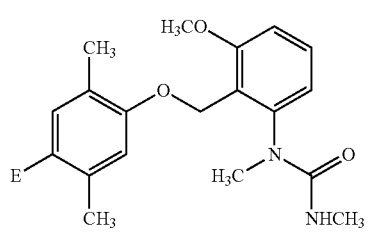 (HF2117)
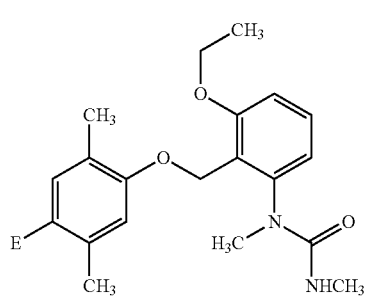 (HF2118)
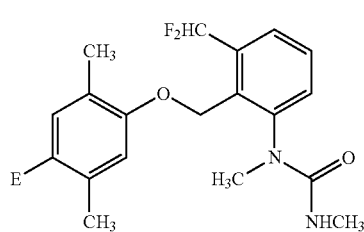 (HF2119)
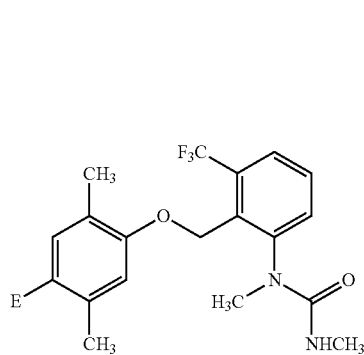 (HF2120)
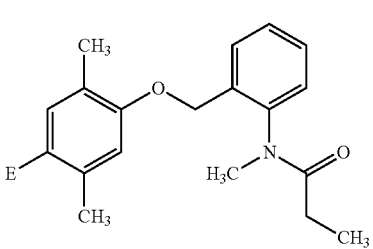 (HF2121)
218
-continued
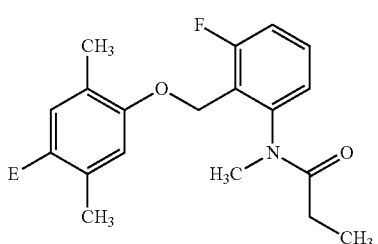 (HF2122)
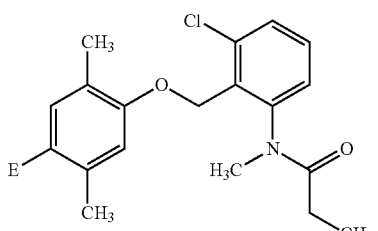 (HF2123)
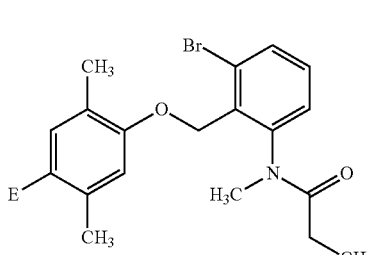 (HF2124)
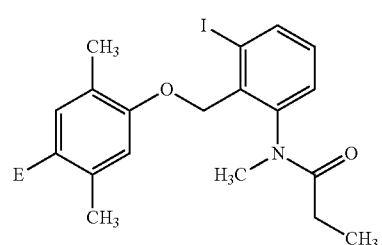 (HF2125)
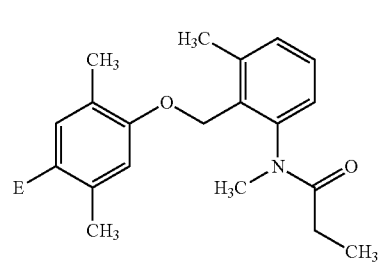 (HF2126)
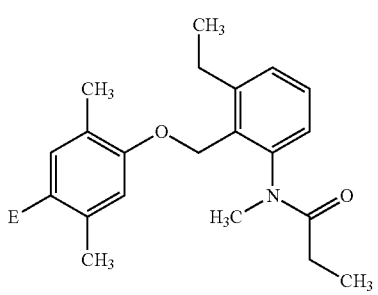 (HF2127)

(HF2128) 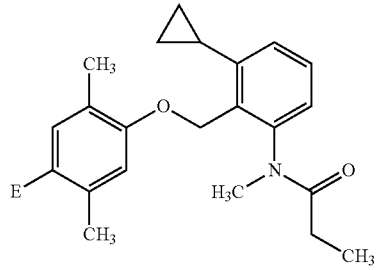
(HF2129) 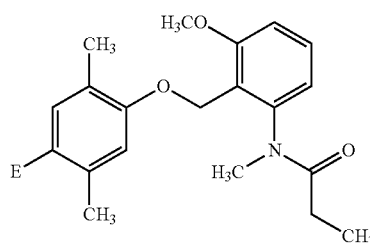
(HF2130) 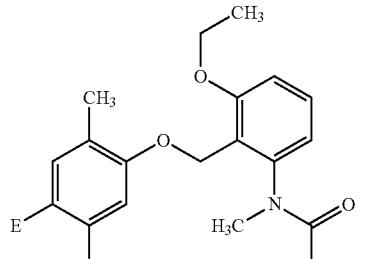
(HF2131) 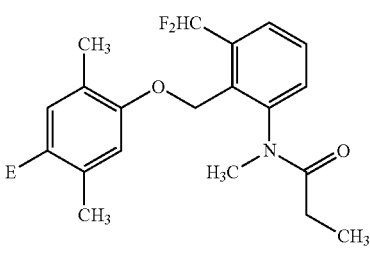
(HF2132) 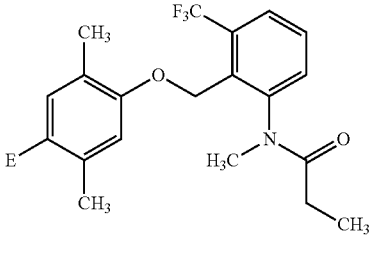
(HG1001) 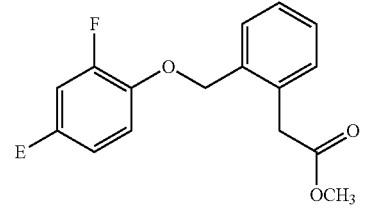
(HG1002) 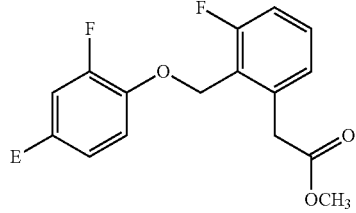
(HG1003)
(HF1004)
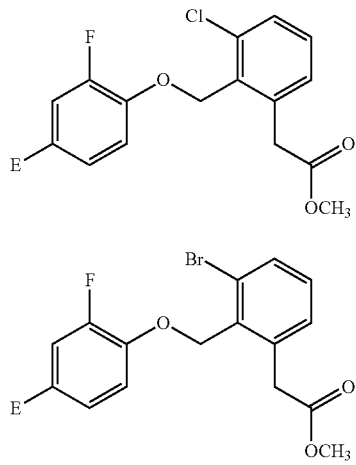
(HF1005)
(HG1006) 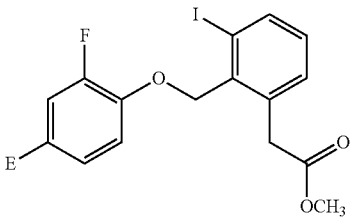
(HG1007) 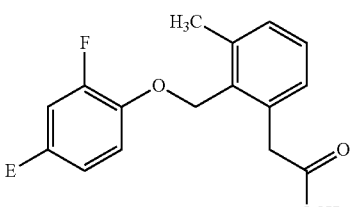
(HG1008) 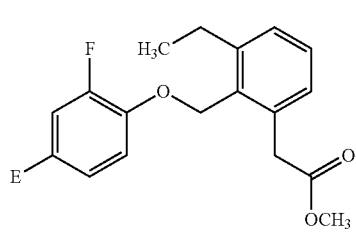

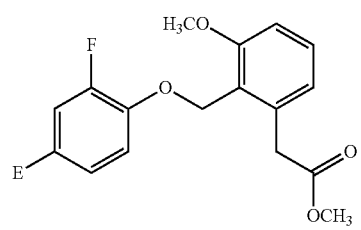
(HG1009)
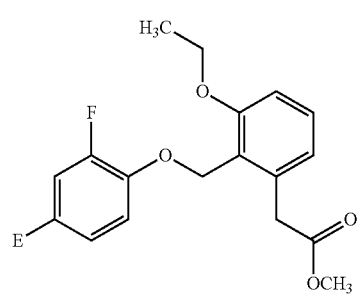
(HG1010)
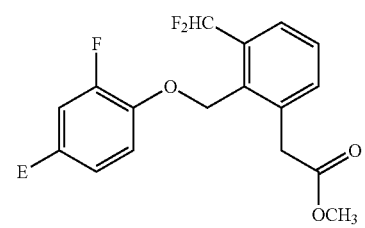
(HG1011)
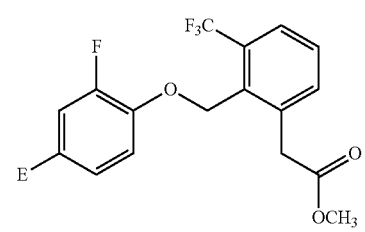
(HG1012)
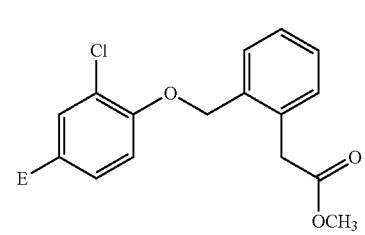
(HG1025)
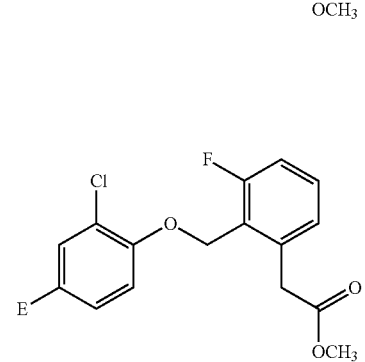
(HG1026)
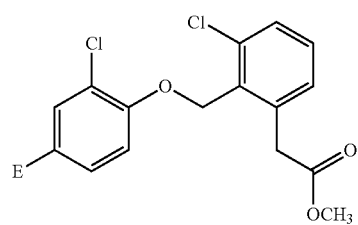
(HG1027)
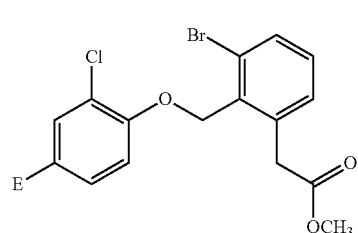
(HF1028)
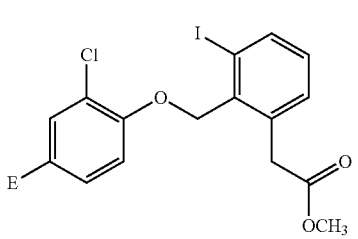
(HF1029)
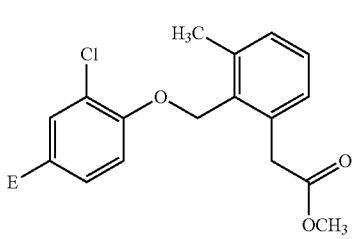
(HG1030)
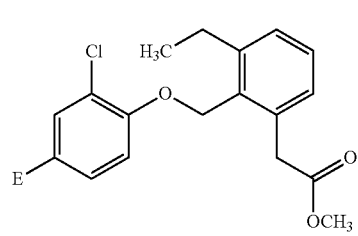
(HG1031)
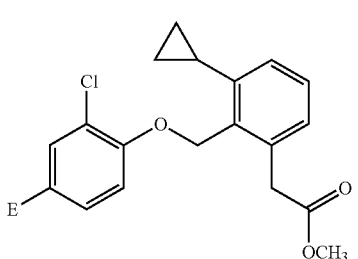
(HG1032)
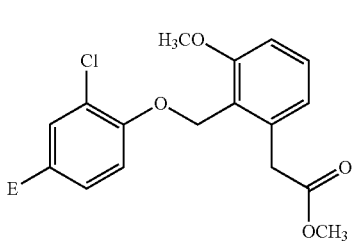
(HG1033)

223
-continued
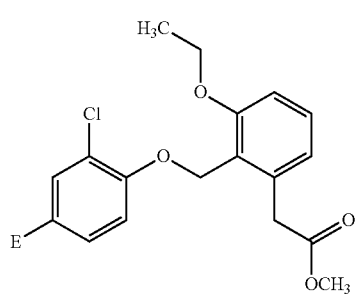
(HG1034)
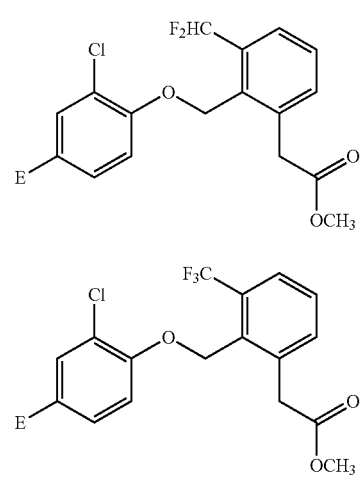
(HG1035)
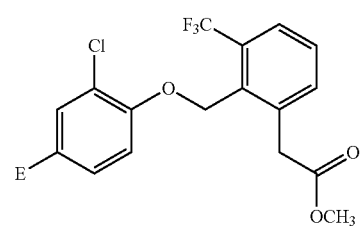
(HG1036)
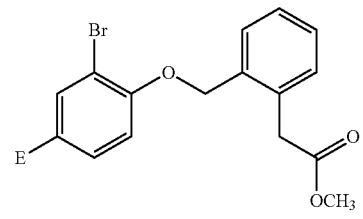
(HG1037)
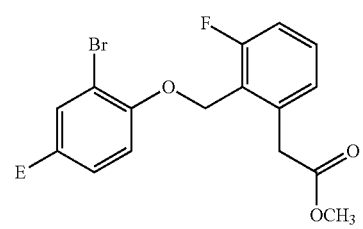
(HG1038)
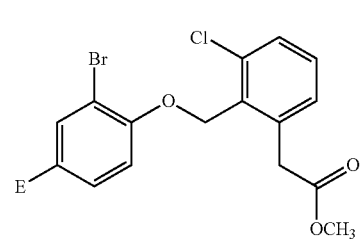
(HG1039)
224
-continued
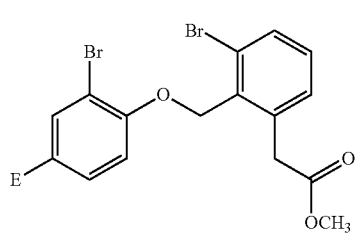
(HF1040)
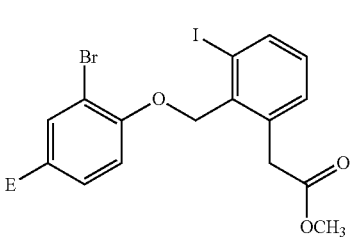
(HF1041)
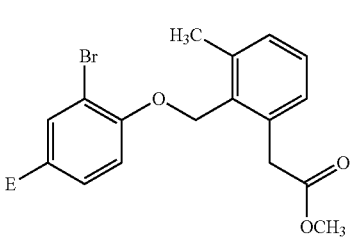
(HG1042)
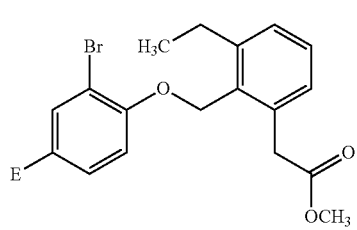
(HG1043)
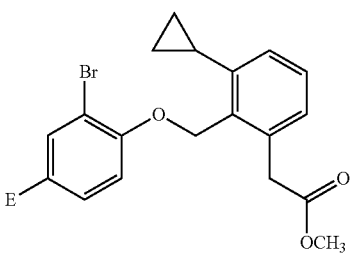
(HG1044)
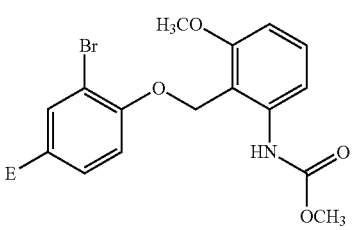
(HG1045)

(HG1046)
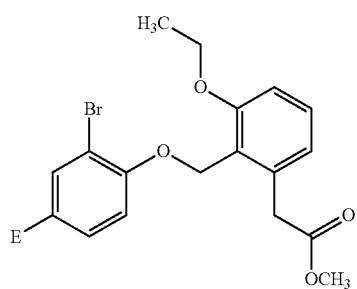
(HG1047)
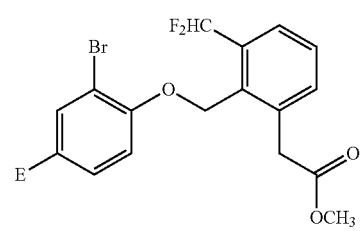
(HG1048)
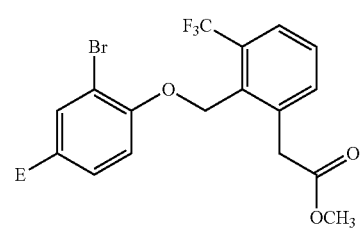
(HG1049)
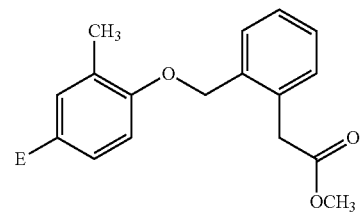
(HG1050)
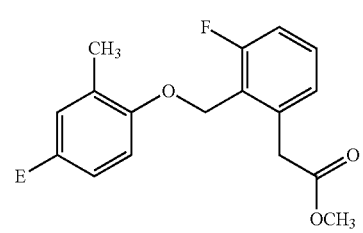
(HG1051)
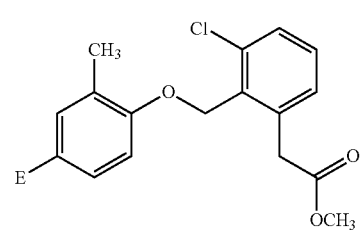
(HF1052)
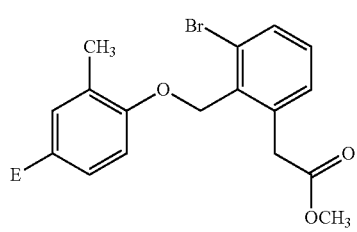
(HF1053)
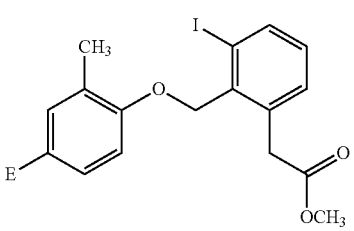
(HG1054)
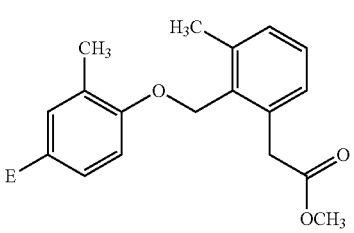
(HG1055)
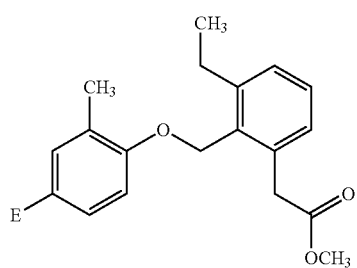
(HG1056)
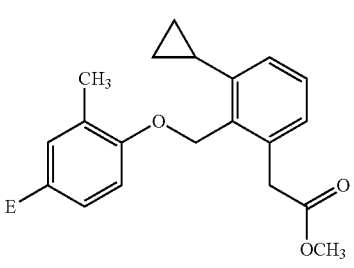
(HG1057)
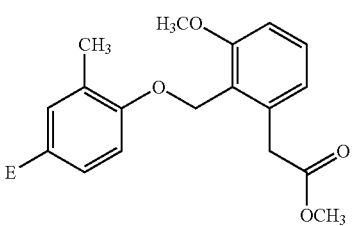

| | |
|---|---|
| (HG1058) 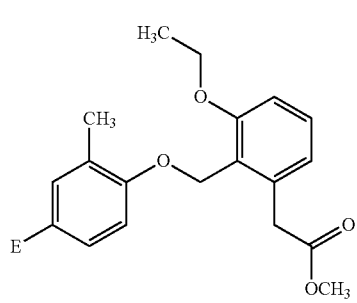 | (HF1064) 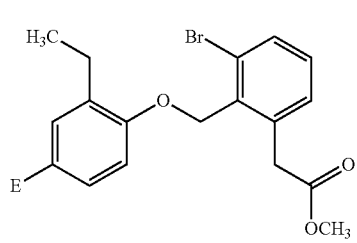 |
| (HG1059) 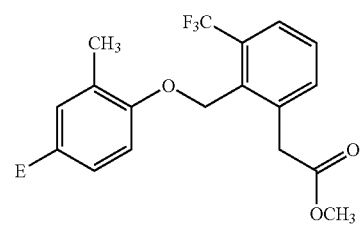 | (HF1065) 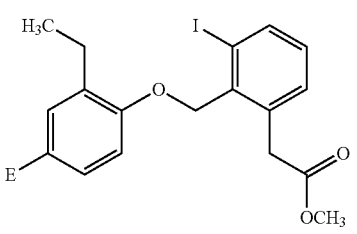 |
| (HG1060) 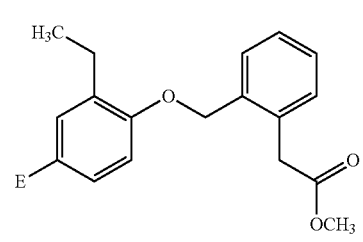 | (HG1066) 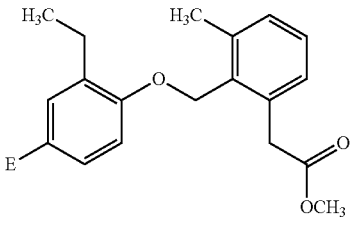 |
| (HG1061) 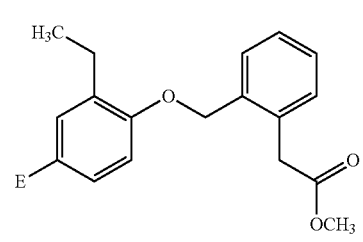 | (HG1067) 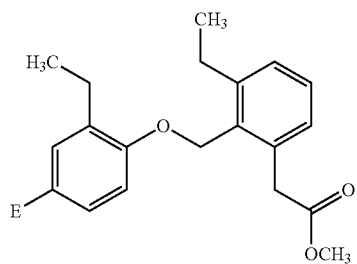 |
| (HG1062) 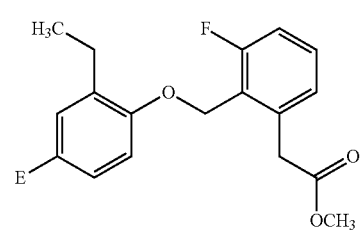 | (HG1068) 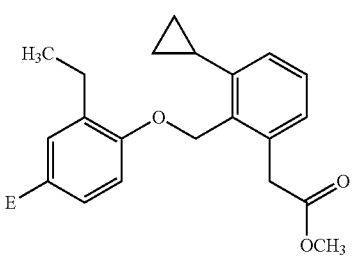 |
| (HG1063) 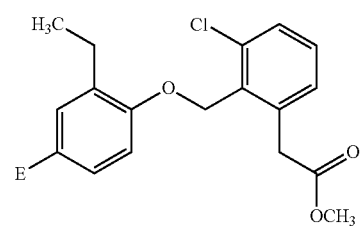 | (HG1069) 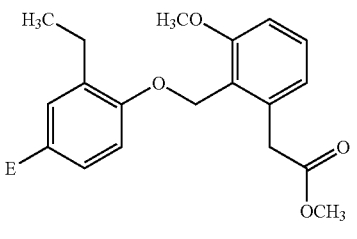 |

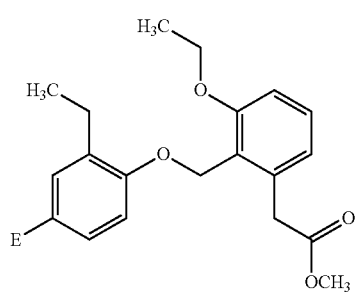
(HG1070)
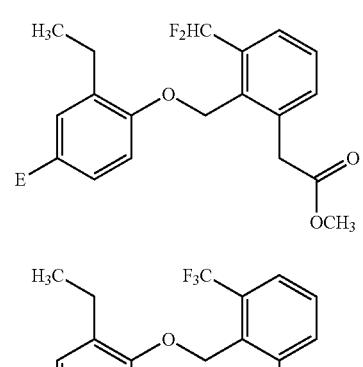
(HG1071)
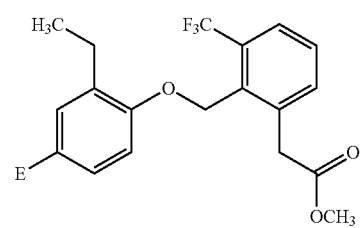
(HG1072)
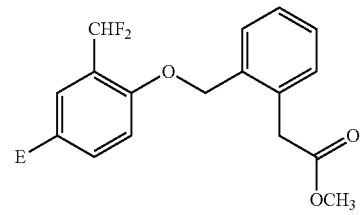
(HG1073)
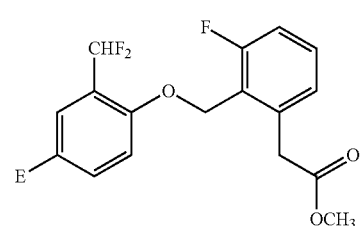
(HG1074)
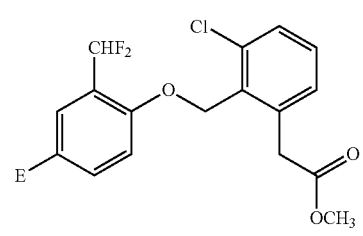
(HG1075)
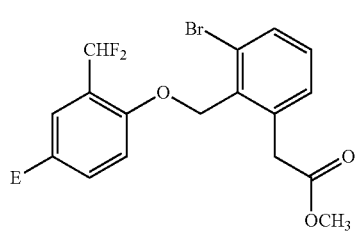
(HF1076)
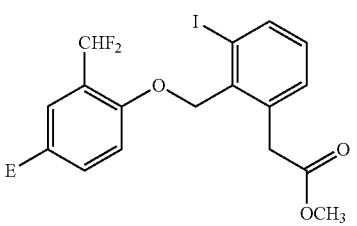
(HF1077)
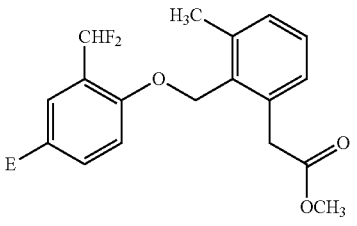
(HG1078)
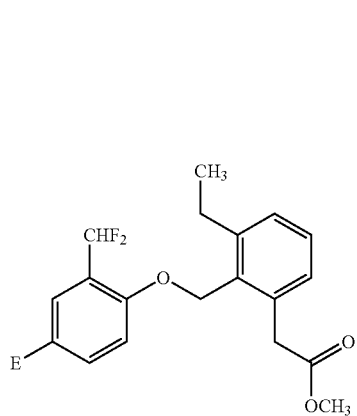
(HG1079)
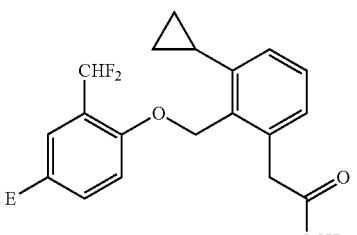
(HG1080)
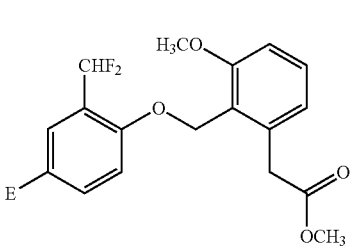
(HG1081)

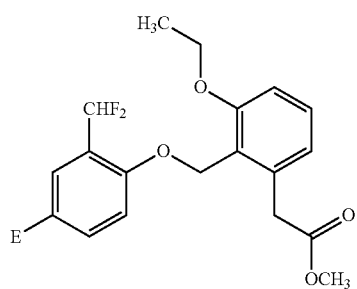
(HG1082)
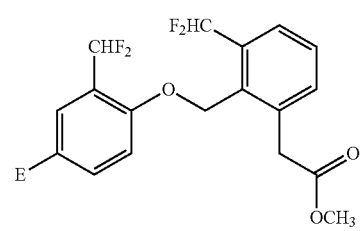
(HG1083)
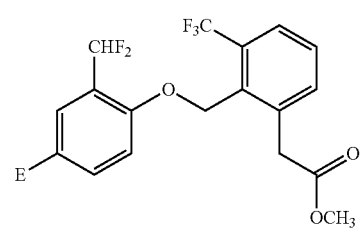
(HG1084)
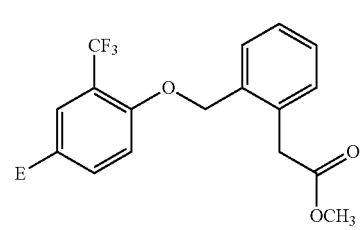
(HG1085)
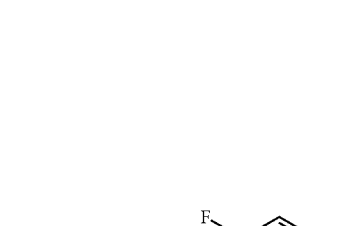
(HG1086)
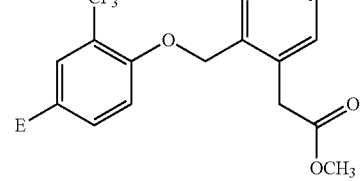
(HG1087)
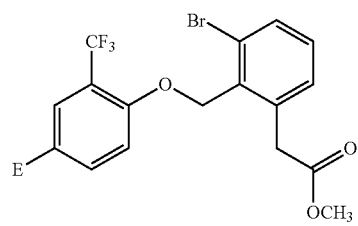
(HF1088)
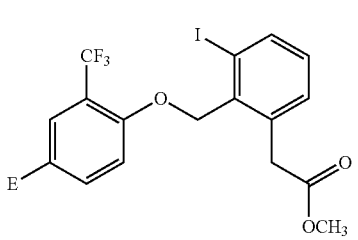
(HF1089)
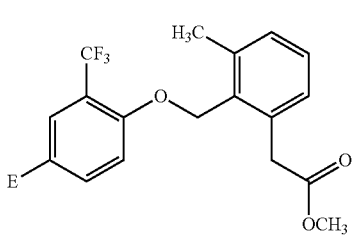
(HG1090)
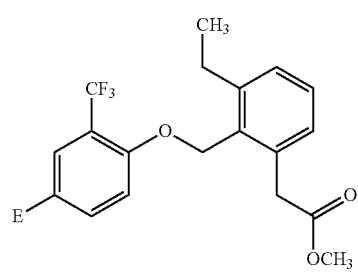
(HG1091)
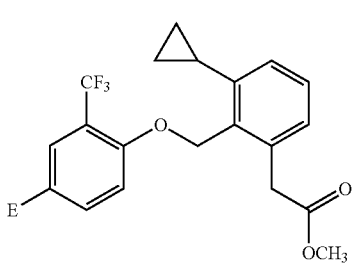
(HG1092)
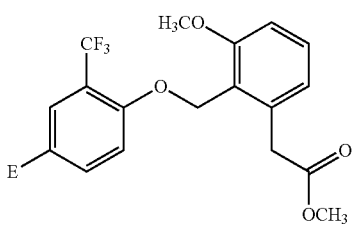
(HG1093)

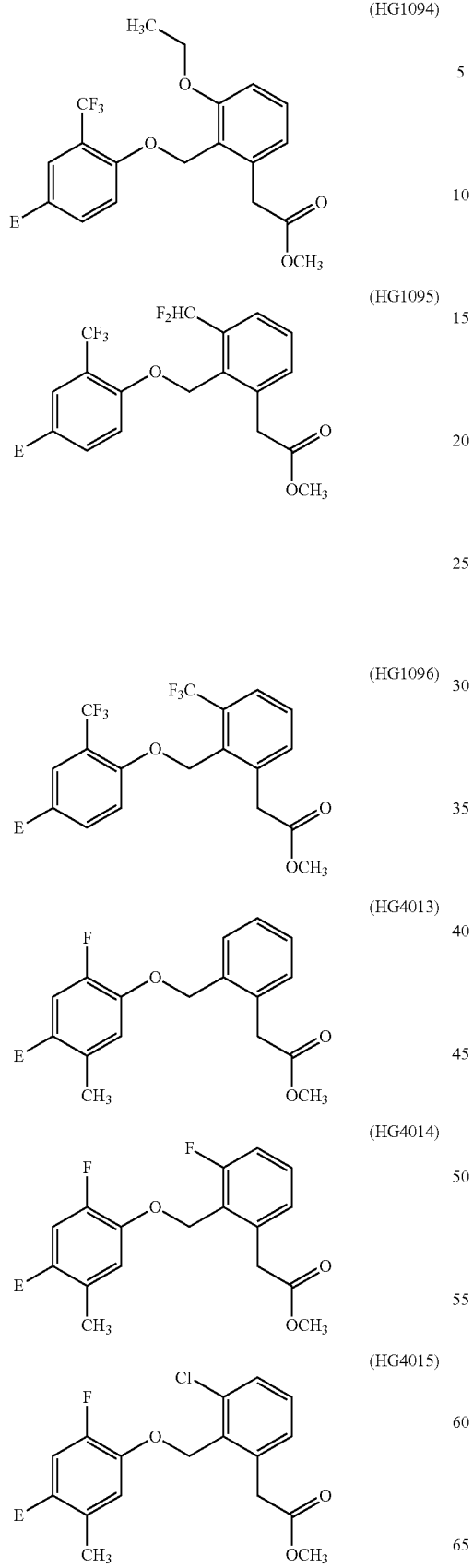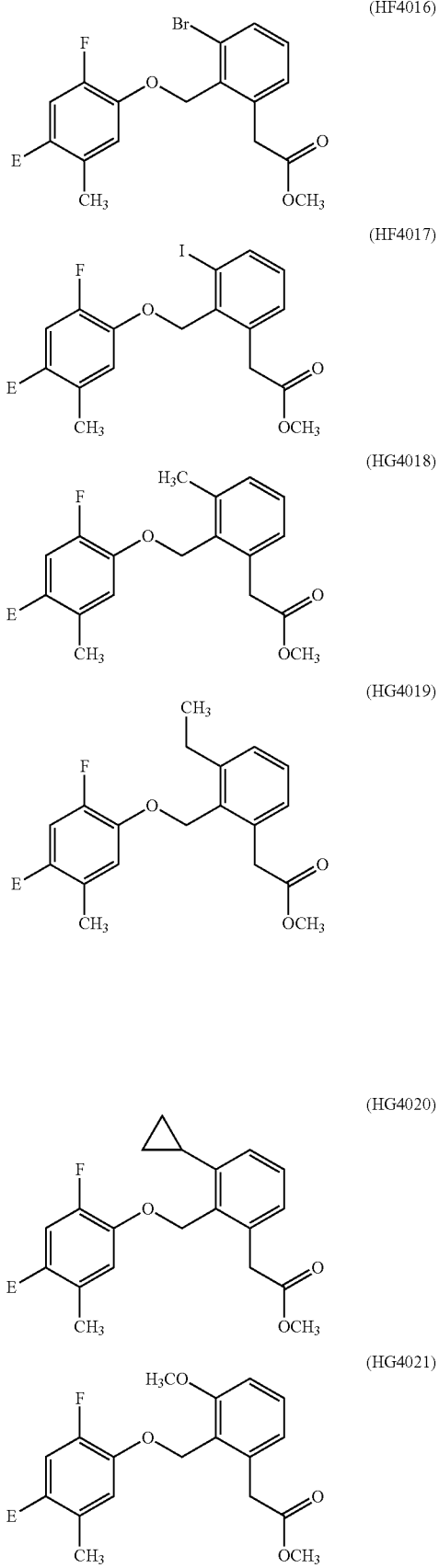

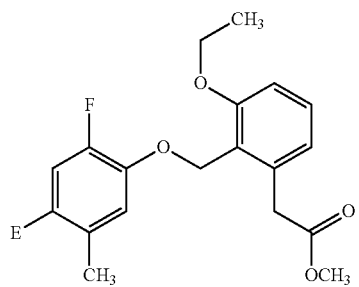 (HG4022)
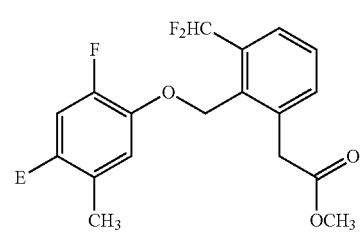 (HG4023)
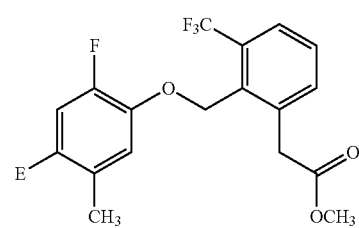 (HG4024)
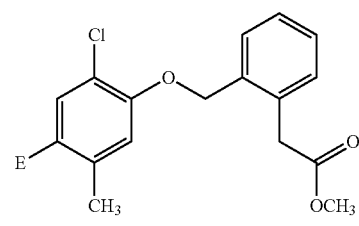 (HG4025)
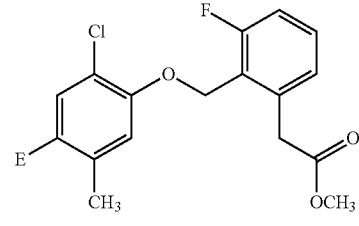 (HG4026)
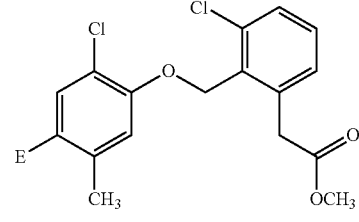 (HG4027)
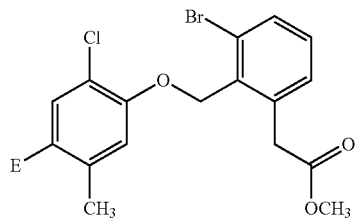 (HF4028)
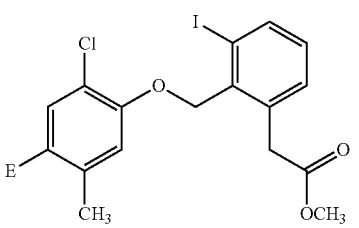 (HF4029)
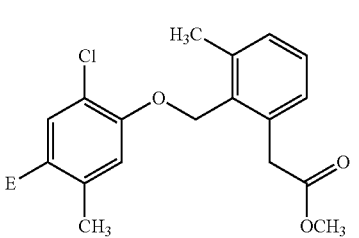 (HG4030)
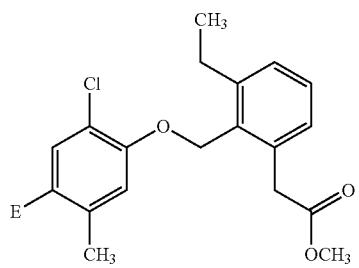 (HG4031)
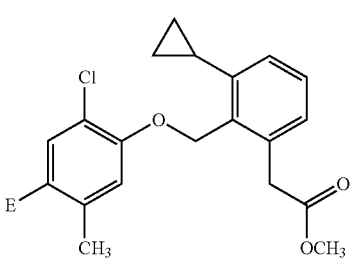 (HG4032)
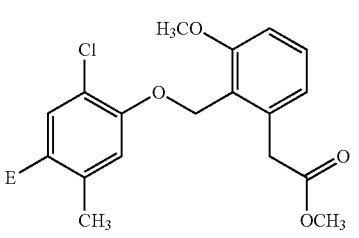 (HG4033)

(HG4034)
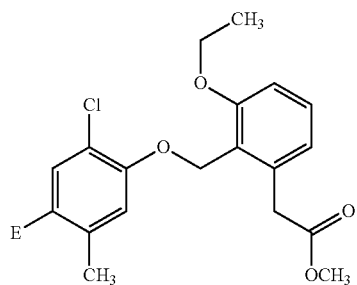
(HG4035)
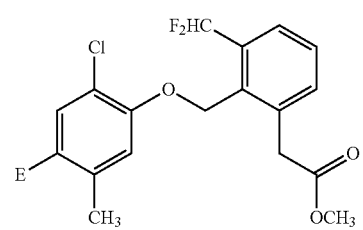
(HG4036)
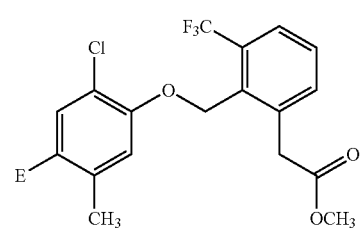
(HG4049)
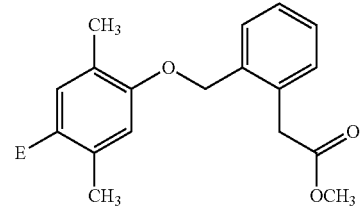
(HG4050)
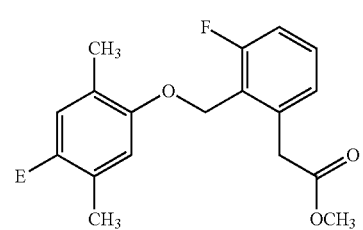
(HG4051)
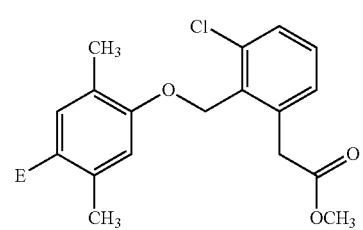
(HF4052)
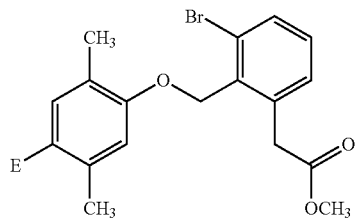
(HF4053)
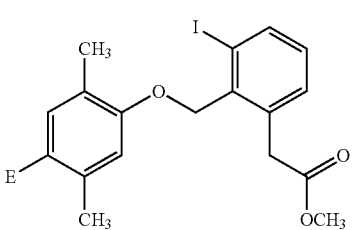
(HG4054)
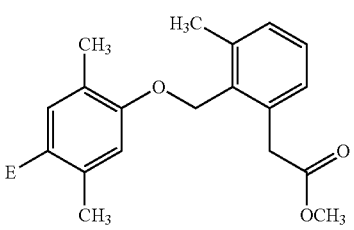
(HG4055)
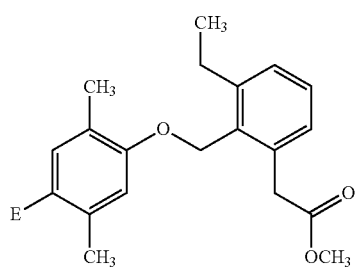
(HG4056)
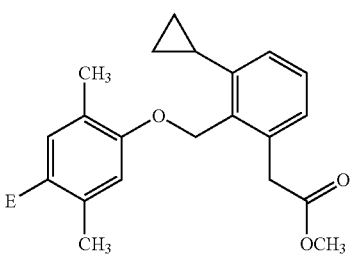
(HG4057)
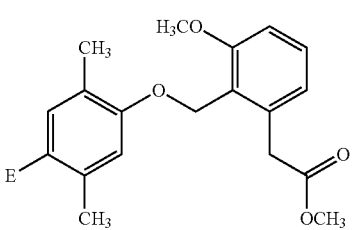

239
-continued
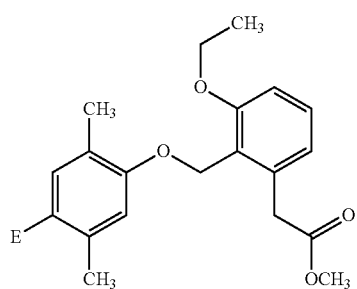
(HG4058)
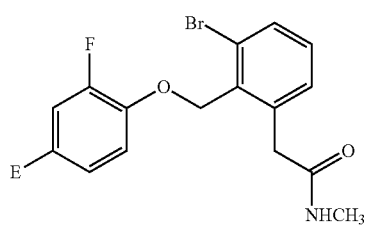
(HG4059)
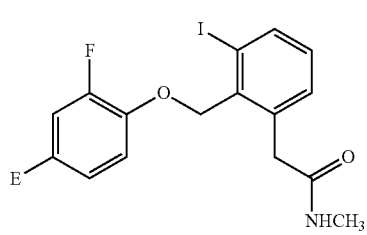
(HG4060)
240
-continued
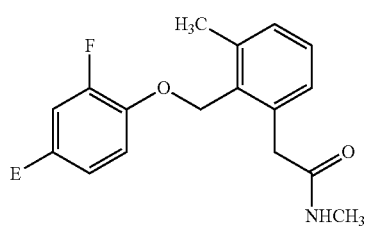
(HH1004)
(HH1005)
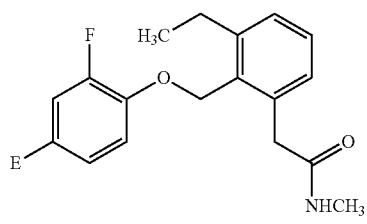
(HH1006)
(HH1007)
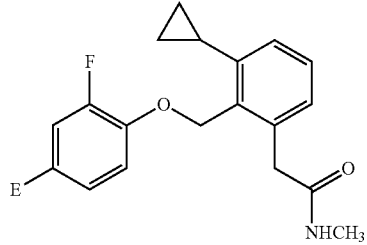
(HH1008)
(HH1009)
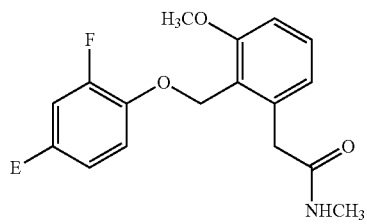
(HH1001)
(HH1002)
(HH1003)

241
-continued
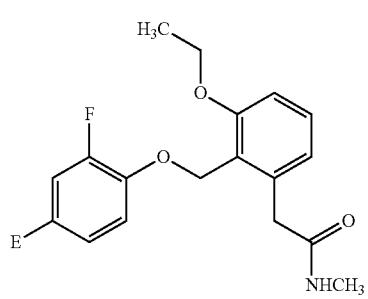
(HH1010)
(HH1011)
(HH1012)
(HH1025)
(HH1026)
(HH1027)
242
-continued
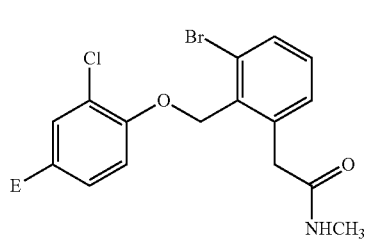
(HH1028)
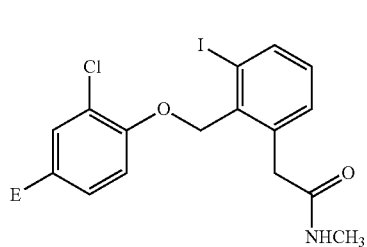
(HH1029)
(HH1030)
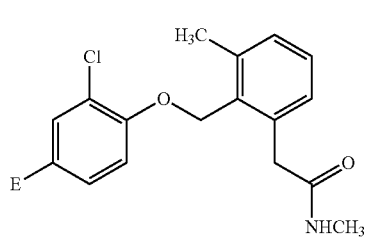
(HH1031)
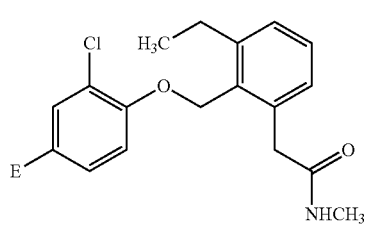
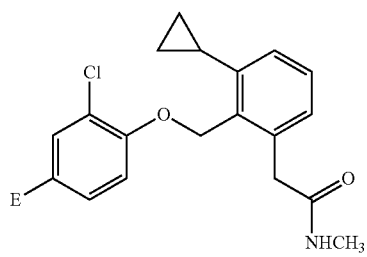
(HH1032)
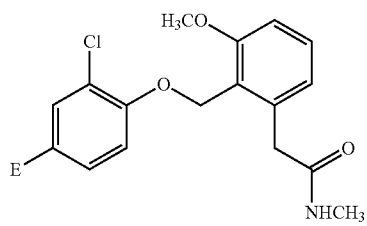
(HH1033)

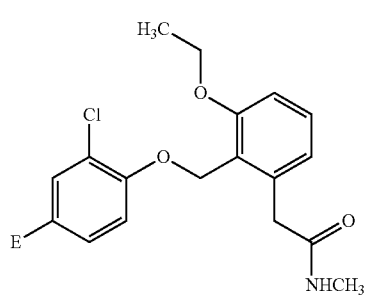 (HH1034)
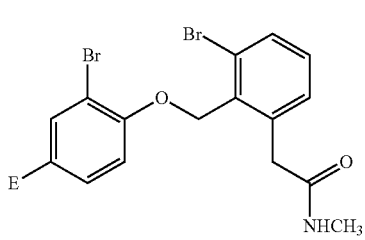 (HH1040)
(HH1041)
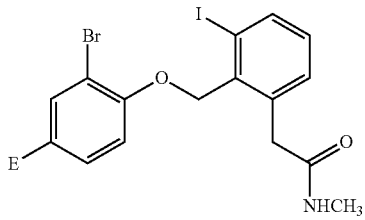
(HH1035)
(HH1036)
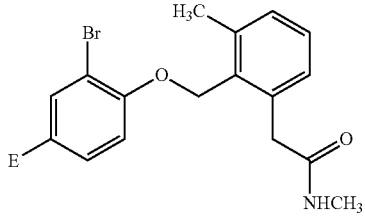 (HH1042)
(HH1043)
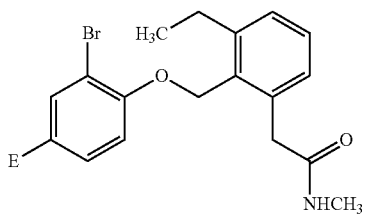
(HH1037)
(HH1038)
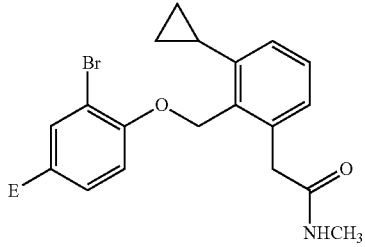 (HH1044)
(HH1045)
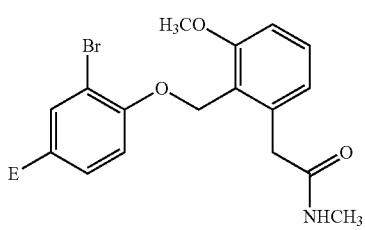
(HH1039)

(HH1046)
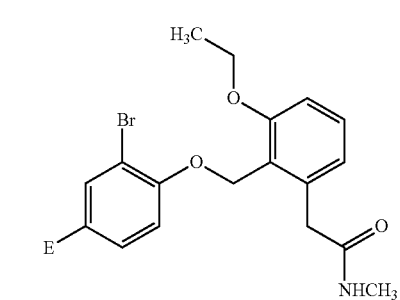
(HH1047)
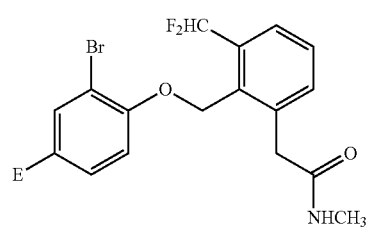
(HH1048)
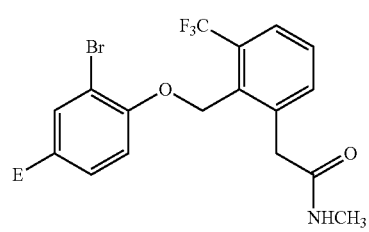
(HH1049)
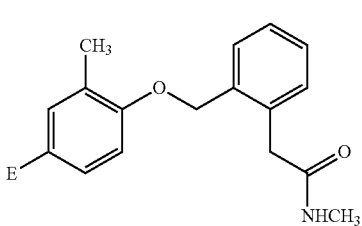
(HH1050)
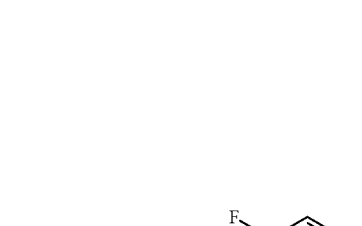
(HH1051)
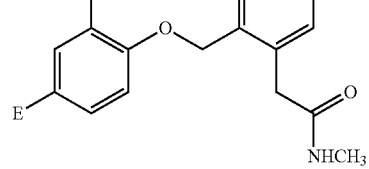
(HH1052)
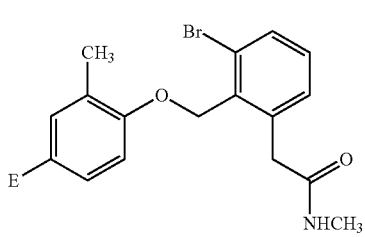
(HH1053)
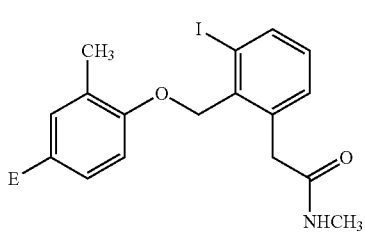
(HH1054)
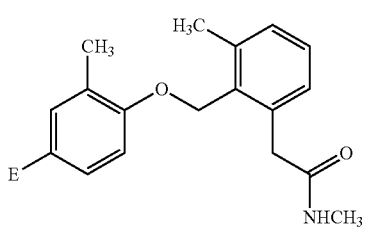
(HH1055)
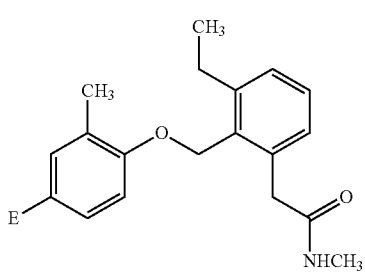
(HH1056)
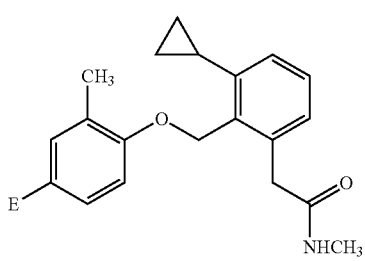
(HH1057)
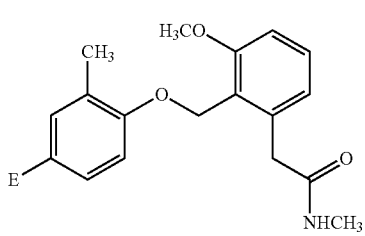

-continued (HH1058)
(HH1059)
(HH1060)
(HH1061)
(HH1062)
(HH1063)

-continued (HH1064)
(HH1065)
(HH1066)
(HH1067)
(HH1068)
(HH1069)

| | |
|---|---|
| (HH1070) | (HH1076) |
| (HH1071) | (HH1077) |
| (HH1072) | (HH1078) |
| (HH1073) | (HH1079) |
| (HH1074) | (HH1080) |
| (HH1075) | (HH1081) |

(HH1082)
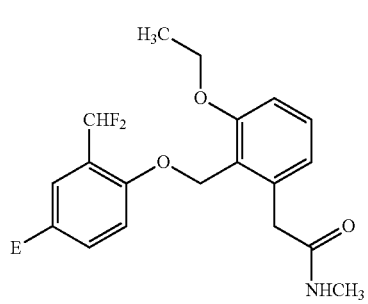
(HH1083)
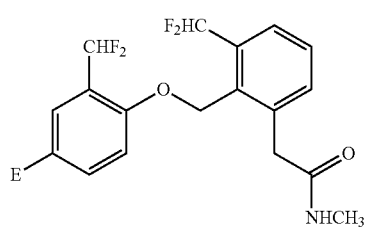
(HH1084)
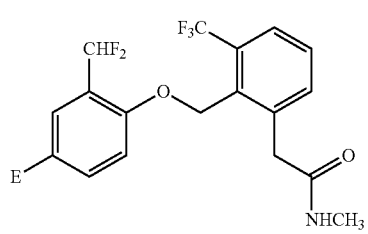
(HH1085)
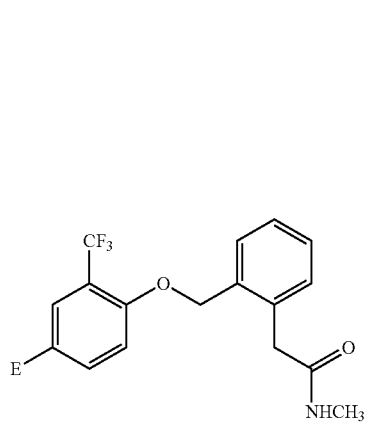
(HH1086)
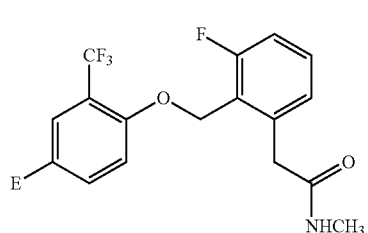
(HH1087)
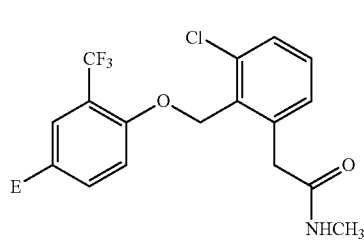
(HH1088)
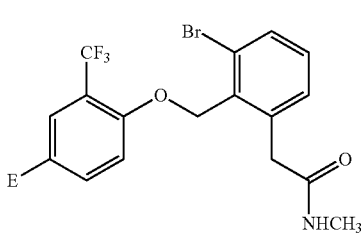
(HH1089)
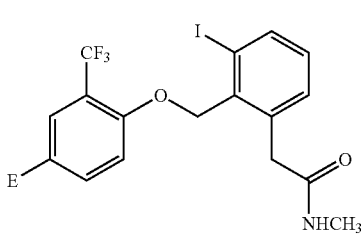
(HH1090)
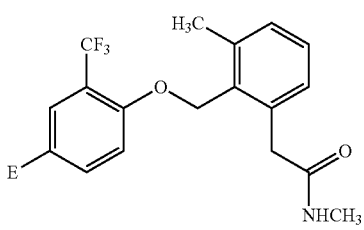
(HH1091)
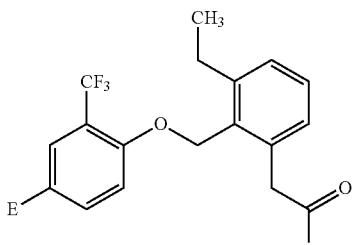
(HH1092)
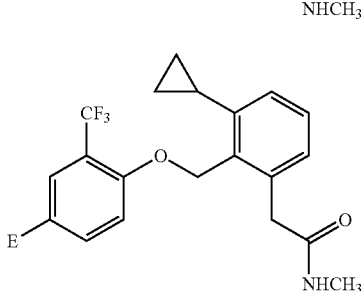
(HH1093)
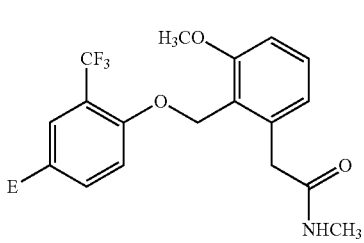

| (HH1094) | (HH4016) |
| (HH1095) | (HH4017) |
| (HH1096) | (HH4018) |
| | (HH4019) |
| (HH4013) | |
| (HH4014) | (HH4020) |
| (HH4015) | (HH4021) |

(HH4022)
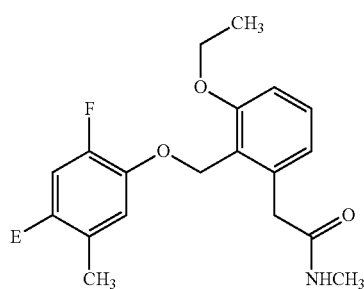
(HH4023)
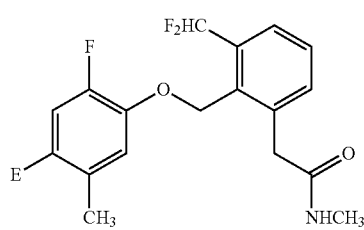
(HH4024)
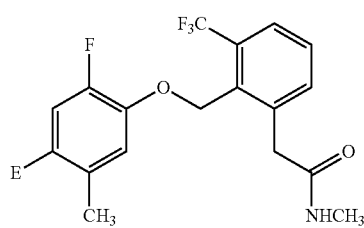
(HH4025)
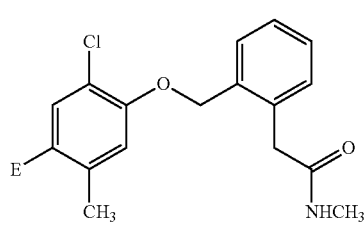
(HH4026)
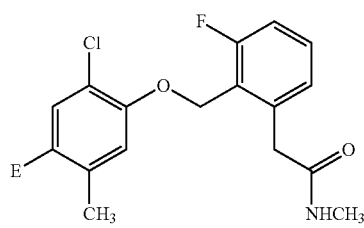
(HH4027)
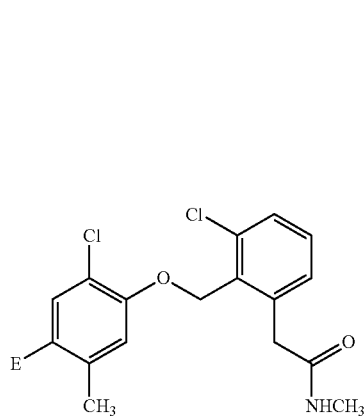
(HH4028)
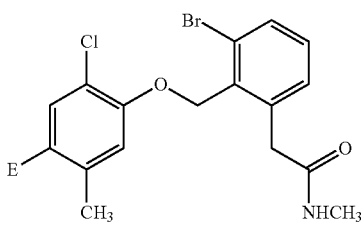
(HH4029)
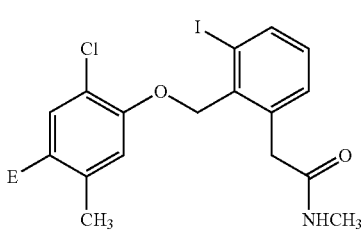
(HH4030)
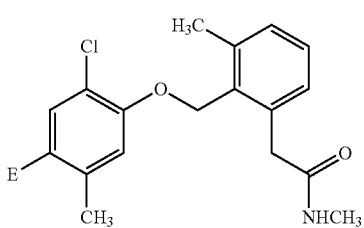
(HH4031)
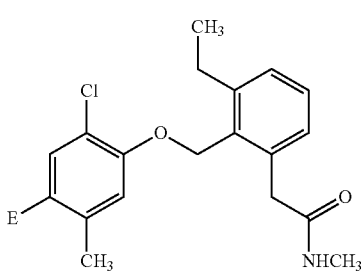
(HH4032)
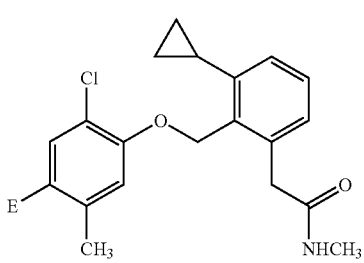
(HH4033)
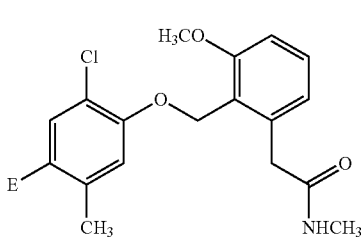

(HH4034) 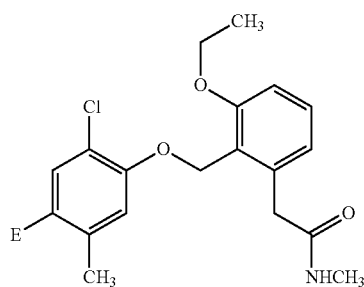
(HH4035) 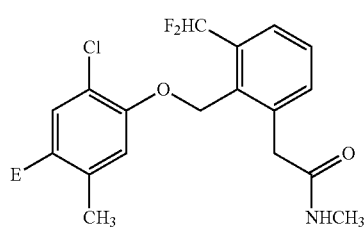
(HH4036) 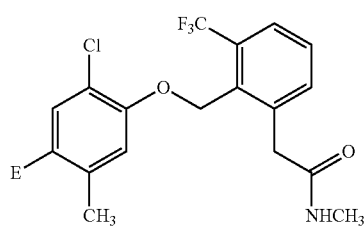
(HH4049) 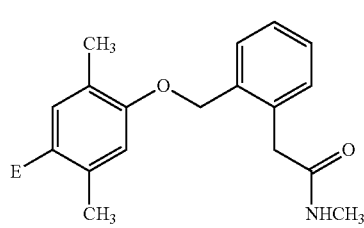
(HH4050) 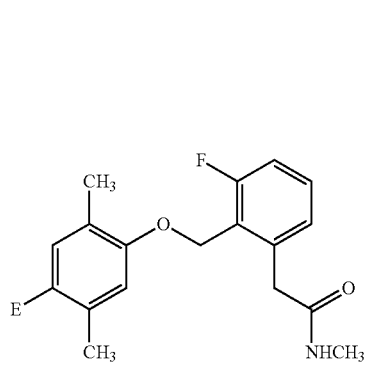
(HH4051) 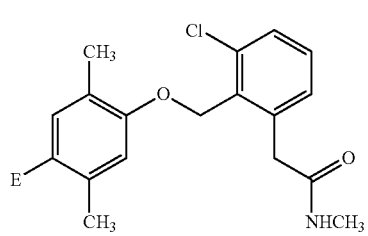
(HH4052) 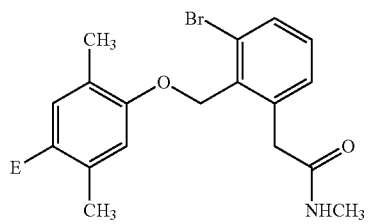
(HH4053) 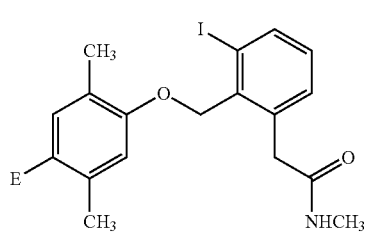
(HH4054) 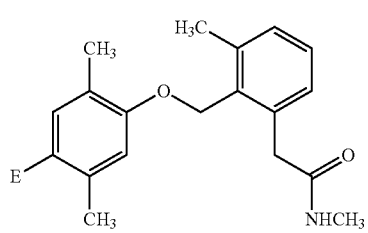
(HH4055) 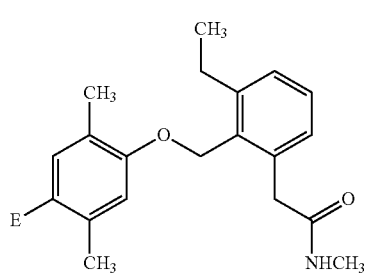
(HH4056) 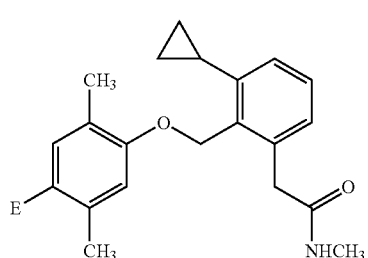
(HH4057) 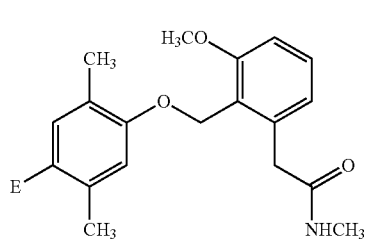

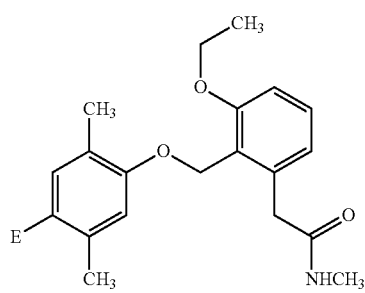
(HH4058)
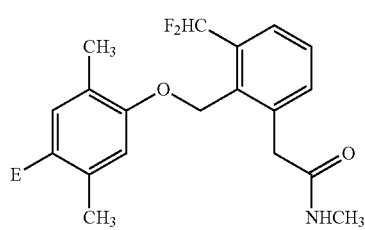
(HH4059)
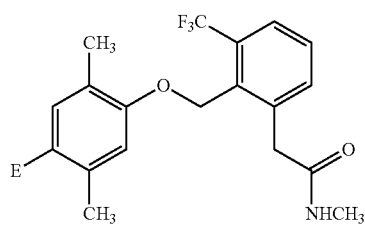
(HH4060)
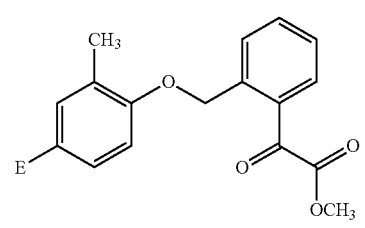
(HI1049)
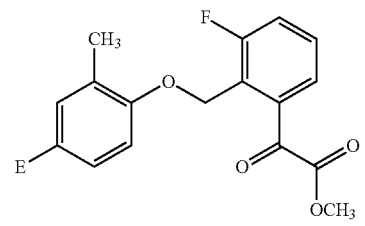
(HI1050)
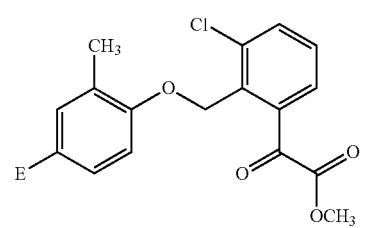
(HI1051)
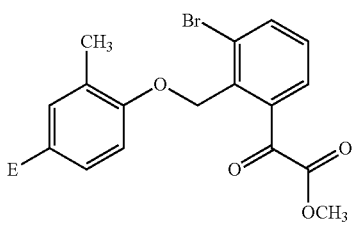
(HI1052)
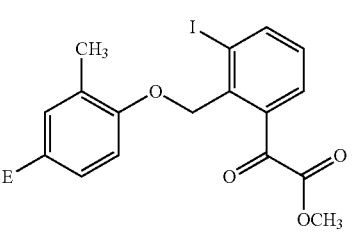
(HI1053)
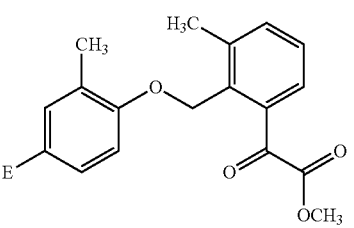
(HI1054)
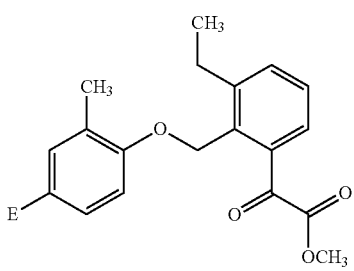
(HI1055)
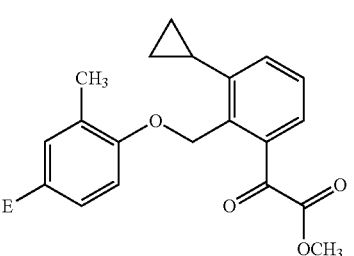
(HI1056)
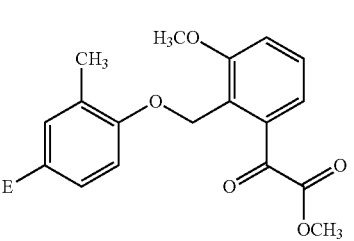
(HI1057)

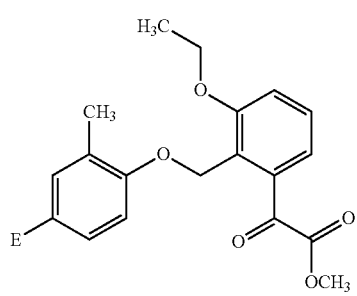
(HI1058)
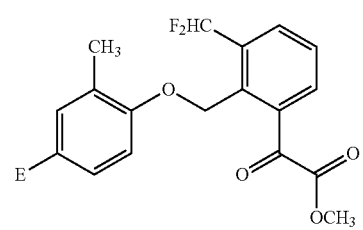
(HI1059)
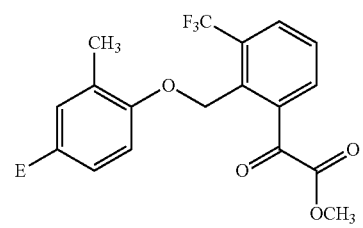
(HI1060)
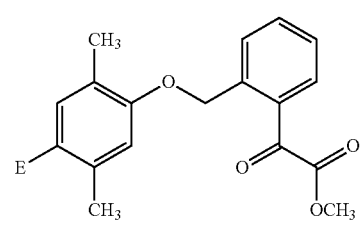
(HI4049)
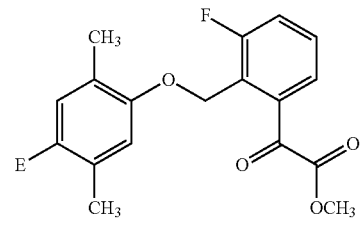
(HI4050)
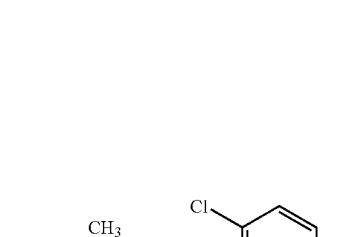
(HI4051)
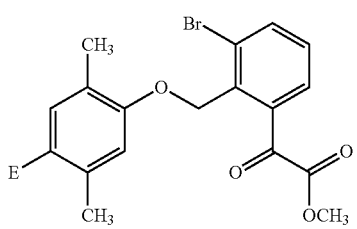
(HI4052)
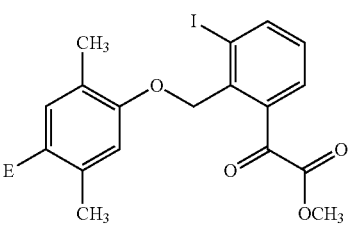
(HI4053)
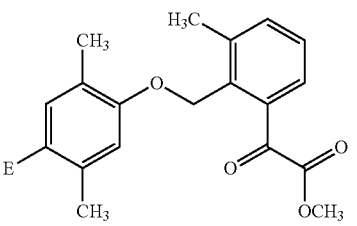
(HI4054)
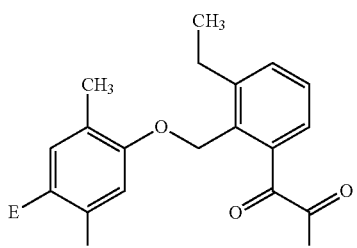
(HI4055)
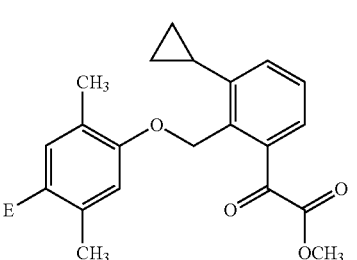
(HI4056)
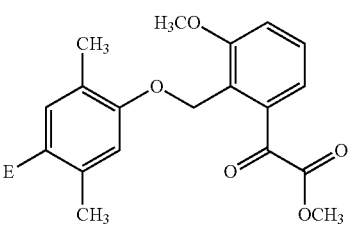
(HI4057)

-continued
(HI4058)
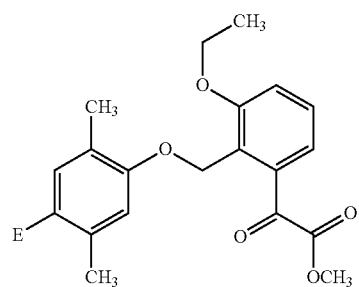
(HI4059)
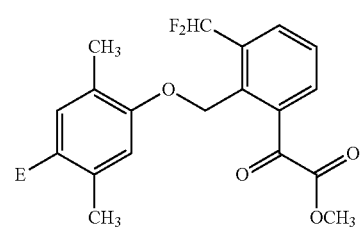
(HI4060)
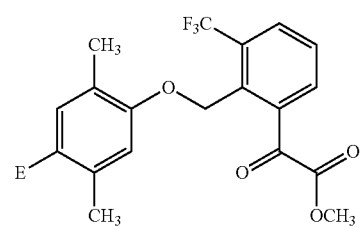
(HJ1049)
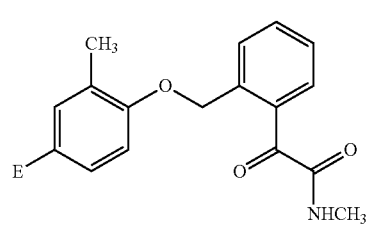
(HJ1050)
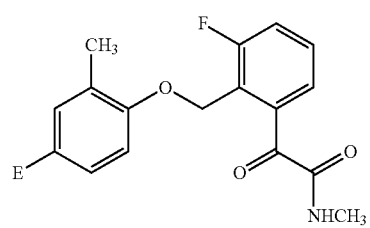
(HJ1051)
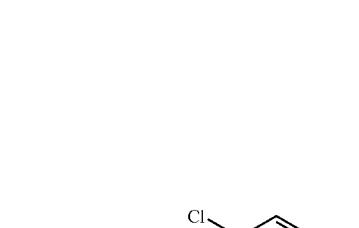
-continued
(HJ1052)
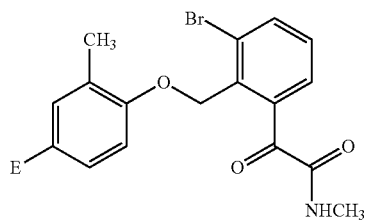
(HJ1053)
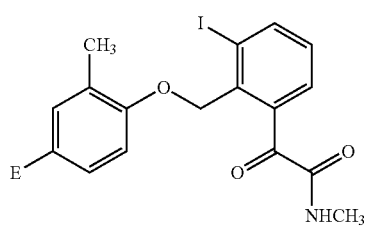
(HJ1054)
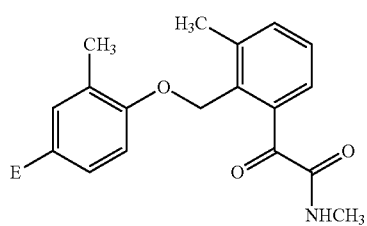
(HJ1055)
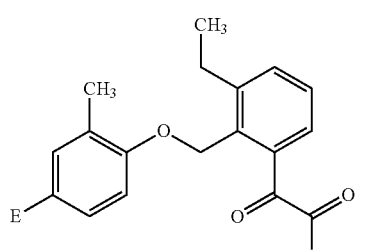
(HJ1056)
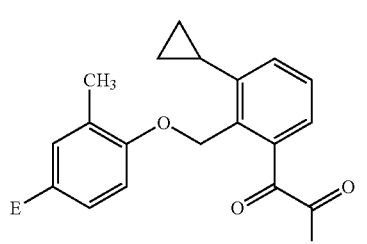
(HJ1057)
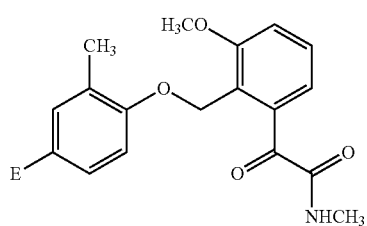

-continued (HJ1058)

(HJ1059)

(HJ1060)

(HJ4049)

(HJ4050)

(HJ4051)

-continued (HJ4052)

(HJ4053)

(HJ4054)

(HJ4055)

(HJ4056)

(HJ4057)

267
-continued
(HJ4058)
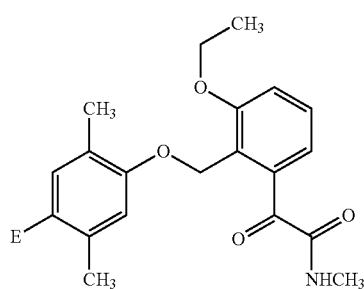
(HJ4059)
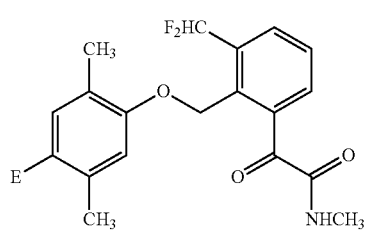
(HJ4060)
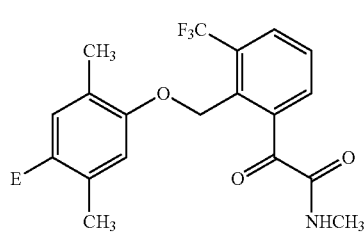
(HK1049)
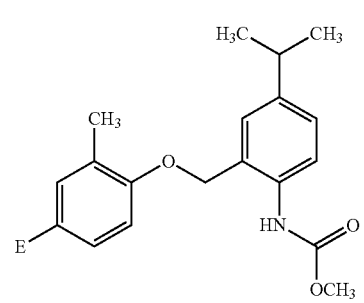
(HK1050)
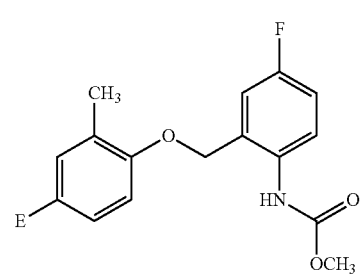
(HK1051)
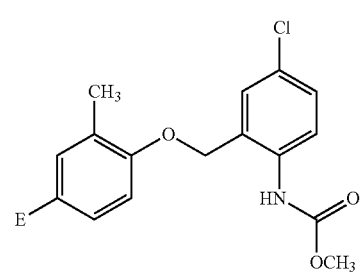
268
-continued
(HK1052)
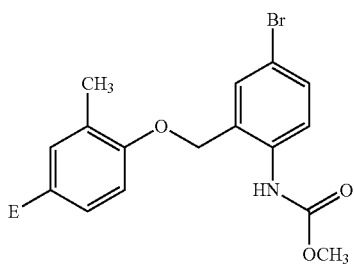
(HK1053)
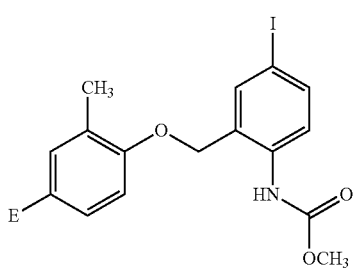
(HK1054)
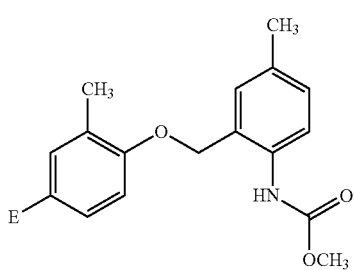
(HK1055)
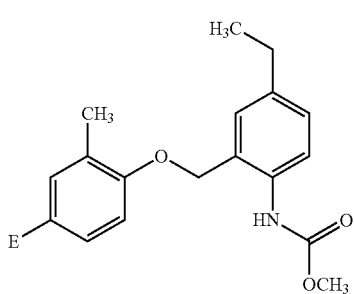
(HK1056)
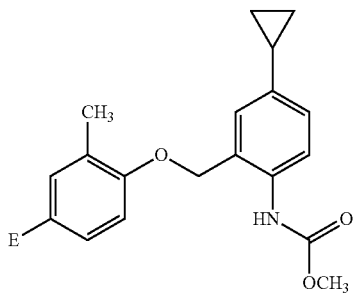

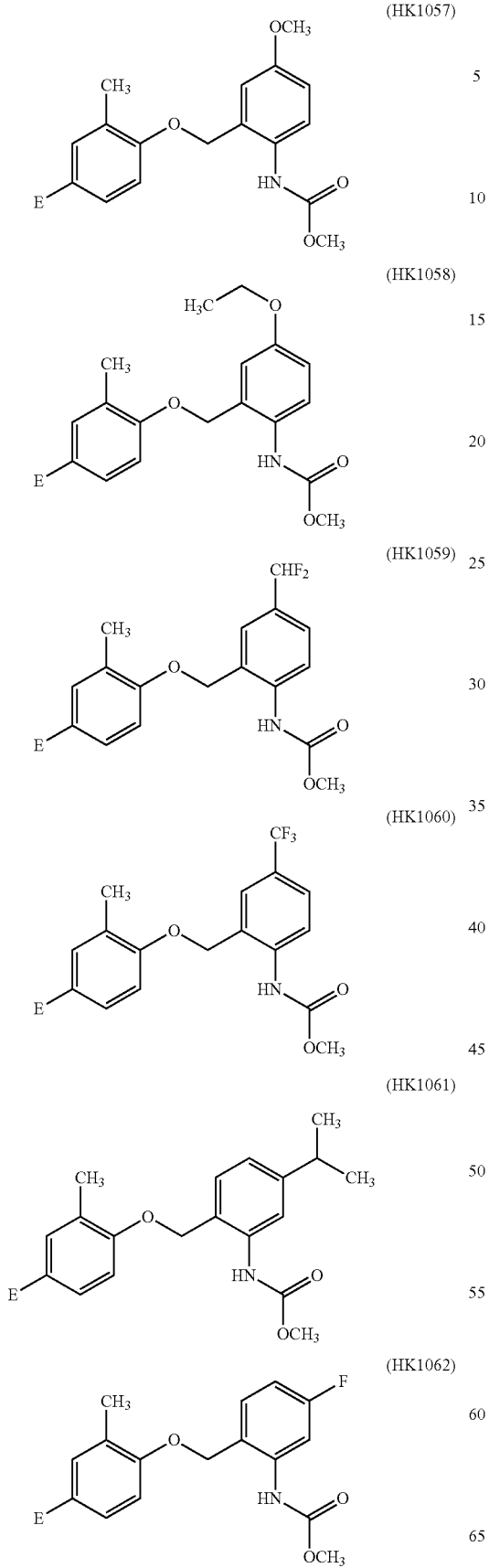
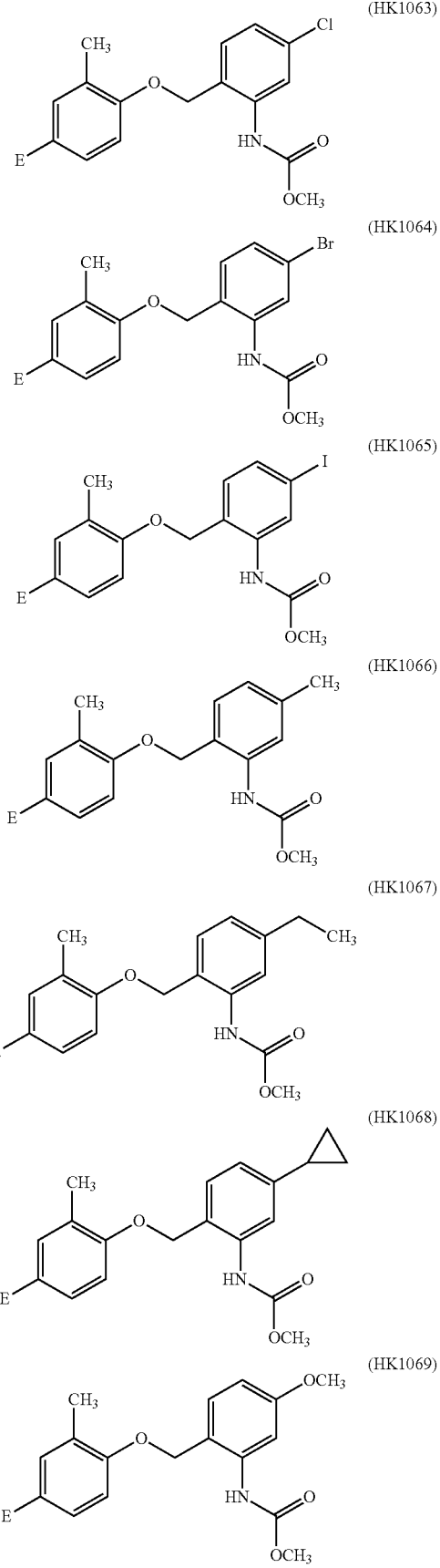

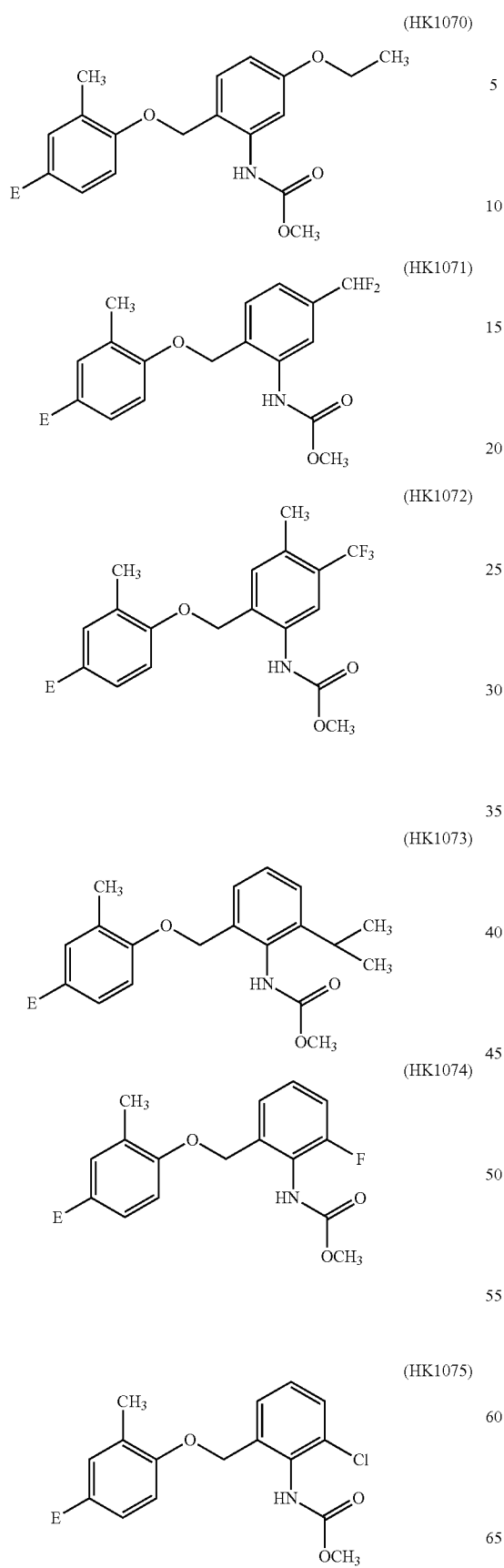
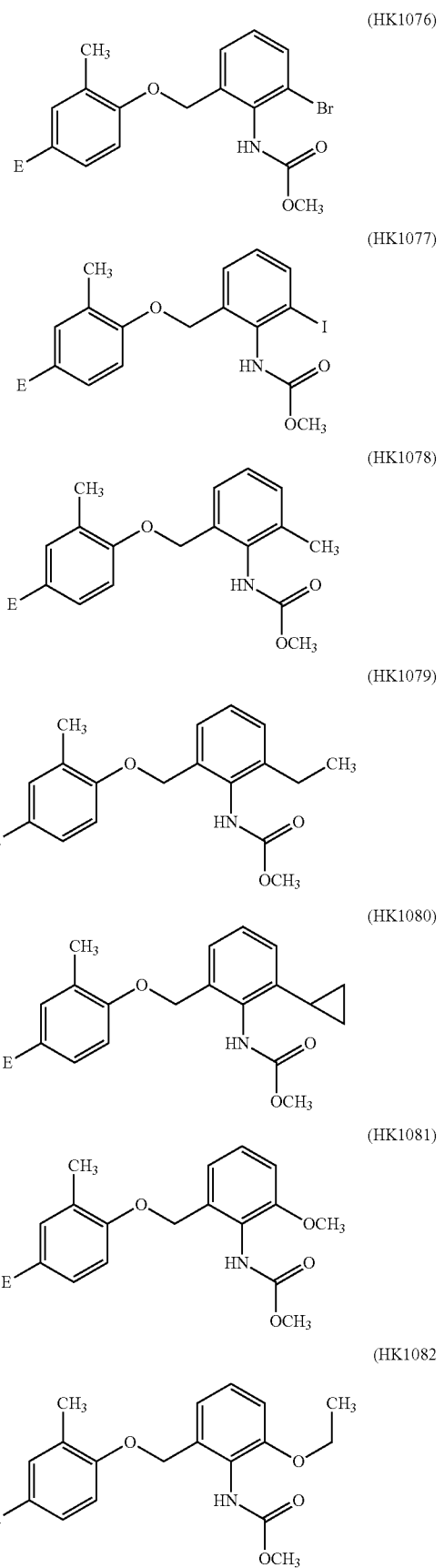

273
-continued
(HK1083)
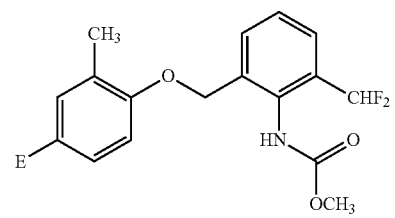
(HK1084)
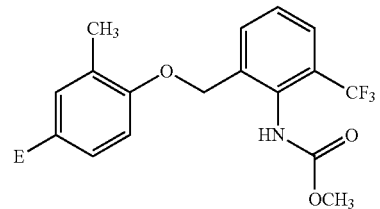
(HL1049)
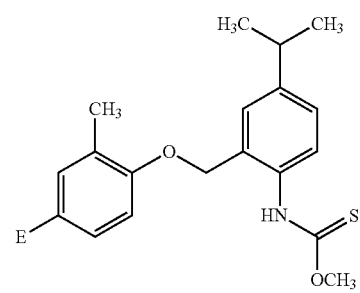
(HL1050)
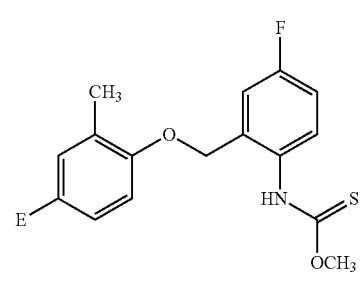
(HL1051)
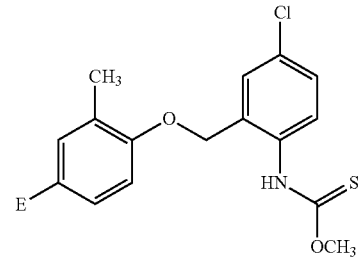
(HL1052)
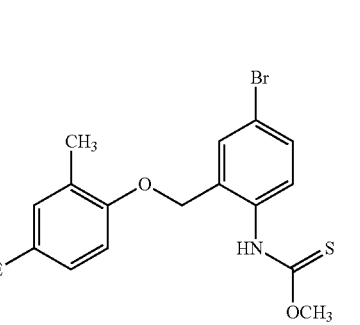
274
-continued
(HL1053)
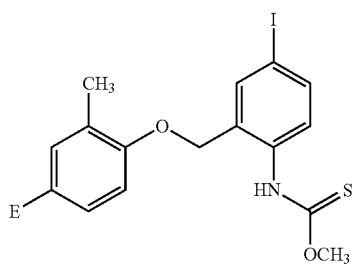
(HL1054)
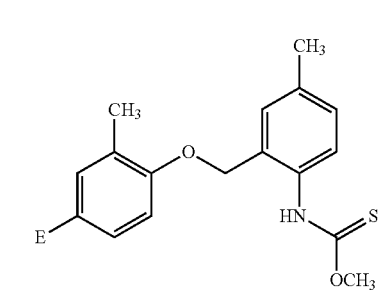
(HL1055)
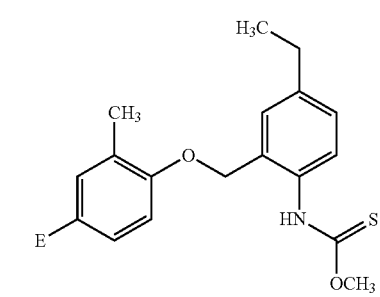
(HL1056)
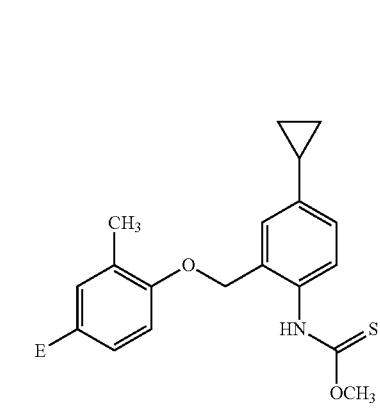
(HL1057)
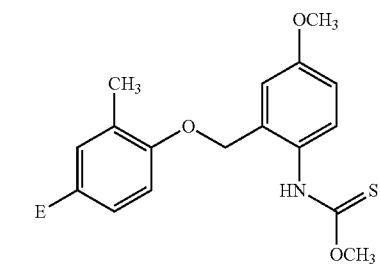

275
-continued
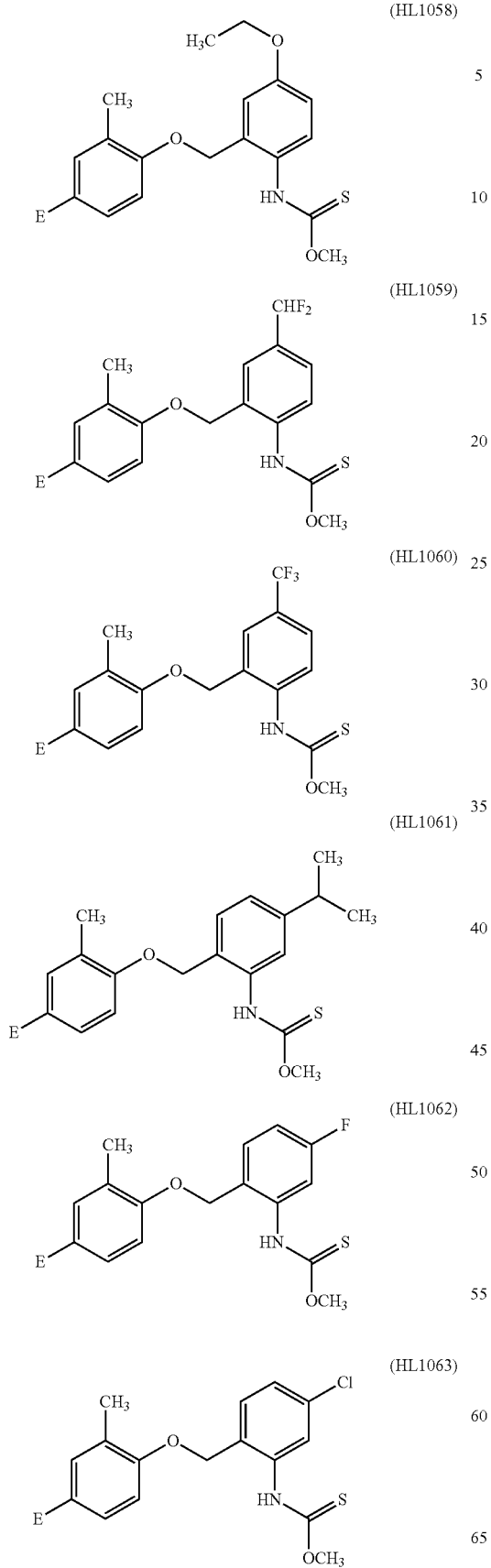
276
-continued
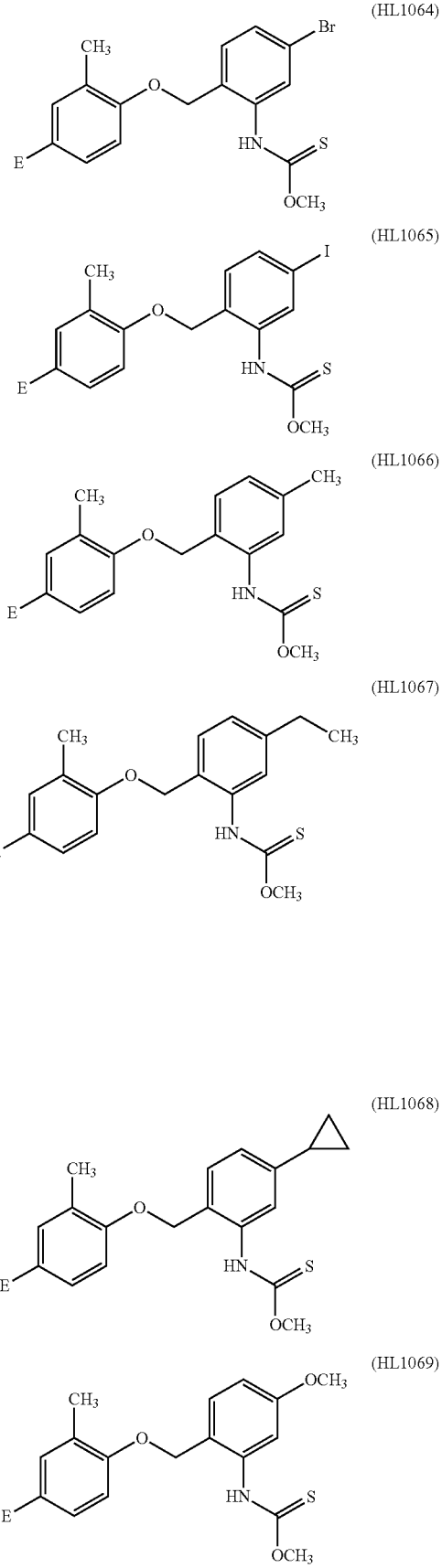

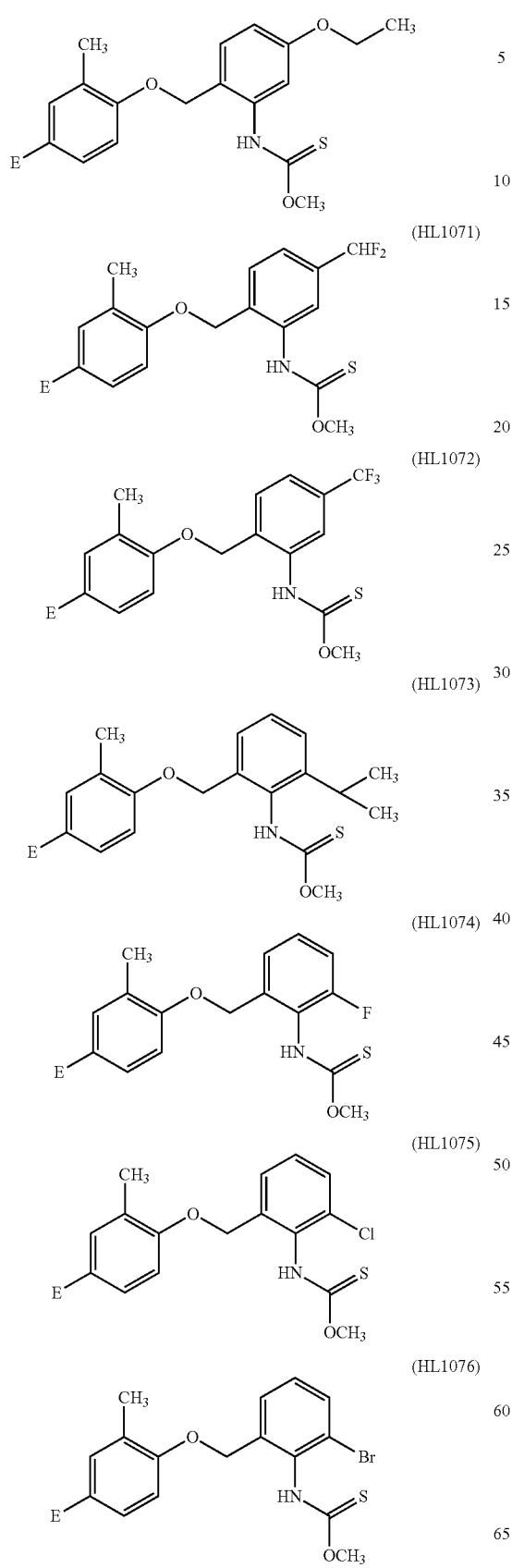
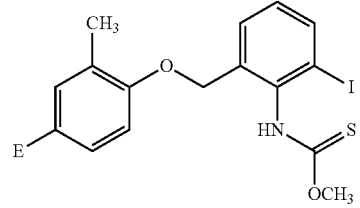
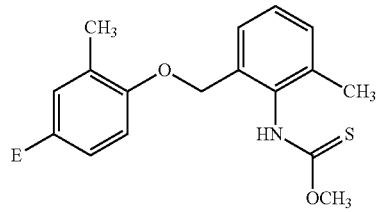
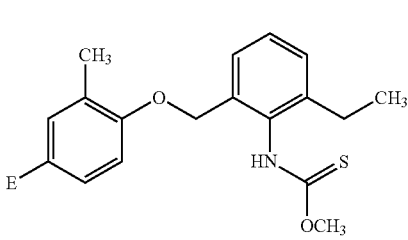
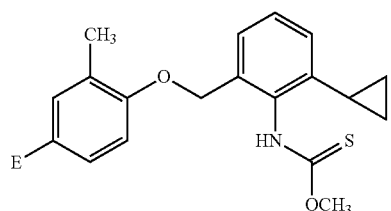
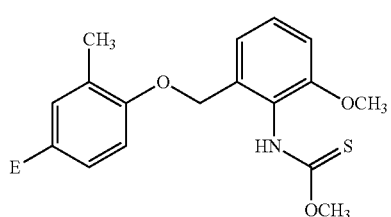
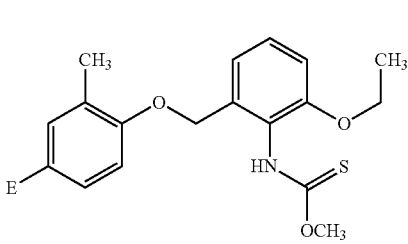
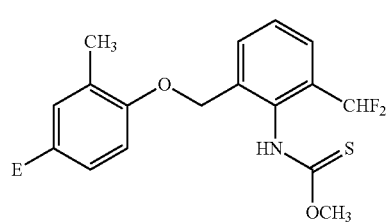

(HL1084)
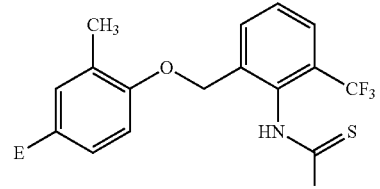
(HM1049)
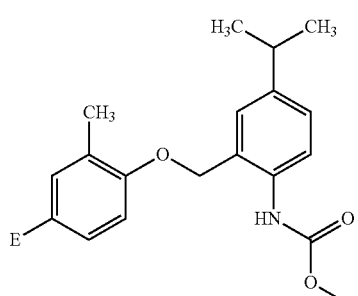
(HM1050)
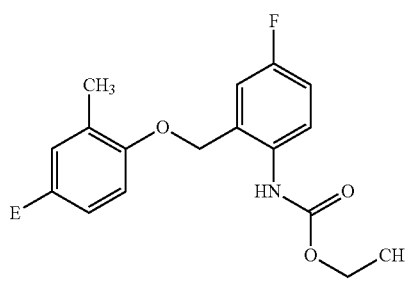
(HM1051)
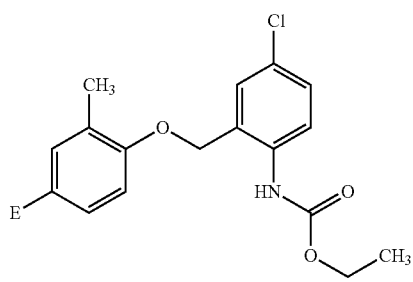
(HM1052)
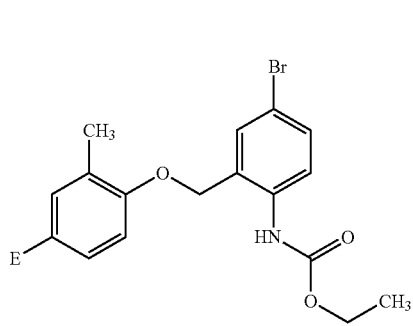
(HM1053)
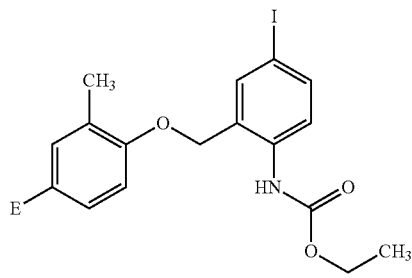
(HM1054)
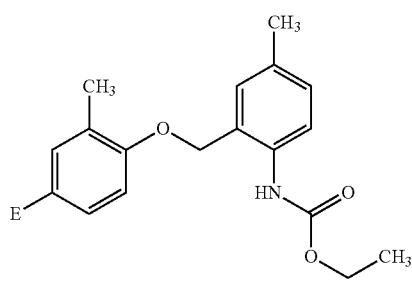
(HM1055)
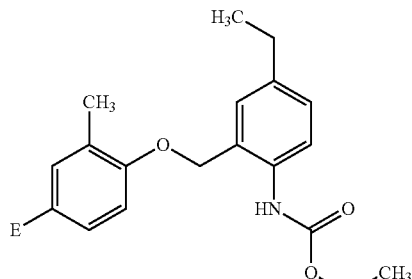
(HM1056)
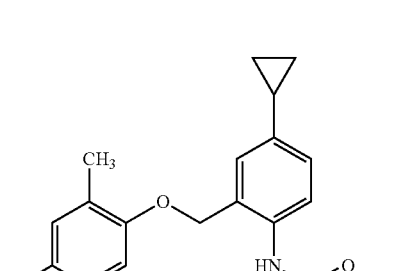
(HM1057)
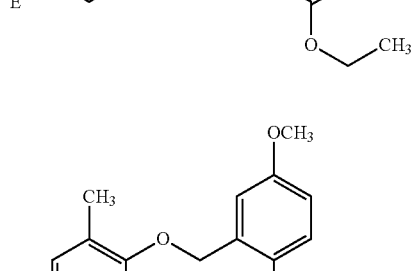

(HM1058)
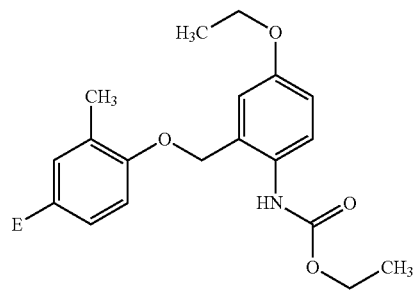
(HM1059)
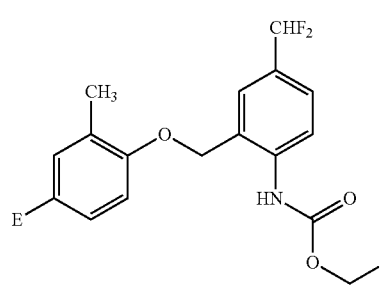
(HM1060)
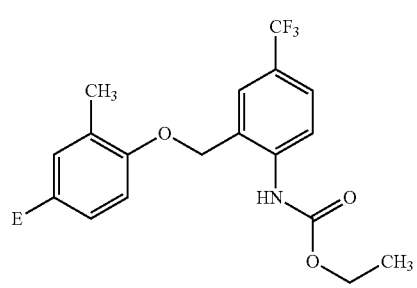
(HM1061)
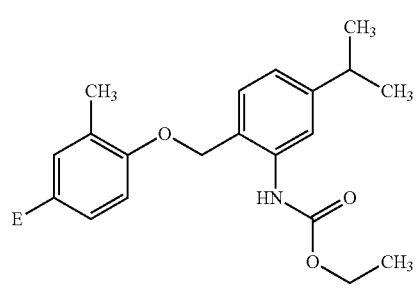
(HM1062)
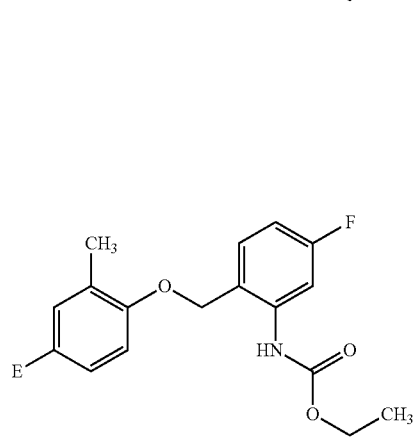
(HM1063)
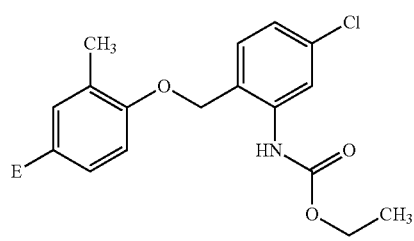
(HM1064)
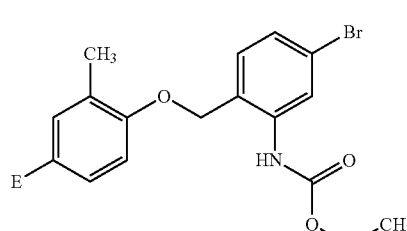
(HM1065)
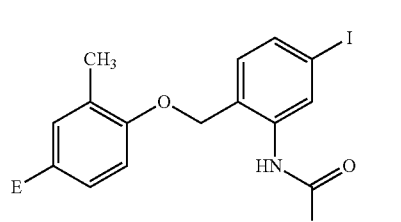
(HM1066)
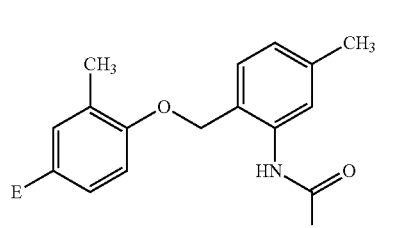
(HM1067)
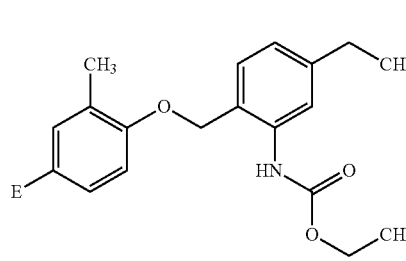
(HM1068)
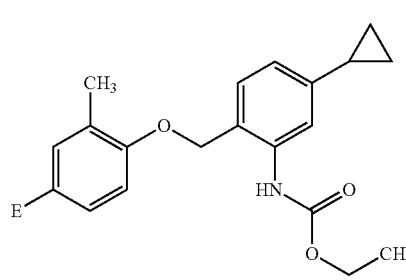

(HM1069)
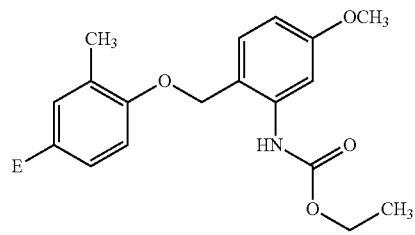
(HM1070)
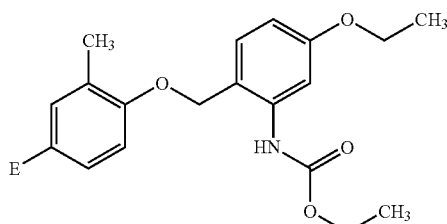
(HM1071)
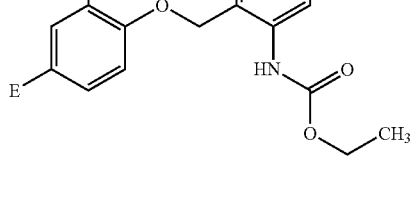
(HM1072)
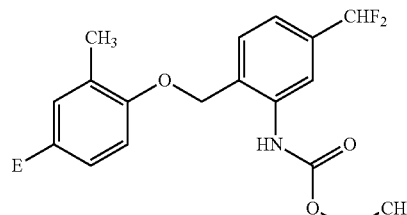
(HM1073)
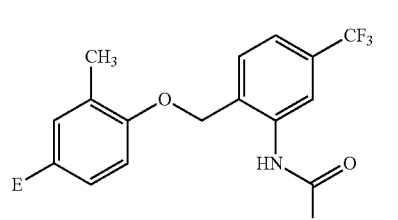
(HM1074)
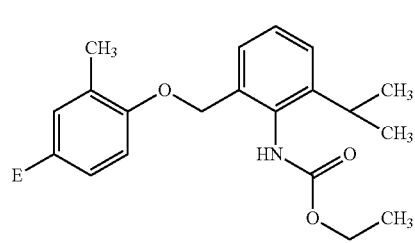
(HM1075)
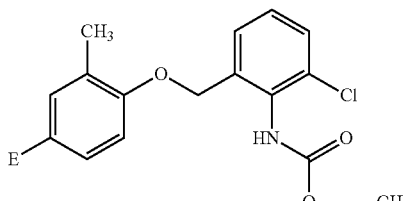
(HM1076)
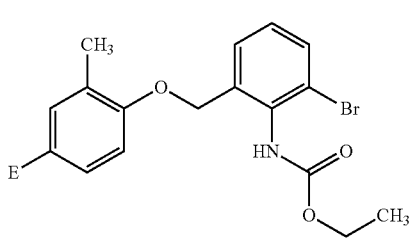
(HM1077)
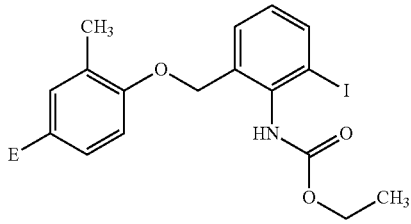
(HM1078)
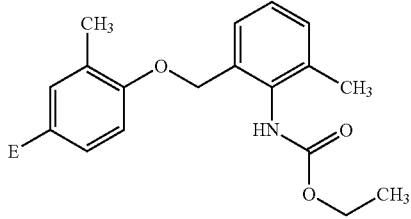
(HM1079)
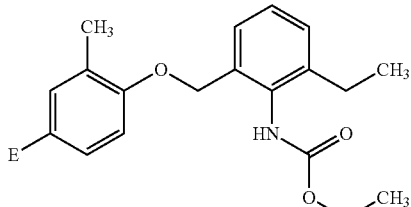
(HM1080)
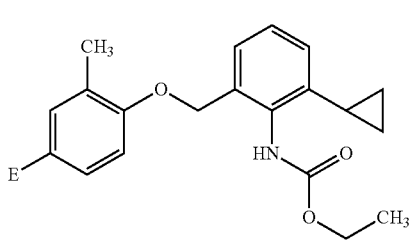

(HM1081)
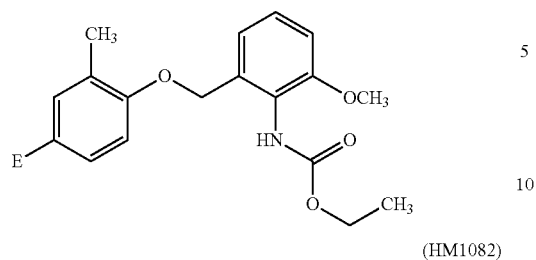
(HM1082)
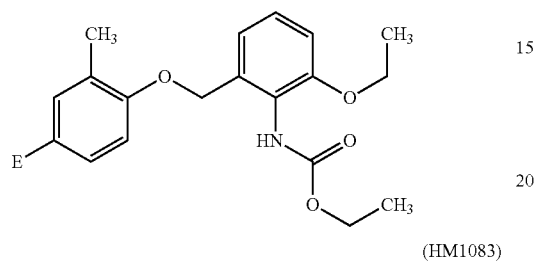
(HM1083)
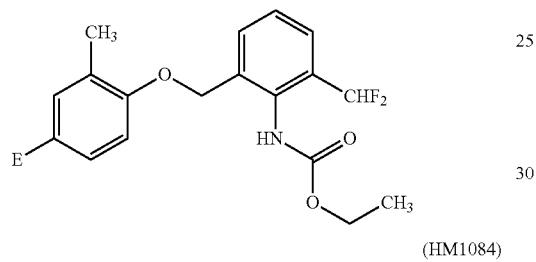
(HM1084)
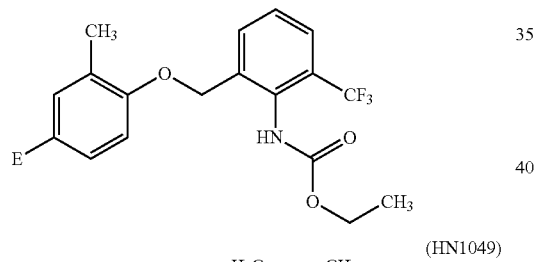
(HN1049)
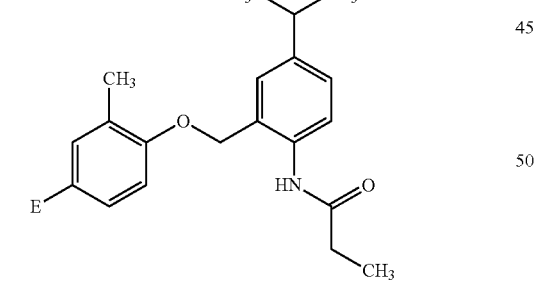
(HN1050)
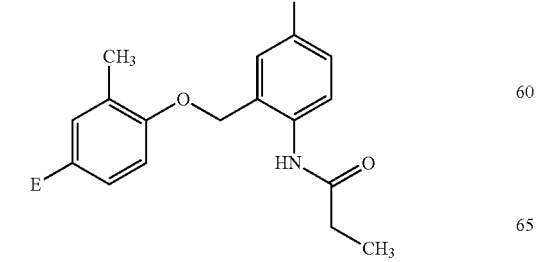
(HN1051)
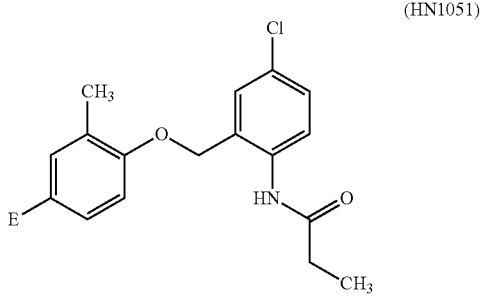
(HN1052)
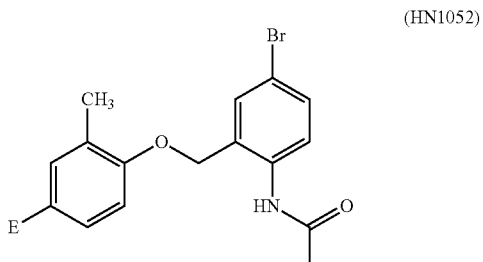
(HN1053)
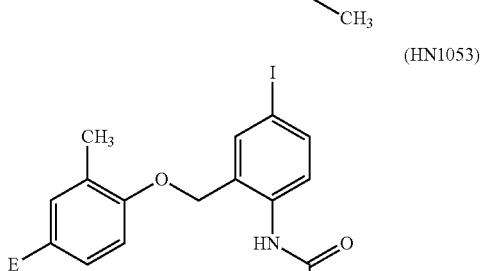
(HN1054)
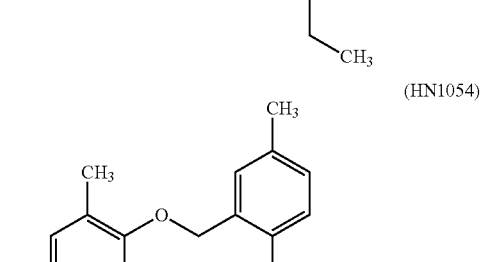
(HN1055)
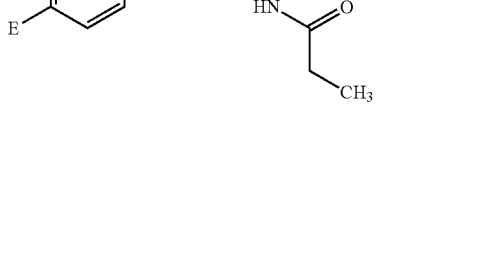

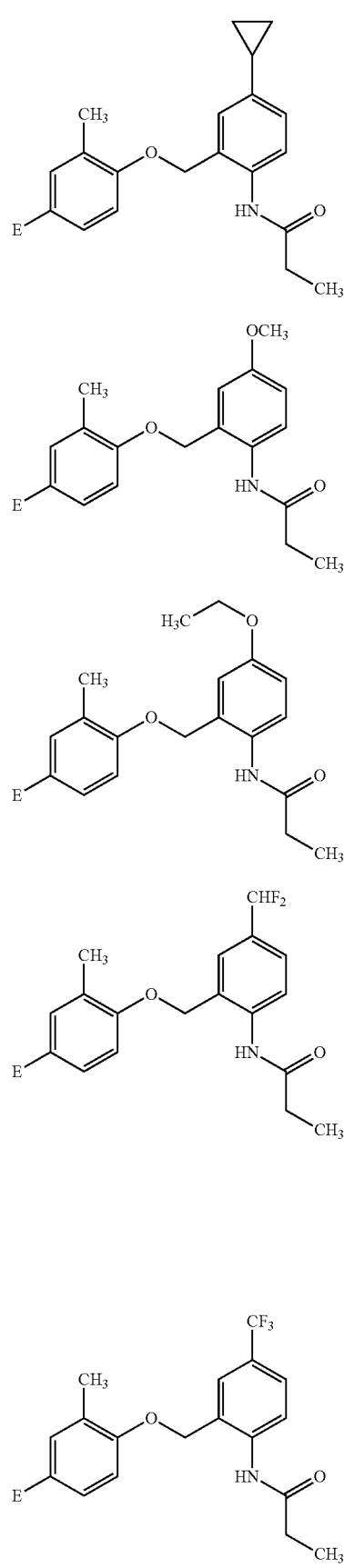
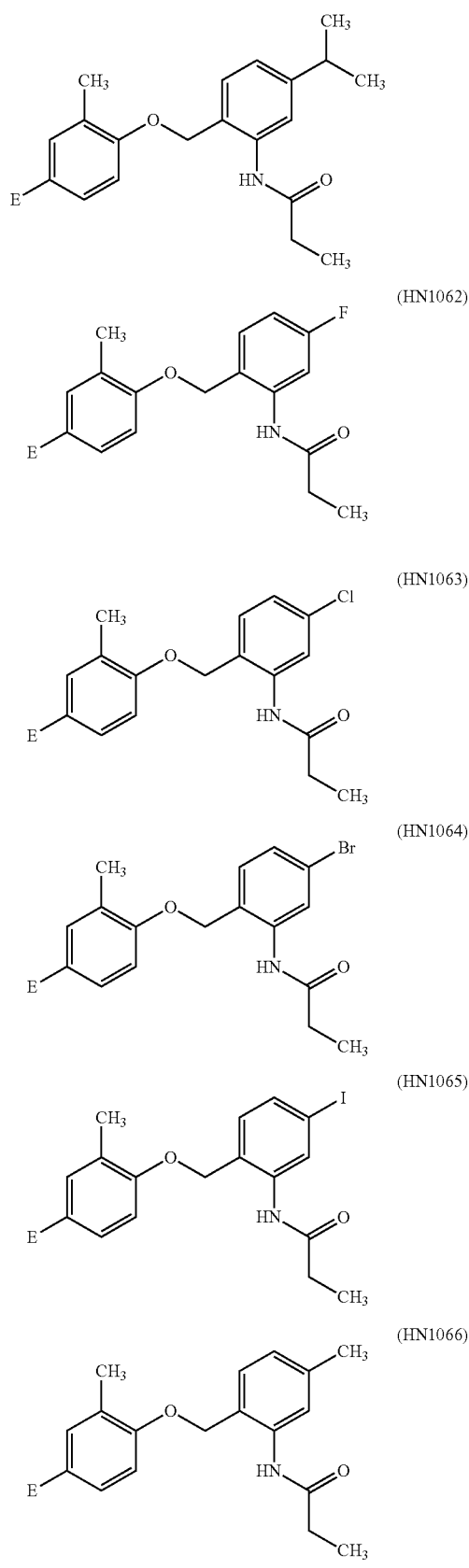

(HN1067)
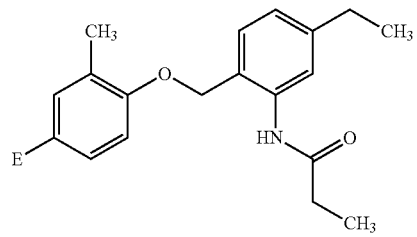
(HN1068)
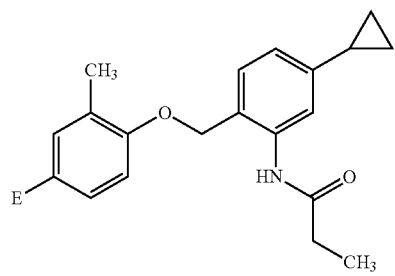
(HN1069)
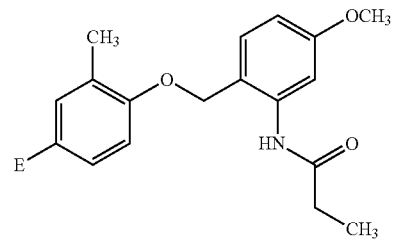
(HN1070)
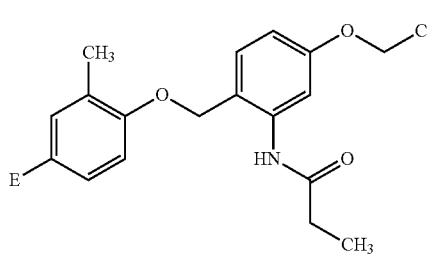
(HN1071)
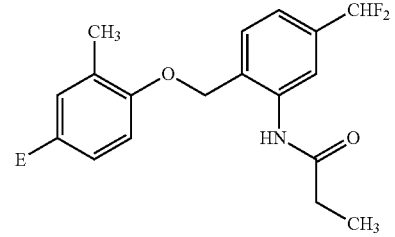
(HN1072)
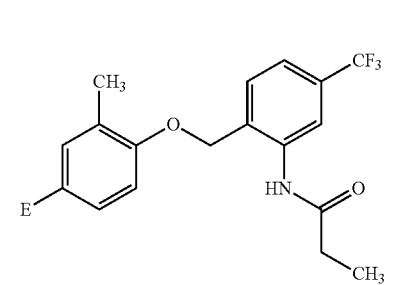
(HN1073)
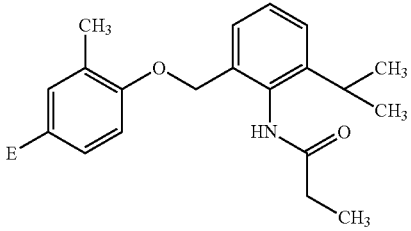
(HN1074)
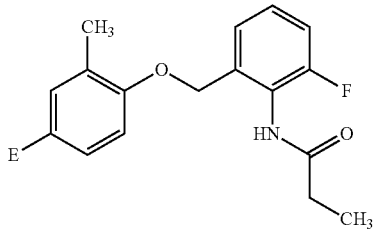
(HN1075)
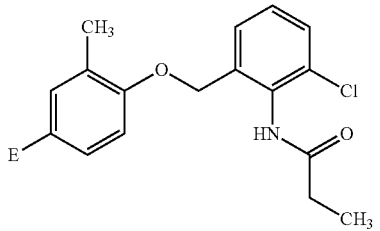
(HN1076)
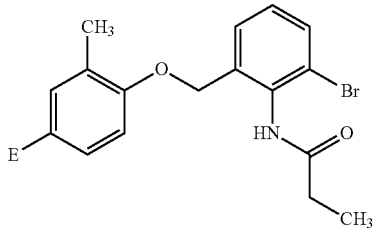
(HN1077)
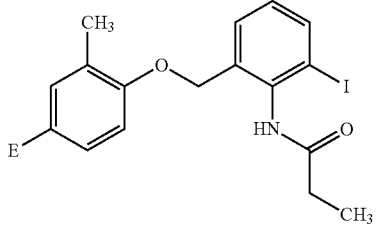
(HN1078)
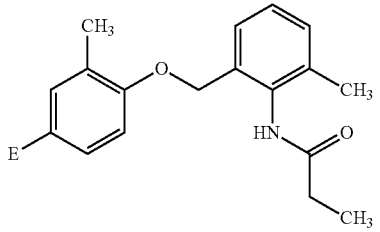

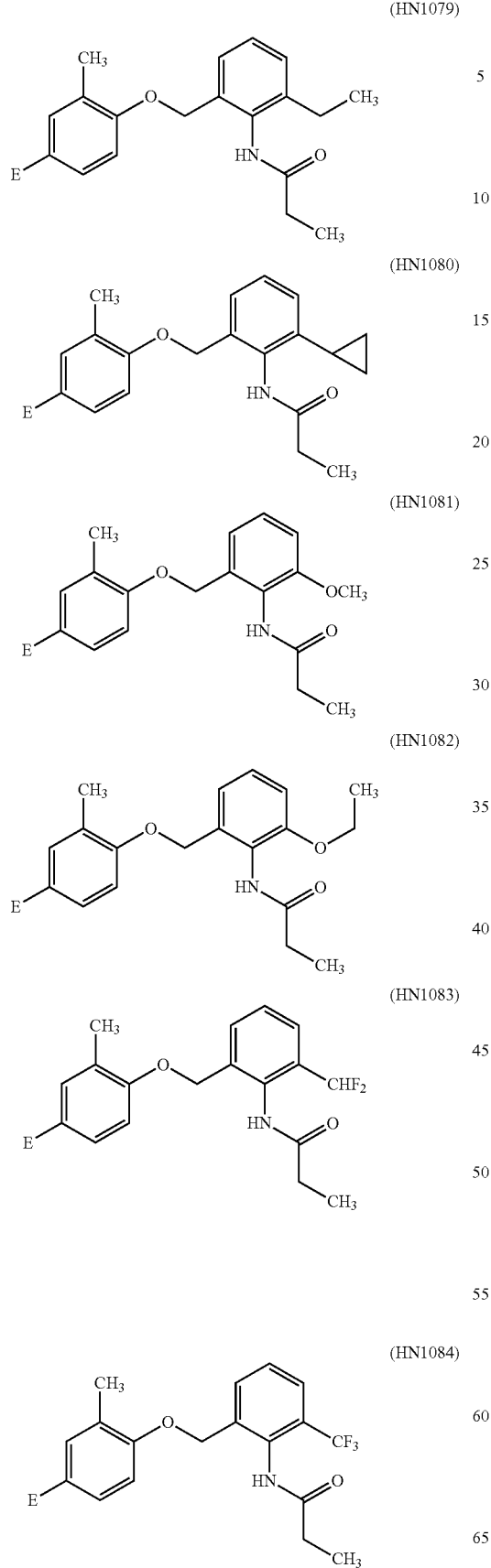
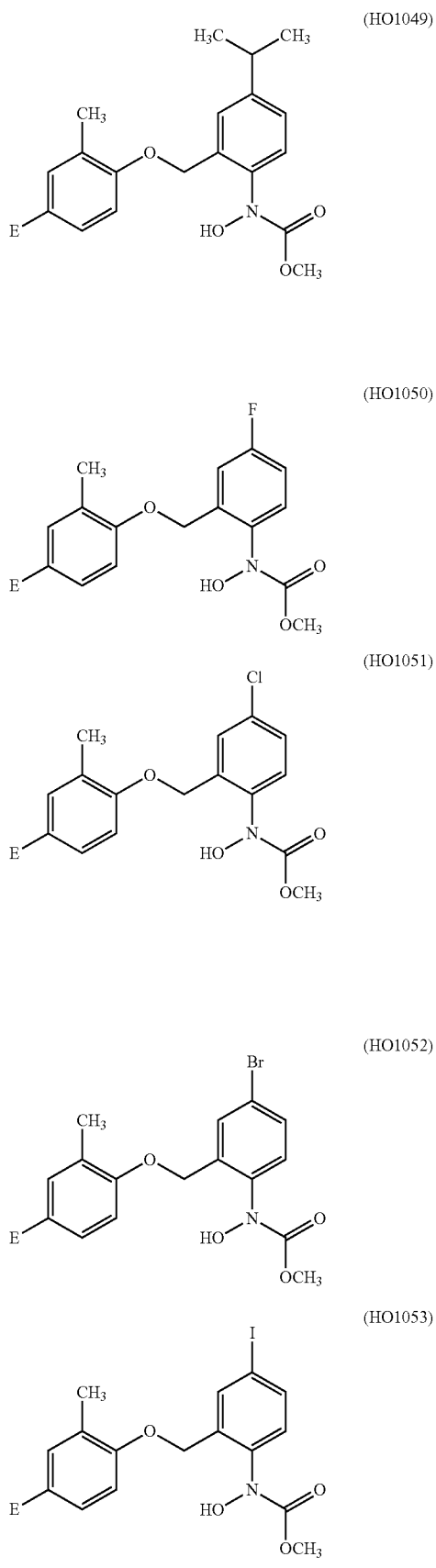

(HO1054)
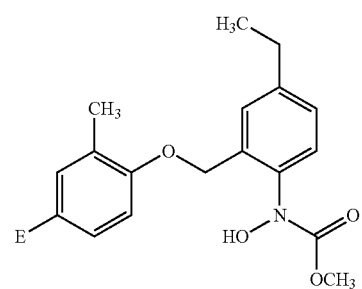
(HO1055)
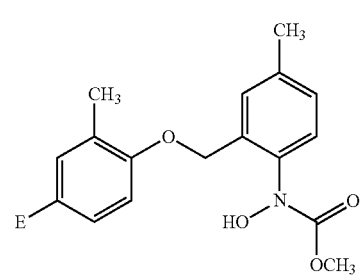
(HO1056)
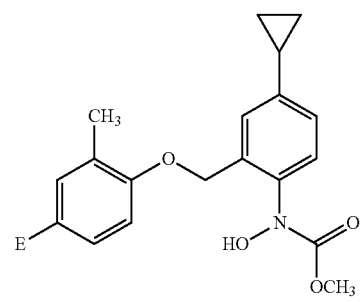
(HO1057)
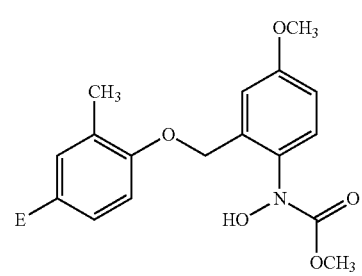
(HO1058)
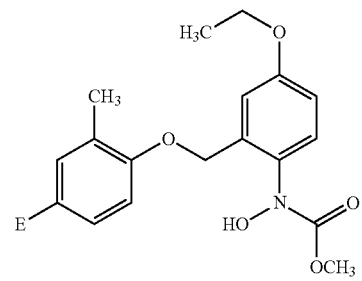
(HO1059)
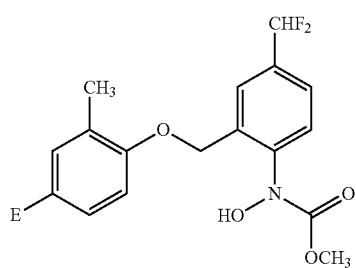
(HO1060)
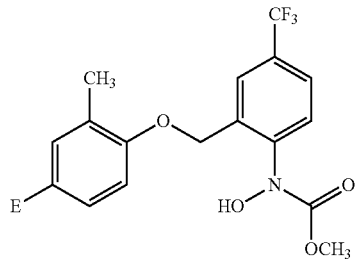
(HO1061)
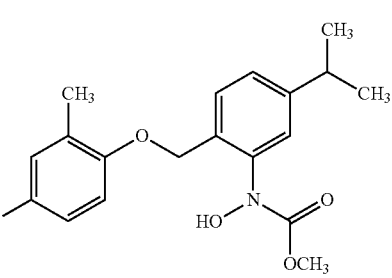
(HO1062)
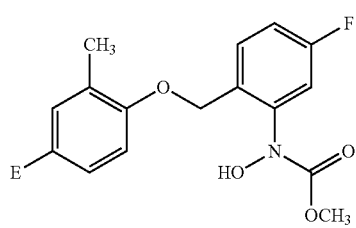
(HO1063)
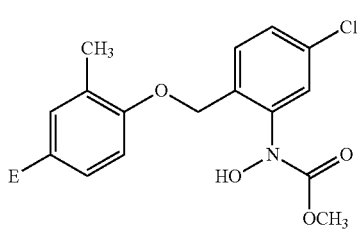
(HO1064)
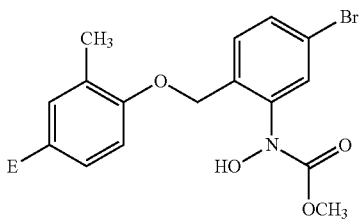

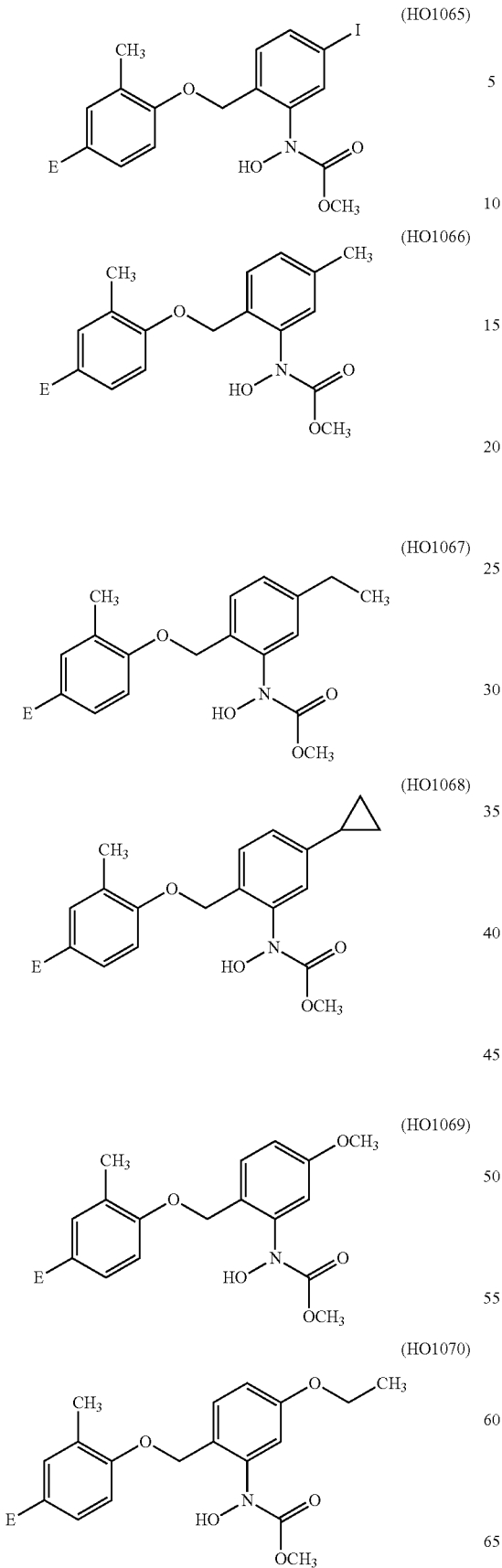
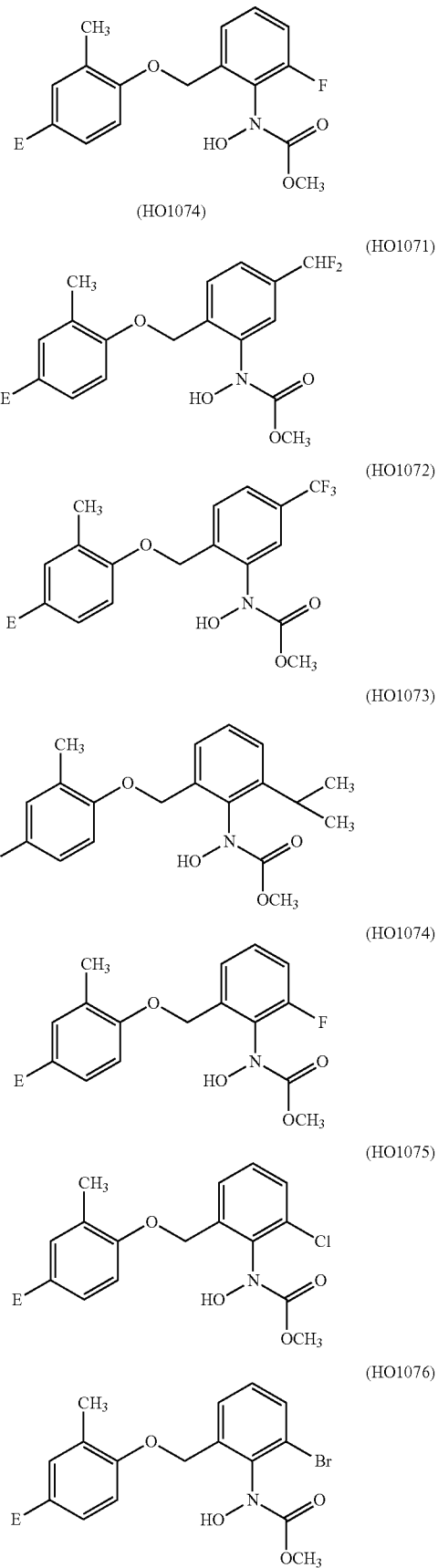

-continued
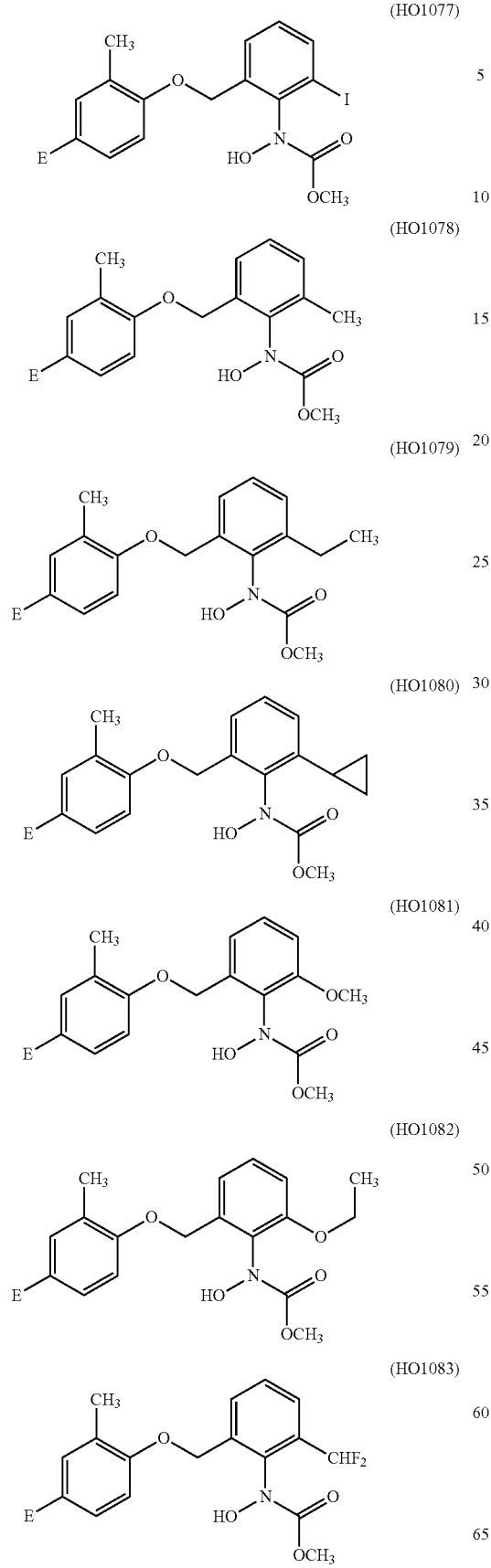
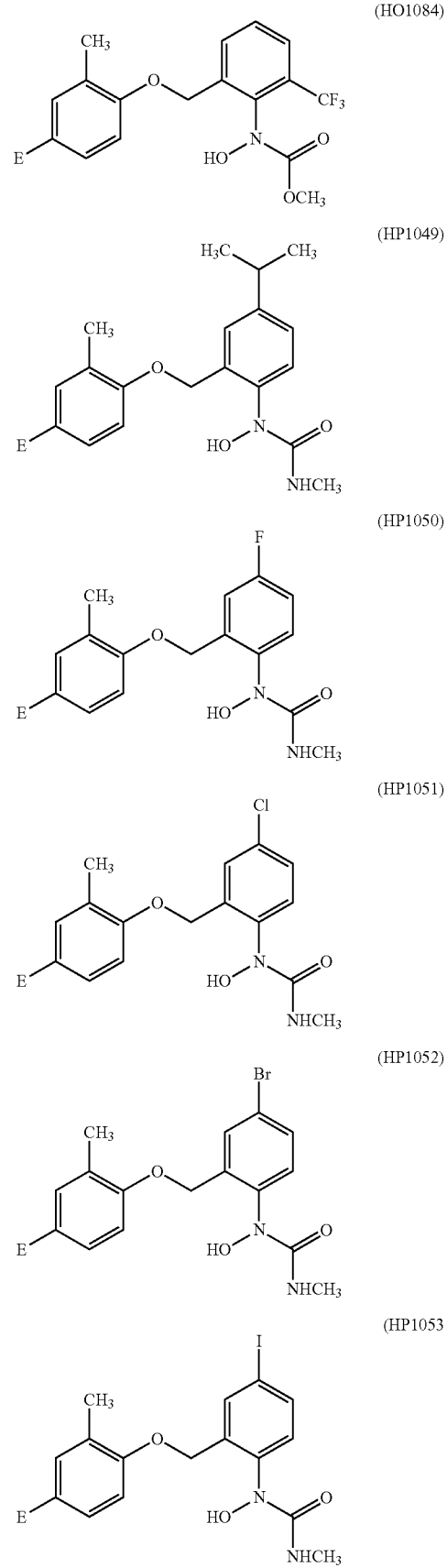

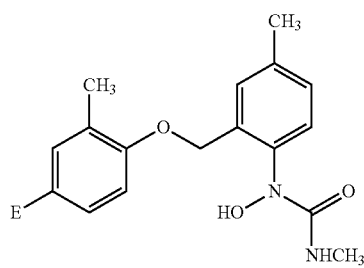
(HP1054)
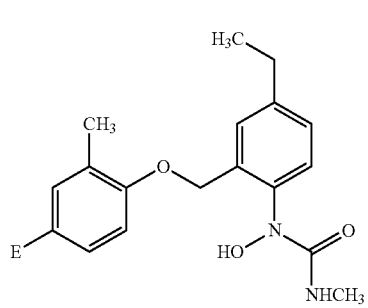
(HP1055)
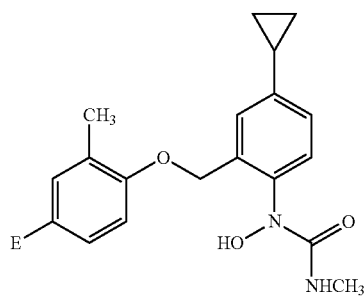
(HP1056)
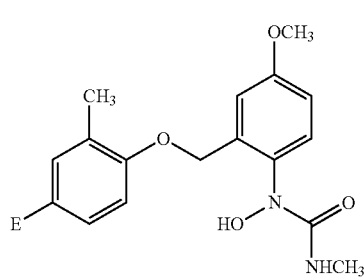
(HP1057)
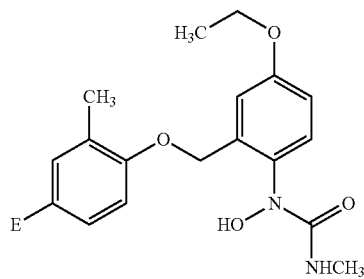
(HP1058)
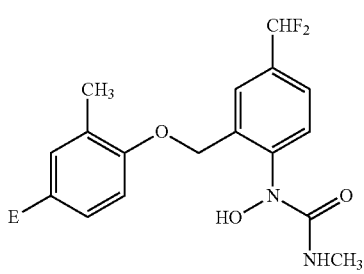
(HP1059)
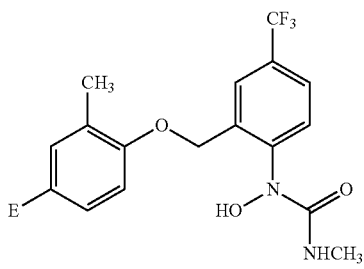
(HP1060)
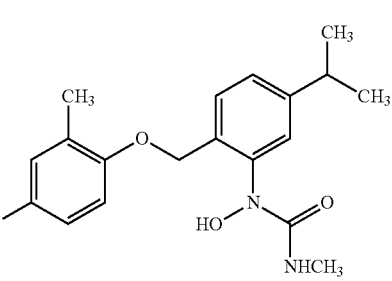
(HP1061)
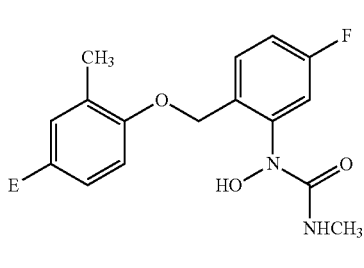
(HP1062)
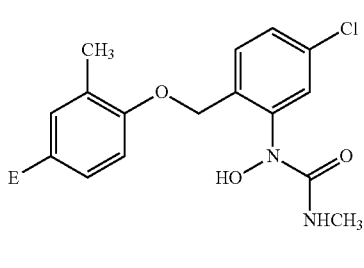
(HP1063)
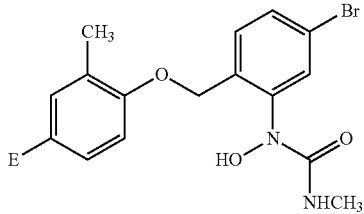
(HP1064)

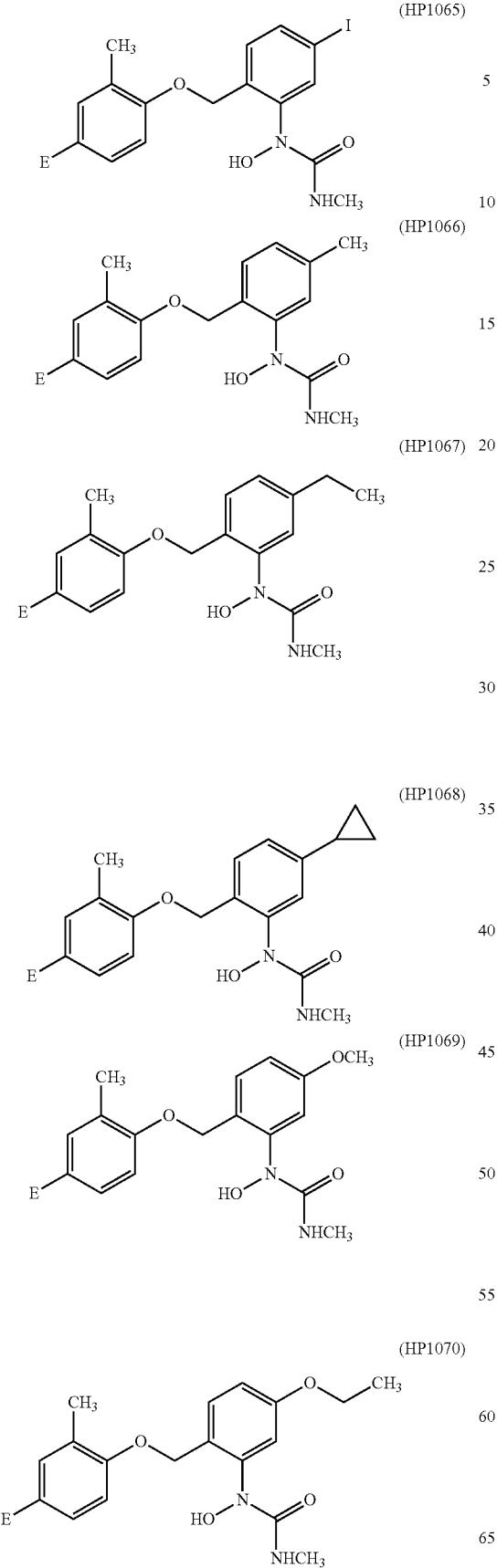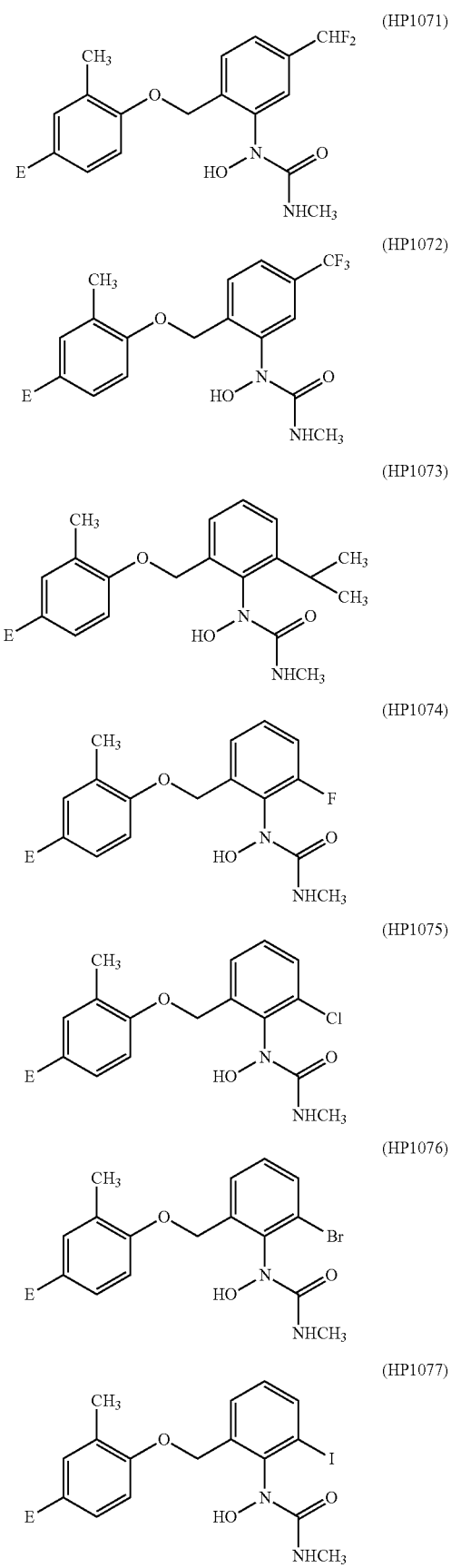

303
-continued
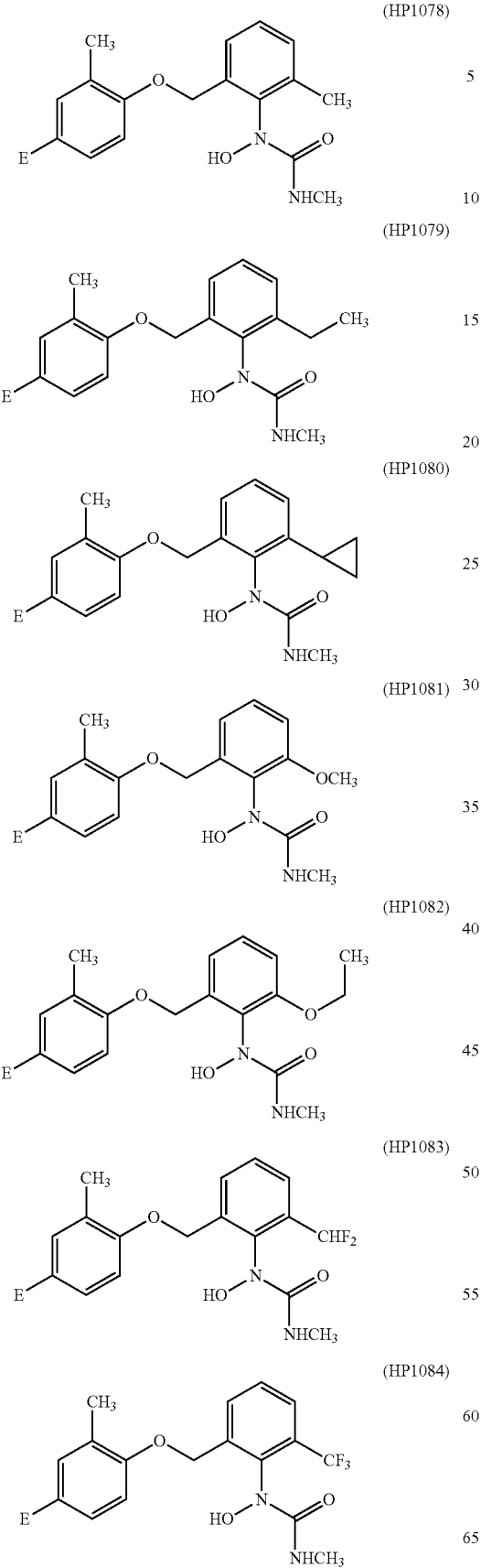
304
-continued
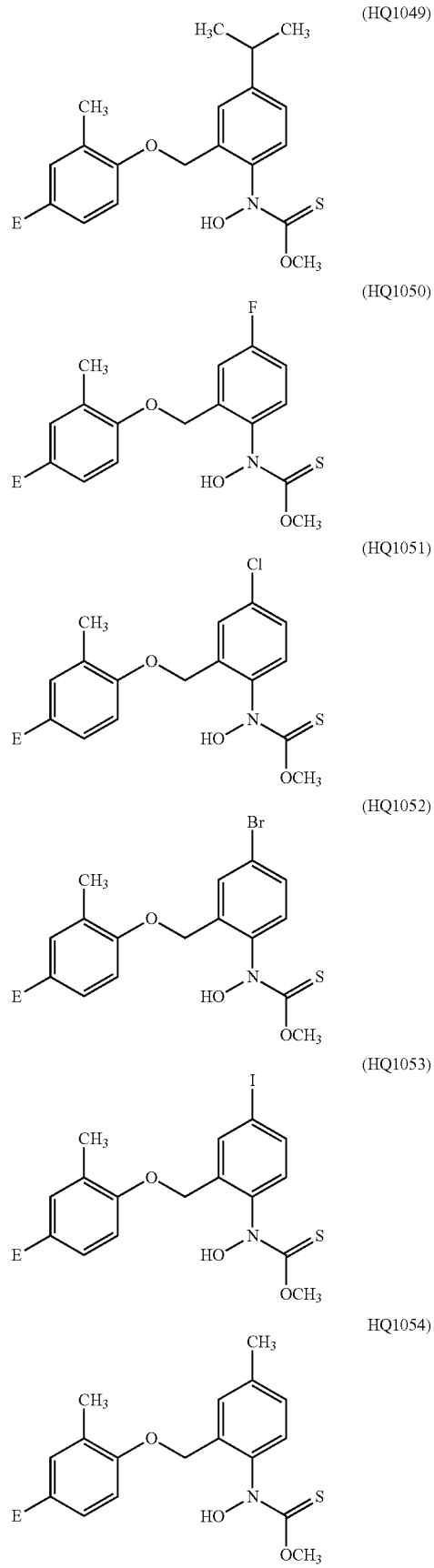

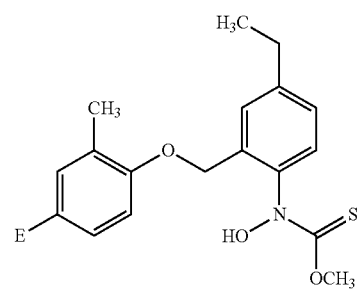
(HQ1055)
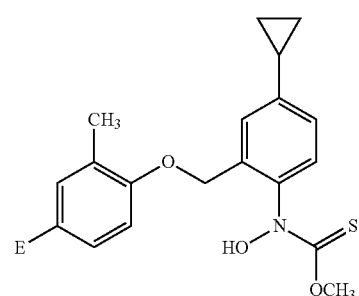
(HQ1056)
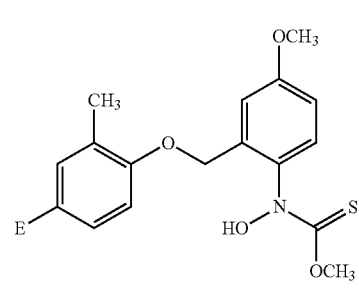
(HQ1057)
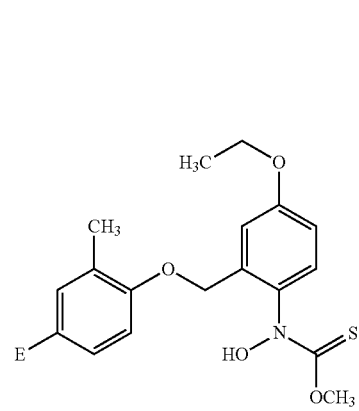
(HQ1058)
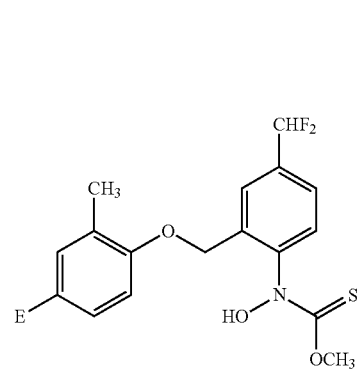
(HQ1059)
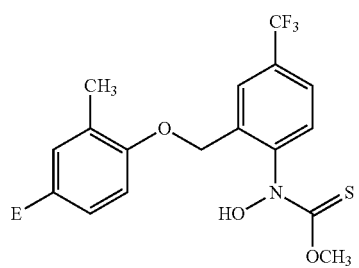
(HQ1060)
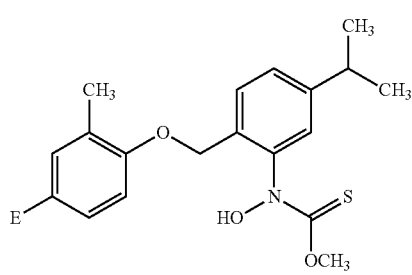
(HQ1061)
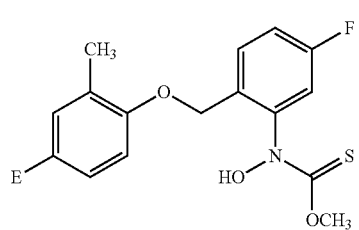
(HQ1062)
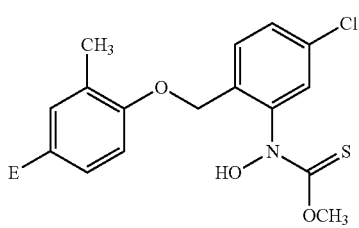
(HQ1063)
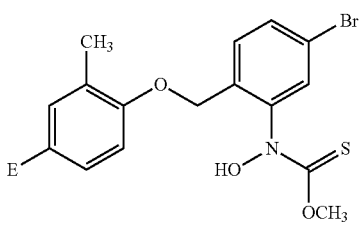
(HQ1064)
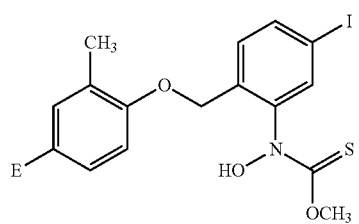
(HQ1065)

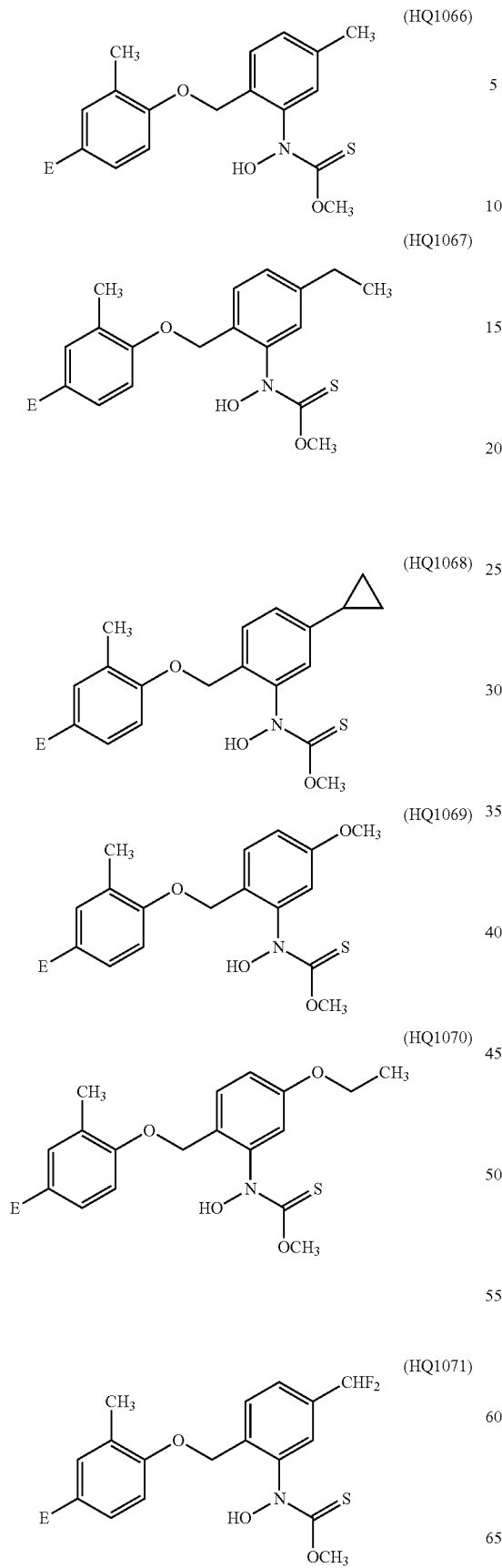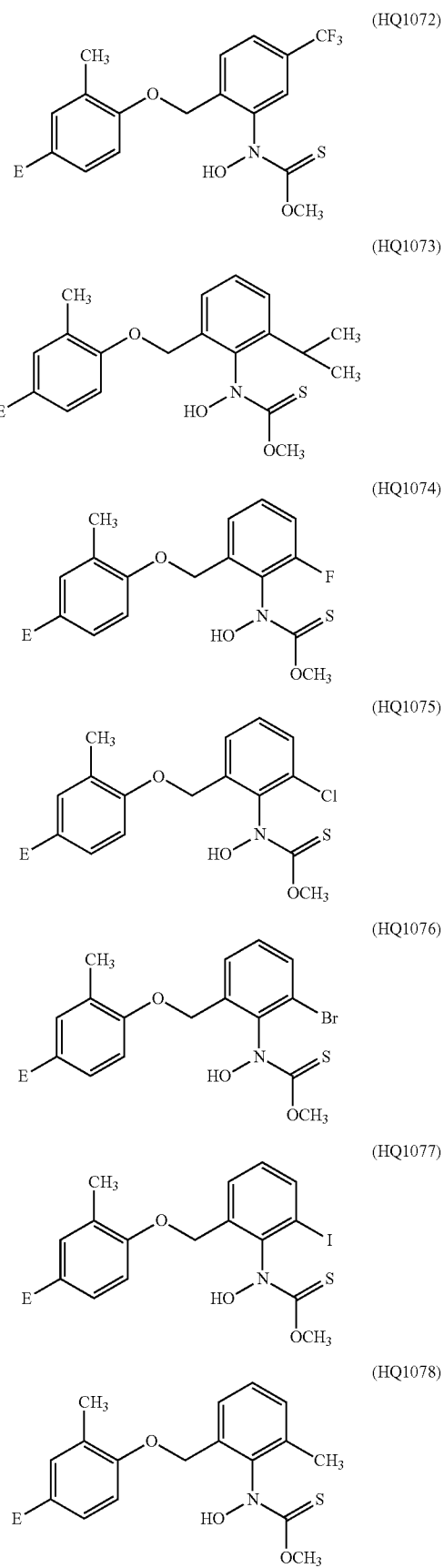

309
-continued
(HQ1079)
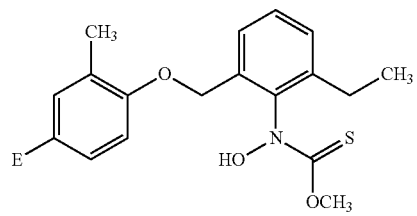
(HQ1080)
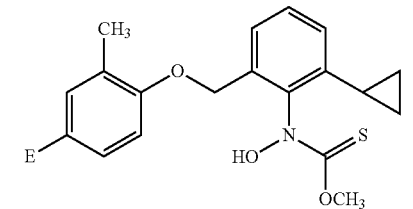
(HQ1081)
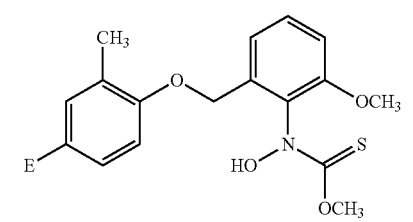
(HQ1082)
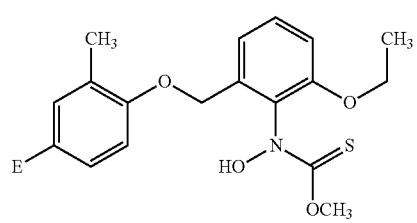
(HQ1083)
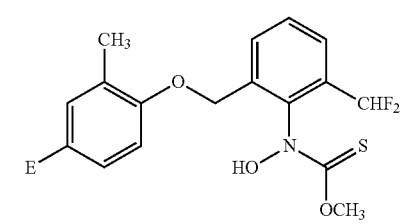
(HQ1084)
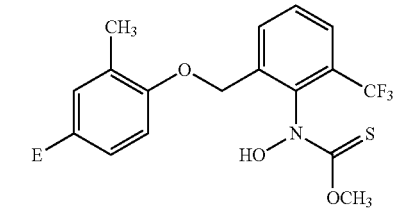
310
-continued
(HR1049)
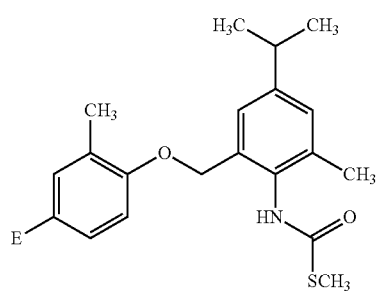
(HR1050)
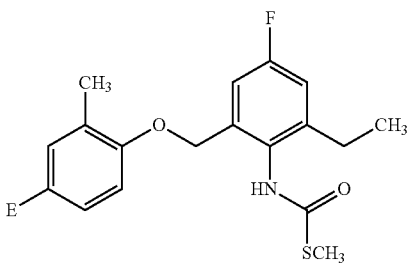
(HR1051)
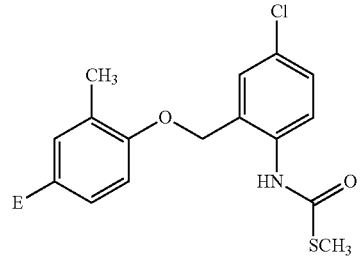
(HR1052)
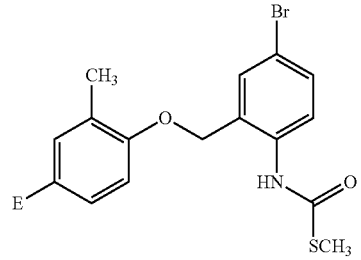
(HR1053)
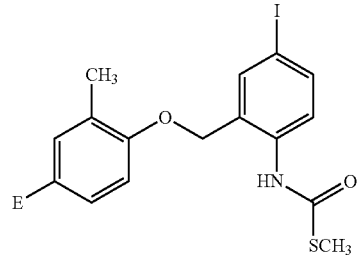
(HR1054)
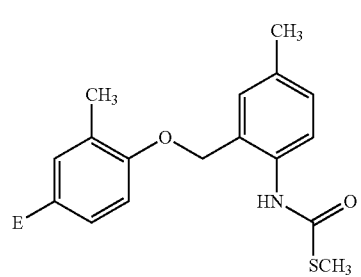

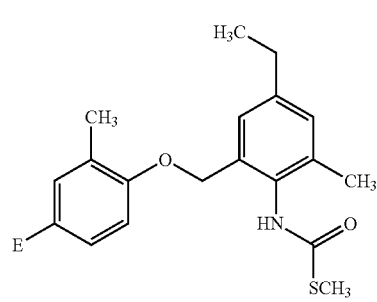
(HR1055)
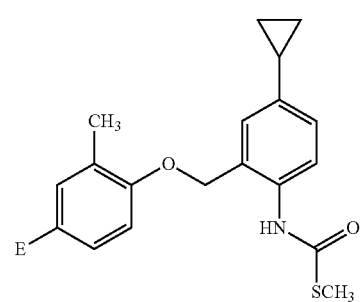
(HR1056)
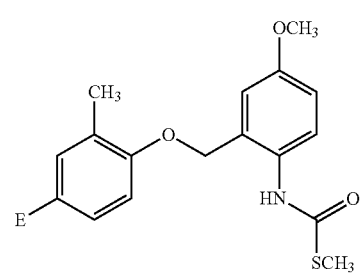
(HR1057)
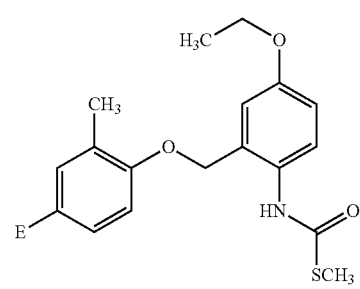
(HR1058)
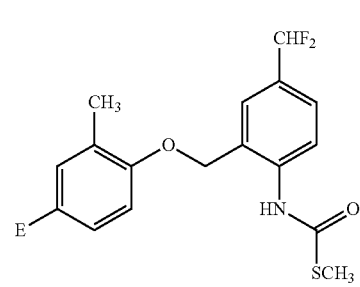
(HR1059)
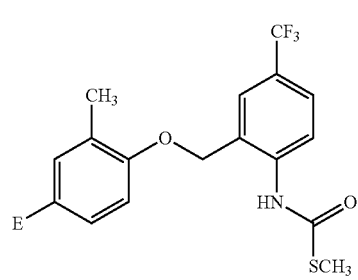
(HR1060)
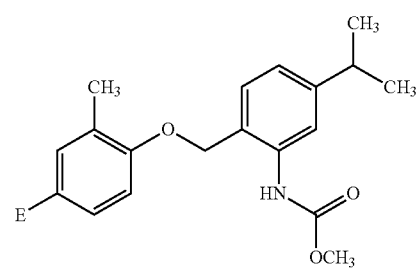
(HR1061)
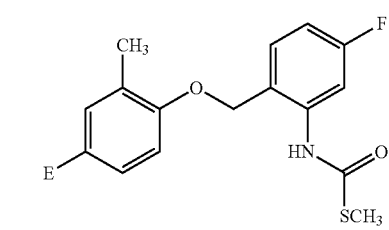
(HR1062)
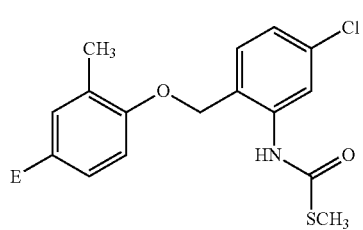
(HR1063)
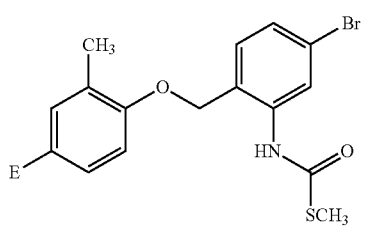
(HR1064)
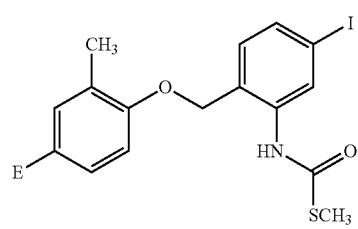
(HR1065)

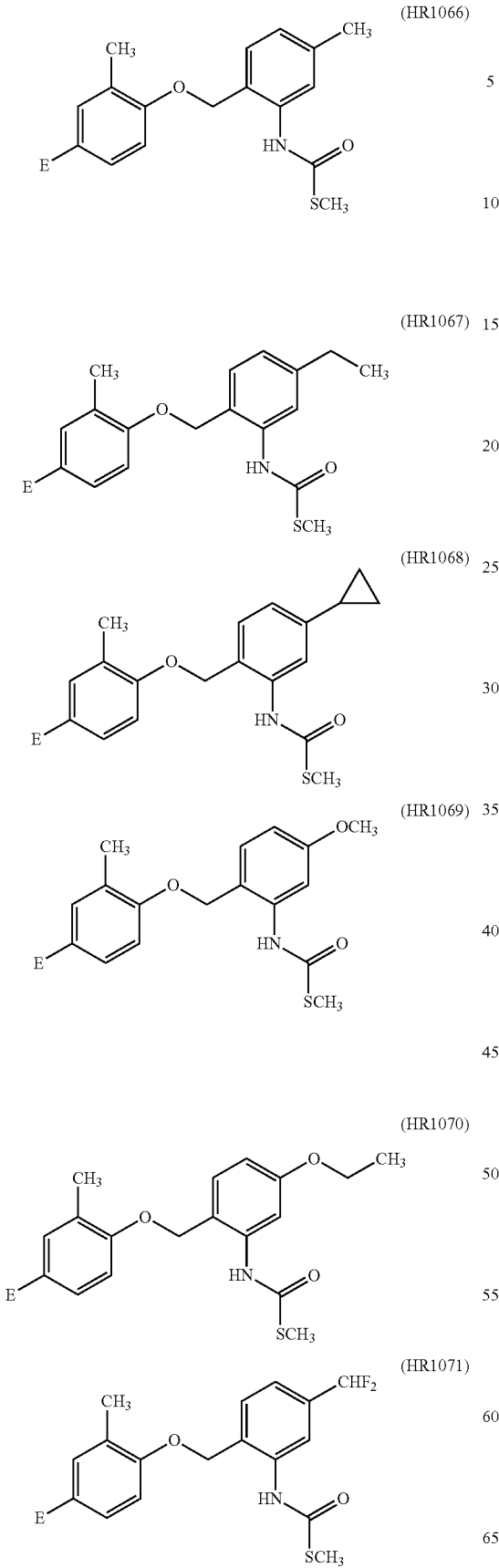
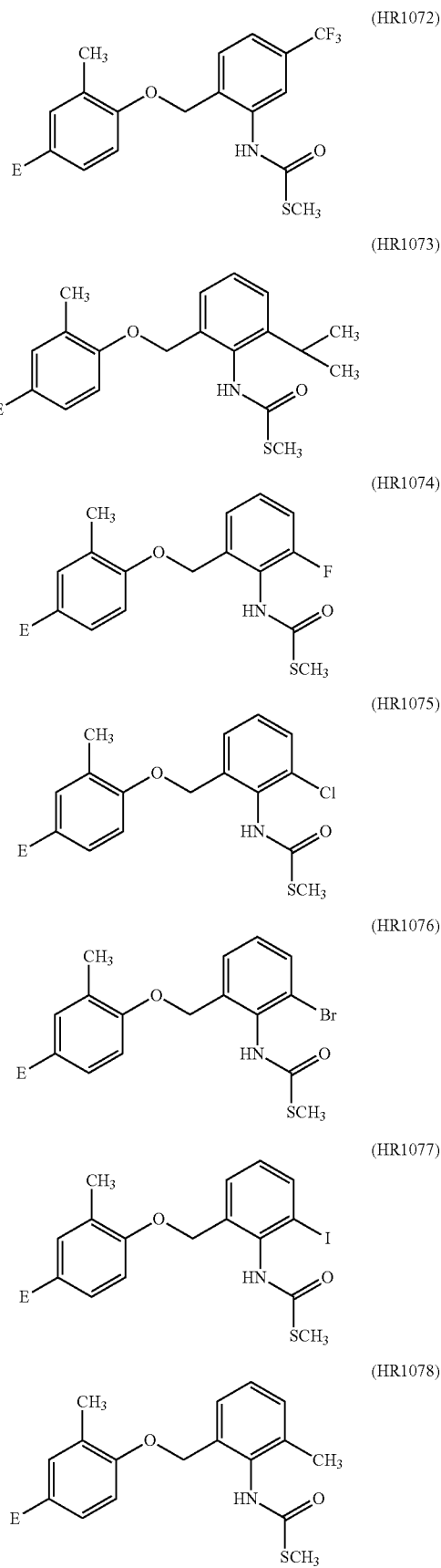

-continued
(HR1079)
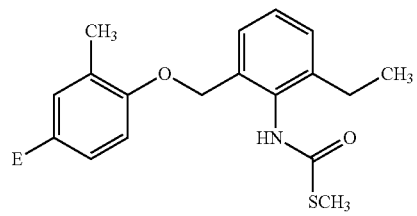
(HR1080)
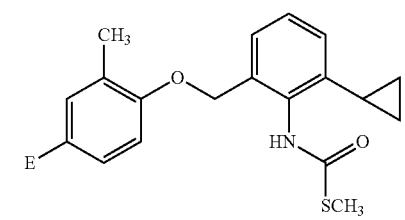
(HR1081)
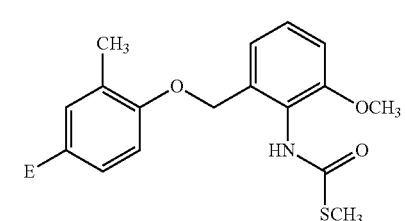
(HR1082)
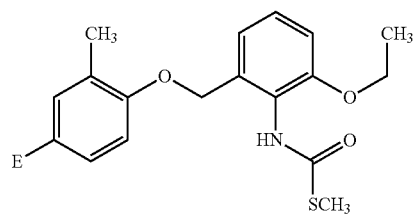
(HR1083)
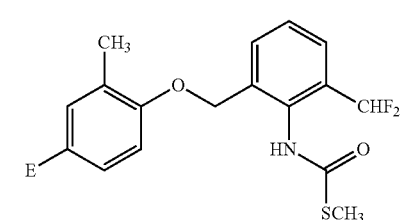
(HR1084)
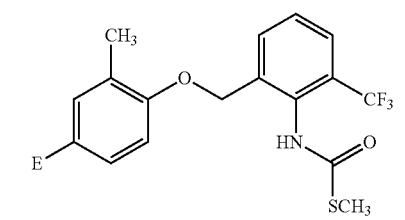
-continued
(HS1049)
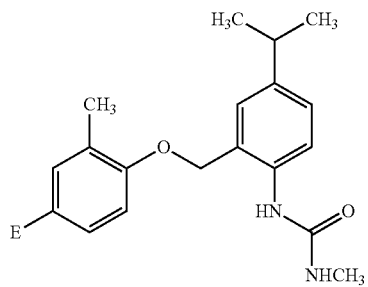
(HS1050)
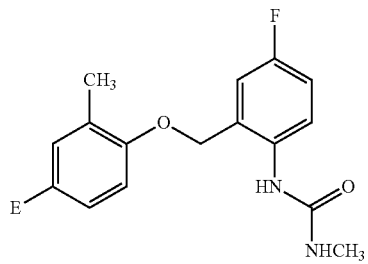
(HS1051)
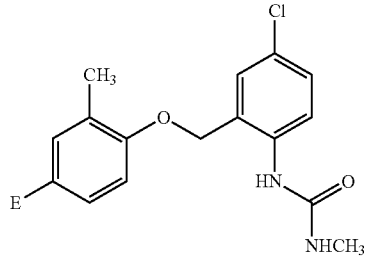
(HS1052)
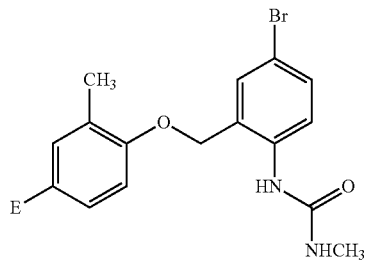
(HS1053)
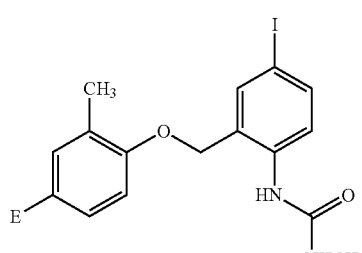
(HS1054)
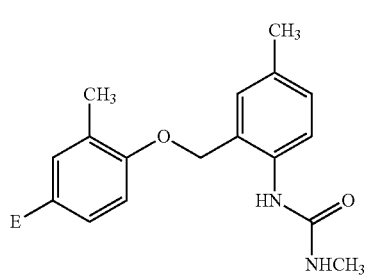

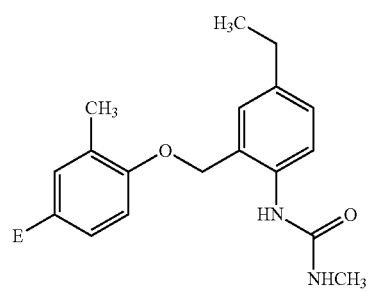 (HS1055)
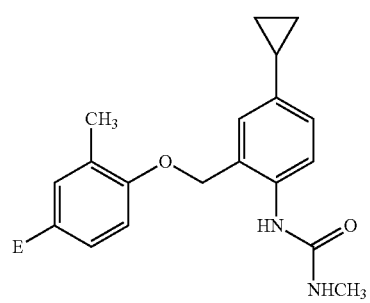 (HS1056)
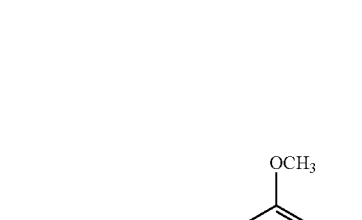 (HS1057)
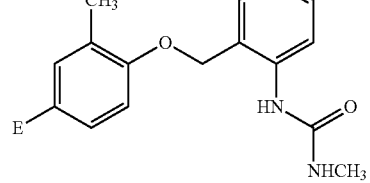 (HS1058)
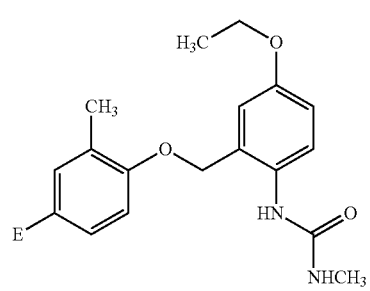 (HS1059)
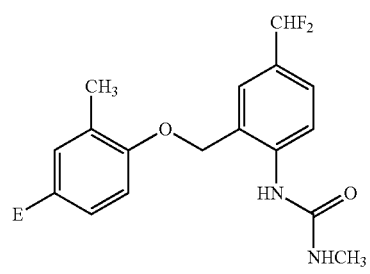 (HS1060)
(HS1061)
(HS1062)
(HS1063)
(HS1064)
(HS1065)

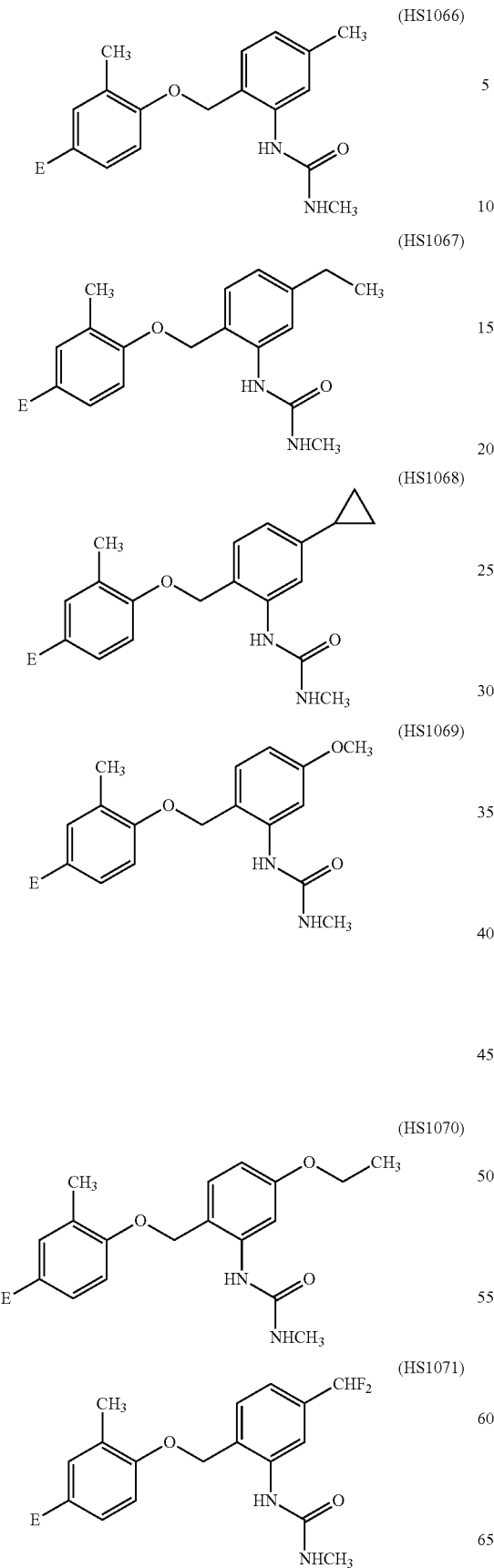
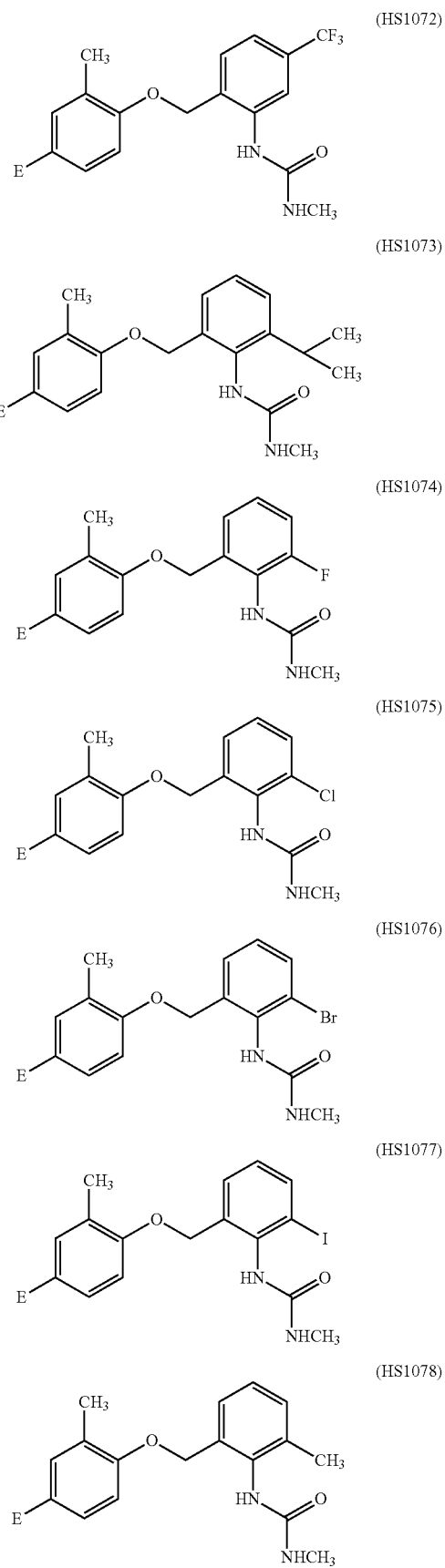

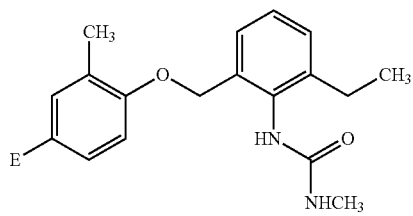
(HS1079)
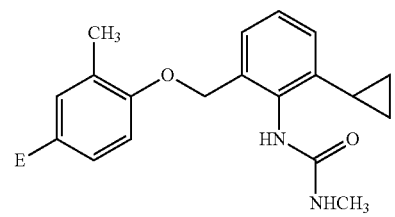
(HS1080)
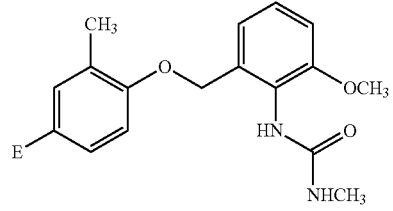
(HS1081)
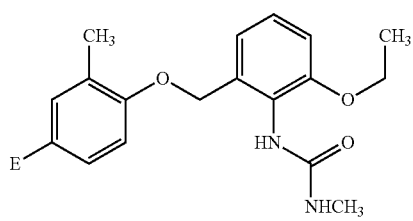
(HS1082)
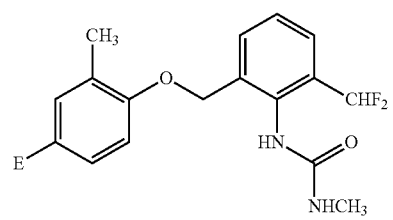
(HS1083)
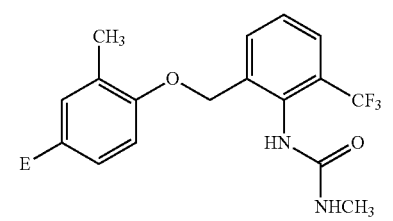
(HS1084)
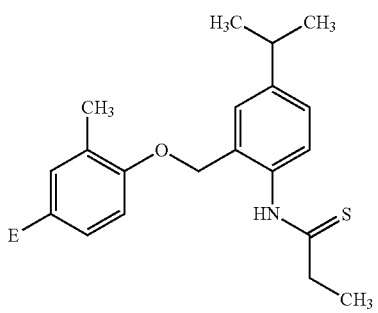
(HT1049)
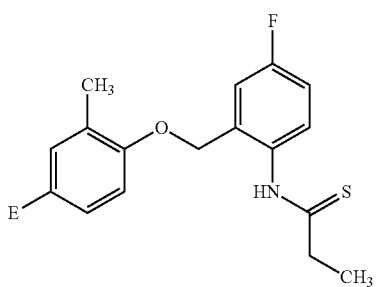
(HT1050)
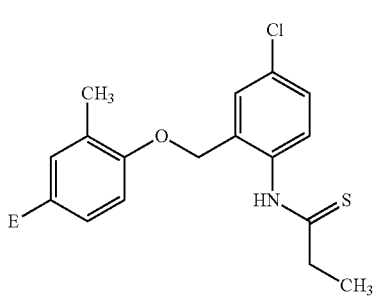
(HT1051)
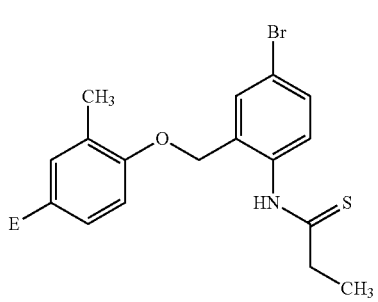
(HT1052)
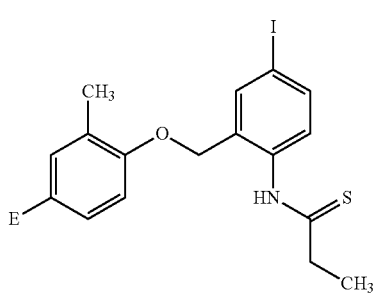
(HT1053)

323
-continued
(HT1055)
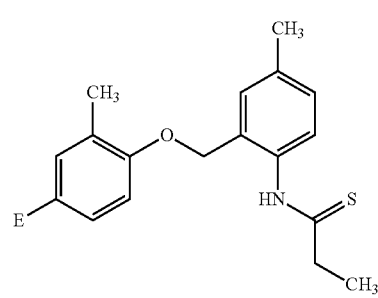
(HT1056)
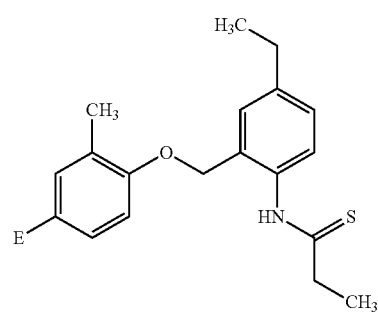
(HT1057)
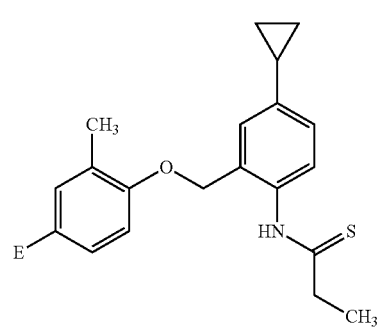
(HT1058)
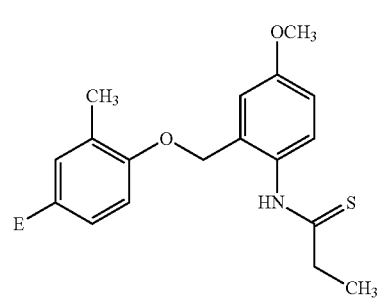
324
-continued
(HT1059)
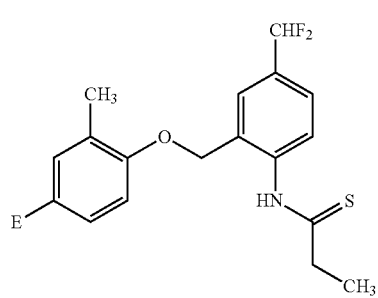
(HT1060)
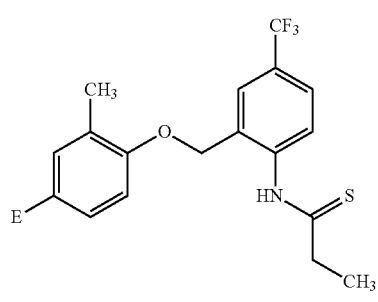
(HT1061)
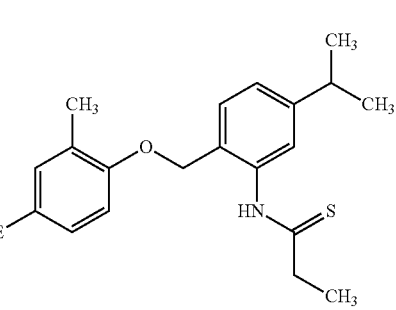
(HT1062)
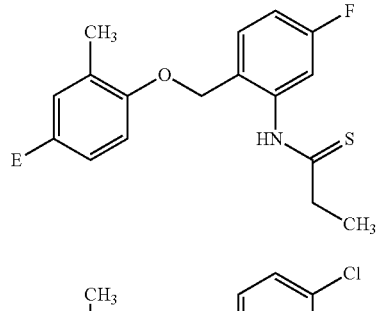
(HT1063)
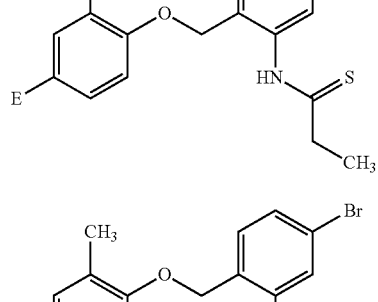
(HT1064)
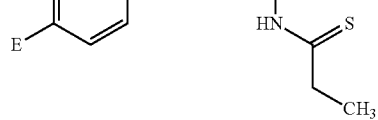
(HT1053)
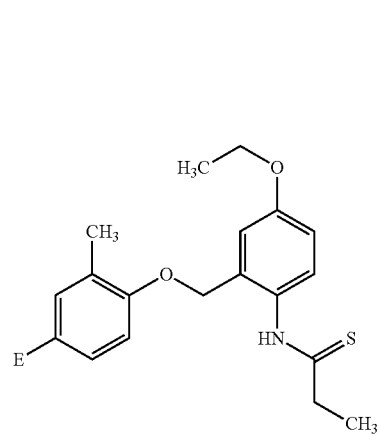

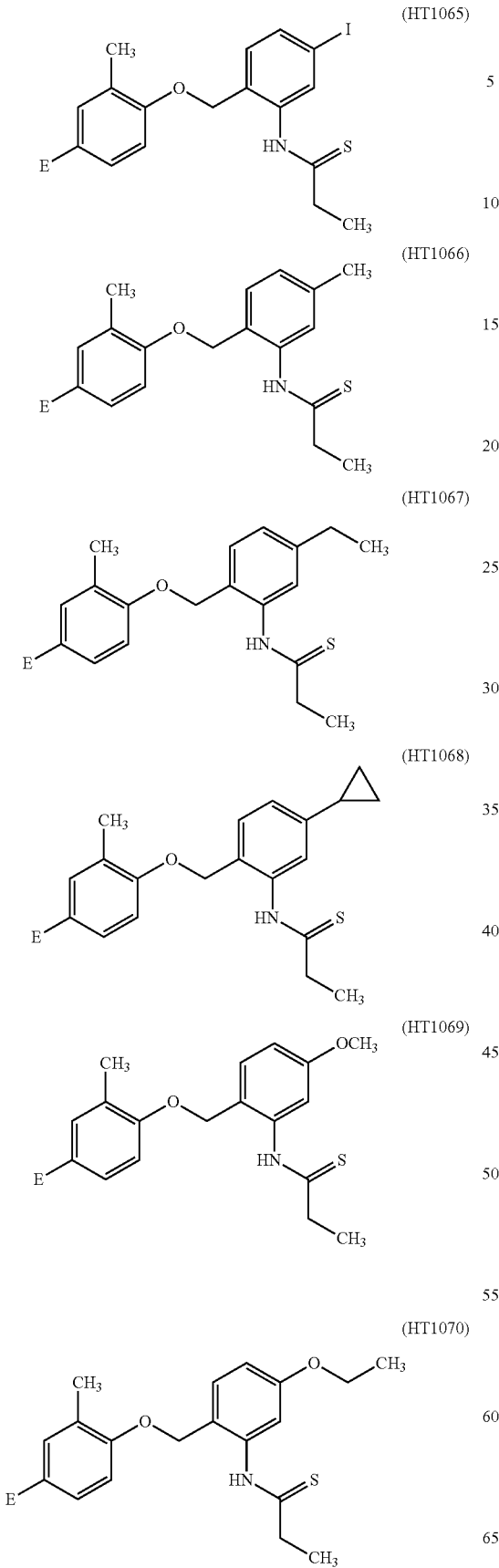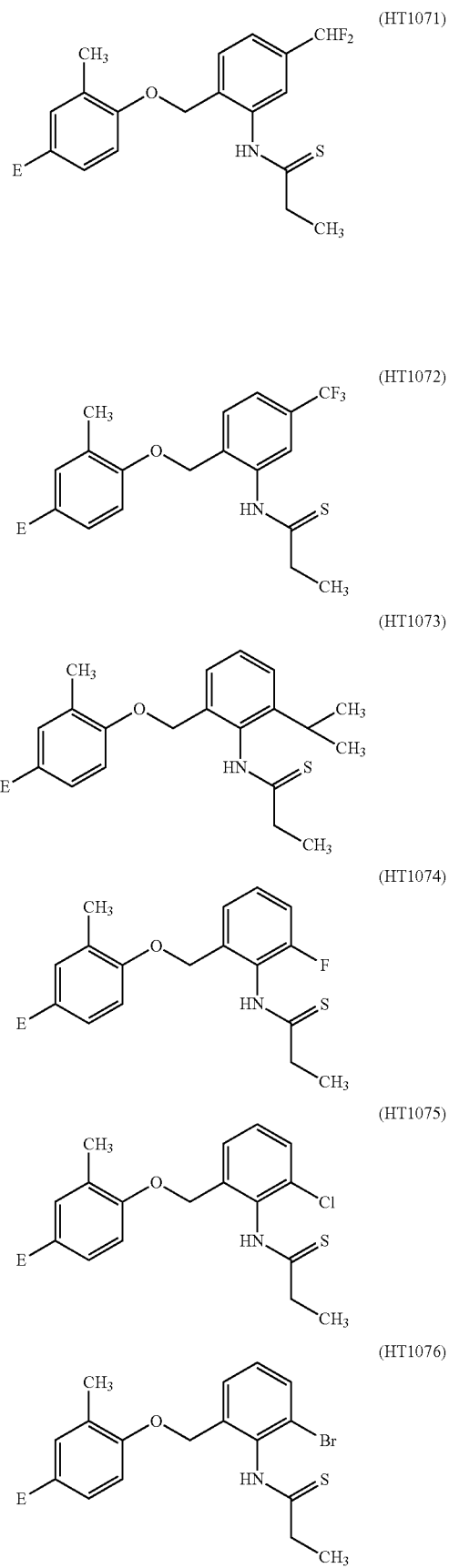

-continued
(HT1077)
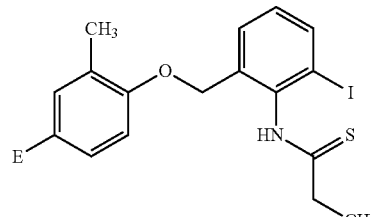
(HT1078)
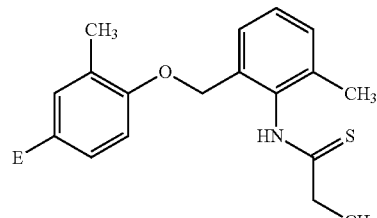
(HT1079)
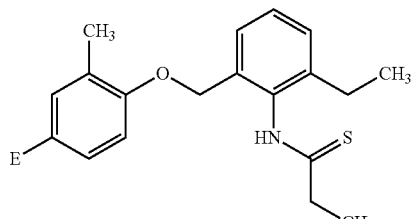
(HT1080)
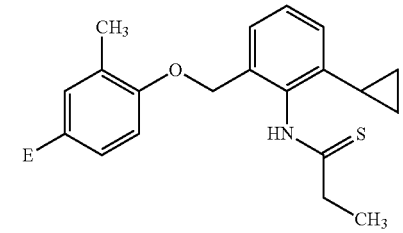
(HT1081)
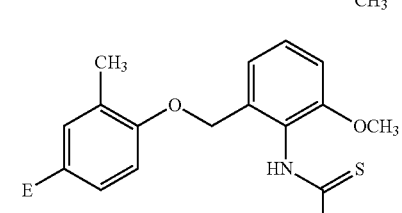
(HT1082)
-continued
(HT1083)
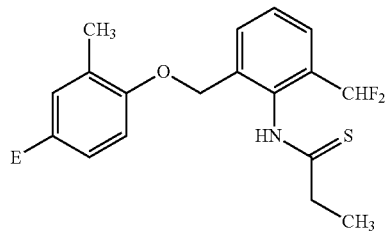
(HT1084)
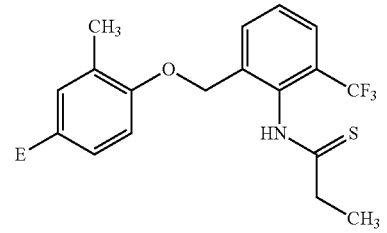
(HU1049)
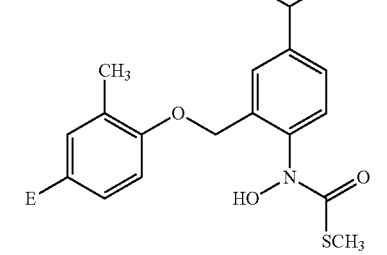
(HU1050)
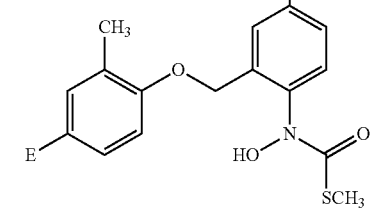
(HU1051)
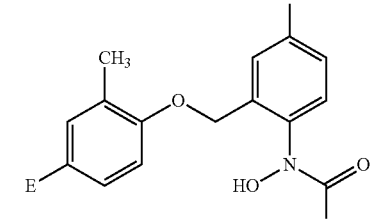
(HU1052)
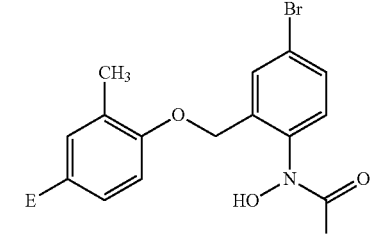

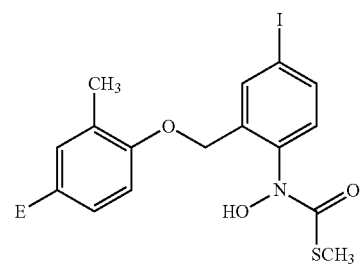
(HU1053)
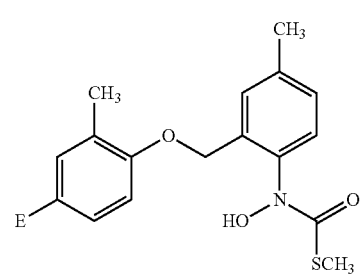
(HU1054)
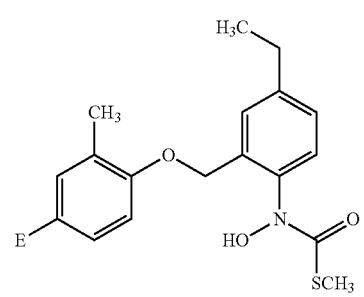
(HU1055)
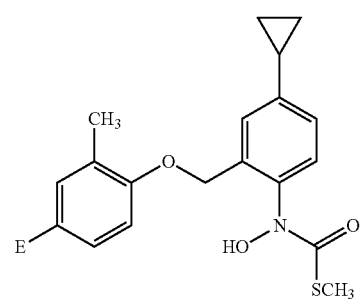
(HU1056)
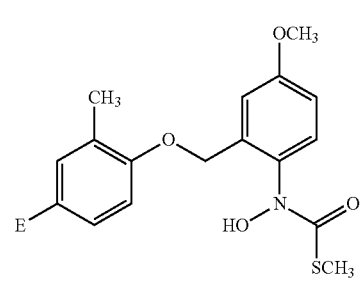
(HU1057)
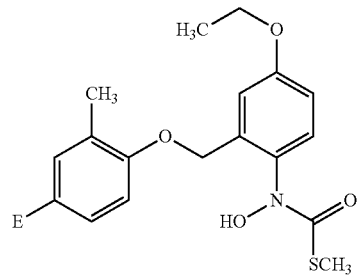
(HU1058)
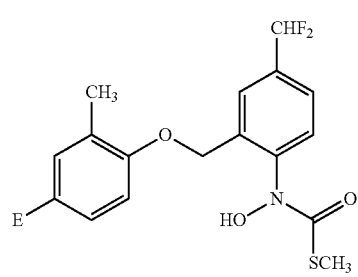
(HU1059)
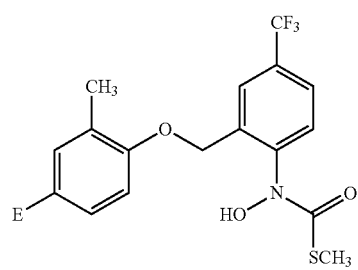
(HU1060)
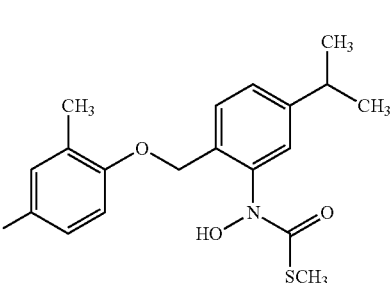
(HU1061)
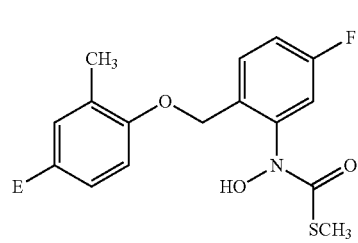
(HU1062)
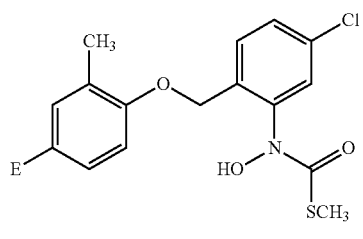
(HU1063)

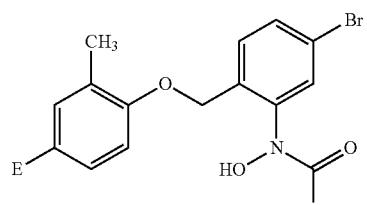
(HU1064)
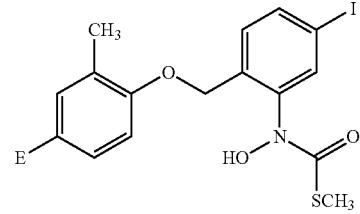
(HU1065)
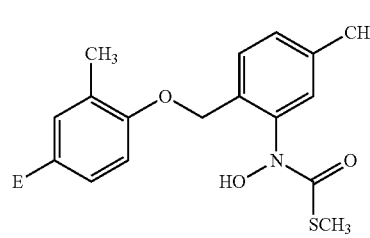
(HU1066)
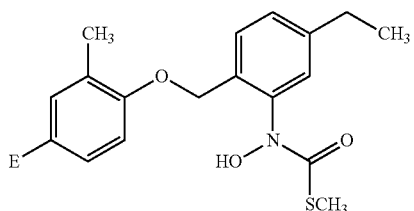
(HU1067)
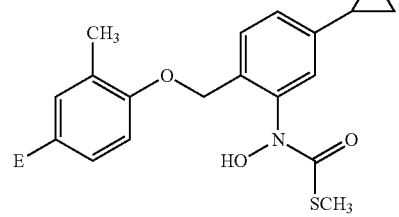
(HU1068)
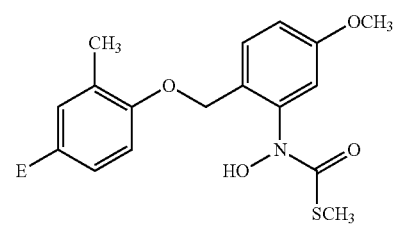
(HU1069)
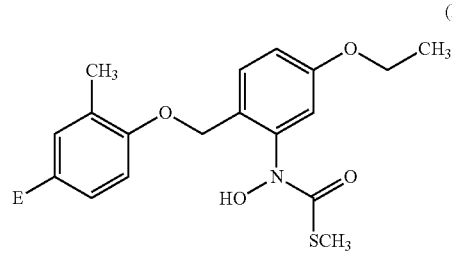
(HU1070)
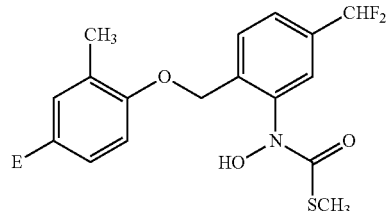
(HU1071)
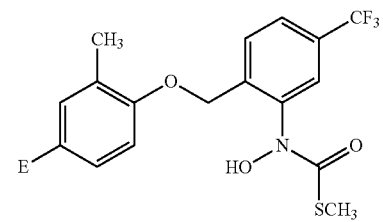
(HU1072)
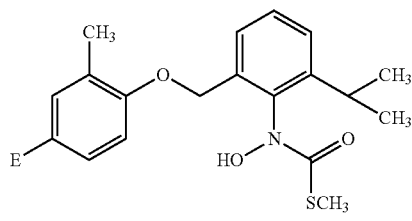
(HU1073)
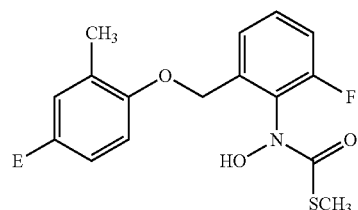
(HU1074)
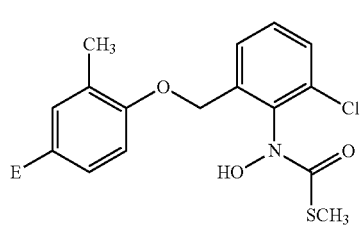
(HU1075)

-continued
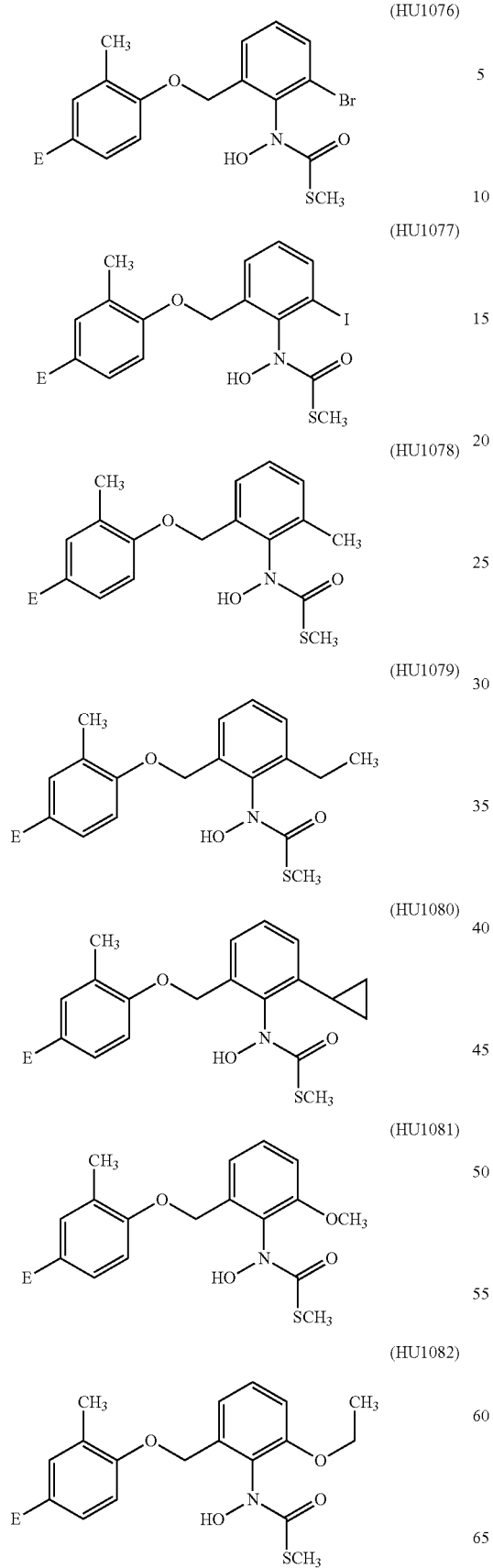
(HU1076)
(HU1077)
(HU1078)
(HU1079)
(HU1080)
(HU1081)
(HU1082)
-continued
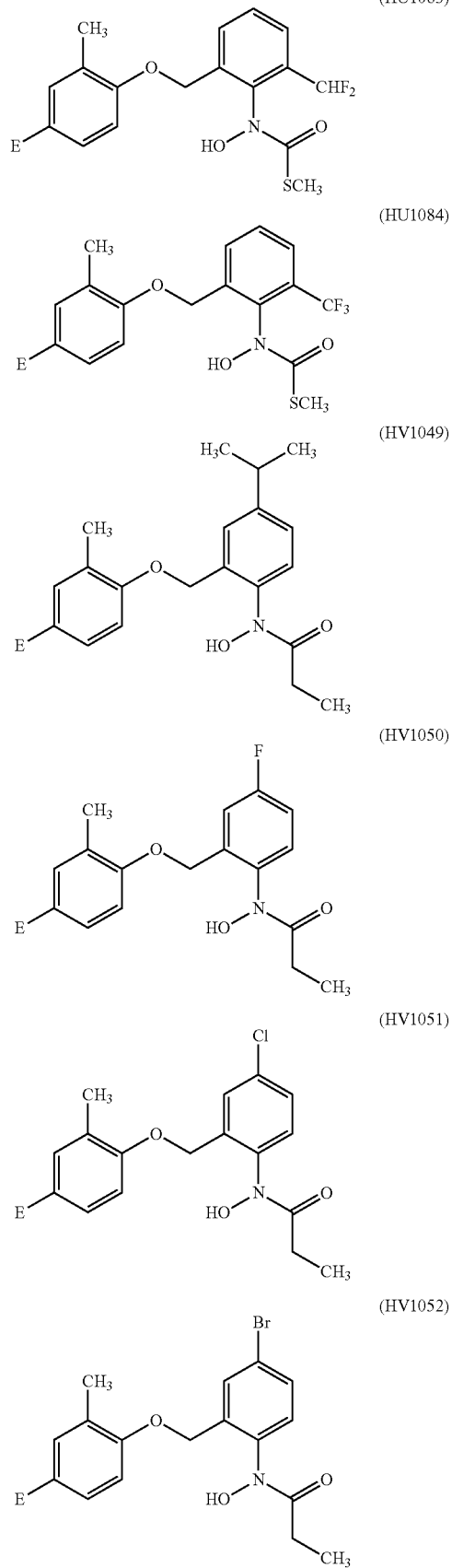
(HU1083)
(HU1084)
(HV1049)
(HV1050)
(HV1051)
(HV1052)

(HV1053) 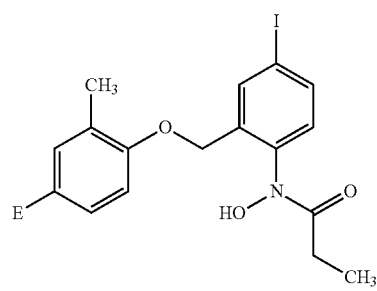
(HV1054) 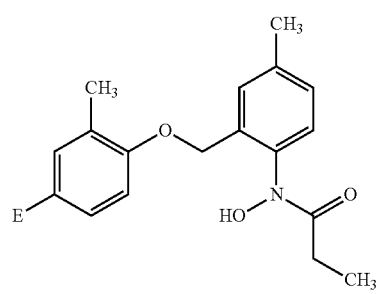
(HV1055) 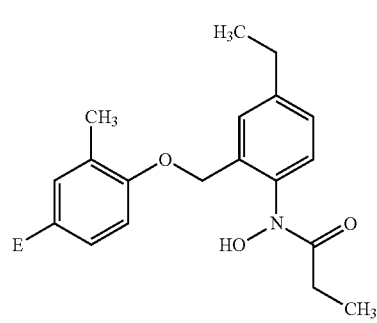
(HV1056) 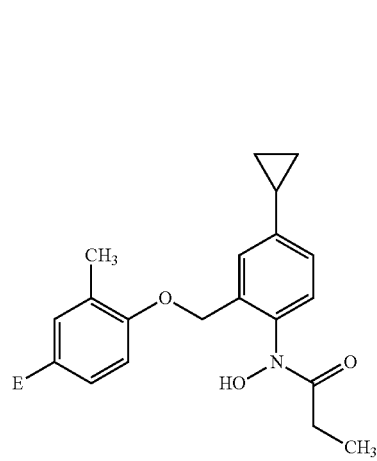
(HV1057) 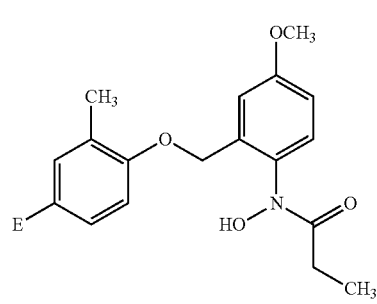
(HV1058) 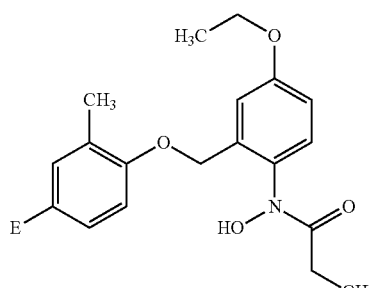
(HV1059) 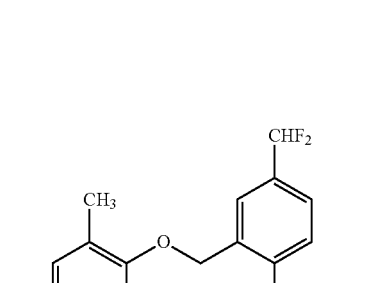
(HV1060) 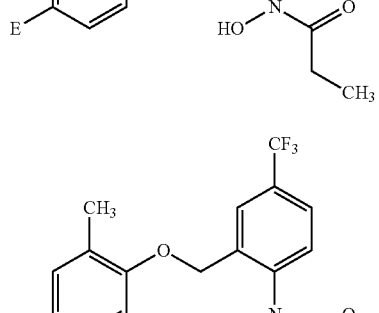
(HV1061) 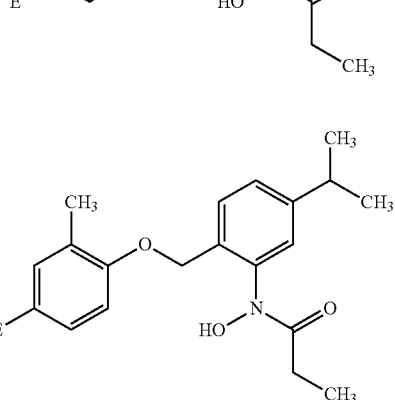
(HV1062) 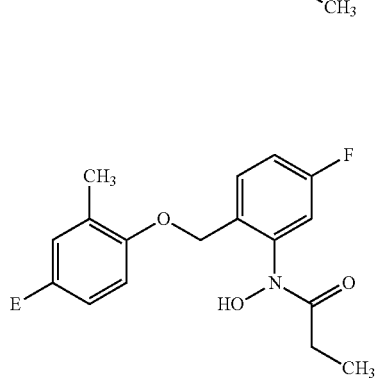

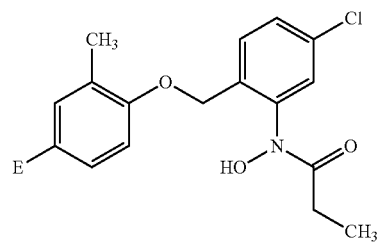 (HV1063)
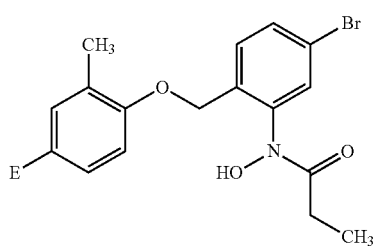 (HV1064)
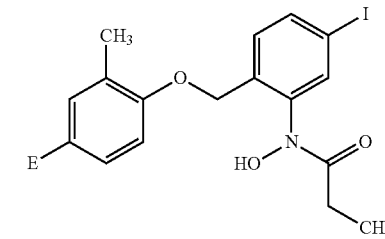 (HV1065)
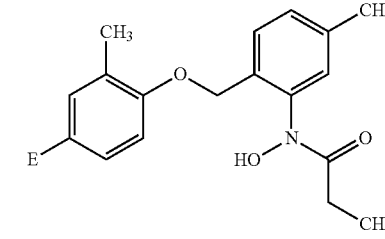 (HV1066)
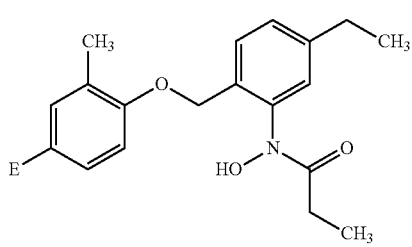 (HV1067)
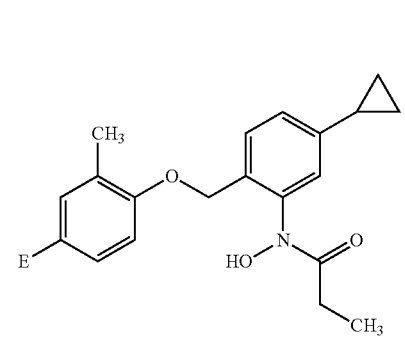 (HV1068)
(HV1069)
(HV1070)
(HV1071)
(HV1072)
(HV1073)
(HV1074)

-continued
(HV1075)
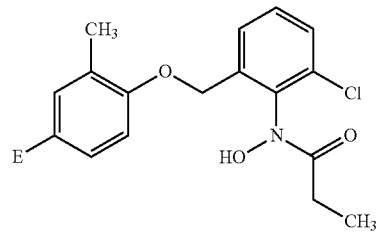
(HV1076)
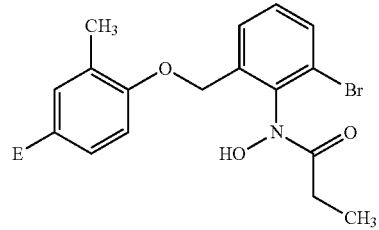
(HV1077)
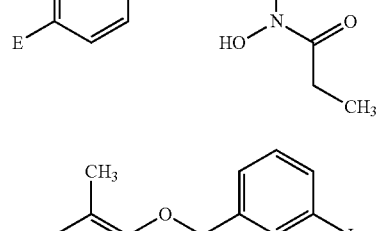
(HV1078)
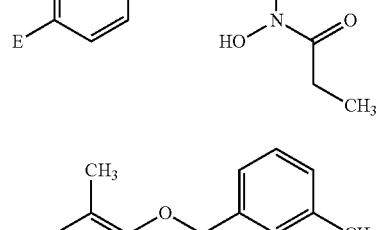
(HV1079)
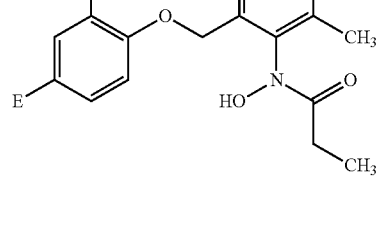
(HV1080)
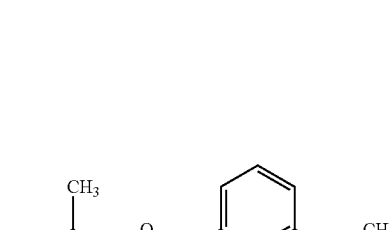
-continued
(HV1081)
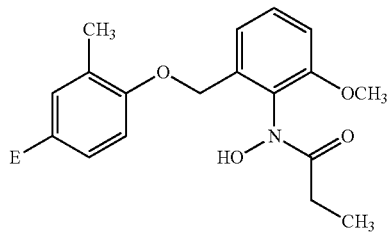
(HV1082)
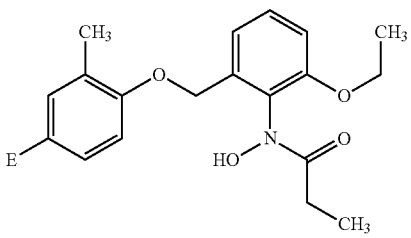
(HV1083)
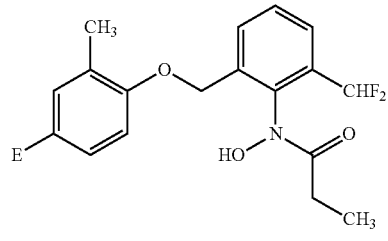
(HV1084)
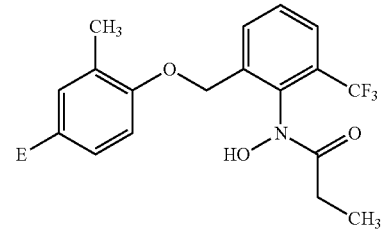
(HW1049)
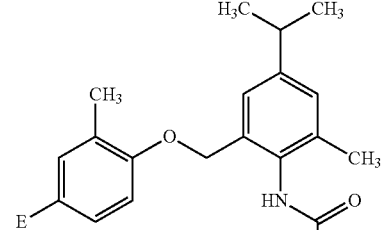
(HW1050)
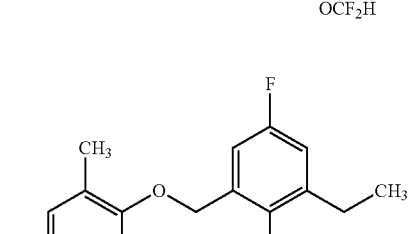

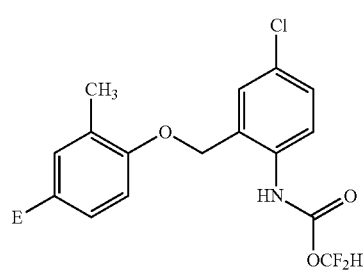
(HW1051)
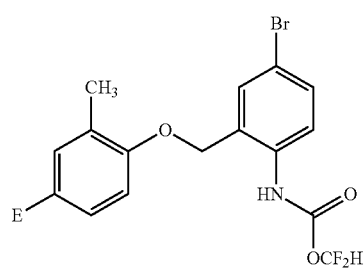
(HW1052)
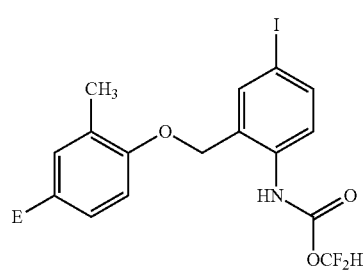
(HW1053)
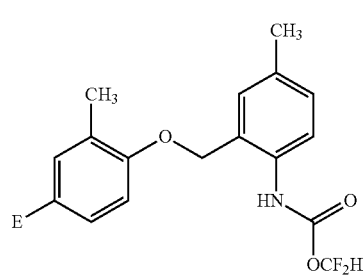
(HW1054)
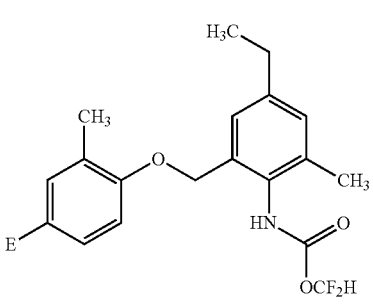
(HW1055)
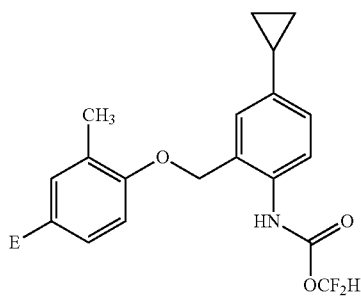
(HW1056)
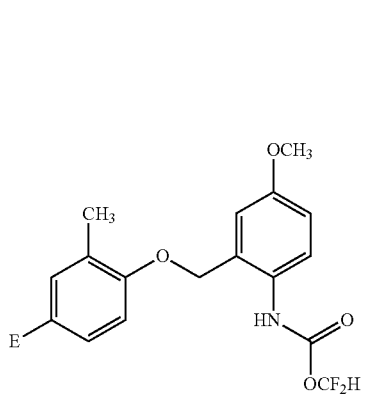
(HW1057)
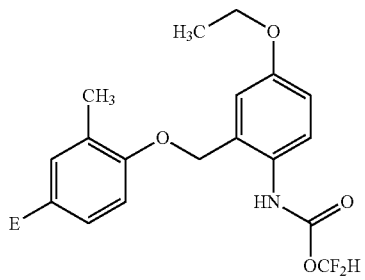
(HW1058)
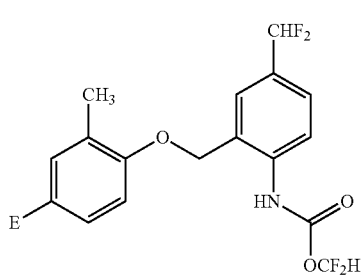
(HW1059)
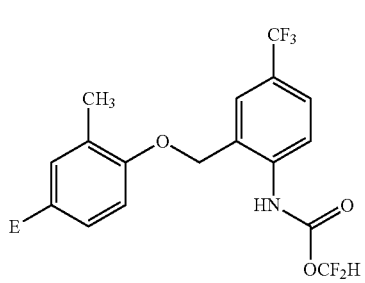
(HW1060)

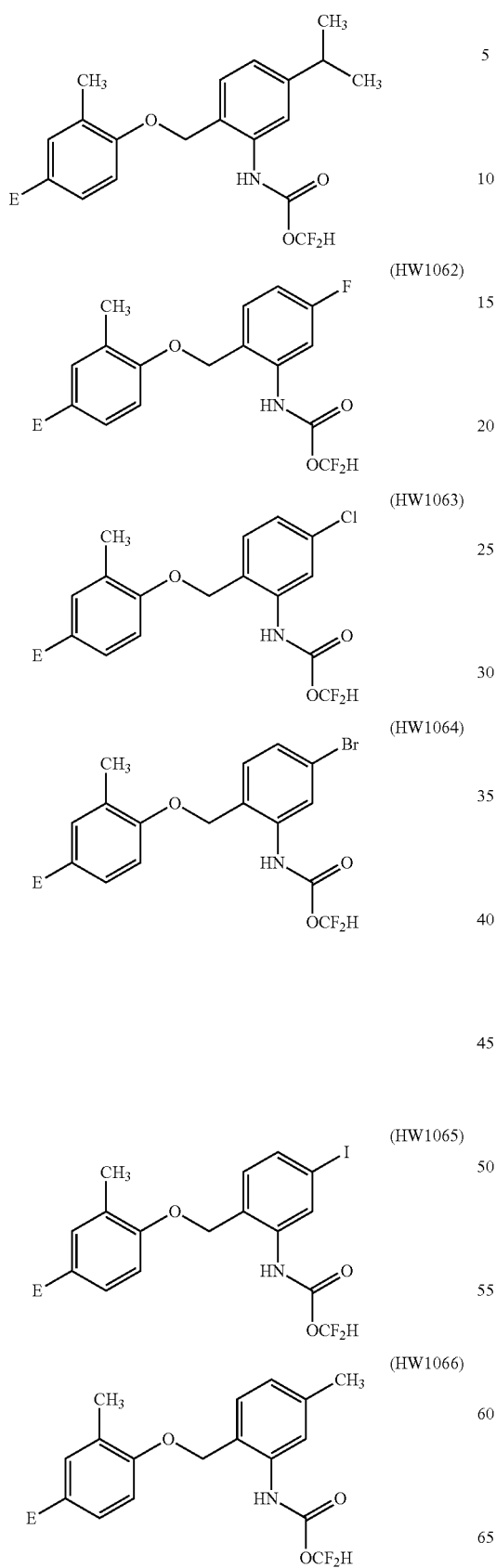
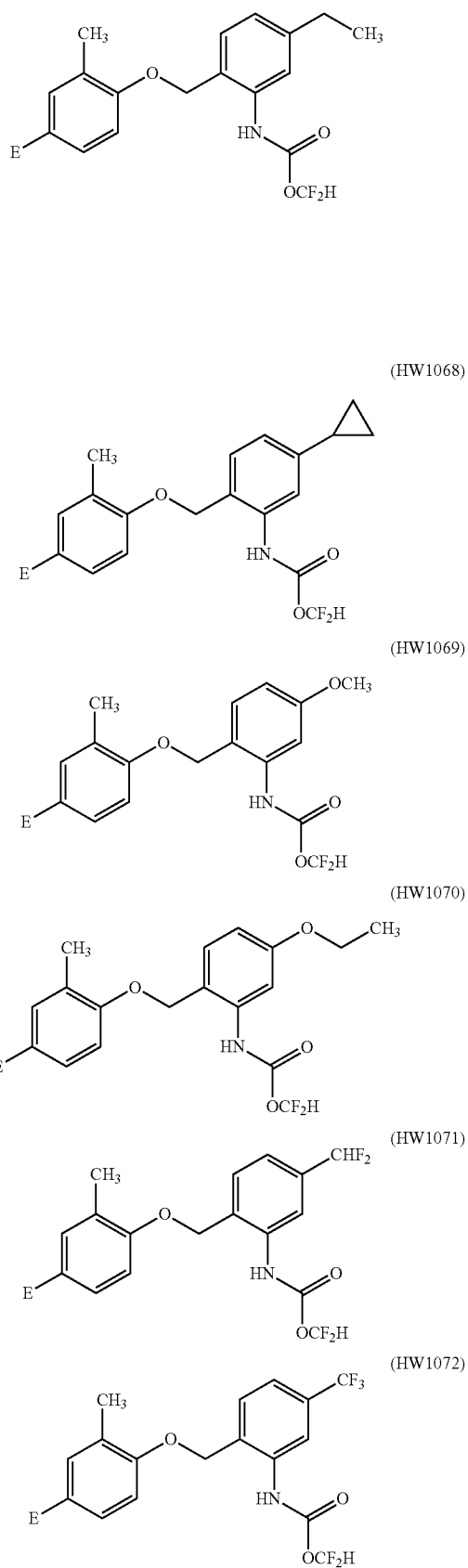

(HW1073)
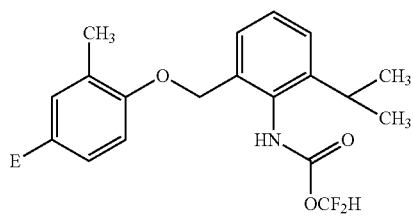

(HW1074)
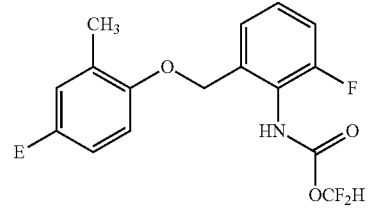

(HW1075)
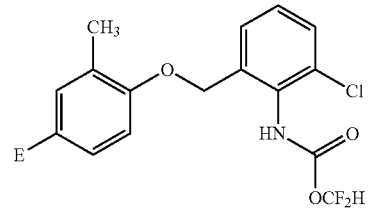

(HW1076)
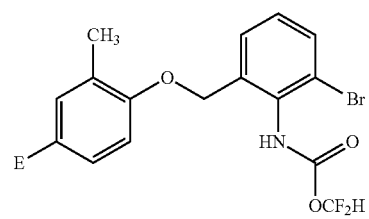

(HW1077)
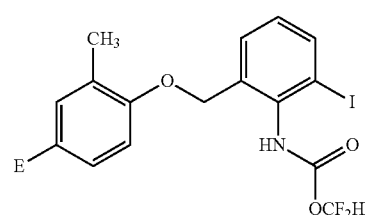

(HW1078)
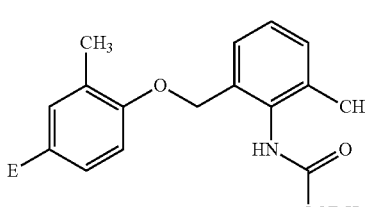

(HW1079)
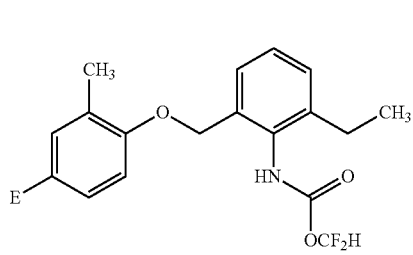

(HW1080)

(HW1081)

(HW1082)

(HW1083)

(HW1084)

[substituent number; E], [0001; 1-Me-PYR3], [0002; 1-Me-4-F-PYR3], [0003; 1-Me-4-Cl-PYR3], [0004; 1-Me-4-Br-PYR3], [0005; 1-Me-4-Me-PYR3], [0006; 1-Me-4-Et-PYR3], [0007; 1-Me-4-OMe-PYR3], [0008; 1-Me-4-OEt-PYR3], [0009; 1-Me-4-CHF2-PYR3], [0010; 1-Me-4-CF3-PYR3], [0011; 1-Me-4-OCHF2-PYR3], [0012; 1-Me-4-OCF3-PYR3], [0013; 1-Me-5-F-PYR3], [0014; 1-Me-5-Cl-PYR3], [0015; 1-Me-5-Br-PYR3], [0016; 1-Me-5-Me-PYR3], [0017; 1-Me-5-Et-PYR3], [0018; 1-Me-5-OMe-PYR3], [0019; 1-Me-5-OEt-PYR3], [0020; 1-Me-5-CHF2-PYR3], [0021; 1-Me-5-CF3-PYR3], [0022; 1-Me-5-OCHF2-PYR3], [0023; 1-Me-5-OCF3-PYR3]

For example, HA1001-0001 is a compound in which a substituent number is 0001 in a compound represented by formula (HA1001), and is a compound having the following structure.

(HA1001-0001)

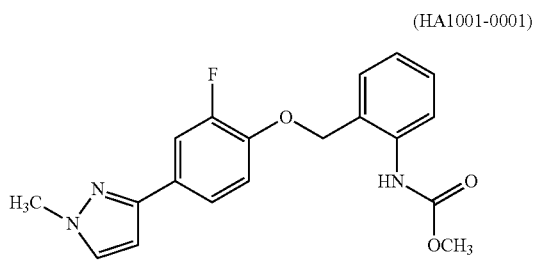 [SMILES: COC(=O)Nc1ccccc1COc1ccc(-c2ccn(C)n2)cc1F]

Formulation Examples will be shown below.

Formulation Example 1

Fifty parts (50 parts) of any one of the present compounds A, 3 parts of calcium ligninsulfonate, 2 parts of laurylmagnesium sulfate, and 45 parts of synthetic hydrated silicon oxide are thoroughly ground and mixed to obtain each formulation.

Formulation Example 2

Twenty parts (20 parts) of any one of the present compounds A and 1.5 parts of sorbitan trioleate are mixed with 28.5 parts of an aqueous solution containing 2 parts of polyvinyl alcohol, and the mixture was finely ground by a wet grinding method. Then, 40 parts of an aqueous solution containing 0.05 part of xanthan gum and 0.1 part of aluminum magnesium silicate is added thereto and 10 parts of propylene glycol is further added, followed by stirring and mixing to obtain each formulation.

Formulation Example 3

Two parts (2 parts) of any one of the present compounds A, 88 parts of kaolin clay, and 10 parts of talc are thoroughly ground and mixed to obtain each formulation.

Formulation Example 4

Five parts (5 parts) of any one of the present compounds A, 14 parts of polyoxyethylene styryl phenyl ether, 6 parts of calcium dodecylbenzenesulfonate, and 75 parts of xylene are thoroughly ground and mixed to obtain each formulation.

Formulation Example 5

Two parts (2 parts) of any one of the present compounds A, 1 part of synthetic hydrated silicon oxide, 2 parts of calcium ligninsulfonate, 30 parts of bentonite, and 65 parts of kaolin clay are thoroughly ground and mixed. After the addition of water, the mixture is thoroughly kneaded and further granulated and dried to obtain each formulation.

Formulation Example 6

Ten parts (10 parts) of any one of the present compounds A, 35 parts of a mixture of a polyoxyethylene alkyl ether sulfate ammonium salt and white carbon (weight ratio of 1:1), and 55 parts of water are finely ground by a wet grinding method to obtain each formulation.

Next, Test Examples will be shown.

Test Example 1: Control Test Against Wheat *Septoria Tritici* Blotch Fungus (*Mycosphaerella graminicola*)

The present compound 1 was diluted to a predetermined concentration (150 ppm) with dimethyl sulfoxide (DMSO). After dispensing 1 μl of the dilution thus obtained into a titer plate (with 96 wells), 150 μl of a liquid medium inoculated in advance with spores of wheat *septoria tritici* blotch fungus was further dispensed. This plate was cultured at 18° C. for 4 days, thereby allowing wheat *septoria tritici* blotch fungus to undergo proliferation, and then the degree of growth of wheat *septoria tritici* blotch fungus was measured by the absorbance at 550 nm of each well of the titer plate. Based on the degree of growth, control activity was calculated using "Equation 1". The present compound exhibited activity of 70% or more.

$$\text{Activity} = 100 \times (A-B)/A \qquad \text{"Equation 1"}$$

where
A: Degree of bacterial growth in non-treated area, or severity of plant in non-treated area
B: Degree of bacterial growth in treated area, or severity of plant in non-treated area Test Example 2

Each of plastic pots was filled with soil and rice (cultivar: NIHONBARE) was sowed and grown in a greenhouse for 20 days. Then, each water dilution prepared by adjusting so as to contain a predetermined concentration (500 ppm) of any one compound of the present compounds 10 and 11 was sprayed over stems and leaves so that it sufficiently adhered to the surface of the leaves of the rice. After spraying, the plant was air-dried and placed for 6 days at 24° C. in the daytime and 20° C. at night under high humidity condition, while being in contact with the rice seedling (cultivar: NIHONBARE) infected by the rice blast fungus (*Magnaporthe grisea*), and then the area of lesion was investigated. As a result, the lesion areas on the plant treated with the present compound 10 or 11 were 30% or less with respect to the lesion area on the non-treated plant.

The control effect was evaluated by visually observing the area of lesion on each of test plants at the time of investigation, and comparing the area of lesion on a plant treated with the present compound with that on an untreated plant. With respect to Test Examples 3 to 9, evaluation was performed in the same manner.

Test Example 3

Each of plastic pots was filled with soil and wheat (cultivar: SHIROGANE) was sowed and grown in a greenhouse for 9 days. Then, each water dilution prepared by adjusting so as to contain a predetermined concentration (500 ppm) of any one compound of the present compounds 2, 6, 7, 10, and 11 was sprayed over stems and leaves of the wheat so that it sufficiently adhered to the surface of the leaves of the wheat. After spraying, the plant was air-dried and cultivated at 20° C. for 5 days under illumination, and then inoculated by sprinkling with spores of wheat rust fungus (*Puccinia recondita*). After the inoculation, the plant was placed at 23° C. for one day under dark and high humidity condition, and cultivated under illumination at 20° C. for 8 days, and then the area of lesion was investigated.

As a result, it has been found that the area of lesion on the plant treated with the present compound 2, 6, 7, 10, or 11 was 30% or less of that on an untreated plant.

Test Example 4

Each of plastic pots was filled with soil and barley (cultivar: NISHINOHOSHI) was sowed and grown in a greenhouse for 7 days. Then, each water dilution prepared by adjusting so as to contain a predetermined concentration (200 ppm) of any one compound of the present compounds 1, 2, 3, 4, 5, 6, 7, 8, 9, 10, and 11 was sprayed over stems and leaves of the barley so that it sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was placed for 3 days in a greenhouse at 23° C. in the daytime and 20° C. at night under high humidity condition and cultivated in a greenhouse for 7 days, and then the area of lesion was investigated. As a result, the area of lesion on the plant treated with the present compound 1, 2, 3, 4, 5, 6, 7, 8, 9, 10, or 11 was 30% or less of that on an untreated plant.

Test Example 5

Each of plastic pots was filled with soil and kidney bean (cultivar: NAGAUZURA SAITOU) was sowed and grown in a greenhouse for 8 days. Then, each water dilution prepared by adjusting so as to contain a predetermined concentration (500 ppm) of any one compound of the present compounds 2, 5, 6, 7, 8, 10, and 11 was sprayed over stems and leaves of the kidney bean so that it sufficiently adhered to the surface of the leaves of the kidney bean. After spraying, the plant was air-dried and a potato dextrose agar (PDA) medium containing hyphae of the kidney bean stem rot fungus (*Sclerotinia sclerotiorum*) was placed on the leaves of the kidney bean. After the inoculation, all kidney beans were placed under high humidity condition only at night. Four days after the inoculation, the area of lesion was investigated. As a result, the area of lesion on the plant treated with the present compound 2, 5, 6, 7, 8, 10, or 11 was 30% or less of that on an untreated plant.

Test Example 6

Each of plastic pots was filled with soil and wheat (cultivar: APOGEE) was sowed and grown in a greenhouse for 10 days. Then, each water dilution prepared by adjusting so as to contain a predetermined concentration (500 ppm) of any one compound of the present compounds 2, 5, 6, 7, and 11 was sprayed over stems and leaves of the wheat so that it sufficiently adhered to the surface of the leaves of the wheat. After spraying, the plant was air-dried. After 4 days, an aqueous suspension containing spores of wheat leaf blotch fungus (*Septoria tritici*) was sprayed to inoculate the spores. After completion of the inoculation, the plant was placed at 18° C. under high humidity condition for 3 days and placed under illumination for 14 to 18 days, and then the area of lesion was investigated. As a result, the area of lesion on the plant treated with the present compound 2, 5, 6, 7, or 11 was 30% or less of that on an untreated plant.

Test Example 7

Each of plastic pots was filled with soil and cucumber (cultivar: SAGAMI HANJIRO) was sowed and grown in a greenhouse for 12 days. Then, each water dilution prepared by adjusting so as to contain a predetermined concentration (500 ppm) of any one compound of the present compounds 2, 5, 6, 7, 8, 9, 10, and 11 was sprayed over stems and leaves of the cucumber so that it sufficiently adhered to the surface of the leaves of the cucumber. After spraying, the plant was air-dried and then inoculated by sprinkling with spores of cucumber powdery mildew fungus (Sphaerotheca *fuliginea*, a QoI-resistant strain in which, among the genes encoding cytochrome b, the amino acid residue at position 143 of cytochrome b is mutated from glycine to alanine). After the inoculation, the plant was cultivated in a greenhouse at 24° C. in the daytime and 20° C. at night for 8 days, and then the area of lesion was investigated. As a result, the area of lesion on the plant treated with the present compound 2, 5, 6, 7, 8, 9, 10, or 11 was 30% or less of that on an untreated plant.

Test Example 8

Each of plastic pots was filled with soil and barley (cultivar: NISHINOHOSHI) was sowed and grown in a greenhouse for 7 days. Then, each water dilution prepared by adjusting so as to contain a predetermined concentration (200 ppm) of any one compound of the present compounds 3, 4, 5, 6, 7, 8, 9, 10, and 11 was sprayed over stems and leaves of the barley so that it sufficiently adhered to the surface of the leaves of the barley. After spraying, the plant was air-dried. After 2 days, an aqueous suspension containing spores of barley scald fungus (*Rhynchosporium secalis*) was sprayed to inoculate the spores. After completion of the inoculation, the plant was placed for 3 days in a greenhouse at 23° C. in the daytime and 20° C. at night under high humidity condition and cultivated in a greenhouse for 7 days, and then the area of lesion was investigated. As a result, the area of lesion on the plant treated with of the present compound 3, 4, 5, 6, 7, 8, 9, 10, or 11 was 30% or less of that on an untreated plant.

Test Example 9

Each of plastic pots was filled with soil and cucumber (cultivar: SAGAMI HANJIRO) was sowed and grown in a greenhouse for 19 days. Then, each water dilution prepared by adjusting so as to contain a predetermined concentration (200 ppm) of the present compounds 2, 3, 4, 5, 7, 8, 9, 10, and 11 was sprayed over stems and leaves of the cucumber so that it sufficiently adhered to the surface of the leaves of the cucumber. After spraying, the plant was air-dried. After one day, an aqueous suspension containing spores of cucumber anthracnose fungus (*Colletotrichum lagenarium*) was sprayed to inoculate the spores. After the inoculation, the plant was placed at 23° C. for one day under high humidity condition, and then cultivated in a greenhouse at 24° C. in the daytime and 20° C. at night for 6 days, and then the area of lesion was investigated. As a result, the area of lesion on the plant treated with the present compound 2, 3, 4, 5, 7, 8, 9, 10, or 11 was 30% or less of that on an untreated plant.

Test Example 10

In accordance with Formulation Example 2, a formulation was obtained from each of the present compounds 2 and 11, and then diluted with water so as to contain 500 ppm of an active ingredient to obtain a dilution.

Thirty (30) heads of cotton aphid (*Aphis gossypii*) (including adults and larvae) were released on the leaves of cucumber grown in a polyethylene cup until the first true leaf was developed. Next day, 20 mL of the dilution was sprayed. After 6 days, the number of the surviving insects was counted and the control value was calculated by the following equation.

Control value (%)={1−(Cb×Tai)/(Cai×Tb)}×100 wherein symbols in the equation represent the followings:
Cb: Number of tested insects in untreated area;
Cai: Number of surviving insects in untreated area;
Tb: Number of tested insects in treated area; and
Tai: Number of surviving insects in treated area.

As a result, the present compound 2 or 11 showed 90% or more of the control value.

The present control agent has control activity against pests and is useful as an active ingredient of a pest control agent.

The invention claimed is:

1. An aromatic compound represented by formula (1):

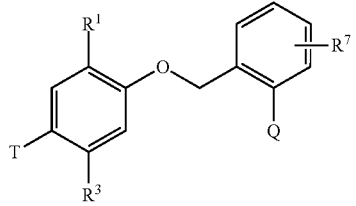

(1)

wherein $R^1$ represents a halogen atom or a C1-C4 alkyl group optionally having one or more halogen atoms;
$R^3$ represents a hydrogen atom, a halogen atom, or a C1-C4 alkyl group optionally having one or more halogen atoms;
$R^7$ represents a C1-C3 alkyl group optionally having one or more halogen atoms, a hydrogen atom, a halogen atom, a C1-C3 alkoxy group optionally having one or more halogen atoms, or a C3-C4 cycloalkyl group optionally having one or more halogen atoms;
T represents the following group T1, T2, or T3;

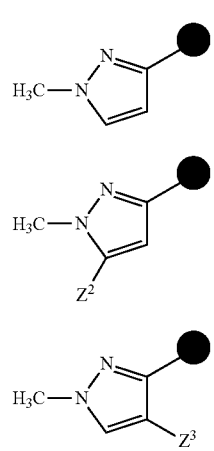

T1

T2

T3

$Z^2$ and $Z^3$ each independently represents a halogen atom, a C1-C3 alkyl group optionally having one or more halogen atoms, or a C1-C3 alkoxy group optionally having one or more halogen atoms;

Q represents the following group Q1, Q2, or Q3;

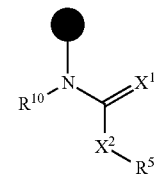

Q1

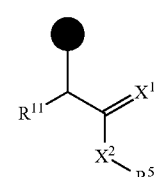

Q2

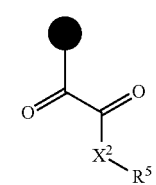

Q3

$R^5$ represents a C1-C3 alkyl group optionally having one or more halogen atoms;
$R^{10}$ represents a hydrogen atom, a hydroxyl group, or a methyl group;
$R^{11}$ represents a hydrogen atom, a hydroxyl group, a methyl group, or a methoxy group;
$X^1$ represents an oxygen atom or a sulfur atom;
$X^2$ represents an oxygen atom, a sulfur atom, $NR^{12}$, or a direct bond; and
$R^{12}$ represents a C1-C3 alkyl group optionally having one or more halogen atoms, or a hydrogen atom.

2. An aromatic compound represented by formula (2):

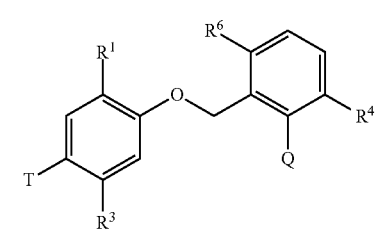

(2)

wherein $R^1$ represents a halogen atom or a C1-C4 alkyl group optionally having one or more halogen atoms;
$R^3$ represents a hydrogen atom, a halogen atom, or a C1-C4 alkyl group optionally having one or more halogen atoms;
$R^4$ and $R^6$ each independently represents a C1-C3 alkyl group optionally having one or more halogen atoms, a hydrogen atom, a halogen atom, a C1-C3 alkoxy group optionally having one or more halogen atoms, or a C3-C4 cycloalkyl group optionally having one or more halogen atoms;
T represents the following group T1, T2, or T3;

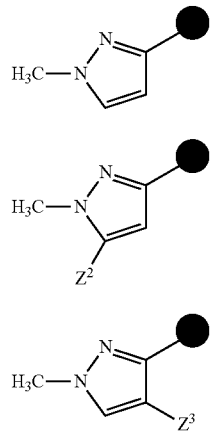

$Z^2$ and $Z^3$ each independently represents a halogen atom, a C1-C3 alkyl group optionally having one or more halogen atoms, or a C1-C3 alkoxy group optionally having one or more halogen atoms;
Q represents the following group Q1, Q2, or Q3;

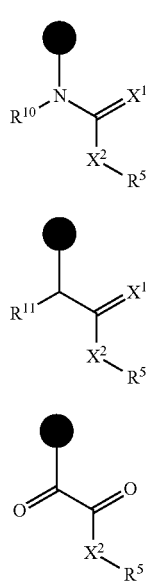

$R^5$ represents a C1-C3 alkyl group optionally having one or more halogen atoms;
$R^{10}$ represents a hydrogen atom, a hydroxyl group, or a methyl group;
$R^{11}$ represents a hydrogen atom, a hydroxyl group, a methyl group, or a methoxy group;
$X^1$ represents an oxygen atom or a sulfur atom;
$X^2$ represents an oxygen atom, a sulfur atom, $NR^{12}$, or a direct bond; and
$R^{12}$ represents a C1-C3 alkyl group optionally having one or more halogen atoms, or a hydrogen atom.

3. The aromatic compound according to claim 2, wherein Q is a group Q1 or Q3.

4. An aromatic compound represented by formula (3):

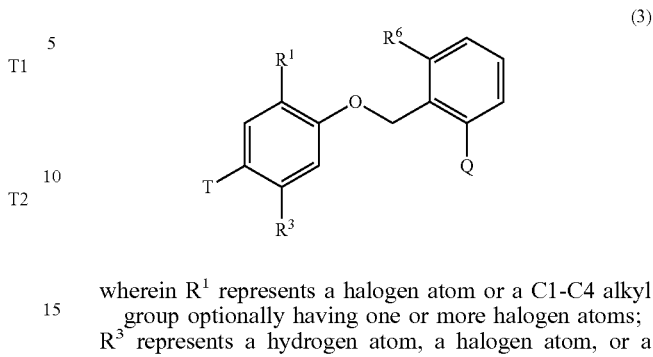

(3)

wherein $R^1$ represents a halogen atom or a C1-C4 alkyl group optionally having one or more halogen atoms;
$R^3$ represents a hydrogen atom, a halogen atom, or a C1-C4 alkyl group optionally having one or more halogen atoms;
$R^6$ represents a C1-C3 alkyl group optionally having one or more halogen atoms, a hydrogen atom, a halogen atom, a C1-C3 alkoxy group optionally having one or more halogen atoms, or a C3-C4 cycloalkyl group optionally having one or more halogen atoms;
T represents the following group T1, T2, or T3;

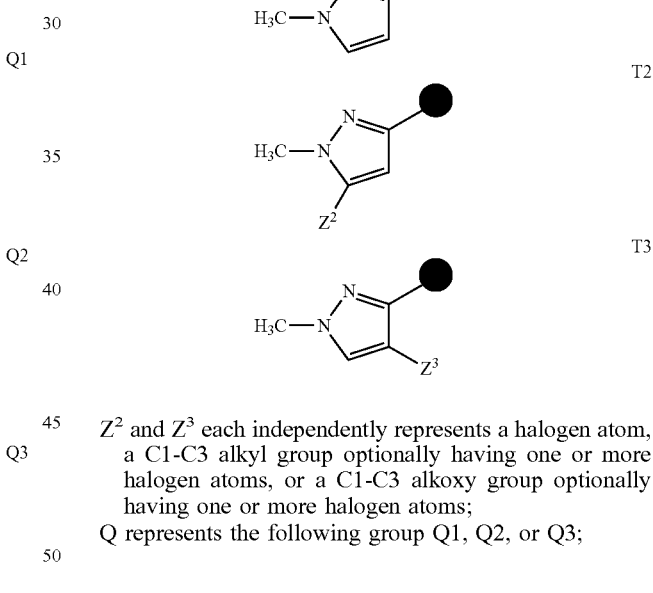

$Z^2$ and $Z^3$ each independently represents a halogen atom, a C1-C3 alkyl group optionally having one or more halogen atoms, or a C1-C3 alkoxy group optionally having one or more halogen atoms;
Q represents the following group Q1, Q2, or Q3;

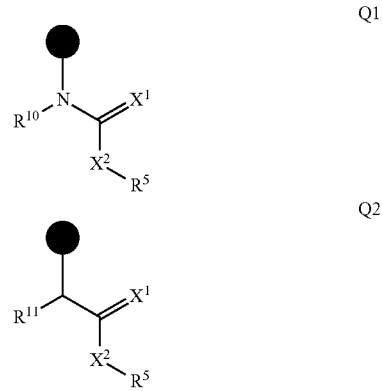

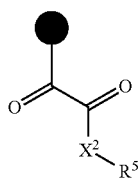

R⁵ represents a C1-C3 alkyl group optionally having one or more halogen atoms;
R¹⁰ represents a hydrogen atom, a hydroxyl group, or a methyl group;
R¹¹ represents a hydrogen atom, a hydroxyl group, a methyl group, or a methoxy group;
X¹ represents an oxygen atom or a sulfur atom;
X² represents an oxygen atom, NR¹², or a direct bond; and
R¹² represents a C1-C3 alkyl group optionally having one or more halogen atoms, or a hydrogen atom.

5. The aromatic compound according to claim 4, wherein R¹ is a C1-C4 alkyl group optionally having one or more halogen atoms; and
X¹ is an oxygen atom.

6. A pest control agent comprising the aromatic compound as defined in claim 1.

7. A method for controlling pests, which comprises treating plants or soil with an effective amount of the aromatic compound as defined in claim 1.

8. A pest control agent comprising the aromatic compound as defined in claim 2.

9. A method for controlling pests, which comprises treating plants or soil with an effective amount of the aromatic compound as defined in claim 2.

10. A pest control agent comprising the aromatic compound as defined in claim 3.

11. A method for controlling pests, which comprises treating plants or soil with an effective amount of the aromatic compound as defined in claim 3.

12. A pest control agent comprising the aromatic compound as defined in claim 4.

13. A method for controlling pests, which comprises treating plants or soil with an effective amount of the aromatic compound as defined in claim 4.

14. A pest control agent comprising the aromatic compound as defined in claim 5.

15. A method for controlling pests, which comprises treating plants or soil with an effective amount of the aromatic compound as defined in claim 5.

* * * * *